US011319510B2

(12) United States Patent
Velasquez et al.

(10) Patent No.: US 11,319,510 B2
(45) Date of Patent: *May 3, 2022

(54) METHOD AND CONSUMER PRODUCT COMPOSITION HAVING ENZYMES FOR CLEANING A SURFACE HAVING SOIL COMPRISING FATTY ACID

(71) Applicant: The Procter & Gamble Company, Cincinnati, OH (US)

(72) Inventors: Juan Esteban Velasquez, Cincinnati, OH (US); Denis Alfred Gonzales, Brussels (BE); Jean-Luc Philippe Bettiol, Etterbeek (BE); Nicholas William Geary, Mariemont, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,894

(22) Filed: Nov. 13, 2018

(65) Prior Publication Data

US 2019/0144794 A1    May 16, 2019

(30) Foreign Application Priority Data

| Nov. 13, 2017 | (EP) | ................................. | 17201300 |
| Nov. 13, 2017 | (EP) | ................................. | 17201309 |
| Jun. 20, 2018 | (EP) | ................................. | 18178709 |
| Oct. 8, 2018  | (EP) | ................................. | 18199084 |
| Oct. 8, 2018  | (EP) | ................................. | 18199086 |
| Oct. 8, 2018  | (EP) | ................................. | 18199093 |

(51) Int. Cl.

| *C11D 3/386* | (2006.01) |
| *A61Q 5/02*  | (2006.01) |
| *C12N 9/04*  | (2006.01) |
| *C12N 9/02*  | (2006.01) |
| *A61K 8/66*  | (2006.01) |
| *C11D 11/00* | (2006.01) |
| *C11D 1/10*  | (2006.01) |
| *C11D 1/12*  | (2006.01) |
| *C11D 1/66*  | (2006.01) |

(52) U.S. Cl.
CPC ............ *C11D 3/38636* (2013.01); *A61K 8/66* (2013.01); *A61Q 5/02* (2013.01); *C11D 3/38654* (2013.01); *C11D 11/0064* (2013.01); *C12N 9/0006* (2013.01); *C12N 9/0069* (2013.01); *C11D 1/10* (2013.01); *C11D 1/126* (2013.01); *C11D 1/662* (2013.01); *C12Y 113/11* (2013.01); *C12Y 402/01092* (2013.01)

(58) Field of Classification Search
None
See application file for complete search history.

(56) References Cited

U.S. PATENT DOCUMENTS

| 2003/0166485 | A1* | 9/2003  | Hage ..................... | C11D 3/3932 |
|              |     |         |                           | 510/314 |
| 2010/0080787 | A1* | 4/2010  | Perrier .................... | A61K 8/66 |
|              |     |         |                           | 424/94.4 |
| 2015/0005223 | A1* | 1/2015  | McConaughy ........ | A61K 8/466 |
|              |     |         |                           | 510/439 |
| 2017/0321160 | A1  | 11/2017 | Lant                      |             |
| 2017/0321161 | A1* | 11/2017 | Lant ................... | C11D 3/38672 |

FOREIGN PATENT DOCUMENTS

WO    9526393 A1    10/1995

OTHER PUBLICATIONS

Hamberg et al. Biochem Biophys Res Commun. Dec. 9, 2005;338(1):169-74. (Year: 2005).*
Hamberg et al., "Fatty acid alpha-dioxygenases", Prostaglandins & other Lipid Mediators 68-69, 2002, pp. 363-374.
International Search Report and Written Opinion dated Jan. 25, 2019, U.S. Appl. No. 16/188,894, 25 pgs.
"Jianhe Xu" East China University of Science and Technology Press, the first edition, Oct. 2008 ,2 Pages.

* cited by examiner

*Primary Examiner* — Christian L Fronda
(74) *Attorney, Agent, or Firm* — James E Oehlenschlager; Jason J Camp

(57) ABSTRACT

A method of cleaning a surface having disposed thereon a soil comprising fatty acid, the method comprising contacting the soil with a consumer product composition comprising a surfactant and a soil transforming enzyme selected from the group consisting of hydroperoxy fatty acid producing enzymes, hydroperoxy fatty acid converting enzymes, multi-domain enzymes, hydroxy fatty acid producing enzymes, and mixtures thereof. The method further comprises converting the fatty acid of the soil into an active fatty acid derivative material selected from the group consisting of hydroperoxy fatty acids, hydroperoxy fatty acid derivatives, hydroxy fatty acids, and mixtures thereof. Consumer product compositions are also provided.

15 Claims, No Drawings
Specification includes a Sequence Listing.

METHOD AND CONSUMER PRODUCT COMPOSITION HAVING ENZYMES FOR CLEANING A SURFACE HAVING SOIL COMPRISING FATTY ACID

REFERENCE TO A SEQUENCE LISTING

This application contains a Sequence Listing in computer readable form. The computer readable form is incorporated herein by reference.

FIELD OF THE INVENTION

The present invention relates to methods of transforming soil comprising fatty acid into an active fatty acid derivative material and consumer product compositions comprising a surfactant and a soil transforming enzyme.

BACKGROUND OF THE INVENTION

Consumer product compositions, such as those for cleaning surfaces, should have a good suds profile in particular a long-lasting suds profile especially in the presence of greasy soils, while providing good soil and/or grease cleaning. Users usually see suds as an indicator of the performance of the detergent composition. Moreover, the user of a detergent composition may also use the suds profile and the appearance of the suds (e.g., density, whiteness) as an indicator that the wash solution still contains active detergent ingredients. Accordingly, it is desirable for a detergent composition to provide "good sudsing profile", which includes good suds height and/or density as well as good suds duration during the initial mixing of the detergent with water and/or during the entire washing operation.

It has been found that some types of soil, in particular greasy soils comprising fatty acids, can act as a suds suppressor, triggering consumers to replace the product more frequently than is necessary. As such there is a need to provide detergent compositions with desirable suds properties, especially in the presence of greasy soils, even more in the presence of greasy soils comprising fatty acids, and that at the same time provide good soil and grease removal.

There is also a desire to utilize less surfactant materials in consumer product composition. However, using less surfactant can decrease the suds generation and/or cleaning performance of the consumer product composition.

There remains a desire to provide a consumer product composition for cleaning surfaces that have soils comprising fatty acid which provide effective suds generation and/or cleaning performance, especially when the consumer product composition contains relatively low amounts of surfactant in the composition.

SUMMARY OF THE INVENTION

The present invention relates to a method of cleaning a surface having disposed thereon a soil comprising fatty acid, the method comprising contacting the soil with a consumer product composition comprising a surfactant and a soil transforming enzyme selected from the group consisting of hydroperoxy fatty acid producing enzymes, hydroperoxy fatty acid converting enzymes, multi-domain enzymes, hydroxy fatty acid producing enzymes, and mixtures thereof. The method further comprises converting the fatty acid of the soil into an active fatty acid derivative material selected from the group consisting of hydroperoxy fatty acids, hydroperoxy fatty acid derivatives, hydroxy fatty acids, and mixtures thereof.

The present invention further relates to consumer product compositions comprising a surfactant selected from the group consisting of anionic surfactants, nonionic surfactants, zwitterionic surfactants, amphoteric surfactants, cationic surfactants, and mixtures thereof; and a soil transforming enzyme selected from the group consisting of hydroperoxy fatty acid producing enzymes, hydroperoxy fatty acid converting enzymes, multi-domain enzymes, hydroxy fatty acid producing enzymes, and mixtures thereof.

DETAILED DESCRIPTION OF THE INVENTION

Definitions

As used herein, the articles "a" and "an" when used in a claim, are understood to mean one or more of what is claimed or described.

As used herein, the term "substantially free of" or "substantially free from" means that the indicated material is present in an amount of no more than about 5 wt %, preferably no more than about 2%, and more preferably no more than about 1 wt % by weight of the composition.

As used therein, the term "essentially free of" or "essentially free from" means that the indicated material is present in an amount of no more than about 0.1 wt % by weight of the composition, or preferably not present at an analytically detectable level in such composition. It may include compositions in which the indicated material is present only as an impurity of one or more of the materials deliberately added to such compositions.

As used herein, the term "detergent composition" refers to a composition or formulation designed for cleaning soiled surfaces. Such compositions include but are not limited to, dishwashing compositions, laundry detergent compositions, fabric softening compositions, fabric enhancing compositions, fabric freshening compositions, laundry pre-wash, laundry pretreat, laundry additives, spray products, dry cleaning agent or composition, laundry rinse additive, wash additive, post-rinse fabric treatment, ironing aid, hard surface cleaning compositions, unit dose formulation, delayed delivery formulation, detergent contained on or in a porous substrate or nonwoven sheet, and other suitable forms that may be apparent to one skilled in the art in view of the teachings herein. Such compositions may be used as a pre-cleaning treatment, a post-cleaning treatment, or may be added during the rinse or wash cycle of the cleaning process. The detergent compositions may have a form selected from liquid, powder, single-phase or multi-phase unit dose or pouch form, tablet, gel, paste, bar, or flake. Preferably the composition is for manual-washing. Preferably, the detergent composition of the present invention is a dishwashing detergent. Preferably the composition is in the form of a liquid.

As used herein the term "fragment" means an amino acid sequence of at least 30, 60, 100, 150 contiguous amino acids of the reference sequences or any integer there-between.

As used herein the term "identity" means the identity between two or more sequences and is expressed in terms of the identity or similarity between the sequences as calculated over the entire length of a sequence aligned against the entire length of the reference sequence. Sequence identity can be measured in terms of percentage identity; the higher the percentage, the more identical the sequences are. The percentage identity is calculated over the length of comparison. For example, the identity is typically calculated over the entire length of a sequence aligned against the entire length of the reference sequence. Methods of alignment of sequences for comparison are well known in the art and identity can be calculated by many known methods. Various programs and alignment algorithms are described in the art. It should be noted that the terms 'sequence identity' and 'sequence similarity' can be used interchangeably.

As used herein the term "increased suds longevity" means an increase in the duration of visible suds in a washing process cleaning soiled articles using the composition comprising one or more hydroperoxy fatty acid producing enzymes, and one or more hydroperoxy fatty acid converting enzymes, compared with the suds longevity provided by the same composition and process in the absence of the hydroperoxy fatty acid producing enzymes and the hydroperoxy fatty acid converting enzymes.

As used herein, the term "soiled surfaces" refers non-specifically to any type of flexible material consisting of a network of natural or artificial fibers, including natural, artificial, and synthetic fibers, such as, but not limited to, cotton, linen, wool, polyester, nylon, silk, acrylic, and the like, as well as various blends and combinations. Soiled surfaces may further refer to any type of hard surface, including natural, artificial, or synthetic surfaces, such as, but not limited to, tile, granite, grout, glass, composite, vinyl, hardwood, metal, cooking surfaces, plastic, and the like, as well as blends and combinations, as well as dishware. Key targeted soiled surfaces by this application are soiled dishware.

As used herein, the term "variant" of hydroperoxy fatty acid producing enzyme or hydroperoxy fatty acid converting enzyme means an amino acid sequence when the hydroperoxy fatty acid producing enzyme or hydroperoxy fatty acid converting enzyme is modified by, or at, one or more amino acids (for example 1, 2, 3, 4, 5, 6, 7, 8, 9 or 10 or more amino acid modifications) selected from substitutions, insertions, deletions and combinations thereof. The variant may have "conservative" substitutions, wherein a substituted amino acid has similar structural or chemical properties to the amino acid that replaces it, for example, replacement of leucine with isoleucine. A variant may have "non-conservative" changes, for example, replacement of a glycine with a tryptophan. Variants may also include sequences with amino acid deletions or insertions, or both. Guidance in determining which amino acid residues may be substituted, inserted, or deleted without abolishing the activity of the protein may be found using computer programs well known in the art. Variants may also include truncated forms derived from a wild-type hydroperoxy fatty acid producing enzyme or hydroperoxy fatty acid converting enzyme, such as for example, a protein with a truncated N-terminus. Variants may also include forms derived by adding an extra amino acid sequence to a wild-type protein, such as for example, an N-terminal tag, a C-terminal tag or an insertion in the middle of the protein sequence.

As used herein, the term "water hardness" or "hardness" means uncomplexed cation ions (i.e., $Ca^{2+}$ or $Mg^{2+}$) present in water that have the potential to precipitate with anionic surfactants or any other anionically charged detergent actives under alkaline conditions, and thereby diminishing the surfactancy and cleaning capacity of surfactants. Further, the terms "high water hardness" and "elevated water hardness" can be used interchangeably and are relative terms for the purposes of the present invention, and are intended to include, but not limited to, a hardness level containing at least 12 grams of calcium ion per gallon water (gpg, "American grain hardness" units).

Consumer Product Compositions

The present invention relates to consumer product compositions comprising a surfactant and a soil transforming enzyme. The consumer product compositions, when used to contact soiled surfaces having disposed thereon soils comprising fatty acid, can convert the fatty acid of the soil into active fatty acid derivative materials. In this regard, the consumer product compositions of the present invention can exhibit improved cleaning performance, or equivalent cleaning performance while utilizing lower levels of surfactant in the consumer product composition.

Consumer product compositions of the present invention include, but are not limited to, compositions for treating hair (human, dog, and/or cat), including, bleaching, coloring, dyeing, conditioning, growing, removing, retarding growth, shampooing, styling; deodorants and antiperspirants; personal cleansing; products, and/or methods relating to treating skin (human, dog, and/or cat), including application of creams, lotions, and other topically applied products for consumer use; shaving; body sprays; compositions for treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; compositions incorporated into products relating to disposable absorbent and/or non-absorbent articles including adult incontinence garments, bibs, diapers, training pants, infant and toddler care wipes; hand soaps, shampoos, lotions, oral care implements; products such as wet or dry bath tissue, facial tissue, disposable handkerchiefs, disposable towels, and/or wipes; compositions incorporated into products relating to catamenial pads, incontinence pads, interlabial pads, panty liners, pessaries, sanitary napkins, tampons and tampon applicators, and/or wipes. In preferred aspects, the consumer product composition is a detergent composition.

Preferred consumer product compositions herein include fabric cleaning compositions, hard surface cleaning compositions, dishwashing compositions, and hair cleaning compositions. Such compositions typically comprise a consumer product adjunct ingredient(s).

A preferred consumer product composition is a manual dishwashing composition, preferably in liquid form. It typically contains from 30% to 95%, preferably from 40% to 90%, more preferably from 50% to 85% by weight of the composition of a liquid carrier in which the other essential and optional components are dissolved, dispersed or suspended. One preferred component of the liquid carrier is water.

Preferably the pH of the consumer product composition of the invention, measured as a 10% product concentration in demineralized water at 20° C., is adjusted to between 3 and 14, more preferably between 4 and 13, more preferably between 6 and 12 and most preferably between 8 and 10. The pH of the consumer product composition can be adjusted using pH modifying ingredients known in the art.

Soil Transforming Enzymes

Consumer product compositions comprising: a) one or more soil-transforming enzymes selected from the group consisting of hydroperoxy fatty acid producing enzymes, hydroperoxy fatty acid converting enzymes, hydroperoxy fatty acid producing and converting enzymes, peroxygenases, fatty acid hydratases, and mixtures thereof; and b)

surfactant. The consumer product composition can further comprise consumer product adjunct ingredients as described herein.

In one aspect, the level of surfactant in the consumer product composition is less than about 2%, preferably less than about 1%, preferably less than about 0.5%, preferably less than about 0.1%, or preferably 0%, by weight of the composition, while still providing enhanced sudsing and/or cleaning benefits against oily and/or greasy soils by transforming such soils into surface active agents. It is believed that the increased sudsing and/or cleaning benefits are due to the conversion of fatty acids into more oxygenated fatty acids with enhanced surfactant properties and decreased tendency to precipitation in the presence of hard water. Furthermore, it is believed that concentrations of surfactants below about 2%, by weight of the composition, can favor the stability and activity of the enzymes in the consumer product composition.

Hydroperoxy Fatty Acid Producing Enzymes

Fatty acids can be oxidized in the presence of molecular oxygen ($O_2$) by the hydroperoxy fatty acid producing enzymes such as dioxygenases to produce hydroperoxy fatty acids. These hydroperoxylated compounds can be further processed enzymatically or transformed spontaneously to a diverse group of oxygenated fatty acids and other derivatives. In the context of the current application, a "hydroperoxy fatty acid producing enzyme" is an enzyme that is capable of converting at least one fatty acid into a mixture of oxygenated compounds, comprising at least a hydroperoxy fatty acid as an intermediate or as a final product. Non-limiting examples of hydroperoxy fatty acid producing enzymes are lipoxygenases (LOX), heme-dependent dioxygenases (DOX), alpha-dioxygenases, diol synthases, and other enzymes containing a domain with dioxygenase activity.

In one embodiment of the present invention, the cleaning composition comprises lipoxygenases. Lipoxygenases (EC 1.13.11.-) are a family of (non-heme), iron- or manganese-containing dioxygenases that catalyze the insertion of molecular oxygen into unsaturated fatty acids to produce the corresponding hydroperoxy fatty acids. The present invention comprises different groups of lipoxygenases, including linoleate lipoxygenases, arachidonate lipoxygenases, and oleate lipoxygenases. Even though linoleate, arachidonate, and oleate lipoxygenases typically recognize linoleic acid/linoleate, arachidonic acid/arachidonate, and oleic acid/oleate as the preferred substrates, respectively, the terms "linoleate lipoxygenases," "arachidonate lipoxygenases," and "oleate lypoxygenases" are used interchangeably herein and do not suggest any substrate specificity, i.e., the respective enzymes may act on any of these substrates.

Regiospecific lipoxygenases catalyze the positional-specific hydroperoxylation of unsaturated fatty acids. For example, animal 12- and 15-lipoxygenases and microbial 15-lipoxygenases convert arachidonic acid into the corresponding 12- and 15-hydroperoxy fatty acids; whereas 11-lipoxygenases from coral and sea urchin produce 11-hydroperoxyfatty acids as intermediate or final products. Similarly, plant and bacterial 9-, and 13-lipoxygenases and fungal 11- and 13-lipoxygenases transform linoleic acid into its 9-, 11-, and 13-hydroperoxy fatty acid derivatives. Furthermore, some dioxygenases are able to catalyze the incorporation of molecular oxygen at several positions of the unsaturated fatty acid.

Non-limiting examples of lipoxygenases that are part of the current invention include the wild-type lipoxygenases listed in Table 1 and variants thereof which exhibit lipoxy- genase activity. Preferred lipoxygenases exhibit at least 20%, preferably at least 30%, preferably at least 40%, preferably at least 50%, preferably at least 60%, preferably at least 70%, preferably at least 80%, preferably at least 90%, preferably at least 95%, preferably at least 98% or preferably even 100% identity to one of more of the wild-type lipoxygenases listed in Table 1.

In embodiments of the present invention, a cleaning composition comprises one or more unsaturated fatty acid (UFA) heme-dioxygenases. In contrast to lipoxygenases with catalytic iron or manganese, the UFA heme-dioxygenases of the COX superfamily are heme-dependent enzymes, use a catalytic Tyr, and can catalyze effectively the conversion of not only polyunsaturated fatty acids (e.g. linoleic acid), but also mono unsaturated fatty acids (e.g. oleic acid).

In other embodiments of the present invention, said UFA heme-dioxygenases are selected from the group comprising 8R-dioxygenases, 8S-dioxygenases, 9R-dioxygenases, 9S-dioxygenases, 10R-dioxygenases, 10S-dioxygenases, and mixtures thereof, preferably 10S-dioxygenases. In another embodiment, said UFA heme-dioxygenases are selected from the group comprising oleate dioxygenases, linoleate dioxygenase, and mixtures thereof, preferably oleate dioxygenases, and more preferably oleate 10S-dioxygenases. Even though oleate and linoleate dioxygenases typically recognize oleic acid/oleate and linoleic acid/linoleate as the preferred substrates, respectively, the terms "oleate dioxygenases" and "linoleate dioxygenases" are used interchangeably herein and do not suggest any substrate specificity, i.e., the respective enzymes may act on any of these substrates.

Regiospecific UFA heme-dioxygenases catalyze the positional-specific hydroperoxylation of UFAs. For example, 10S-dioxygenases from *Pseudomonas aeruginosa* or *Nostoc punctiforme* convert oleic acid into the corresponding 10S-hydroperoxy derivative. Furthermore, some UFA heme-dioxygenases are able to catalyze the incorporation of molecular oxygen at several positions of the UFA.

Non-limiting examples of UFA heme-dioxygenases that are part of the current invention include the wild-type UFA heme-dioxygenases listed in Table 1 and variants thereof which exhibit dioxygenase activity. Preferred UFA heme-dioxygenases exhibit at least 20%, preferably at least 30%, preferably at least 40%, preferably at least 50%, preferably at least 60%, preferably at least 70%, preferably at least 80%, preferably at least 90%, preferably at least 95%, preferably at least 98% or preferably even 100% identity to one of more of the wild-type dioxygenases listed in Table 1.

TABLE 1

Lipoxygenases and UFA Heme-Dioxygenases

| Origin | SEQ ID |
|---|---|
| Linoleate 8R-dioxygenases | |
| *Gaeumannomyces graminis* | 1 |
| Linolenate 9R-lipoxygenases (EC 1.13.11.61) | |
| *Nostoc* sp. PCC 7120 | 2 |
| *Acaryochloris marina* | 3 |
| Linoleate 9S-lipoxygenases (EC 1.13.11.58) | |
| *Avena sativa* | 4 |
| *Oryza sativa* subsp. *Japonica* | 5 |
| *Magnaporthe oryzae* | 6 |

TABLE 1-continued

Lipoxygenases and UFA Heme-Dioxygenases

| Origin | SEQ ID |
|---|---|
| Linoleate 10R-dioxygenases | |
| *Aspergillus fumigatus* | 7 |
| *Aspergillus nidulans* | 8 |
| *Aspergillus terreus* | 9 |
| *Aspergillus clavatus* | 10 |
| *Penicillium marneffei* | 11 |
| *Penicillium decumbens* | 12 |
| *Penicillium chrysogenum* | 13 |
| *Aspergillus niger* | 14 |
| Linoleate 10S-lipoxygenases | |
| *Nostoc punctiforme* | 15 |
| Oleate 10S-dioxygenases | |
| *Pseudomonas aeruginosa* | 16 |
| *Pseudomonas aeruginosa* | 17 |
| Linoleate 11-lipoxygenases (EC 1.13.11.45) | |
| *Fusarium oxysporum* | 18 |
| *Gaeumannomyces graminis* var. *avenae* | 19 |
| *Colletotrichum gloeosporioides* | 20 |
| Linoleate 13S-lipoxygenases (EC 1.13.11.12) | |
| *Arabidopsis thaliana* | 21 |
| *Oryza sativa* subsp. *Japonica* | 22 |
| Linoleate 9/13-lipoxygenases (EC 1.13.11.B6) | |
| *Pseudomonas aeruginosa* | 23 |
| *Momordica charantia* | 24 |
| Arachidonate 5-lipoxygenases (EC 1.13.11.34) | |
| *Homo sapiens* | 25 |
| Arachidonate 8-lipoxygenases (EC 1.13.11.40) | |
| *Plexaura homomalla* | 26 |
| Arachidonate 12-lipoxygenases (E.C. 1.13.11.31) | |
| *Homo sapiens* | 27 |
| *Homo sapiens* | 28 |
| *Homo sapiens* | 29 |
| *Physcomitrella patens* | 30 |
| Arachidonate 15-lipoxygenase (EC 1.13.11.33) | |
| *Homo sapiens* | 31 |
| *Pseudomonas aeruginosa* | 32 |
| *Cyanothece* sp. | 33 |
| *Nostoc punctiforme* | 34 |
| *Hordeum vulgare* | 35 |

In another embodiment of the present invention, the cleaning composition comprises alpha-dioxygenases. Alpha-dioxygenases are another class of dioxygenases (DOX) that convert saturated and unsaturated fatty acids to their corresponding 2-hydroperoxy fatty acids via stereoselective dioxygenation. The resulting hydroperoxy fatty acids can undergo spontaneous decarboxylation to shorter aldehydes. Alpha-dioxygenases differs from lipoxygenases and heme-dioxygenases in that an unsaturated carbon bond is not required during the oxidation. They are generally encoded by different species of plants and fungi, where they are up-regulated during the host defense response against pathogen attack, but homologs are also found in bacteria.

Non-limiting examples of alpha-dioxygenases that are part of the current invention include the wild-types listed in Table 2 and variants thereof which exhibit alpha-dioxygenase activity. Preferred alpha-dioxygenases exhibit at least 20%, preferably at least 30%, preferably at least 40%, preferably at least 50%, preferably at least 60%, preferably at least 70%, preferably at least 80%, preferably at least 90%, preferably at least 95%, preferably at least 98% or preferably even 100% identity as calculated over the entire length of a sequence aligned against the entire length of at least one reference sequence selected from the group consisting of wild-type alpha-dioxygenases listed in Table 2.

TABLE 2

Alpha-Dioxygenases

| Origin | SEQ ID |
|---|---|
| Alpha-dioxygenases | |
| *Arabidopsis thaliana* | 36 |
| *Arabidopsis thaliana* | 37 |
| *Fusarium graminearum* | 38 |
| *Fusarium verticillioides* | 39 |
| *Fusarium oxysporum* | 40 |
| *Oryza sativa* (Rice) | 41 |

Hydroperoxy Fatty Acid Converting Enzymes

Hydroperoxy fatty acids can be converted catalytically or spontaneously to oxygenated derivatives including hydroxy-, dihydroxy-, oxo-, epoxy-, and keto fatty acids, divinyl ethers, and aldehydes (Andreou, A., et al. (2009), *Prog. Lipid Res.* 48(3-4): 148-170). The cleaning composition of invention may further comprise one or more hydroperoxy fatty acid converting enzymes, which are capable of converting the hydroperoxy fatty acids into one or more derivatives of hydroperoxy fatty acids. Preferably the hydroperoxy fatty acid converting enzymes are selected from the group consisting of: cyclooxygenases (EC 1.14.99.1), allene oxide synthases (EC 4.2.1.92), hydroperoxide isomerases (EC 4.2.1.92, EC 5.3.99.1, EC 5.4.4.5, EC 5.4.4.6), hydroperoxide lyases (EC 4.2.1.92), hydroperoxide dehydratases (EC 4.2.1.92), divinyl ether synthases (EC 4.2.1.121, EC 4.2.1.B8, EC 4.2.1.B9), 9,12-octadecadienoate 8-hydroperoxide 8R-isomerases (EC 5.4.4.5), 9,12-octadecadienoate 8-hydroperoxide 8S-isomerases (EC 5.4.4.6), 7,10-hydroperoxide diol synthases, epoxy alcohol synthases, and mixtures thereof. Preferably the hydroperoxy fatty acid converting enzymes are selected from the group consisting of: hydroperoxide isomerases (EC 4.2.1.92, EC 5.3.99.1, EC 5.4.4.5, EC 5.4.4.6), hydroperoxide lyases (EC 4.2.1.92), hydroperoxide dehydratases (EC 4.2.1.92), 7,10-hydroperoxide diol synthases, epoxy alcohol synthases, and mixtures thereof, preferably 7,10-hydroperoxide diol synthases.

Non-limiting examples of hydroperoxy fatty acid converting enzymes include the wild-types listed in Table 2 and variants thereof which exhibit hydroperoxy fatty acid converting enzyme activity. Preferred hydroperoxy fatty acid converting enzymes exhibit at least 20%, preferably at least 30%, preferably at least 40%, preferably at least 50%, preferably at least 60%, preferably at least 70%, preferably at least 80%, preferably at least 90%, preferably at least 95%, preferably at least 98% or preferably even 100% identity to one of more of the wild-types listed in Table 3. Preferred hydroperoxy fatty acid converting enzymes can also be fragments (e.g., N-terminal domain or C-terminal domain) of the wild-types listed in Table 3.

TABLE 3

Hydroperoxy Fatty Acid Converting Enzymes

| Origin | SEQ ID |
|---|---|
| Cyclooxygenases (EC 1.14.99.1) | |
| Homo sapiens | 42 |
| Hydroperoxide isomerases (EC 4.2.1.92, EC 5.3.99.1, EC 5.4.4.5, EC 5.4.4.6) | |
| Pseudomonas aeruginosa | 43 |
| Pseudomonas aeruginosa | 44 |
| Homo sapiens | 45 |
| Hydroperoxide lyases (EC 4.2.1.92) | |
| Nostoc punctiforme | 46 |
| Hydroperoxide dehydratases, allene oxide synthases (EC 4.2.1.92) | |
| Aspergillus terreus | 47 |
| Arabidopsis thaliana | 48 |
| Plexaura homomalla | 49 |
| Fusarium oxysporum | 50 |
| Colletotrichum graminicola | 51 |
| Glomerella cingulate | 52 |
| Aspergillus niger | 53 |
| Divinyl ether synthases (EC 4.2.1.121, EC 4.2.1.B8, EC 4.2.1.B9) | |
| Solanum tuberosum | 54 |
| Allium sativum | 55 |
| 9,12-Octadecadienoate 8-hydroperoxide 8R-isomerases (EC 5.4.4.5) | |
| Asperigullus nidalus | 56 |
| Aspergillus fumigatus | 57 |
| 9,12-Octadecadienoate 8-hydroperoxide 8S-isomerases (EC 5.4.4.6) | |
| Gaeumannomyces graminis | 1 |
| 7,10-Hydroperoxide diol synthases | |
| Pseudomonas aeruginosa | 43 |
| Pseudomonas aeruginosa | 44 |
| Epoxy alcohol synthases | |
| Magnaporthe oryzae | 58 |
| Glomerella cingulate | 59 |
| Fusarium oxysporum | 60 |

The derivatives of hydroperoxy fatty acids formed from the conversion of hydroperoxy fatty acids by the hydroperoxy fatty acid converting enzymes preferably are selected from the group consisting of dihydroxy fatty acids, epoxy fatty acids, oxo fatty acids, divinyl ether fatty acids, alkenals, aldehydes, epoxy alcohols, and mixtures thereof, preferably dihydroxy fatty acids.

Multi-Domain Enzymes

In another embodiment of the present invention, at least one hydroperoxy fatty acid producing enzyme and at least one hydroperoxy fatty acid converting enzyme are linked together in a polypeptide chain. In another embodiment, the cleaning composition comprises one or more multi-domain polypeptide chain which comprises polypeptide domains comprising a) a hydroperoxy fatty acid producing domain, and b) a hydroperoxy fatty acid converting domain, preferably said hydroperoxy fatty acid producing domain is a dioxygenase (DOX) domain or a lipoxygenase (LOX) and preferably said hydroperoxy fatty acid converting domain is selected from the group consisting of: allene oxide synthase (AOS) domain, epoxy alcohol synthase (EAS) domain, hydroperoxide lyase (HPL) domain, and hydroperoxide isomerase (HPI) domain. In the first step of the reaction, the DOX domains of these enzymes convert the unsaturated fatty acid into a hydroperoxy fatty acid, frequently followed by an additional transformation catalyzed by the HPI, AOS, or EAS domain. It is believed that when both enzymes are linked together the rate of conversion and the selectivity towards desirable derivatives of hydroperoxy fatty acids can be enhanced.

Several examples of multi-domain enzymes comprising: a) a hydroperoxy fatty acid producing domain and b) hydroperoxy fatty acid converting domain are found in nature. Examples of these multi-domain enzymes included in the current invention are the diol synthases. In the context of the current application, a "diol synthase" is an enzyme that is capable of converting at least one unsaturated fatty acid into a mixture of oxylipins, comprising at least a dihydroxy fatty acid. At least two different classes of diol synthases have been reported in the art. The class I fungal diol synthases, also referred as Psi-factor producing oxygenases (Ppo), contain an N-terminal dioxygenase (DOX) domain and a C-terminal cytochrome P450/hydroperoxide isomerase (HPI) domain; while the class II bacterial diol synthases consists of an N-terminal allene oxide synthase (AOS) domain and a C-terminal lipoxygenase (LOX) domain. In the first step of the reaction, the unsaturated fatty acid (e.g., linoleic acid) is converted to a hydroperoxy fatty acid derivative by the DOX or LOX domain, frequently followed by isomerization to a dihydroxy fatty acid by the HPI domain or the AOS domain.

Several amino acid residues are conserved in class I diol synthases. For example, in the DOX domain, the YR(W/F)H motif containing the catalytic Tyr is highly conserved. In the HPI domain, the SRS-4 region motif ANQXQ, the EXXG motif, and the heme signature motif (G/E)(P/A)HX(C/S)(L/F/G) are also frequently found in diol synthases. The His and Cys residues of the heme motif and the last Asn of the SRS-4 region have been associated with the isomerization step and the type of oxylipins generated during the reaction.

The present invention comprises different groups of diol synthases, including linoleate diol synthases and oleate diol synthases. Even though oleate diol synthases typically recognize oleic acid/oleate as the preferred substrate and linoleate diol synthases recognize linoleic acid/linoleate as the preferred substrate, the terms "oleate diol synthase" and "linoleate diol synthase" are used interchangeably herein and do not suggest any substrate specificity, i.e., the respective enzymes can act on both substrates.

Based on the reaction products, several diol synthases have been characterized: 5,8-linoleate diol synthases (5,8-LDS), 7,8-linoleate diol synthases (7,8-LDS), 8,11-linoleate diol synthases (8,11-LDS), and 9,14-linoleate diol synthases (9,14-LDS). Although they are frequently referred as linoleate diol synthases, they can convert substrates different than linoleate (e.g., oleate).

Non-limiting examples of diol synthases included in current invention are listed in Table 4. For instance, A. nidulans PpoA (SEQ ID NO: 56) converts C16 and C18 unsaturated fatty acids, including palmitoleic acid, oleic acid, linoleic acid, and α-linolenic acid, into 5,8-dihydroxy fatty acids, and converts C20 unsaturated fatty acids, including eicosenoic acid, eicosadienoic acid and eicosatrienoic acid, to 7,10-dihydroxy fatty acids (Brodhun, F., et al. (2009), J. Biol. Chem. 284(18): 11792-11805 and Jerneren, F., et al. (2010), Biochim. Biophys. Acta, Mol. Cell Biol. Lipids 1801(4): 503-507). In another example, G. graminis 7,8-LDS (SEQ ID NO: 67) converts oleic acid, linoleic acid, and α-linolenic acid into 7,8-dihydroxy fatty acids as major products, but this enzyme does not show activity when γ-linolenic acid, eicosatrienoic acid, arachidonis acid, and eicosapentaenoic acid are used as substrates. Similarly, *G. cingulate* 7,8-LDS (SEQ ID NO: 66) converts palmitoleic acid, oleic acid, linoleic acid, and α-linolenic acid to 7,8-dihydroxy fatty acids, but also processes eicosenoic acid, eicosadienoic acid, dihomo-γ-linolenic acid, and arachidonic acid to 8-hydroperoxy fatty acids by using only the N-terminal dioxygenase domain (Seo, M.-J., et al. (2016), *Appl. Microbiol. Biotechnol.* 100(7): 3087-3099). Furthermore, *Penicillium chrysogenum* 8,11-LDS (SEQ ID NO: 70) converts linoleic acid and α-linolenic acid to 8,11-dihydroxy fatty acids, whereas oleic acid and palmitoleic acid are converted to 8-hydroxy fatty acids. Interestingly, the Q898E or Q898L variants of *G. cingulate* 7,8-LDS also converts linoleic acid to the 8,11-dihydroxy fatty acid (Shin, K.-C., et al. (2016), *J. Lipid Res.* 57(2): 207-218). *Nostoc* sp. PCC 7120 9,14-LDS (SEQ ID NO: 2) converts linoleic acid into the 9,14-dihydroxy fatty acid as the main product with 9,10-dihydroxy, 8-11-dihydroxy, and 9-hydroxy fatty acids; α-linolenic acid to 9,16-dihydroxy, 9,13-dihidroxy, and 9-hydroxy fatty acids; and γ-linolenic acid to 9,14-dihidroxy and 9-hydroxy fatty acids (Lang, I., et al. (2008), *Biochem. J.* 410(2): 347-357).

TABLE 4

Diol Synthases

| Origin | SEQ ID |
|---|---|
| 5,8-Linoleate diol synthases (EC 1.13.11.60, EC 5.4.4.5) | |
| *Aspergiullus nidulans* PpoA | 56 |
| *Aspergillus fumigatus* PpoA | 61 |
| *Aspergillus terreus* PpoA | 62 |
| *Aspergillus kawachii* PpoA | 63 |
| *Aspergillus clavatus* PpoA | 64 |
| *Aspergillus niger* PpoA | 65 |
| 7,8-Linoleate diol synthases (EC 1.13.11.60, EC 5.4.4.6) | |
| *Glomerella cingulate* | 66 |
| *Gaeumannomyces graminis* | 67 |
| *Magnaporthe oryzae* | 68 |
| 8,11-Linoleate diol synthases | |
| *Penicillium oxalicum* | 69 |
| *Penicillium chrysogenum* | 70 |
| *Penicillium digitatum* | 71 |
| 9,14-Linoleate diol synthases (EC 1.13.11.B1) | |
| *Nostoc* sp. PCC 7120 | 2 |
| *Acaryochloris marina* | 72 |
| *Nostoc* sp. NIES-4103 | 73 |

Other dihydroxylation patterns have been observed in nature, but the enzymes have not been characterized yet. For example, *Bacillus megaterium* ALA2 and *Clavibacter* sp. ALA2 produce 12,13-dihydroxy fatty acids from linoleic acid. In another example, the red alga *Gracilariopsis lemaneiformis* produces 9,10-dihydroxy, 12,12-dihydroxy, and 12-hydroxy fatty acids from arachidonic acid. Finally, *Leptomitus lacteus* converts linoleic acid to 8,11-dihydroxy, 11,16-dihydroxy, 11,17-dihydroxy, 7-hydroxy, and 8-hydroxy fatty acids. Thus, diol synthases, can be used to convert unsaturated fatty acids into different hydroxylated products (Kim, K.-R. and D.-K. Oh (2013), *Biotechnol. Adv.* 31(8): 1473-1485).

In another embodiment, the diol synthases are selected from the group consisting of: linoleate diol synthases (EC 1.13.11.44), 5,8-linoleate diol synthases (EC 1.13.11.60 and EC 5.4.4.5), 7,8-linoleate diol synthases (EC 1.13.11.60 and EC 5.4.4.6), 9,14-linoleate diol synthases (EC 1.13.11.B1), 8,11-linoleate diol synthases, oleate diol synthases, and mixtures thereof.

In another embodiment, the diol synthases have at least 60%, preferably at least 70%, preferably at least 80%, preferably at least 85%, preferably at least 90%, preferably at least 95%, preferably at least 98% or preferably even 100% identity to one or more of the wild-type diol synthases selected from the group consisting of *Aspergillus nidulans* PpoA (SEQ ID NO: 56), *Aspergillus fumigatus* PpoA (SEQ ID NO: 61), *Aspergillus terreus* PpoA (SEQ ID NO: 62), *Aspergillus kawachii* PpoA (SEQ ID NO: 63), *Aspergillus clavatus* PpoA (SEQ ID NO: 64), *Aspergillus niger* PpoA (SEQ ID NO: 65), *Glomerella cingulate* 7,8-LDS (SEQ ID NO: 66), *Gaeumannomyces graminis* 7,8-LDS (SEQ ID NO: 67), *Magnaporthe oryzae* 7,8-LDS (SEQ ID NO: 68), *Nostoc punctiforme* 8,11-LDS (SEQ ID NO: 69), *Penicillium chrysogenum* 8,11-LDS (SEQ ID NO: 70), *Penicillium digitatum* 8,11-LDS (SEQ ID NO: 71), *Nostoc* sp. PCC 7120 9,14-LDS (SEQ ID NO: 2), *Acaryochloris marina* putative 9,14-LDS (SEQ ID NO: 72) and *Nostoc* sp. NIES-4103 putative 9,14-LDS (SEQ ID NO: 73).

Preferably the diol synthases are 5,8-linoleate diol synthases (EC 1.13.11.60 and EC 5.4.4.5). Preferably the 5,8-linoleate diol synthases (EC 1.13.11.60 and EC 5.4.4.5) have at least 60%, preferably at least 70%, preferably at least 80%, preferably at least 85%, preferably at least 90%, preferably at least 95%, preferably at least 98% or preferably even 100% identity to one or more of the wild-type diol synthases selected from the group consisting of *Aspergillus nidulans* PpoA (SEQ ID NO: 56), *Aspergillus fumigatus* PpoA (SEQ ID NO: 61), *Aspergillus terreus* PpoA (SEQ ID NO: 62), *Aspergillus kawachii* PpoA (SEQ ID NO: 63), *Aspergillus clavatus* PpoA (SEQ ID NO: 64), and *Aspergillus niger* PpoA (SEQ ID NO: 65), and mixtures thereof, more preferably *Aspergillus nidulans* PpoA (SEQ ID NO: 56).

In another example of multi-domain enzymes comprising: a) a hydroperoxy fatty acid producing domain and b) hydroperoxy fatty acid converting domain, enzymes containing a dioxygenase (DOX) or lipoxygenase (LOX) domain and an allene oxide synthase (AOS) domain produce a diverse series of oxygenated derivatives of unsaturated fatty acids and are included in the current invention. Non-limiting examples of these DOX-AOS or AOS-LOX enzymes are listed in Table 5. In further another example, enzymes can contain a dioxygenase (DOX) domain and an epoxy alcohol synthase (EAS) domain and also are included in the current invention. Non-limiting examples of these DOX-EAS enzymes are listed in Table 5.

TABLE 5

Other Multi-domain Enzymes

| Origin | SEQ ID |
|---|---|
| 8R-LOX-AOS | |
| *Plexaura homomalla* | 49 |
| 9S-DOX-AOS | |
| *Fusarium oxysporum* | 50 |
| *Colletotrichum graminicola* | 51 |
| *Glomerella cingulate* | 52 |
| 9R-DOX-AOS | |
| *Aspergillus niger* | 53 |
| 10R-DOX-EAS | |
| *Magnaporthe oryzae* | 58 |
| *Glomerella cingulate* | 59 |
| *Fusarium oxysporum* | 60 |

Preferably the hydroperoxy fatty acid producing enzymes are present in an amount of from 0.0001 wt % to 1 wt %, by weight of the composition, based on active protein in the composition. More preferably the hydroperoxy fatty acid producing enzymes are present in the amounts of from 0.001 wt % to 0.2 wt %, by weight of the composition, based on active protein in the composition.

In one embodiment of the present invention, the fatty acids being converted by the hydroperoxy fatty acid producing enzymes are selected from the group consisting of: mono unsaturated fatty acids, di unsaturated fatty acids, tri unsaturated fatty acids, tetra unsaturated fatty acids, penta unsaturated fatty acids, hexa unsaturated fatty acids, saturated fatty acids, and mixtures thereof; preferably myristoleic acid, myristic acid, pentadecanoic acid, palmitoleic acid, palmitic acid, sapienic acid, margaric acid, oleic acid, elaidic acid, vaccenic acid, linoleic acid, linoelaidic acid, α-linolenic acid, γ-linolenic acid, stearic acid, gadoleic acid, arachidic acid, behenic acid, α-eleostearic acid, β-eleostearic acid, ricinoleic acid, eicosenic acid, arachidonic acid, eicosapentaenoic acid, erucic acid, docosadienoic acid, docosahexaenoic acid, tetracosenoic acid, and mixtures thereof, preferably palmitoleic acid, oleic acid, linoleic acid, α-linolenic acid, γ-linolenic acid, and mixtures thereof, more preferably oleic acid.

In another embodiment, the resultant hydroperoxy fatty acids formed from the conversion reaction of the fatty acids with the hydroperoxy fatty acid producing enzymes are selected from the group consisting of 2-hydroperoxy fatty acids, 8R-hydroperoxy fatty acids, 8S-hydroperoxy fatty acids, 9R-hydroperoxy fatty acids, 9S-hydroperoxy fatty acids, 10R-hydroperoxy fatty acids, 11R-hydroperoxy fatty acids, 11S-hydroperoxy fatty acids, 12R-hydroperoxy fatty acids, 12S-hydroperoxy fatty acids, 13R-hydroperoxy fatty acids, 13S-hydroperoxy fatty acids, 14R-hydroperoxy fatty acids, 14S-hydroperoxy fatty acids, 15S-hydroperoxy fatty acids, their derivatives, and mixtures thereof; preferably 2R-hydroperoxy fatty acids, unsaturated 5S-hydroperoxy fatty acids, unsaturated 8R-hydroperoxy fatty acids, unsaturated 9R-hydroperoxy fatty acids, unsaturated 11R-hydroperoxy fatty acids, unsaturated 12R-hydroperoxy fatty acids, unsaturated 12S-hydroperoxy fatty acids, unsaturated 13S-hydroperoxy fatty acids, unsaturated 15S-hydroperoxy fatty acids, their derivatives, and mixtures thereof; more preferably 2R-hydroperoxy fatty acids. The resulting hydroperoxy fatty acids can undergo spontaneous or enzymatic transformations to monohydroxy fatty acids, dihydroxy fatty acids, epoxy fatty acids, oxo fatty acids, divinyl ether fatty acids, alkenals, aldehydes, epoxy alcohols or other derivatives. Non-limiting examples of monohydroxy fatty acids are 2-hydroxy fatty acids, unsaturated 5-hydroxy fatty acids, unsaturated 8-hydroxy fatty acids, unsaturated 9-hydroxy fatty acids, unsaturated 11-hydroxy fatty acids, unsaturated 12-hydroxy fatty acids, unsaturated 13-hydroxy fatty acids, unsaturated 15-hydroxy fatty acids, their derivatives, and mixtures thereof. Non-limiting examples of dihydroxy fatty acids are 5,8-dihydroxy fatty acids, 7,8-dihydroxy fatty acids, 7,10-dihydroxy fatty acids, 8,11-dihydroxy fatty acids, 9,14-dihydroxy fatty acids, and mixtures thereof. Non-limiting examples of aldehydes are 1-alkanals, alken-1-als, alkadien-1-als, alkatrien-1-als, alkatetraen-1als, and mixtures thereof.

Hydroxy Fatty Acid Producing Enzymes

The soil transforming enzyme of the present invention can be a hydroxy fatty acid producing enzyme, preferably selected from the group consisting of peroxygenases, fatty acid hydratases, and mixtures thereof.

Peroxygenases

Fatty acids can be oxidized in the presence of hydrogen peroxide ($H_2O_2$) by peroxygenases to produce hydroxyfatty acids. In another embodiment of the present invention, the cleaning composition comprises one or more enzymes selected from the group consisting of: unspecific peroxygenases (EC 1.11.2.1), plant seed peroxygenases (EC 1.11.2.3), fatty acid peroxygenases (EC 1.11.2.4), and mixtures thereof. Peroxygenases, also known as hydroperoxide oxidoreductases, can catalyze the conversion of fatty acids into hydroxylated derivatives using hydrogen peroxide as co-substrate. Non-limiting examples of peroxygenases, included in the present invention are listed in table 6. For instance, *Sphingomonas paucimobilis* peroxygenase catalyzes the hydroxylation of fatty acids at the α-position, while the *Bacillus subtilis* peroxygenase catalyzes hydroxylation at α-position (40%) and β-position (60%).

TABLE 6

| Peroxygenases | |
|---|---|
| Origin | SEQ ID |
| Unspecific peroxygenases (EC 1.11.2.1) | |
| *Agrocybe aegerita* | 74 |
| Fatty acid peroxygenases (EC 1.11.2.4) | |
| *Bacillus subtilis* | 75 |
| *Sphingomonas paucimobilis* | 76 |
| *Clostridium acetobutylicum* | 77 |

In one embodiment of the present invention, the fatty acids being converted by the peroxygenases are selected from the group consisting of: mono unsaturated fatty acids, di unsaturated fatty acids, tri unsaturated fatty acids, tetra unsaturated fatty acids, penta unsaturated fatty acids, hexa unsaturated fatty acids, saturated fatty acids, and mixtures thereof; preferably myristoleic acid, myristic acid, pentadecanoic acid, palmitoleic acid, palmitic acid, sapienic acid, margaric acid, oleic acid, elaidic acid, vaccenic acid, linoleic acid, linoelaidic acid, α-linolenic acid, γ-linolenic acid, stearic acid, gadoleic acid, arachidic acid, behenic acid, α-eleostearic acid, β-eleostearic acid, ricinoleic acid, eicosenic acid, arachidonic acid, eicosapentaenoic acid, erucic acid, docosadienoic acid, docosahexaenoic acid, tetracosenoic acid, and mixtures thereof, preferably palmitoleic acid, oleic acid, linoleic acid, α-linolenic acid, γ-linolenic acid, and mixtures thereof, more preferably oleic acid.

In another embodiment, the resultant hydroxy fatty acids formed from the conversion reaction of the fatty acids with the peroxygenases are selected from the group consisting of 2-hydroxy fatty acids, 3-hydroxy fatty acids, 4-hydroxy fatty acids, 5-hydroxy fatty acids, 6-hydroxy fatty acids, and mixtures thereof; preferably 2-hydroxy fatty acids, 3-hydroxy fatty acids, and mixtures thereof.

Fatty Acid Hydratases

Unsaturated fatty acids can be hydrated in the presence of water ($H_2O$) by fatty acid hydratases to produce hydroxy fatty acids. In another embodiment, the cleaning composition comprises one or more fatty acid hydratases (EC 4.2.1.53). Fatty acid hydratases catalyze the regio-specific and irreversible addition of water to a double bond of unsaturated fatty acids to produce hydroxy fatty acids. Hydration of unsaturated fatty acids is common in bacteria. For instance, *Stenotrophomonas nitritireducens* hydrates linoleic acid at the C-10 position, whereas *Enterococcus gallinarum, Flavobacterium* sp., *Lactobacillus* sp., *Pedio-* coccus acidilactici, and *Selenomonas ruminantium* hydrate oleic acid. Oleate hydratases can convert cis-9 and cis-12 unsaturated fatty acids into either 10- or 13-hydroxy fatty acids or 10,13-dihydroxy fatty acids. Non-limiting example of oleate hydratases are listed in table 7.

TABLE 7

Fatty Acid Hydratases

| Origin | SEQ ID |
|---|---|
| Oleate hydratases (EC 4.2.1.53) | |
| *Elizabethkingia meningoseptica* | 78 |
| *Macrococcus caseolyticus* | 79 |
| *Streptococcus pyogenes* | 80 |

In one embodiment of the present invention, the fatty acids being converted by the hydratases are selected from the group consisting of: mono unsaturated fatty acids, di unsaturated fatty acids, tri unsaturated fatty acids, tetra unsaturated fatty acids, penta unsaturated fatty acids, hexa unsaturated fatty acids, and mixtures thereof; preferably myristoleic acid, palmitoleic acid, sapienic acid, oleic acid, elaidic acid, vaccenic acid, linoleic acid, linoelaidic acid, α-linolenic acid, γ-linolenic acid, gadoleic acid, α-eleostearic acid, (3-eleostearic acid, ricinoleic acid, eicosenic acid, arachidonic acid, eicosapentaenoic acid, erucic acid, docosadienoic acid, docosahexaenoic acid, tetracosenoic acid, and mixtures thereof; preferably palmitoleic acid, oleic acid, linoleic acid, α-linolenic acid, γ-linolenic acid, and mixtures thereof; more preferably oleic acid.

In another embodiment, the resultant hydroxy fatty acids formed from the conversion reaction of the fatty acids with the hydratases are selected from the group consisting of 10-hydroxy fatty acids, 13-hydroxy fatty acids, 10,13-dihydroxy fatty acids, and mixtures thereof.

Additional Considerations

The present invention also includes variants of enzymes. Variants of enzymes, as used herein, include a sequence resulting when a wild-type protein of the respective protein is modified by, or at, one or more amino acids (for example 1, 2, 5 or 10 amino acids). The invention also includes variants in the form of truncated forms derived from a wild-type enzyme, such as a protein with a truncated N-terminus or a truncated C-terminus. Some enzymes may include an N-terminal signal peptide that is likely removed upon secretion by the cell. The present invention includes variants without the N-terminal signal peptide. Bioinformatic tools, such as SignalP ver 4.1 (Petersen T N., Brunak S., von Heijne G. and Nielsen H. (2011), Nature Methods, 8:785-786), can be used to predict the existence and length of such signal peptides. The invention also includes variants derived by adding an extra amino acid sequence to a wild-type protein, such as for example, an N-terminal tag, a C-terminal tag or an insertion in the middle of the protein sequence. Non-limiting examples of tags are maltose binding protein (MBP) tag, glutathione S-transferase (GST) tag, thioredoxin (Trx) tag, His-tag, and any other tags known by those skilled in art. Tags can be used to improve solubility and expression levels during fermentation or as a handle for enzyme purification.

It is important that variants of enzymes retain and preferably improve the ability of the wild-type protein to catalyze the conversion of the unsaturated fatty acids. Some performance drop in a given property of variants may of course be tolerated, but the variants should retain and preferably improve suitable properties for the relevant application for which they are intended. Screening of variants of one of the wild-types can be used to identify whether they retain and preferably improve appropriate properties.

The variants may have "conservative" substitutions. Suitable examples of conservative substitution includes one conservative substitution in the enzyme, such as a conservative substitution in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80. Other suitable examples include 10 or fewer conservative substitutions in the protein, such as five or fewer. An enzyme of the invention may therefore include 1, 2, 3, 4, 5, 6, 7, 8, 9, 10 or more conservative substitutions. An enzyme can be produced to contain one or more conservative substitutions by manipulating the nucleotide sequence that encodes that enzyme using, for example, standard procedures such as site-directed mutagenesis or PCR.

Examples of amino acids which may be substituted for an original amino acid in an enzyme and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

A variant includes a "modified enzyme" or a "mutant enzyme" which encompasses proteins having at least one substitution, insertion, and/or deletion of an amino acid. A modified enzyme may have 1, 2, 3, 4, 5, 6, 7, 8, 9 or 10 or more amino acid modifications (selected from substitutions, insertions, deletions and combinations thereof).

Enzymes can be modified by a variety of chemical techniques to produce derivatives having essentially the same or preferably improved activity as the unmodified enzymes, and optionally having other desirable properties. For example, carboxylic acid groups of the protein, whether carboxyl-terminal or side chain, may be provided in the form of a salt of a pharmaceutically-acceptable cation or esterified, for example to form a C1-C6 alkyl ester, or converted to an amide, for example of formula CONR1R2 wherein R1 and R2 are each independently H or C1-C6 alkyl, or combined to form a heterocyclic ring, such as a 5- or 6-membered ring Amino groups of the enzyme, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C20 alkyl or dialkyl amino or further converted to an amide. Hydroxyl groups of the protein side chains may be converted to alkoxy or ester groups, for example C1-C20 alkoxy or C1-C20 alkyl ester, using well-recognized techniques. Phenyl and phenolic rings of the protein side chains may be substituted with one or more halogen atoms, such as F, Cl, Br or I, or with C1-C20 alkyl, C1-C20 alkoxy, carboxylic acids and esters thereof, or amides of such carboxylic acids. Methylene groups of the protein side chains can be extended to homologous C2-C4 alkylenes. Thiols can be protected with any one of a number of well-recognized protecting groups, such as acetamide groups. Those skilled in the art will also recognize methods for introducing cyclic structures into the proteins of this disclosure to select and provide conformational constraints to the structure that result in enhanced stability.

Identity, or homology, percentages as mentioned herein in respect of the present invention are those that can be calculated with the GAP program, obtainable from GCG (Genetics Computer Group Inc., Madison, Wis., USA). Alternatively, a manual alignment can be performed.

For enzyme sequence comparison the following settings can be used: Alignment algorithm: Needleman and Wunsch, J. Mol. Biol. 1970, 48: 443-453. As a comparison matrix for amino acid similarity the Blosum62 matrix is used (Henikoff S. and Henikoff J. G., P.N.A.S. USA 1992, 89: 10915-10919). The following gap scoring parameters are used: Gap penalty: 12, gap length penalty: 2, no penalty for end gaps.

A given sequence is typically compared against the full-length sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80 to obtain a score.

The enzymes may be incorporated into the cleaning composition via an additive particle, such as an enzyme granule or in the form of an encapsulate, or may be added in the form of a liquid formulation. Preferably the enzyme is incorporated into the cleaning composition via an encapsulate. Encapsulating the enzymes promote the stability of the enzymes in the composition and helps to counteract the effect of any hostile compounds present in the composition, such as bleach, protease, surfactant, chelant, etc.

The hydroperoxy fatty acid producing enzymes are present in an additive particle may be the only enzymes in the additive particle or may be present in the additive particle in combination with one or more additional co-enzymes.

Where necessary, the composition comprises, provides access to or forms in situ any additional substrate necessary for the effective functioning of the enzyme. For example, molecular oxygen is provided as an additional substrate for lipoxygenases, heme-dioxygenases, alpha-dioxygenases, diol synthases, and other enzymes containing the DOX domain. Molecular oxygen can be obtained from the atmosphere or from a precursor that can be transformed to produce oxygen in situ. In many applications, oxygen from the atmosphere can be present in sufficient amounts. Similarly, hydrogen peroxide is provided as an additional substrate for peroxygenases and can be added to the cleaning composition or produce in situ during the cleaning process, e.g. by the action of alcohol oxidases on their corresponding substrates. Furthermore, water is required as an additional substrates for fatty acid hydratases and can be part of the cleaning composition or added during the cleaning process.

Surfactant

The consumer product compositions of the present invention further comprise a surfactant, preferably at a level of from about 0.01% to about 60%, preferably from about 5% to about 50%, more preferably from about 8% to about 40%, by weight of the composition.

In some aspects, the consumer product composition comprises relatively low levels of surfactant, as the soil transforming enzymes can convert fatty acid-containing soils into active fatty acid derivative materials directly on the surface being cleaned in order to aid in cleaning the soil from the surface. Such active fatty acid derivative materials can therefore reduce the need to incorporate larger amounts of surfactant in the consumer product composition. In addition, lower levels of surfactant can favor the stability and activity of the soil transforming enzymes utilized herein. As such, the consumer product composition preferably comprises from about 0.01% to about 2%, preferably from about 0.01% to about 1.5%, preferably from about 0.01% to about 1%, preferably from about 0.01% to about 0.5%, preferably from about 0.01% to about 0.2%, preferably from about 0.01% to about 0.1%, by weight of the composition, of surfactant.

Suitable surfactants are selected from the group consisting of anionic surfactants, nonionic surfactants, zwitterionic surfactants, amphoteric surfactants, cationic surfactants, and mixtures thereof. Anionic and nonionic surfactants are typically employed if the composition is a laundry detergent or hair shampoo. Cationic surfactants are typically employed if the composition is a fabric softener or hair conditioner.

Anionic surfactants suitable for use in the compositions include alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278.

Exemplary anionic surfactants for use in the composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

The compositions may contain a nonionic surfactant. The compositions may contain up to from 0.01% to about 30%, alternatively from about 0.01% to about 20%, more alternatively from about 0.1% to about 10%, by weight of the composition, of a nonionic surfactant. In some examples, the nonionic surfactant may comprise an ethoxylated nonionic surfactant. Suitable for use herein are the ethoxylated alcohols and ethoxylated alkyl phenols of the formula $R(OC_2H_4)n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)nOH$, wherein R1 is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

Suitable cationic surfactants include those which can deliver fabric care benefits, non-limiting examples which include: fatty amines; quaternary ammonium surfactants; and imidazoline quat materials.

Non-limiting examples of cationic surfactants are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate; 1, 2 di (stearoyloxy) 3 trimethyl ammoniumpropane chloride; dialkylenedimethylammonium salts such as dicanoladimethylammonium chloride, di(hard)tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

Cationic surfactants can serve as conditioning agents in the consumer product compositions, such as in fabric softening compositions or hair conditioning compositions.

Amphoteric detersive surfactants suitable for use in the hair care composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present hair care composition include cocoamphoacetate, cocoamphodiacetate, lauroamphoacetate, lauroamphodiacetate, and mixtures thereof.

Zwitterionic detersive surfactants suitable for use in the hair care composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non-limiting examples of suitable zwitterionic or amphoteric surfactants are described in U.S. Pat. Nos. 5,104,646 and 5,106,609, which are incorporated herein by reference in their entirety. Non-limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

In one aspect, it can be preferred that the consumer product composition is free of sulfate surfactants. In such aspects, the surfactant is preferably a sugar-based surfactant or amino acid-based surfactant, such as surfactant selected from the group consisting of decyl glucoside, isethionates, glutamates, and mixtures thereof.

In one aspect, the consumer product compositions can comprise an anionic surfactant and co-surfactant selected from the group consisting of amphoteric surfactant, zwitterionic surfactant and mixtures thereof. Preferably the amphoteric surfactant is an amine oxide surfactant and the zwitterionic surfactant is a betaine surfactant.

Preferably the weight ratio of the anionic surfactants to the co-surfactant(s) is less than 9:1, more preferably from 5:1 to 1:1, more preferably from 4:1 to 2:1. Preferably the primary co-surfactant system is an amphoteric surfactant. Preferably, the primary co-surfactant system is an amine oxide surfactant, and wherein the composition comprises anionic surfactant and amine oxide surfactant in a weight ratio of less than 9:1, more preferably from 5:1 to 1:1, more preferably from 4:1 to 2:1, preferably from 3:1 to 2.5:1. Preferably the composition of the present invention, wherein the surfactant system comprises one or more anionic surfactants and one or more co-surfactants, wherein the anionic surfactants are a mixture of alkyl sulfates and alkyl alkoxy sulfates, the co-surfactants are alkyl dimethyl amine oxides, and wherein the weight ratio of the anionic surfactants to the co-surfactants is from 4:1 to 2:1.

Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or branched alkyl moiety.

The composition may further comprise a C10AO, especially n-decyl dimethyl amine, and preferably comprises less than 5% preferably less than 3% by weight of total amine oxide of a C8 amine oxide such as a C8 dimethyl amine oxide.

The co-surfactant can be a zwitterionic surfactant. Suitable examples of zwitterionic surfactants include betaines, preferably alkyl betaines, alkylamidobetaine, and mixtures thereof. Cocoamidopropylbetaine is most preferred.

The consumer product composition can further comprise a co-surfactant comprising a non-ionic surfactant. Suitable non-ionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol. Highly preferred non-ionic surfactants are the condensation products of guerbet alcohols with from 2 to 18 moles, preferably 2 to 15, more preferably 5-12 of ethylene oxide per mole of alcohol. Preferably, the non-ionic surfactants are an alkyl ethoxylated surfactants, preferably comprising from 9 to 15 carbon atoms in its alkyl chain and from 5 to 12 units of ethylene oxide per mole of alcohol. Other suitable non-ionic surfactants for use herein include fatty alcohol polyglycol ethers, alkylpolyglucosides and fatty acid glucamides, preferably alkylpolyglucosides. Preferably the alkyl polyglucoside surfactant is a C8-C16 alkyl polyglucoside surfactant, preferably a C8-C14 alkyl polyglucoside surfactant, preferably with an average degree of polymerization of between 0.1 and 3, more preferably between 0.5 and 2.5, even more preferably between 1 and 2. Most preferably the alkyl polyglucoside surfactant has an average alkyl carbon chain length between 10 and 16, preferably between 10 and 14, most preferably between 12 and 14, with an average degree of polymerization of between 0.5 and 2.5 preferably between 1 and 2, most preferably between 1.2 and 1.6. C8-C16 alkyl polyglucosides are commercially available from several suppliers (e.g., Simusol® surfactants from Seppic Corporation; and Glucopon® 600 CSUP, Glucopon® 650 EC, Glucopon® 600 CSUP/MB, and Glucopon® 650 EC/MB, from BASF Corporation). Preferably, the composition comprises the anionic surfactant and the non-ionic surfactant in a ratio of from 2:1 to 50:1, preferably 2:1 to 10:1.

Consumer Product Adjunct Ingredients

The consumer product composition herein may optionally comprise a number of other consumer product adjunct ingredients such as enzyme stabilizers, co-enzymes, salts, hydrotropes, chelants, builders, dispersants, dye transfer inhibitors, bleach, stabilizers/thickeners, perfume, conditioning agents, hueing agents, structurants, solvents, aqueous carrier, and mixtures thereof. Consumer product adjunct ingredients also include scrubbing particles, malodor control agents, pigments, dyes, opacifiers, pH adjusters and buffering means (e.g., carboxylic acids such as citric acid, HCl, NaOH, KOH, alkanolamines, phosphoric and sulfonic acids, carbonates such as sodium carbonates, bicarbonates, sesquicarbonates, borates, silicates, phosphates, imidazole and alike).

Enzyme Stabilizers

Preferably the composition of the invention further comprises an enzyme stabilizer, selected from the group consisting of chemical and physical stabilizers, preferably the physical stabilizer comprises encapsulating the enzyme. Suitable enzyme stabilizers may be selected from the group consisting of (a) univalent, bivalent and/or trivalent cations preferably selected from the group of inorganic or organic salts of alkaline earth metals, alkali metals, aluminum, iron, copper and zinc, preferably alkali metals and alkaline earth metals, preferably alkali metal and alkaline earth metal salts with halides, sulfates, sulfites, carbonates, hydrogencarbonates, nitrates, nitrites, phosphates, formates, acetates, propionates, citrates, maleates, tartrates, succinates, oxalates, lactates, and mixtures thereof. In a preferred embodiment the salt is selected from the group consisting of sodium chloride, calcium chloride, potassium chloride, sodium sulfate, potassium sulfate, sodium acetate, potassium acetate, sodium formate, potassium formate, calcium lactate, calcium nitrate and mixtures thereof. Most preferred are salts selected from the group consisting of calcium chloride, potassium chloride, potassium sulfate, sodium acetate, potassium acetate, sodium formate, potassium formate, calcium lactate, calcium nitrate, and mixtures thereof, and in particular potassium salts selected from the group of potassium chloride, potassium sulfate, potassium acetate, potassium formate, potassium propionate, potassium lactate and mixtures thereof. Most preferred are potassium acetate and potassium chloride. Preferred calcium salts are calcium formate, calcium lactate and calcium nitrate including calcium nitrate tetrahydrate. Calcium and sodium formate salts may be preferred. These cations are present at at least 0.01 wt %, preferably at least 0.03 wt %, more preferably at least 0.05 wt %, most preferably at least 0.25 wt % up to 2 wt % or even up to 1 wt % by weight of the total composition. These salts are formulated from 0.1 wt % to 5 wt %, preferably from 0.2 wt % to 4 wt %, more preferably from 0.3 wt % to 3 wt %, most preferably from 0.5 wt % to 2 wt % relative to the total weight of the composition. Further enzyme stabilizers can be selected from the group (b) carbohydrates selected from the group consisting of oligosaccharides, polysaccharides and mixtures thereof, such as a monosaccharide glycerate as described in WO201219844; (c) mass efficient reversible protease inhibitors selected from the group consisting of phenyl boronic acid and derivatives thereof, preferably 4-formyl phenylboronic acid; (d) alcohols such as 1,2-propane diol, propylene glycol; (e) peptide aldehyde stabilizers such as tripeptide aldehydes such as Cbz-Gly-Ala-Tyr-H, or disubstituted alaninamide; (f) carboxylic acids such as phenyl alkyl dicarboxylic acid as described in WO2012/19849 or multiply substituted benzyl carboxylic acid comprising a carboxyl group on at least two carbon atoms of the benzyl radical such as described in WO2012/19848, phthaloyl glutamine acid, phthaloyl asparagine acid, aminophthalic acid and/or an oligoaminobiphenyl-oligocarboxylic acid; and (g) mixtures thereof.

Co-Enzymes

Preferred compositions of the invention comprise one or more additional co-enzymes selected from the group consisting of amylases, lipases, proteases, cellulases, lipoxygenases, diol synthases, and mixtures thereof. Even more preferred compositions of the invention comprise one or more co-enzymes selected from lipases, proteases, cellulases, amylases and any combination thereof. Most preferably compositions of the invention comprise one or more co-enzymes selected from lipases, proteases, amylases and any combination thereof.

It may be particularly preferred for the compositions of the present invention to additionally comprise a protease co-enzyme. Since oleic acid and other foam suppressing unsaturated fatty acids are present in body soils or even human skin, as protease enzyme acts as a skin care agent, or breaks down proteinaceous soils, fatty acids released are broken down, preventing suds suppression.

It may be particularly preferred for the compositions of the present invention to additionally comprise an amylase co-enzyme. Since oily soils are commonly entrapped in starchy soils, the amylase and unsaturated fatty acid transforming enzymes work synergistically together: fatty acid soils are released by breakdown of starchy soils with amylase, thus, the unsaturated fatty acid transforming enzyme is particularly effective in ensuring there is no negative impact on suds in the wash liquor.

It may be particularly preferred for the compositions of the present invention to additionally comprise a lipase co-enzyme. Lipases break down fatty ester soils into fatty acids which are then acted upon by the hydroperoxy fatty acid producing enzymes, peroxygenases, and fatty acid hydratases into suds or cleaning boosting agents.

In another embodiment of the present invention, the consumer product composition comprises one or more co-enzymes selected from the group consisting of: unspecific monooxygenase (EC 1.14.14.1), alkane 1-monooxygenase (EC 1.14.15.3), oleate 12-hydroxylases (EC 1.14.18.4), linoleate isomerases (EC 5.2.1.5), linoleate (10E,12Z)-isomerases (EC 5.3.3.B2), fatty acid decarboxylases (OleT-like), iron-dependent decarboxylases (UndA-like), other CYP450 monooxygenases, and mixtures thereof.

Co-enzyme, when present, is typically present in an amount of from about 0.0001% to about 1%, preferably from about 0.0005% to about 0.5%, more preferably from about 0.005% to about 0.1%, by weight of the composition, based on active protein.

Salt

The composition of the present invention may optionally comprise from 0.01% to 3%, preferably from 0.05% to 2%, more preferably from 0.2% to 1.5%, or most preferably 0.5% to 1%, by weight of the total composition of a salt, preferably a monovalent, divalent inorganic salt or a mixture thereof, preferably sodium chloride. Most preferably the composition alternatively or further comprises a multivalent metal cation in the amount of from 0.01 wt % to 2 wt %, preferably from 0.1% to 1%, more preferably from 0.2% to 0.8% by weight of the composition, preferably the multivalent metal cation is magnesium, aluminum, copper, calcium or iron, more preferably magnesium, most preferably said multivalent salt is magnesium chloride. It is believed that use of a multivalent cation helps with the formation of protein/protein, surfactant/surfactant or hybrid protein/surfactant network at the oil water and air water interface that is strengthening the suds.

Hydrotrope

The composition of the present invention may optionally comprise from 1% to 10%, or preferably from 0.5% to 10%, more preferably from 1% to 6%, or most preferably from 0.1% to 3%, or combinations thereof, by weight of the total composition of a hydrotrope, preferably sodium cumene sulfonate. Other suitable hydrotropes for use herein include anionic-type hydrotropes, particularly sodium, potassium, and ammonium xylene sulfonate, sodium, potassium and ammonium toluene sulfonate, sodium potassium and ammonium cumene sulfonate, and mixtures thereof, as disclosed in U.S. Pat. No. 3,915,903.

Chelant

The detergent composition herein can comprise a chelant at a level of from 0.1% to 20%, preferably from 0.2% to 5%, more preferably from 0.2% to 3% by weight of total composition.

Suitable chelants include citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Other suitable chelants for the compositions of the present invention comprise carboxylate chelants, amino carboxylate chelants, amino phosphonate chelants, and mixtures thereof. Preferably the chelants are selected from the group consisting of MGDA (methylglycine-N,N-diacetic acid), GLDA (glutamic-N,N-diacetic acid), and mixtures thereof.

Builders

The compositions may also contain from about 0.1% to 80% by weight of the composition of a builder. Compositions in liquid form generally contain from about 1% to 10% by weight of the composition of the builder component. Compositions in granular form generally contain from about 1% to 50% by weight of the composition of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites.

Dispersants

The compositions may contain from about 0.1%, to about 10%, by weight of the composition of dispersants. Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Dye Transfer Inhibiting Agents

The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Bleach System

Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzenesulphonate, benzoylvalerolactam, dodecanoyloxybenzenesulphonate. Other bleaching agents include metal complexes of transitional metals with ligands of defined stability constants.

Stabilizer/Thickener

The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Conditioning Agents

The consumer product composition may comprise one or more conditioning agents. Conditioning agents include materials that are used to give a particular conditioning or softening benefit to surfaces, such as hair or fabrics. The conditioning agents useful in the consumer product compositions of the present invention typically comprise a water-insoluble, water-dispersible, non-volatile, liquid that forms emulsified, liquid particles. Suitable conditioning agents are those characterized generally as silicones, organic conditioning oils or combinations thereof, or those conditioning agents which otherwise form liquid, dispersed particles in the aqueous surfactant matrix.

Cationic surfactants, such as quaternary ammonium compounds described hereinabove, can also be utilized as conditioning agents in the present compositions.

One or more conditioning agents are present from about 0.01% to about 10%, from about 0.1% to about 8%, and from about 0.2% to about 4%, by weight of the composition.

Silicones

Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked.

In some examples, the organosilicone may comprise a cyclic silicone. The cyclic silicone may comprise a cyclomethicone of the formula $[(CH_3)_2SiO]_n$ where n is an integer that may range from about 3 to about 7, or from about 5 to about 6.

In some examples, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In some examples, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In some examples, the functionalized siloxane polymer may comprise an aminosilicone.

In some examples, the organosilicone may comprise amine ABn silicones and quat ABn silicones. Such organosilicones are generally produced by reacting a diamine with an epoxide.

In some examples, the functionalized siloxane polymer may comprise silicone-urethanes. These are commercially available from Wacker Silicones under the trade name SLM-21200®.

Silicone materials typically serve as conditioning agents in the consumer product compositions, such as in fabric softening compositions or hair conditioning compositions.

Organic Conditioning Materials

The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Perfume

The consumer product adjunct ingredient can comprise a perfume, which is a neat perfume added to the consumer product composition in addition to the microcapsule. Therefore, the consumer product composition can comprise a neat perfume and a microcapsule comprising a perfume as the core material of the microcapsule. The neat perfume and the perfume of the microcapsule can be the same or can be different.

Hueing Agents

The composition may comprise a hueing agent (sometimes referred to as shading, bluing or whitening agents). Typically the hueing agent provides a blue or violet shade to treated surfaces, such as fabric. Hueing agents can be used either alone or in combination to create a specific shade of hueing and/or to shade different surface types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents further include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive or hydrolysed Reactive, Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes U.S. Pat. No. 8,268,016 B2, or dyes as disclosed in U.S. Pat. No. 7,208,459 B2, and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

In some examples, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In some examples, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15), Monastral Blue and mixtures thereof.

Structurants

Useful structurant materials that may be added to adequately suspend the benefit agent containing delivery particles include polysaccharides, for example, gellan gum, waxy maize or dent corn starch, octenyl succinated starches, derivatized starches such as hydroxyethylated or hydroxypropylated starches, carrageenan, guar gum, pectin, xanthan gum, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey, U.S.A.

Solvents

The composition of the present invention may optionally comprise an organic solvent. Suitable organic solvents include C4-14 ethers and diethers, polyols, glycols, alkoxylated glycols, C6-C16 glycol ethers, alkoxylated aromatic alcohols, aromatic alcohols, aliphatic linear or branched alcohols, alkoxylated aliphatic linear or branched alcohols, alkoxylated C1-C5 alcohols, C8-C14 alkyl and cycloalkyl hydrocarbons and halohydrocarbons, and mixtures thereof. Preferably the organic solvents include alcohols, glycols, and glycol ethers, alternatively alcohols and glycols. The composition comprises from 0% to less than 50%, preferably from 0.01% to 25%, more preferably from 0.1% to 10%, or most preferably from 0.5% to 5%, by weight of the total composition of an organic solvent, preferably an alcohol, more preferably an ethanol, a polyalkyleneglycol, more preferably polypropyleneglycol, and mixtures thereof.

Aqueous Carrier

The compositions herein can be in the form of pourable liquids (under ambient conditions). Such compositions will therefore typically comprise a carrier, which is present at a level of from about 20 wt % to about 95 wt %, or even from about 60 wt % to about 85 wt %. The carrier may comprise water, or a miscible mixture of water and organic solvent, and in one aspect may comprise water with minimal or no significant concentrations of organic solvent, except as otherwise incidentally incorporated into the composition as minor ingredients of other components.

The carrier useful in embodiments of the composition of the present invention includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Method of Cleaning a Surface

The present invention relates to a method of cleaning a surface having disposed thereon a soil comprising fatty acid, said method comprising the steps of: (a) contacting said soil disposed on said surface with a consumer product composition comprising a surfactant and a soil transforming enzyme selected from the group consisting of: (i) alpha-dioxygenases and UFA heme-dioxygenases; (ii) hydroperoxy fatty acid producing enzymes selected from the group consisting of lipoxygenases and UFA heme-dioxygenases; and hydroperoxy fatty acid converting enzymes selected from the group consisting of cyclooxygenases (EC 1.14.99.1), allene oxide synthases (EC 4.2.1.92), hydroperoxide isomerases (EC 4.2.1.92, EC 5.3.99.1, EC 5.4.4.5, EC 5.4.4.6), hydroperoxide lyases (EC 4.2.1.92), hydroperoxide dehydratases (EC 4.2.1.92), divinyl ether synthases (EC 4.2.1.121, EC 4.2.1.B8, EC 4.2.1.B9), 9,12-octadecadienoate 8-hydroperoxide 8R-isomerases (EC 5.4.4.5), 9,12-octadecadienoate 8-hydroperoxide 8S-isomerases (EC 5.4.4.6), 7,10-hydroperoxide diol synthases, epoxy alcohol synthases, and mixtures thereof, wherein said hydroperoxy fatty acid converting enzymes are capable of transforming the reaction product of said hydroperoxy fatty acid producing enzymes; (iii) multi-domain enzymes comprising a hydroperoxy fatty acid domain comprising a heme-dioxygenase or lipoxygenase domain and a hydroperoxy fatty acid converting domain selected from the group consisting of allene oxide synthase domain, epoxy alcohol synthase domain, hydroperoxide lyase domain, and hydroperoxide isomerase domain; (iv) hydroxy fatty acid producing enzymes selected from the group consisting of peroxygenase, fatty acid hydratases, and mixtures thereof; and (iv) mixtures thereof; and (b) converting said fatty acid of said soil on said surface into an active fatty acid derivative material selected from the group consisting of hydroperoxy fatty acids, hydroperoxy fatty acid derivatives, hydroxy fatty acids, and mixtures thereof.

The method of the present invention can form active fatty acid derivative material in situ on the surface, thereby creating additional cleaning action from the consumer product composition during use. This can provide enhanced cleaning benefits and/or allow the use of reduced surfactant levels in the consumer product composition.

The method can further comprise the step of removing the consumer product composition from the surface, e.g. by rinsing the composition from the surface (e.g. with water) or mechanically removing the composition from the surface (e.g. by wiping composition from the surface).

The method can further include the step of diluting the consumer product composition with water to form a diluted consumer product composition and then contacting the surface with the diluted consumer product composition.

Preferred surfaces treated with the consumer product composition of the present invention include surfaces selected from the group consisting of hair, skin, fabric, dishware, tableware, and household hard surfaces.

In one aspect, the fatty acid of the soil is selected from the group consisting of mono unsaturated fatty acids, di unsaturated fatty acids, tri unsaturated fatty acids, tetra unsaturated fatty acids, penta unsaturated fatty acids, hexa unsaturated fatty acids, saturated fatty acids, and mixtures thereof. Preferably the fatty acid of the soil is selected from the group consisting of myristoleic acid, palmitoleic acid, sapienic acid, oleic acid, elaidic acid, vaccenic acid, linoleic acid, linoelaidic acid, α-linolenic acid, γ-linolenic acid, gadoleic acid, α-eleostearic acid, β-eleostearic acid, ricinoleic acid, eicosenic acid, arachidonic acid, eicosapentaenoic acid, erucic acid, docosadienoic acid, docosahexaenoic acid, tetracosenoic acid, and mixtures thereof. Preferably the fatty acid of the soil is selected from the group consisting of palmitoleic acid, oleic acid, linoleic acid, α-linolenic acid, γ-linolenic acid, and mixtures thereof. Preferably the fatty acid of the soil is oleic acid.

In one aspect, the active fatty acid derivative material formed via the method is hydroperoxy fatty acid selected from the group consisting of 2-hydroperoxy fatty acids, 8R-hydroperoxy fatty acids, 8S-hydroperoxy fatty acids, 9R-hydroperoxy fatty acids, 9S-hydroperoxy fatty acids, 10R-hydroperoxy fatty acids, 11R-hydroperoxy fatty acids, 11S-hydroperoxy fatty acids, 12R-hydroperoxy fatty acids, 12S-hydroperoxy fatty acids, 13R-hydroperoxy fatty acids, 13S-hydroperoxy fatty acids, 14R-hydroperoxy fatty acids, 14S-hydroperoxy fatty acids, 15S-hydroperoxy fatty acids, derivatives thereof, and mixtures thereof; preferably selected from the group consisting of 2R-hydroperoxy fatty acids, unsaturated 8R-hydroperoxy fatty acids, unsaturated 9R-hydroperoxy fatty acids, unsaturated 11R-hydroperoxy fatty acids, unsaturated 12R-hydroperoxy fatty acids, unsaturated 12S-hydroperoxy fatty acids, unsaturated 13S-hydroperoxy fatty acids, unsaturated 15S-hydroperoxy fatty acids, derivatives thereof, and mixtures thereof; and more preferably 2R-hydroperoxy fatty acids.

In one aspect, the active fatty acid derivative material formed via the method is hydroperoxy fatty acid derivative selected from the group consisting of dihydroxy fatty acids, epoxy fatty acids, oxo fatty acids, divinyl ether fatty acids, alkenals, aldehydes, epoxy alcohols, and mixtures thereof; preferably dihydroxy fatty acids.

In one aspect, the active fatty acid derivative material formed via the method is hydroxy fatty acid selected from the group consisting of 2-hydroxy fatty acids, 3-hydroxy fatty acids, 4-hydroxy fatty acids, 5-hydroxy fatty acids, 6-hydroxy fatty acids, and mixtures thereof; preferably 2-hydroxy fatty acids, 3-hydroxy fatty acids, and mixtures thereof.

The present invention further relates to a method of cleaning a surface comprising the steps of includes a method of manually washing soiled articles, preferably dishware, comprising the step of: delivering a composition of the invention into a volume of water to form a wash solution and immersing the soiled articles in the wash solution, wherein the soil on the soiled articles comprise at least one unsaturated fatty acid selected from the group consisting of: mono unsaturated fatty acids, di unsaturated fatty acids, tri unsaturated fatty acids, tetra unsaturated fatty acids, penta unsaturated fatty acids, hexa unsaturated fatty acids, and mixtures thereof. Preferred unsaturated fatty acids include: myristoleic acid, palmitoleic acid, sapienic acid, oleic acid, elaidic acid, vaccenic acid, linoleic acid, linoelaidic acid, α-linolenic acid, γ-linolenic acid, gadoleic acid, α-eleostearic acid, β-eleostearic acid, ricinoleic acid, eicosenic acid, arachidonic acid, eicosapentaenoic acid, erucic acid, docosadienoic acid, docosahexaenoic acid, tetracosenoic acid, and mixtures thereof, more preferably palmitoleic acid, oleic acid, linoleic acid, α-linolenic acid, γ-linolenic acid, and mixtures thereof, more preferably oleic acid.

Preferably the resultant hydroperoxy fatty acids formed from the conversion reaction of the fatty acids with the hydroperoxy fatty acid producing enzymes are selected from the group consisting of 8R-hydroxyperoxy fatty acids, 8S-hydroxyperoxy fatty acids, 9R-hydroperoxy fatty acids, 9S-hydroperoxy fatty acids, 10R-hydroperoxy fatty acids, 11R-hydroperoxy fatty acids, 11S-hydroperoxy fatty acids, 12R-hydroperoxy fatty acids, 12S-hydroperoxy fatty acids, 13R-hydroperoxy fatty acids, 13S-hydroperoxy fatty acids, 14R-hydroperoxy fatty acids, 14S-hydroperoxy fatty acids, 15S-hydroperoxy fatty acids, their derivatives, and mixtures thereof; preferably unsaturated 8R-hydroperoxy fatty acids, unsaturated 8S-hydroperoxy fatty acids, unsaturated 9R-hydroperoxy fatty acids, unsaturated 10R-hydroperoxy fatty acids, their derivatives, and mixtures thereof.

The derivatives of hydroperoxy fatty acids formed from the conversion of hydroperoxy fatty acids by the hydroperoxy fatty acid converting enzymes preferably can be selected from the group consisting of monohydroxy fatty acids, dihydroxy fatty acids, epoxy fatty acids, oxo fatty acids, divinyl ether fatty acids, alkenals, aldehydes, epoxy alcohols, and mixtures thereof, preferably dihydroxy fatty acids.

Preferably each of the hydroperoxy fatty acid producing enzymes, and hydroperoxy fatty acid converting enzymes, are present at a concentration of from 0.005 ppm to 15 ppm, preferably from 0.01 ppm to 5 ppm, more preferably from 0.02 ppm to 0.5 ppm, in an aqueous wash liquor during the washing process. As such, the composition herein will be applied in its diluted form to the dishware. Soiled surfaces e.g. dishes are contacted with an effective amount, typically from 0.5 mL to 20 mL (per 25 dishes being treated), preferably from 3 mL to 10 mL, of the detergent composition of the present invention, preferably in liquid form, diluted in water. The actual amount of detergent composition used will be based on the judgment of user, and will typically depend upon factors such as the particular product formulation of the composition, including the concentration of active ingredients in the composition, the number of soiled dishes to be cleaned, the degree of soiling on the dishes, and the like. Generally, from 0.01 mL to 150 mL, preferably from 3 mL to 40 mL of a liquid detergent composition of the invention is combined with from 2,000 mL to 20,000 mL, more typically from 5,000 mL to 15,000 mL of water in a sink having a volumetric capacity in the range of from 1,000 mL to 20,000 mL, more typically from 5,000 mL to 15,000 mL. The soiled dishes are immersed in the sink containing the diluted compositions then obtained, where contacting the soiled surface of the dish with a cloth, sponge, or similar article cleans them. The cloth, sponge, or similar article may be immersed in the detergent composition and water mixture prior to being contacted with the dish surface, and is typically contacted with the dish surface for a period of time ranged from 1 to 10 seconds, although the actual time will vary with each application and user. The contacting of cloth, sponge, or similar article to the surface is preferably accompanied by a concurrent scrubbing of the surface.

Alternatively, the composition of the present invention can be delivered directly onto the dishware or by contacting a cleaning implement (such as a sponge) comprising the composition with the dishware, before cleaning the dishware with the composition in the presence in water, and optionally, rinsing. Such direct application dishwashing methods are particularly beneficial for cleaning greasy dishware, and especially where the grease has been baked on.

The present invention includes the use one or more hydroperoxy fatty acid producing enzymes, and one or more hydroperoxy fatty acid converting enzymes to provide increased suds longevity in an aqueous wash liquor comprising soil, wherein the soil comprises fatty acid. The enzymes are preferably comprised in a detergent composition, especially a detergent composition of the present invention, which is used for manually washing dishes.

The present invention further relates to use of the consumer product composition described herein to convert fatty acid of a soil disposed on a surface into an active fatty acid derivative material selected from the group consisting of hydroperoxy fatty acids, hydroperoxy fatty acid derivatives, hydroxy fatty acids, and mixtures thereof.

Test Methods

The following assays set forth must be used in order that the invention described and claimed herein may be more fully understood.

Test Method 1—Glass Vial Suds Mileage Method

The objective of the glass vial suds mileage test method is to measure the evolution of suds volume over time generated by a certain solution of detergent composition in the presence of a greasy soil, e.g., olive oil. The steps of the method are as follows:

1. Test solutions are prepared by subsequently adding aliquots at room temperature of: a) 10 g of an aqueous detergent solution at specified detergent concentration and water hardness, b) 1.0 g of an aqueous protein (or mixture of proteins) solution at specified concentration and water hardness), and c) 0.11 g of olive oil (Bertolli®, Extra Virgin Olive Oil), into a 40 mL glass vial (dimensions: 95 mm H×27.5 mm D). For the reference samples, the protein solutions are substituted with 1.0 mL of demineralized water.
2. The test solutions are mixed in the closed test vials by stirring at room temperature for 2 minutes on a magnetic stirring plate (IKA, model #RTC B S001; VWR magnetic stirrer, catalog #58949-012; 500 RPM), followed by manually shaking for 20 seconds with an upwards downwards movement (about 2 up and down cycles per second, +/−30 cm up and 30 cm down).

3. Following the shaking, the test solutions in the closed vials are further stirred on a magnetic stirring plate (IKA, model #RTC B S001; VWR magnetic stirrer, catalog #58949-012; 500 RPM) for 60 minutes inside a water bath at 46° C. to maintain a constant temperature. The samples are then shaken manually for another 20 seconds as described above and the initial suds heights (H1) are recorded with a ruler.
4. The samples are incubated for an additional 30 minutes inside the water bath at 46° C. while stirring (IKA, model #RTC B S001; VWR magnetic stirrer, catalog #58949-012; 500 RPM), followed by manual shaking for another 20 seconds as described above. The final suds heights (H2) are recorded.
5. Protein solutions that produce larger suds heights (H1 and H2), preferably combined with lower drops in suds height between H1 and H2, are more desirable.

Test Method 2—Small Sink Suds Mileage Method

The evolution of the suds volume generated by a solution of a liquid detergent composition can be determined while adding soil loads periodically as follows. An aliquot of 500 mL of solution of the liquid detergent composition in 15 dH hard water (final concentration of 0.12 w %, initial temperature 46° C.) is added into a cylindrical container (dimensions: 150 mm D×150 mm H). The container is incubated in a water bath during the test to maintain the temperature of the solution between 46° C. and 40° C. An initial suds volume is generated in the container by mechanical agitation at 135 rpm for 120 seconds with a paddle (dimensions: 50 mm×25 mm) positioned in the middle of the container.

Then, an aliquot of 0.5 mL of greasy soil (composition: see Table 3, 0.5 mL) is dosed into the solution using a 20-mL syringe and an automated pump (KDS Legato 110 Single Syringe I/W Pump), while the paddle rotates into the solution at 135 rpm for 14 seconds. After mixing, the solution is incubated for 166 additional seconds before the next cycle. The soil injecting, paddling, and incubation steps are repeated every 180 seconds until the end-point is reached and the amount of soil additions needed is recorded. The end-point occurs when a clear suds-free ring that circles the impeller at least half way around is observed two or more consecutive times. The complete process is repeated a number of times and the average of the number of additions for all the replicates is calculated for each liquid detergent composition.

Finally, the suds mileage index is then calculated as: (average number of soil additions for test liquid detergent composition)/(average number of soil additions for reference liquid detergent composition)×100. Pending on the test purpose the skilled person could choose to select an alternative water hardness, solution temperature, product concentration or soil type.

TABLE 3

| Greasy Soil Composition | |
| --- | --- |
| Ingredient | Weight % |
| Crisco oil | 12.730 |
| Crisco shortening | 27.752 |
| Lard | 7.638 |
| Refined Rendered Edible Beef Tallow | 51.684 |
| Oleic Acid, 90% (Techn) | 0.139 |
| Palmitic Acid, 99+% | 0.036 |
| Stearic Acid, 99+% | 0.021 |

Test Method 3—Large Sink Suds Mileage Method

The evolution of the suds volume generated by a solution of a detergent composition can be determined while adding soil loads periodically as follows. A stream of hard water (15 dH) fills a sink (cylinder dimensions: 300 mm D×288 mm H) to 4 L with a constant pressure of 4 bar. Simultaneously, an aliquot of the detergent composition (final concentration 0.12 w %) is dispensed through a pipette with a flow rate of 0.67 mL/sec at a height of 37 cm above the bottom of the sink surface. An initial suds volume is generated in the sink due to the pressure of the water. The temperature of the solution is maintained at 46° C. during the test.

After recording the initial suds volume (average suds height×sink surface area), a fixed amount of greasy soil (composition: see Table 3, 4 mL) is injected in the middle of the sink, while a paddle (dimensions: 10 cm×5 cm, positioned in the middle of the sink at the air liquid interface at an angle of 45 degrees) rotates 20 times into the solution at 85 rpm. This step is followed immediately by another measurement of the total suds volume. The soil injecting, paddling, and measuring steps are repeated until the measured suds volume reaches a minimum level, which is set at 400 cm$^3$. The amount of soil additions needed to get to that level is recorded. The complete process is repeated a number of times and the average of the number of additions for all the replicates is calculated for each detergent composition.

Finally, the suds mileage index is then calculated as: (average number of soil additions for test detergent composition)/(average number of soil additions for reference detergent composition)×100.

Pending on the test purpose the skilled person could choose to select an alternative water hardness, solution temperature, product concentration or soil type.

EXAMPLES

The following examples are provided to further illustrate the present invention and are not to be construed as limitations of the present invention, as many variations of the present invention are possible without departing from its spirit or scope.

Example 1a—*Pseudomonas aeruginosa* Strain 42A2 10S-DOX

*Pseudomonas aeruginosa* 10S-DOX (SEQ ID NO: 18) is a hydroperoxy fatty acid producing enzyme (oleate 10S-dioxygenase) that converts unsaturated fatty acids (e.g. oleic acid and linoleic acid) into the corresponding hydroperoxylated materials and that is included as part of the current invention. A codon optimized gene (SEQ ID NO: 55) encoding for a *P. aeruginosa* strain 42A2 10S-DOX variant, including an N-terminal amino acid sequence containing a His-tag, a MBP tag and a TEV protease cleavage site (SEQ ID NO: 56), is designed and synthesized. After gene synthesis, the protein is expressed and purified by Genscript (Piscataway, N.J.). In brief, the complete synthetic gene sequence is subcloned into a pET28a vector for heterologous expression. *Escherichia coli* BL21 (DE3) cells are transformed with the recombinant plasmid and a single colony is inoculated into LB medium containing kanamycin. Cultures are incubated at 15° C. for 16 h at 200 rpm and isopropyl β-D-1-thiogalactopyranoside (IPTG) is added (final concentration 1 mM) to induce protein expression. Cells are harvested by centrifugation and the pellets are lysed by sonication. After centrifugation, the supernatant is collected and the protein is purified by one-step purification using a nickel affinity column and standard protocols known in the art. The protein is stored in a buffer containing 50 mM Tris-HCl, 150 mM NaCl, and 10% Glycerol at pH 8.0. The final protein concentration is 0.12 mg/mL as determined by Bradford protein assay with BSA as a standard (ThermoFisher, catalog #23236).

Example 1b—*Nostoc punctiforme* HPL

*Nostoc punctiforme* HPL (SEQ ID NO: 40) is an enzyme (hydroperoxide lyase, EC 4.2.1.92) that converts hydroperoxide fatty acids (e.g. 10S-hydroperoxy linoleate) into smaller fatty acids and alcohols and that is included as part of the current invention. A codon optimized gene (SEQ ID NO: 62) encoding for a *N. punctiforme* HPL variant, including an N-terminal amino acid sequence containing a His-tag, a MBP tag and a TEV protease cleavage site (SEQ ID NO: 63), is designed and synthesized. After gene synthesis, the protein is expressed and purified by Genscript (Piscataway, N.J.). In brief, the complete synthetic gene sequence is subcloned into a pET28a vector for heterologous expression. *Escherichia coli* BL21 (DE3) cells are transformed with the recombinant plasmid and a single colony is inoculated into TB medium containing kanamycin at 37° C. When the OD600 reaches about 0.8-1.0, protein expression is induced by adding isopropyl β-D-1-thiogalactopyranoside (IPTG) (final concentration 0.1 mM) and δ-aminolevulinic acid (final concentration 0.25 mM). Cultures are incubated at 16° C. for 16 h at 200 rpm. Cells are harvested by centrifugation and the pellets are lysed by sonication. After centrifugation, the supernatant is collected and the protein is purified by two-step purification using nickel affinity columns and standard protocols known in the art. The protein is stored in 1×PBS buffer (pH 7.4) containing 10% Glycerol. The final protein concentration is 1.58 mg/mL as determined by Bradford protein assay with BSA as a standard (ThermoFisher, catalog #23236) and purity of about 75% as estimated by densitometric analysis of the Coomassie Blue-stained SDS-PAGE gel under reducing condition.

Example 1c—Hydroperoxy Fatty Acid Producing & Converting Enzymes Detergent Compositions The evolution of suds volume generated by a certain solution of detergent composition in presence of a soil, i.e., olive oil or greasy soil, is followed under specific conditions (e.g., water hardness, solution temperature, detergent concentrations, etc.). The following solutions are prepared:
A. Hard water (15 dH): 0.75 g $MgCl_2.6H_2O$ (Sigma-Aldrich, catalog #M9272), 2.10 g $CaCl_2.6H_2O$ (Sigma-Aldrich, catalog #21108), and 0.689 g $NaHCO_3$ (Sigma-Aldrich, catalog #31437) are dissolved in 5 L of demineralized water.
B. Detergent solution of a control reference detergent composition ("solution DG-R") is prepared using Fairy Dark Green, as commercially available in the UK in February 2017, diluted in hard water (15 dH) prepared as above, at targeted detergent concentration of 0.12%.
C. Protein solutions: Proteins are diluted in demineralized water to the required concentration before proceeding with the suds mileage method.
D. Greasy soil: A grease soil is prepared according to the composition described in Table 3.

Example 2: Exemplary Manual Dish-Washing Detergent Compositions

Manual dish-washing detergent compositions comprising:
a) the hydroperoxy fatty acid producing enzyme *Pseudomonas aeruginosa* strain 42A2 10S-DOX (SEQ ID NO: 18) and b) the hydroperoxy fatty acid converting enzyme(s) *Pseudomonas aeruginosa* strain 42A2 7,10-DS/HP-isomerase (SEQ ID NO: 38) or *Nostoc punctiforme* HPL_ (SEQ ID NO: 40) according to the invention are shown in Table 5. The enzymes can be produced following the protocols described on Examples 1a and 1b or similar procedures described in the art (Estupinan, M., et al. (2015)). PLoS One 10(7): e0131462/0131461-e0131462/0131420).

TABLE 5

Detergent Compositions

| Ingredient | Wt % | Wt % |
|---|---|---|
| Sodium alkyl ethoxy sulfate (C1213EO0.6S) | 22.91% | 22.91% |
| n-C12-14 Di Methyl Amine Oxide | 7.64% | 7.64% |
| Lutensol ® XP80 (non-ionic surfactant supplied by BASF) | 0.45% | 0.45% |
| Sodium Chloride | 1.2% | 1.2% |
| Poly Propylene Glycol (MW 2000) | 1% | 1% |
| Ethanol | 2% | 2% |
| Sodium Hydroxide | 0.24% | 0.24% |
| *Pseudomonas aeruginosa* strain 42A2 10S-DOX (SEQ ID NO: 18) | 0.1% | 0.1% |
| *Pseudomonas aeruginosa* strain 42A2 7,10-DS/HP-isomerase (SEQ ID NO: 38) | 0.1% | 0.0% |
| *Nostoc punctiforme* HPL (SEQ ID NO: 40) | 0.0% | 0.1% |
| Minors (perfume, preservative, dye) + water | To 100% | To 100% |
| pH (@ 10% solution) | 9 | 9 |

Examples of Automatic Dishwashing Compositions

The following are non-limited examples of consumer product compositions of the present invention in the form of automatic dishwashing compositions.

| Ingredients | EX 3 | EX 4 | EX 5 | EX 6 | EX 7 |
|---|---|---|---|---|---|
| Sodium carbonate | 8.0 | 7.4 | 4.0 | 3.5 | 0 |
| Sodium sulphate | 5.0 | 2.8 | 1 | 5.0 | 5.0 |
| Sodium silicate | 0.2 | 0.2 | 0 | 0.1 | 0.3 |
| MGDA | 1.5 | 2.5 | 5.0 | 2.5 | 5.0 |
| Sodium percarbonate | 1.0 | 1.0 | 2.0 | 1.0 | 2.0 |
| Sulfonated polymer | 0.25 | 0.4 | 1.2 | 0.5 | 0.5 |
| Protease | 0.025 | 0.035 | 0.035 | 0.25 | 0.035 |
| Amylase | 0.0017 | 0.0055 | 0.009 | 0.005 | 0.002 |
| *Asperigullus nidalus* PpoA (SEQ ID NO: 1) | 0.1 | 0.1 | 0.1 | 0.1 | 0.001 |
| Bleach Activator | 0.001 | 0.001 | 0.002 | 0.002 | 0.002 |
| SLF180 | 0.5 | 0.5 | 0.75 | 0.5 | 0.75 |
| Lutensol TO7 | 0.5 | 0.5 | 0.9 | 0.9 | 0.5 |
| Liquid polymer | 0.5 | 0.5 | 0 | 0.5 | 0 |
| Miscellaneous | balance to 18 g | balance to 18 g | balance to 18 g | balance to 18 g | balance to 18 g |

Wherein values in the table above are given as gram of active material.

| | |
|---|---|
| Amylase | Stainzyme plus ® supplied by Novozymes |
| Bleach Activator | PAAN by Weylchem |
| Lutensol TO7 | Nonionic surfactant supplied by BASF |
| Liquid polymer | GT 101 supplied by Nippon Shokubi |
| MGDA | Three-sodium Methyl glycine diacetate supplied by BASF |
| Protease | Ultimase ® supplied by DuPont |
| Sulfonated polymer | Acusol 588 supplied by Dow Chemicals |
| SLF180 | Nonionic surfactant supplied by BASF |

Examples of Shampoo Compositions

The following are non-limited examples of consumer product compositions of the present invention in the form of shampoo compositions for cleaning hair.

| Ingredients | EX 8 wt % | EX 9 wt % |
|---|---|---|
| Water Purified | Q.S to 100 | Q.S to 100 |
| Sodium Laureth-3 Sulfate | 21.6 | 21.6 |
| Sodium Lauryl Sulfate | 34.5 | 34.5 |
| Laureth-4 | 0.9 | 0.9 |
| Dimethicone 330M cps | 0.5 | 0.5 |
| Glycol Distearate | 1.5 | 1.5 |
| Polyquatemium-6 | 0.32 | 0.32 |
| *Asperigullus nidalus* PpoA (SEQ ID NO: 1) | 0.1 | 0.001 |
| Sodium Benzoate | 0.27 | 0.27 |
| Citric acid 50% Solution | 0.52 | 0.52 |
| Methylchloroisothiazolinone/methylisothiazolinone | 0.035 | 0.035 |
| Sodium chloride | 1.66 | 1.66 |
| Fragrance | 0.65 | 0.65 |
| DL-Panthenol 56% solution | 0.05 | 0.05 |
| Panthenyl Ethyl ether | 0.03 | 0.03 |
| Glycol Distearate | 1.5 | 1.5 |

| Ingredient | EX 10 | EX 11 | EX 12 | EX 13 | EX 14 | EX 15 | EX 16 |
|---|---|---|---|---|---|---|---|
| Sodium lauryl ether sulfate (SLE3S) |  | 6 | 10 | 6 | 6 | 9 |  |
| Sodium cocoyl isethionate |  |  |  |  |  |  | 8.5 |
| Sodium lauryl sulfate (SLS) | 1.5 | 7 | 1.5 | 7 | 7 | 6 |  |
| Sodium lauryl ether sulfate (SLE1S) | 10.5 |  |  |  |  |  |  |
| Disodium laureth sulfosuccinate |  |  |  |  |  |  | 8.5 |
| Sodium lauryl sulfoacetate |  |  |  |  |  |  | 2.5 |
| Sodium Lauroyl Sarcosinate |  |  |  |  |  |  | 0.75 |
| Cocoamidopropyl Hydroxysultaine |  |  |  |  |  |  | 1.5 |
| Cocoamidopropyl Betaine | 1 | 2 | 2 | 2 | 2 | 2 | 2 |
| Coconut monoethanol amide (CMEA) |  | 0.85 |  | 0.85 |  |  |  |
| Cetyl alcohol |  |  | 1 |  |  |  |  |
| Stearyl alcohol |  |  | 2 |  |  |  |  |
| Dimethicone | 1 | 1 | 1 | 1 | 1 |  | 0.5 |
| Ethylene glycol distearate (EGDS) | 1.5 | 1.5 | 1.5 | 1.5 | 1.5 |  |  |
| Jaguar ® C500[1] | 0.25 | 0.25 | 0.15 |  |  |  |  |
| Synthetic Cationic Polymer AMT[2] |  |  |  | 0.1 |  |  |  |
| Polydiallyldimethylammonium chloride (DADMAC) |  |  |  |  | 0.1 |  |  |
| *Asperigullus nidalus* PpoA (SEQ ID NO: 1) | 0.01 | 0.1 | 0.001 | 0.01 | 0.001 | 0.1 | 0.01 |
| Excel Guar[3] |  |  |  |  |  | 0.1 | .15 |
| pH | 6 | 6 | 6 | 6 | 6 | 6 |  |
| Water-USP Purified & Minors | Q.S. to 100 | Q.S. to 100 | Q.S. to 100 | Q.S. to 100 | Q.S. to 100 | Q.S. to 100 | Q.S. to 100 |

[1] Cationic polymer derived from a natural gum with low aqueous viscosity
[2] Cationic synthetic copolymer
[3] Cationic plant derived polymer Examples 17 to 22: Granular Laundry Detergent Compositions for Hand Washing or Washing Machines, Typically Top-Loading Washing Machines

| Ingredient | 17 | 18 | 19 | 20 | 21 | 22 |
|---|---|---|---|---|---|---|
|  | % weight |  |  |  |  |  |
| LAS | 11.33 | 10.81 | 7.04 | 4.20 | 3.92 | 2.29 |
| Quaternary ammonium | 0.70 | 0.20 | 1.00 | 0.60 | — | — |
| AE3S | 0.51 | 0.49 | 0.32 | — | 0.08 | 0.10 |
| AE7 | 8.36 | 11.50 | 12.54 | 11.20 | 16.00 | 21.51 |
| Sodium Tripolyphosphate | 5.0 | — | 4.0 | 9.0 | 2.0 | — |
| Zeolite A | — | 1.0 | — | 1.0 | 4.0 | 1.0 |
| Sodium silicate 1.6R | 7.0 | 5.0 | 3.0 | 3.0 | 3.0 | 5.0 |
| Sodium carbonate | 20.0 | 17.0 | 23.0 | 14.0 | 14.0 | 16.0 |
| Polyacrylate MW 4500 | 1.0 | 0.6 | 1.0 | 1.0 | 1.5 | 1.0 |
| Polymer 6 | 0.1 | 0.2 | — | — | 0.1 | — |
| Carboxymethyl cellulose | 1.0 | 0.3 | 1.0 | 1.0 | 1.0 | 1.0 |
| Acid Violet 50 | 0.05 | — | 0.02 | — | 0.04 | — |
| Violet DD | — | 0.03 | — | 0.03 | — | 0.03 |
| Protease 2 | 0.10 | 0.10 | 0.10 | 0.10 | — | 0.10 |
| Amylase | 0.03 | — | 0.03 | 0.03 | 0.03 | 0.03 |
| Lipase | 0.03 | 0.07 | 0.30 | 0.10 | 0.07 | 0.40 |
| Polishing enzyme | 0.002 | — | 0.05 | — | 0.02 | — |
| Nuclease | 0.001 | 0.001 | 0.01 | 0.05 | 0.002 | 0.02 |
| Dispersin B | 0.001 | 0.001 | 0.05 | — | 0.001 | — |
| Optical Brightener 1 | 0.200 | 0.001 | 0.300 | 0.650 | 0.050 | 0.001 |

-continued

| Ingredient | 17 | 18 | 19 | 20 | 21 | 22 |
|---|---|---|---|---|---|---|
| | | | % weight | | | |
| Optical Brightener 2 | 0.060 | — | 0.650 | 0.180 | 0.200 | 0.060 |
| Optical Brightener 3 | 0.100 | 0.060 | 0.050 | — | 0.030 | 0.300 |
| Chelant 1 | 0.60 | 0.80 | 0.60 | 0.25 | 0.60 | 0.60 |
| DTI 1 | 0.32 | 0.15 | 0.15 | — | 0.10 | 0.10 |
| DTI 2 | 0.32 | 0.15 | 0.30 | 0.30 | 0.10 | 0.20 |
| *Asperigullus nidalus* PpoA (SEQ ID NO: 1) | 0.01 | 0.1 | 0.001 | 0.1 | 0.01 | 0.01 |
| Sodium Percarbonate | 4.6 | 5.2 | 5.0 | 5.7 | 4.5 | 7.3 |
| Nonanoyloxybenzensulfonate | 1.9 | 0.0 | 1.66 | 0.0 | 0.33 | 0.75 |
| Tetraacetylethylenediamine | 0.58 | 1.2 | 0.51 | 0.0 | 0.015 | 0.28 |
| Photobleach | 0.0030 | 0.0 | 0.0012 | 0.0030 | 0.0021 | — |
| S-ACMC | 0.1 | 0.0 | 0.0 | 0.0 | 0.06 | 0.0 |
| Polyetheramine | 0.5 | 2 | 0.5 | 1 | 0.5 | 4 |
| Sulfate/Moisture | | | Balance | | | |

Examples 23-28: Granular Laundry Detergent Compositions Typically for Front-Loading Automatic Washing Machines

| Ingredient | 23 | 24 | 25 | 26 | 27 | 28 |
|---|---|---|---|---|---|---|
| | | | % weight | | | |
| LAS | 6.08 | 5.05 | 4.27 | 3.24 | 2.30 | 1.09 |
| AE3S | — | 0.90 | 0.21 | 0.18 | — | 0.06 |
| AS | 0.34 | — | — | — | — | — |
| AE7 | 4.28 | 5.95 | 6.72 | 7.98 | 9.20 | 10.35 |
| Quaternary ammonium | 0.5 | — | — | 0.3 | — | — |
| Crystalline layered silicate | 4.1 | — | 4.8 | — | — | — |
| Zeolite A | 5.0 | — | 2.0 | — | 2.0 | 2.0 |
| Citric acid | 3.0 | 4.0 | 3.0 | 4.0 | 2.5 | 3.0 |
| Sodium carbonate | 11.0 | 17.0 | 12.0 | 15.0 | 18.0 | 18.0 |
| Sodium silicate 2R | 0.08 | — | 0.11 | — | — | — |
| Optical Brightener 1 | — | 0.25 | 0.05 | 0.01 | 0.10 | 0.02 |
| Optical Brightener 2 | — | — | 0.25 | 0.20 | 0.01 | 0.08 |
| Optical Brightener 3 | — | 0.06 | 0.04 | 0.15 | — | 0.05 |
| DTI 1 | 0.08 | — | 0.04 | — | 0.10 | 0.01 |
| DTI 2 | 0.08 | — | 0.04 | 0.10 | 0.10 | 0.02 |
| *Asperigullus nidalus* PpoA (SEQ ID NO: 1) | 0.01 | 0.01 | 0.1 | 0.1 | 0.001 | 0.1 |
| Soil release agent | 0.75 | 0.72 | 0.71 | 0.72 | — | — |
| Acrylic/maleic acid copolymer | 1.1 | 3.7 | 1.0 | 3.7 | 2.6 | 3.8 |
| Carboxymethyl cellulose | 0.2 | 1.4 | 0.2 | 1.4 | 1.0 | 0.5 |
| Protease 3 | 0.20 | 0.20 | 0.30 | 0.15 | 0.12 | 0.13 |
| Amylase 3 | 0.20 | 0.15 | 0.20 | 0.30 | 0.15 | 0.15 |
| Lipase | 0.05 | 0.15 | 0.10 | — | — | — |
| Amylase 2 | 0.03 | 0.07 | — | — | 0.05 | 0.05 |
| Cellulase 2 | — | — | — | — | 0.10 | 0.10 |
| Polishing enzyme | 0.003 | 0.005 | 0.020 | — | — | — |
| Nuclease | 0.002 | 0.010 | 0.020 | 0.020 | 0.010 | 0.003 |
| Dispersin B | 0.002 | 0.010 | 0.020 | 0.020 | 0.010 | 0.002 |
| Tetraacetylehtylenediamine | 3.6 | 4.0 | 3.6 | 4.0 | 2.2 | 1.4 |
| Sodium percabonate | 13.0 | 13.2 | 13.0 | 13.2 | 16.0 | 14.0 |
| Chelant 3 | — | 0.2 | — | 0.2 | — | 0.2 |
| Chelant 2 | 0.2 | — | 0.2 | — | 0.2 | 0.2 |
| MgSO$_4$ | — | 0.42 | — | 0.42 | — | 0.4 |
| Perfume | 0.5 | 0.6 | 0.5 | 0.6 | 0.6 | 0.6 |
| Suds suppressor agglomerate | 0.05 | 0.10 | 0.05 | 0.10 | 0.06 | 0.05 |
| Soap | 0.45 | 0.45 | 0.45 | 0.45 | — | — |
| Acid Violet 50 | 0.04 | — | 0.05 | — | 0.04 | — |
| Violet DD | — | 0.04 | — | 0.05 | — | 0.04 |
| S-ACMC | 0.01 | 0.01 | — | 0.01 | — | — |
| Direct Violet 9 (active) | — | — | 0.0001 | 0.0001 | — | — |
| Polyetheramine | 0.5 | 2 | 0.5 | 1 | 0.5 | 4 |
| Sulfate/Water & Miscellaneous | | | Balance | | | |

Examples 29-35: Heavy Duty Liquid Laundry Detergent Compositions

| Ingredients | 29 | 30 | 31 | 32 % weight | 33 | 34 | 35 |
|---|---|---|---|---|---|---|---|
| $AE_{1.8}S$ | 6.77 | 5.16 | 1.36 | 1.30 | — | — | — |
| $AE_3S$ | — | — | — | — | 0.45 | — | — |
| LAS | 0.86 | 2.06 | 2.72 | 0.68 | 0.95 | 1.56 | 3.55 |
| HSAS | 1.85 | 2.63 | 1.02 | — | — | — | — |
| AE9 | 6.32 | 9.85 | 10.20 | 7.92 | — | — | — |
| AE8 | — | — | — | — | — | — | 35.45 |
| AE7 | — | — | — | — | 8.40 | 12.44 | — |
| $C_{12-14}$ dimethyl Amine Oxide | 0.30 | 0.73 | 0.23 | 0.37 | — | — | — |
| $C_{12-18}$ Fatty Acid | 0.80 | 1.90 | 0.60 | 0.99 | 1.20 | — | 15.00 |
| Citric Acid | 2.50 | 3.96 | 1.88 | 1.98 | 0.90 | 2.50 | 0.60 |
| Optical Brightener 1 | 1.00 | 0.80 | 0.10 | 0.30 | 0.05 | 0.50 | 0.001 |
| Optical Brightener 3 | 0.001 | 0.05 | 0.01 | 0.20 | 0.50 | — | 1.00 |
| Sodium formate | 1.60 | 0.09 | 1.20 | 0.04 | 1.60 | 1.20 | 0.20 |
| DTI 1 | 0.32 | 0.05 | — | 0.60 | 0.10 | 0.60 | 0.01 |
| DTI 2 | 0.32 | 0.10 | 0.60 | 0.60 | 0.05 | 0.40 | 0.20 |
| *Asperigullus nidalus* PpoA (SEQ. ID NO: 1) | 0.01 | 0.01 | 0.01 | 0.1 | 0.1 | 0.01 | 0.001 |
| Sodium hydroxide | 2.30 | 3.80 | 1.70 | 1.90 | 1.70 | 2.50 | 2.30 |
| Monoethanolamine | 1.40 | 1.49 | 1.00 | 0.70 | — | — | — |
| Diethylene glycol | 5.50 | — | 4.10 | — | — | — | — |
| Chelant 1 | 0.15 | 0.15 | 0.11 | 0.07 | 0.50 | 0.11 | 0.80 |
| 4-formyl-phenylboronic acid | — | — | — | — | 0.05 | 0.02 | 0.01 |
| Sodium tetraborate | 1.43 | 1.50 | 1.10 | 0.75 | — | 1.07 | — |
| Ethanol | 1.54 | 1.77 | 1.15 | 0.89 | — | 3.00 | 7.00 |
| Polymer 1 | 0.10 | — | — | — | — | — | 2.00 |
| Polymer 2 | 0.30 | 0.33 | 0.23 | 0.17 | — | — | — |
| Polymer 3 | — | — | — | — | — | — | 0.80 |
| Polymer 4 | 0.80 | 0.81 | 0.60 | 0.40 | 1.00 | 1.00 | — |
| 1,2-Propanediol | — | 6.60 | — | 3.30 | 0.50 | 2.00 | 8.00 |
| Structurant | 0.10 | — | — | — | — | — | 0.10 |
| Perfume | 1.60 | 1.10 | 1.00 | 0.80 | 0.90 | 1.50 | 1.60 |
| Perfume encapsulate | 0.10 | 0.05 | 0.01 | 0.02 | 0.10 | 0.05 | 0.10 |
| Protease | 0.80 | 0.60 | 0.70 | 0.90 | 0.70 | 0.60 | 1.50 |
| Mannanase | 0.07 | 0.05 | 0.045 | 0.06 | 0.04 | 0.045 | 0.10 |
| Amylase 1 | 0.30 | — | 0.30 | 0.10 | — | 0.40 | 0.10 |
| Amylase 2 | — | 0.20 | 0.10 | 0.15 | 0.07 | — | 0.10 |
| Xyloglucannase | 0.20 | 0.10 | — | — | 0.05 | 0.05 | 0.20 |
| Lipase | 0.40 | 0.20 | 0.30 | 0.10 | 0.20 | — | — |
| Polishing enzyme | — | 0.04 | — | — | — | 0.004 | — |
| Nuclease | 0.05 | 0.03 | 0.01 | 0.03 | 0.03 | 0.003 | 0.003 |
| Dispersin B | — | — | — | 0.05 | 0.03 | 0.001 | 0.001 |
| Acid Violet 50 | 0.05 | — | — | — | — | — | 0.005 |
| Direct Violet 9 | — | — | — | — | — | 0.05 | — |
| Violet DD | — | 0.035 | 0.02 | 0.037 | 0.04 | — | — |
| Dye control agent | 0.2 | 0.3 | 0.2 | 0.03 | 1.2 | 0.3 | 0.3 |
| Water, dyes & minors | | | | Balance | | | |
| pH | | | | 8.2 | | | |

Based on total cleaning and/or treatment composition weight. Enzyme levels are reported as raw material.

Examples 36 to 47: Unit Dose Compositions

These examples provide various formulations for unit dose laundry detergents and comprise double compartment unit dose products comprising one powder and one liquid compartment. The film used to encapsulate the compositions is PVA. Each example is prepared by combining a liquid compartment composition selected from compositions A-E with a powder compartment composition selected from compositions F-K.

| | Example | | | | | |
|---|---|---|---|---|---|---|
| | 36 | 37 | 38 | 39 | 40 | 41 |
| Liquid composition | 15 g A | 17 g B | 20 g C | 19 g C | 15 g C | 25 g C |
| Solid composition | 15 g L | 14 g F | 15 g G | 18 g H | 15 g I | 12 g J |

| | Example | | | | | |
|---|---|---|---|---|---|---|
| | 42 | 43 | 44 | 45 | 46 | 47 |
| Liquid composition | 20 g D | 18 g D | 22 g D | 32 g E | 32 g E | 27 g E |
| Solid composition | 20 g K | 13 g L | 15 g F | 17 g G | 12 g H | 18 g I |

The following Examples A-E are liquid compositions of the unit dose products:

| Ingredients | A | B | C | D | E |
|---|---|---|---|---|---|
| | % weight of compartment | | | | |
| LAS | 19.09 | 16.76 | 8.59 | 6.56 | 3.44 |
| AE3S | 1.91 | 0.74 | 0.18 | 0.46 | 0.07 |
| AE7 | 14.00 | 17.50 | 26.33 | 28.08 | 31.59 |
| Citric Acid | 0.6 | 0.6 | 0.6 | 0.6 | 0.6 |
| C12-15 Fatty Acid | 14.8 | 14.8 | 14.8 | 14.8 | 14.8 |
| Polymer 3 | 4.0 | 4.0 | 4.0 | 4.0 | 4.0 |
| Chelant 2 | 1.2 | 1.2 | 1.2 | 1.2 | 1.2 |
| Optical Brightener 1 | 0.20 | 0.25 | 0.01 | 0.01 | 0.50 |
| Optical Brightener 2 | 0.20 | — | 0.25 | 0.03 | 0.01 |
| Optical Brightener 3 | 0.18 | 0.09 | 0.30 | 0.01 | — |
| DTI 1 | 0.10 | — | 0.20 | 0.01 | 0.05 |
| DTI 2 | — | 0.10 | 0.20 | 0.25 | 0.05 |
| Glycerol | 6.1 | 6.1 | 6.1 | 6.1 | 6.1 |
| Monoethanol amine | 8.0 | 8.0 | 8.0 | 8.0 | 8.0 |
| Tri-isopropanol amine | — | — | 2.0 | — | — |
| Tri-ethanol amine | — | 2.0 | — | — | — |
| Cumene sulfonate | — | — | — | — | 2.0 |
| Protease | 0.80 | 0.60 | 0.07 | 1.00 | 1.50 |
| Mannanase | 0.07 | 0.05 | 0.05 | 0.10 | 0.01 |
| Amylase 1 | 0.20 | 0.11 | 0.30 | 0.50 | 0.05 |
| Amylase 2 | 0.11 | 0.20 | 0.10 | — | 0.50 |
| Polishing enzyme | 0.005 | 0.05 | — | — | — |
| Nuclease | 0.005 | 0.05 | 0.005 | 0.010 | 0.005 |
| Dispersin B | 0.010 | 0.05 | 0.005 | 0.005 | — |
| *Asperigullus nidalus* PpoA (SEQ ID NO: 1) | 0.1 | 0.1 | 0.01 | 0.01 | 0.01 |
| Cyclohexyl dimethanol | — | — | — | 2.0 | — |
| Acid violet 50 | 0.03 | 0.02 | | | |
| Violet DD | | | 0.01 | 0.05 | 0.02 |
| Structurant | 0.14 | 0.14 | 0.14 | 0.14 | 0.14 |
| Perfume | 1.9 | 1.9 | 1.9 | 1.9 | 1.9 |
| Water, solvents and miscellaneous | To 100% | | | | |
| pH | 7.5-8.2 | | | | |

The following Examples F-K are powder/solid compositions of the unit dose products:

| Ingredient | F | G | H | I | J | K |
|---|---|---|---|---|---|---|
| | % weight | | | | | |
| Sodium carbonate | 20.0 | 35.0 | 30.0 | 29.0 | 28.0 | 18.0 |
| Carboxymethyl cellulose | 2.0 | 1.0 | — | — | 2.5 | 0.6 |
| Sodium silicate 2R | 5.0 | — | 5.0 | 3.2 | 20.0 | — |
| Tetraacetyl ethylenediamine | 20.0 | 15.0 | 18.0 | 15.0 | — | 25.0 |
| Sodium percarbonate | 50.0 | 44.0 | 45.0 | 45.0 | 29.0 | 50.0 |
| Polyetheramine | 0.5 | 2 | 0.5 | 1 | 0.5 | 4 |
| Sulfate/Water & Miscellaneous | Balance | | | | | |

Based on total cleaning and/or treatment composition/compartment weight. Enzyme levels are reported as raw material.

For Examples 17-47 above, the following definitions apply:

| | |
|---|---|
| AE1.8S | is $C_{12-15}$ alkyl ethoxy (1.8) sulfate |
| AE3S | is $C_{12-15}$ alkyl ethoxy (3) sulfate |
| AE7 | is $C_{12-13}$ alcohol ethoxylate, with an average degree of ethoxylation of 7 |
| AE8 | is $C_{12-13}$ alcohol ethoxylate, with an average degree of ethoxylation of 8 |
| AE9 | is $C_{12-13}$ alcohol ethoxylate, with an average degree of ethoxylation of 9 |
| Amylase 1 | is Stainzyme ®, 15 mg active/g |
| Amylase 2 | is Natalase ®, 29 mg active/g |
| Amylase 3 | is Stainzyme ® Plus, 20 mg active/g, |
| AS | is $C_{12-14}$ alkylsulfate |
| Cellulase 2 | is Celluclean ™, 15.6 mg active/g |
| Xyloglucanase | is Whitezyme ®, 20 mg active/g |
| Chelant 1 | is diethylene triamine pentaacetic acid |
| Chelant 2 | is 1-hydroxyethane 1,1-diphosphonic acid |
| Chelant 3 | is sodium salt of ethylenediamine-N,N'-disuccinic acid, (S,S) isomer (EDDS) |
| Dispersin B | is a glycoside hydrolase, reported as 1000 mg active/g |
| DTI 1 | is poly(4-vinylpyridine-1-oxide) (such as Chromabond S-403E ®). |
| DTI 2 | is poly(1-vinylpyrrolidone-co-1-vinylimidazole) (such as Sokalan HP56 ®). |
| HSAS | is mid-branched alkyl sulfate as disclosed in U.S. Pat. No. 6,020,303 and U.S. Pat. No. 6,060,443 |
| LAS | is linear alkylbenzenesulfonate having an average aliphatic carbon chain length $C_9$-$C_{15}$ (HLAS is acid form). |
| Lipase | is Lipex ®, 18 mg active/g |
| Mannanase | is Mannaway ®, 25 mg active/g |
| Nuclease | is a Phosphodiesterase SEQ ID NO 1, reported as 1000 mg active/g |
| Optical Brightener 1 | is disodium 4,4'-bis{[4-anilino-6-morpholino-s-triazin-2-yl]-amino}-2,2'-stilbenedisulfonate |
| Optical Brightener 2 | is disodium 4,4'-bis-(2-sulfostyryl)biphenyl (sodium salt) |
| Optical Brightener 3 | is Optiblanc SPL10 ® from 3V Sigma |
| Perfume encapsulate | is a core-shell melamine formaldehyde perfume microcapsules |
| Photobleach | is a sulfonated zinc phthalocyanine |
| Polishing enzyme | is Para-nitrobenzyl esterase, reported as 1000 mg active/g |
| Polyetheramine | as described in present disclosure. |
| Polymer 1 | is bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = 20-30, x = 3 to 8 or sulphated or sulfonated variants thereof |
| Polymer 2 | is ethoxylated ($EO_{15}$) tetraethylene pentamine |
| Polymer 3 | is ethoxylated polyethylenimine |
| Polymer 4 | is ethoxylated hexamethylene diamine |
| Polymer 5 | is Acusol 305, provided by Rohm&Haas |
| Polymer 6 | is a polyethylene glycol polymer grafted with vinyl acetate side chains, provided by BASF. |
| Protease | is Purafect Prime ®, 40.6 mg active/g |
| Protease 2 | is Savinase ®, 32.89 mg active/g |

-continued

| | |
|---|---|
| Protease 3 | is Purafect ®, 84 mg active/g |
| Quaternary ammonium | is $C_{12-14}$ Dimethylhydroxyethyl ammonium chloride |
| S-ACMC | is Reactive Blue 19 Azo-CM-Cellulose provided by Megazyme |
| Soil release agent | is Repel-o-tex ® SF2, supplied by Solvay |
| Structurant | is Hydrogenated Castor Oil |
| Violet DD | is a thiophene azo polymeric hueing dye provided by Milliken |

All percentages and ratios given for enzymes are based on active protein. All percentages and ratios herein are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. A consumer product composition having improved cleaning performance and/or increased sudsing longevity in the presence of greasy soils that comprise both saturated and unsaturated fatty acids comprising:
   (a) a surfactant selected from the group consisting of anionic surfactants, nonionic surfactants, zwitterionic surfactants, amphoteric surfactants, cationic surfactants, and mixtures thereof; and
   (b) alpha-dioxygenases
   wherein the alpha-dioxygenases convert saturated and unsaturated fatty acids to their corresponding 2-hydroperoxy fatty acids via stereoselective dioxygenation.

2. The consumer product composition of claim 1, wherein said alpha-dioxygenases is at least one of linoleate 8R-dioxygenases, linolenate 9R-lipoxygenases (EC 1.13.11.61), linoleate 9S-lipoxygenases (EC 1.13.11.58), linoleate 10R-dioxygenases, oleate 10S-dioxygenases, linoleate 10S-dioxygenases, linoleate 11-lipoxygenases (EC 1.13.11.45), linoleate 13S-lipoxygenases (EC 1.13.11.12), linoleate 9/13-lipoxygenases (EC 1.13.11.B6), arachidonate 5-lipoxygenases (EC 1.13.11.34), arachidonate 8-lipoxygenases (EC 1.13.11.40), arachidonate 12-lipoxygenases (E.C. 1.13.11.31), arachidonate 15-lipoxygenase (EC 1.13.11.33), alpha-dioxygenases, or mixtures thereof.

3. The consumer product composition of claim 2, wherein said hydroperoxy fatty acid producing enzyme that is at least one of linoleate 8R-dioxygenases, linolenate 9R-lipoxygenases (EC 1.13.11.61), linoleate 9S-lipoxygenases (EC 1.13.11.58), linoleate 10R-dioxygenases, linoleate 10S-dioxygenases, alpha-dioxygenases, and mixtures thereof.

4. The consumer product composition of claim 1, wherein said consumer product composition comprises from about 0.01% to about 60% of said surfactant, by weight of said consumer product composition.

5. The consumer product composition of claim 1, wherein said consumer product composition comprises from about 0.01% to about 2%, of said surfactant, by weight of said consumer product composition.

6. The consumer product composition of claim 1, wherein said consumer product composition comprises from about 0.01% to about 1%, of said surfactant, by weight of said consumer product composition.

7. The consumer product composition of claim 1, wherein said surfactant comprises anionic surfactant.

8. The consumer product composition of claim 1, wherein said surfactant comprises nonionic surfactant.

9. The consumer product composition of claim 1, wherein said surfactant comprises cationic surfactant.

10. The consumer product composition of claim 1, wherein said surfactant is selected from the group consisting of decyl glucoside, isethionates, glutamates, and mixtures thereof, and wherein consumer product composition is free of sulfate surfactant.

11. The consumer product composition of claim 1, wherein said consumer product composition further comprises a consumer product adjunct ingredient selected from the group consisting of enzyme stabilizers, co-enzymes, salts, hydrotropes, chelants, builders, dispersants, dye transfer inhibitors, bleach, stabilizers/thickeners, perfume, conditioning agents, hueing agents, structurants, solvents, aqueous carrier, and mixtures thereof.

12. The consumer product composition of claim 1, further comprises UFA heme-dioxygenases.

13. The consumer product composition of claim 1, further comprises at least one of lipoxygenases and UFA heme-dioxygenases; and hydroperoxy fatty acid converting enzymes selected from the group consisting of cyclooxygenases (EC 1.14.99.1), allene oxide synthases (EC 4.2.1.92), hydroperoxide isomerases (EC 4.2.1.92, EC 5.3.99.1, EC 5.4.4.5, EC 5.4.4.6), hydroperoxide lyases (EC 4.2.1.92), hydroperoxide dehydratases (EC 4.2.1.92), divinyl ether synthases (EC 4.2.1.121, EC 4.2.1.B8, EC 4.2.1.B9), 9,12-octadecadienoate 8-hydroperoxide 8R-isomerases (EC 5.4.4.5), 9,12-octadecadienoate 8-hydroperoxide 8S-isomerases (EC 5.4.4.6), 7,10-hydroperoxide diol synthases, epoxy alcohol synthases, or mixtures thereof; wherein said hydroperoxy fatty acid converting enzymes are capable of transforming the reaction product of said hydroperoxy fatty acid producing enzymes.

14. The consumer product composition of claim 1, further comprises multi-domain enzymes comprising a hydroperoxy fatty acid domain comprising a heme-dioxygenase or lipoxygenase domain and a hydroperoxy fatty acid converting domain that is at least one of allene oxide synthase domain, epoxy alcohol synthase domain, hydroperoxide lyase domain, or hydroperoxide isomerase domain.

15. The consumer product composition of claim 1, further comprises hydroxy fatty acid producing enzymes that are at least one of peroxygenase, fatty acid hydratases, or mixtures thereof.

* * * * *

SEQUENCE LISTING

```
<160> NUMBER OF SEQ ID NOS: 80

<210> SEQ ID NO 1
<211> LENGTH: 1165
<212> TYPE: PRT
<213> ORGANISM: Gaeumannomyces graminis

<400> SEQUENCE: 1

Met Thr Val Ser Thr His His Asp Asp Ser Pro Gly Leu Ser Gly Arg
1               5                   10                  15

Leu Arg Asp Leu Leu His His Val Phe Gly Asn Gln Lys Ser Pro Thr
                20                  25                  30

Val Tyr Pro Asn Ala Pro Gly Asn Ser Ala Lys Pro Val Pro Thr Gly
            35                  40                  45

Leu Ala Asp Asp Ile Asp Lys Leu Gly Phe Lys Asp Ile Asp Thr Leu
        50                  55                  60

Leu Ile Phe Leu Asn Ser Ala Val Lys Gly Val Asn Asp Asp Gln Gln
65                  70                  75                  80

Phe Leu Leu Glu Lys Met Ile Gln Leu Leu Ala Lys Leu Pro Pro Ala
                85                  90                  95

Ser Arg Glu Gly Lys Lys Leu Thr Asp Gly Leu Ile Asn Asp Leu Trp
            100                 105                 110

Asp Ser Leu Asp His Pro Pro Val Ala Ser Leu Gly Lys Gly Phe Ser
        115                 120                 125

Phe Arg Glu Pro Asp Gly Ser Asn Asn Ile His Leu Pro Ser Leu
    130                 135                 140

Gly Ala Ala Asn Thr Pro Tyr Ala Arg Ser Thr Lys Pro Leu Val Phe
145                 150                 155                 160

Gln Asn Pro Asn Pro Asp Pro Ala Thr Ile Phe Asp Thr Leu Met
                165                 170                 175

Val Arg Asp Pro Ala Lys Phe Arg Pro His Pro Asn Lys Ile Ser Ser
            180                 185                 190

Met Leu Phe Tyr Leu Ala Thr Ile Ile Thr His Asp Ile Phe Gln Thr
        195                 200                 205

Ser Pro Arg Asp Phe Asn Ile Asn Leu Thr Ser Ser Tyr Leu Asp Leu
    210                 215                 220
```

```
Ser Pro Leu Tyr Gly Arg Asn His Asp Glu Gln Met Ala Val Arg Thr
225                 230                 235                 240

Gly Lys Asp Gly Leu Leu Lys Pro Asp Thr Phe Ser Ser Lys Arg Val
            245                 250                 255

Ile Gly Phe Pro Pro Gly Val Gly Ala Phe Leu Ile Met Phe Asn Arg
        260                 265                 270

Phe His Asn Tyr Val Val Thr Gln Leu Ala Lys Ile Asn Glu Gly Gly
    275                 280                 285

Arg Phe Lys Arg Pro Thr Thr Pro Asp Asp Thr Ala Gly Trp Glu Thr
    290                 295                 300

Tyr Asp Asn Ser Leu Phe Gln Thr Gly Arg Leu Ile Thr Cys Gly Leu
305                 310                 315                 320

Tyr Ile Asn Ile Val Leu Gly Asp Tyr Val Arg Thr Ile Leu Asn Leu
                325                 330                 335

Asn Arg Ala Asn Thr Thr Trp Asn Leu Asp Pro Arg Thr Lys Glu Gly
                340                 345                 350

Lys Ser Leu Leu Ser Lys Pro Thr Pro Glu Ala Val Gly Asn Gln Val
            355                 360                 365

Ser Val Glu Phe Asn Leu Ile Tyr Arg Trp His Cys Thr Ile Ser Glu
370                 375                 380

Arg Asp Asp Lys Trp Thr Thr Asn Ala Met Arg Glu Ala Leu Gly Gly
385                 390                 395                 400

Gln Asp Pro Ala Thr Ala Lys Met Glu Asp Val Met Arg Ala Leu Gly
                405                 410                 415

Met Phe Glu Lys Asn Ile Pro Asp Glu Pro Glu Lys Arg Thr Leu Ala
            420                 425                 430

Gly Leu Thr Arg Gln Ser Asp Gly Ala Phe Asp Asp Thr Glu Leu Val
            435                 440                 445

Lys Ile Leu Gln Glu Ser Ile Glu Asp Val Ala Gly Ala Phe Gly Pro
450                 455                 460

Asn His Val Pro Ala Cys Met Arg Ala Ile Glu Ile Leu Gly Ile Lys
465                 470                 475                 480

Gln Ser Arg Thr Trp Asn Val Ala Thr Leu Asn Glu Phe Arg Gln Phe
                485                 490                 495

Ile Gly Leu Thr Pro His Asp Ser Phe Tyr His Met Asn Pro Asp Pro
            500                 505                 510

Lys Ile Cys Lys Ile Leu Ala Gln Met Tyr Asp Ser Pro Asp Ala Val
            515                 520                 525

Glu Leu Tyr Pro Gly Ile Met Ala Glu Ala Lys Pro Pro Phe Ser
530                 535                 540

Pro Gly Ser Gly Leu Cys Pro Pro Tyr Thr Thr Ser Arg Ala Ile Leu
545                 550                 555                 560

Ser Asp Ala Val Ser Leu Val Arg Gly Asp Arg Phe Tyr Thr Val Asp
                565                 570                 575

Tyr Thr Pro Arg Asn Ile Thr Asn Trp Gly Phe Asn Glu Ala Ser Thr
            580                 585                 590

Asp Lys Ala Val Asp Trp Gly His Val Ile Tyr Lys Leu Phe Arg
    595                 600                 605

Ala Phe Pro Asn His Phe Leu Pro Asn Ser Val Tyr Ala His Phe Pro
    610                 615                 620

Phe Val Val Pro Ser Glu Asn Lys Leu Ile Phe Glu Gly Leu Gly Ala
625                 630                 635                 640
```

```
Ala Asn Lys Tyr Ser Trp Asp Pro Pro Lys Ala Arg Ala Pro Ile Gln
            645                 650                 655

Phe Ile Arg Ser His Lys Ala Val Leu Glu Val Leu Ser Asn Gln Lys
            660                 665                 670

Asp Tyr Lys Val Thr Trp Gly Pro Ala Ile Lys Met Leu Ser Gly Asp
            675                 680             685

Pro Ala Thr Ser Phe Ala Leu Ala Gly Asp Glu Pro Ala Asn Ala Ala
            690                 695             700

Ser Arg His His Val Ile Ala Ala Leu Thr Ala Pro Lys Gln Trp Arg
705                 710                 715                 720

Asp Glu Val Arg Arg Phe Tyr Glu Val Thr Thr Arg Asp Leu Leu Arg
                725                 730                 735

Arg His Gly Ala Pro Val His Gly Val Gly Ala Gly Pro Arg Thr His
                740                 745                 750

Glu Val Asp Val Ile Arg Asp Val Ile Gly Leu Ala His Ala Arg Phe
            755                 760                 765

Met Ala Ser Leu Phe Ser Leu Pro Leu Lys Glu Gly Lys Glu Glu
770                 775                 780

Gly Ala Tyr Gly Glu His Glu Leu Tyr Arg Ser Leu Val Thr Ile Phe
785             790                 795                 800

Ala Ala Ile Phe Trp Asp Ser Asp Val Cys Asn Ser Leu Lys Leu His
                805                 810                 815

Gln Ala Ser Lys Ala Ala Ala Asp Lys Met Ser Ala Leu Ile Ala Glu
                820                 825                 830

His Val Arg Glu Met Glu Ala Gly Thr Gly Phe Leu Gly Ala Leu Gly
                835                 840                 845

Lys Leu Lys Asp Leu Ile Thr Gly Asn Asp Val His Ala Asn Gly Asn
850                 855                 860

Gly Val Tyr Thr Asn Gly Asn Gly Val Tyr Thr Asn Gly Asn Gly Val
865                 870                 875                 880

His Thr Asn Gly Asn Gly Val His Thr Asn Gly Asn Gly Val Pro His
                885                 890                 895

Ala Ala Pro Ser Leu Arg Ser Phe Gly Asp Gln Leu Leu Gln Arg Met
                900                 905             910

Leu Ser Gln Asp Gly Arg Ser Ile Glu Glu Thr Val Ser Gly Thr Ile
            915                 920                 925

Leu Pro Val Val Met Ala Gly Thr Ala Asn Gln Thr Gln Leu Leu Ala
            930                 935                 940

Gln Cys Leu Asp Tyr Tyr Leu Gly Val Gly Glu Lys His Leu Pro Glu
945                 950                 955                 960

Met Lys Arg Leu Ala Met Leu Asn Thr Ser Glu Ala Asp Glu Lys Leu
                965                 970                 975

Leu Lys Tyr Thr Met Glu Gly Cys Arg Ile Arg Gly Cys Val Ala Leu
            980                 985                 990

Tyr Arg Ala Val Val Thr Asp Gln Ala Val Asp Asp Thr Ile Pro Cys
            995                 1000                1005

Ile Pro Asn Lys Asp Asp Pro Thr Phe Ala Arg Pro Leu Ser Asn
        1010                1015                1020

Pro Gln Val Ala Glu Ser Ala Arg Thr Leu Lys Leu Ser Thr Gly
        1025                1030                1035

Thr Arg Met Leu Val Asp Leu Thr Thr Ala Ser His Asp Pro Ala
        1040                1045                1050

Ala Phe Pro Asp Pro Asp Glu Val Arg Leu Asp Arg Pro Leu Glu
```

-continued

```
             1055                1060                1065

Ser  Tyr  Val  His  Phe  Gly  Leu  Gly  Pro  His  Arg  Cys  Ala  Gly  Glu
             1070                1075                1080

Pro  Ile  Ser  Gln  Ile  Ala  Leu  Ser  Ser  Val  Met  Lys  Val  Leu  Leu
             1085                1090                1095

Gln  Leu  Asp  Gly  Leu  Arg  Arg  Ala  Ala  Gly  Pro  Arg  Gly  Glu  Ile
             1100                1105                1110

Arg  Ser  Tyr  Pro  Ala  Ser  Gln  Trp  Pro  Gly  Gln  Ala  Gly  Arg  Pro
             1115                1120                1125

Pro  Arg  Asp  Pro  Ala  Trp  Ser  Gly  Leu  Arg  Thr  Phe  Thr  Ser  Ala
             1130                1135                1140

Asp  Gln  Ser  Ala  Phe  Ser  Pro  Leu  Ala  Thr  Thr  Met  Lys  Ile  Asn
             1145                1150                1155

Trp  Glu  Gly  Arg  Gly  Asp  Leu
             1160                1165

<210> SEQ ID NO 2
<211> LENGTH: 773
<212> TYPE: PRT
<213> ORGANISM: Nostoc sp.

<400> SEQUENCE: 2

Met  Asp  Leu  Asn  Thr  Tyr  Leu  Lys  Leu  Leu  Asn  Leu  Leu  Asp  Ser  Glu
1                 5                   10                  15

Ser  Gln  Lys  Ile  Met  Leu  Glu  Leu  Gln  Ala  Met  Phe  Ser  Ala  Ala  Gly
                 20                   25                  30

Leu  Ala  Leu  Arg  Gly  Arg  Gly  Thr  His  Thr  Asp  Gly  Ile  Ile  Val  Lys
                 35                   40                  45

Gly  Asn  Leu  Thr  Val  Leu  His  Ser  Ser  Asp  Val  Pro  Ser  His  Ser  Leu
         50                       55                  60

Phe  Thr  Pro  Gly  Lys  Lys  Tyr  Asp  Val  Ile  Phe  Arg  His  Ala  Asn  Ile
65                       70                  75                          80

Val  Gly  Gly  Ala  Lys  Asp  Asp  Ala  Leu  Ile  Asn  Gly  Arg  Gly  Ser  Ala
                 85                   90                  95

Ile  Arg  Ile  Gly  Asn  Ile  Gly  Asp  Asp  Leu  Ser  Lys  Pro  Arg  Leu  Leu
                100                  105                 110

Asp  Leu  Val  Leu  Asn  Thr  Gly  Glu  Val  Phe  Gly  Leu  Pro  Thr  Ala  Arg
                115                  120                 125

Leu  Tyr  His  Gln  Phe  Phe  Gly  Ser  Asp  Phe  His  Gln  Lys  Ser  Asp  Met
         130                      135                 140

Leu  Ala  Ser  Gly  Ser  Leu  Arg  Arg  Tyr  Ala  Val  Glu  Ala  Ala  Leu  Arg
145                      150                 155                         160

Asn  Pro  Asp  Ser  Phe  Thr  Glu  Leu  Tyr  Tyr  His  Thr  Gln  Leu  Cys  Tyr
                 165                  170                 175

Glu  Trp  Val  Asp  Ser  Lys  Lys  Lys  Ser  Arg  Tyr  Ala  Arg  Phe  Arg  Leu
                 180                  185                 190

Leu  Asn  Pro  Asn  Gln  Ser  Thr  Glu  Gly  Gly  Leu  Leu  Asp  Asp  Ser  Val
                 195                  200                 205

Glu  Ile  Gly  Pro  Arg  Leu  Val  Leu  Pro  Arg  Lys  Arg  Gly  Asp  Thr  Arg
         210                      215                 220

Glu  Lys  Asn  Tyr  Leu  Arg  Asn  Glu  Phe  Arg  Gln  Arg  Leu  Thr  Asp  Gly
225                      230                 235                         240

Asn  Ile  Val  Glu  Tyr  Val  Leu  Gln  Ala  Gln  Phe  Arg  Ser  Ile  Glu  Asp
                 245                  250                 255
```

-continued

Val Ala Val Asp Cys Ser Asn Ile Trp Asp Pro Asn Thr Tyr Pro Trp
            260                 265                 270

Leu Asp Ile Ala Ala Ile Val Leu Asn Gln Asp Glu Ser Glu Asn Asp
        275                 280                 285

Tyr Tyr Gln Glu Ile Ala Tyr Asn Pro Gly Asn Thr His Tyr Asp Leu
    290                 295                 300

Lys Leu Pro Asn Ser Tyr Ser Val Asp Asp Phe Ala Ser Leu Gly Val
305                 310                 315                 320

Ser Gly Ala Leu Val His Tyr Phe Gly Ser Ile Val Arg Ala Glu Arg
            325                 330                 335

Thr Gln Tyr Leu Tyr Gly Ser Lys Asp Asp Leu Pro Gly Lys Pro Val
        340                 345                 350

Tyr Phe Pro Leu Pro Val Thr Glu Ile Pro Ser Lys Arg Phe Leu Phe
    355                 360                 365

Leu Leu Glu Lys Tyr Asn Phe Leu Thr Asp Asn Ser Tyr Pro Ser Asp
370                 375                 380

Gly Glu His Asp Lys Ile Glu Ala Leu Val Ser Ala Met Pro Thr Thr
385                 390                 395                 400

Ala Leu Asp Leu Ala Val Gly Thr Thr Asp Pro Thr Asp Ile Pro Asp
            405                 410                 415

Ser Tyr Phe Leu Glu Arg Arg Leu Asn Gly Tyr Asn Pro Gly Ala Ile
        420                 425                 430

Arg Glu Ser Ser Gly Gln Glu Gly Trp Thr His Glu Leu Thr His Asn
    435                 440                 445

Leu Ala Lys Tyr Asp Ile Lys Pro Gly Leu His Phe Pro Asp Phe Val
450                 455                 460

Gln Cys Arg Leu Phe Val Asp Lys Gln Asn Gly Val Lys Leu His Ser
465                 470                 475                 480

Ile Lys Ile Asp Asp His Glu Ile Thr Pro Cys Gln Glu Gln Trp Gln
            485                 490                 495

Tyr Ala Lys Arg Thr Tyr Leu Gln Ala Glu Phe Leu Ser Gln Glu Leu
        500                 505                 510

Lys Leu His Leu Ala Arg Cys His Phe Asn Ile Glu Gln Tyr Val Met
    515                 520                 525

Ala Ile Lys Arg Arg Leu Ala Pro Thr His Pro Val Arg Ala Phe Ile
530                 535                 540

Asn Pro His Leu Glu Gly Leu Ile Phe Ile Asn Ser Ser Ala Val Pro
545                 550                 555                 560

Lys Ile Ile Gly Ser Thr Gly Phe Ile Pro Ile Ala Ser Met Leu Thr
            565                 570                 575

Gln Gly Ser Ile Val Asp Val Met Lys Asn Glu Leu Ser Lys Leu Ser
        580                 585                 590

Tyr Met Trp Asn Pro Ile Ala Asp Leu Pro Arg Asp Ile Pro Gly Asp
    595                 600                 605

Leu Phe Thr Pro Ala Ala Thr Ala Tyr Trp Glu Leu Leu Asn Asn Tyr
610                 615                 620

Val Glu Gln Gly Leu Leu Gln Pro Phe Glu Asp Glu Leu Arg Thr Glu
625                 630                 635                 640

Val Asn Ala Ile Gln Val Asp Glu Leu Phe Ala Glu Leu Lys Glu Arg
            645                 650                 655

Ser Leu Tyr Ser Gly Asp Gln Pro Pro Lys Tyr Asp Ser Ser Glu Leu
        660                 665                 670

Lys Ser Leu Leu Met Tyr Ile Ile Tyr His Ser Ser Phe Leu His Ser

```
            675                 680                 685
Trp Ala Asn Phe Lys Gln Tyr Asp Asp Ala Gly Asn Pro Asn His Val
    690                 695                 700

Ser Met Gly Asp Tyr Ser Gln Tyr Asp Gln Gln Thr Gln Asp Lys Ile
705                 710                 715                 720

Arg Phe Ser Gln Arg Ser Leu Thr Trp Val Leu Ser Ser Ile Arg Tyr
                725                 730                 735

Asn Ser Val Ala Val Tyr Gly Ser Asp Leu Leu Lys Gln Leu Ile Arg
                740                 745                 750

Glu Lys Ser Ser Ile Leu Glu Pro Gly Leu Pro Leu Glu Asp Leu Met
                755                 760                 765

Met Ser Ile Asn Ile
            770

<210> SEQ ID NO 3
<211> LENGTH: 805
<212> TYPE: PRT
<213> ORGANISM: Acaryochloris marina

<400> SEQUENCE: 3

Met Asp Ser Arg Asp Pro Arg Thr Glu His Val Asp Asp Glu Phe Lys
1               5                   10                  15

Lys Leu Ile Ser Asn Ile Ala Arg Ala Phe Gly Arg Thr Ala Gln Ile
                20                  25                  30

Lys Gly Arg Arg Ala Thr His Ser Tyr Gly Thr Val Ala Lys Gly Val
            35                  40                  45

Leu Lys Val Leu Asp Thr Leu Asp Ile Pro Gln His Gln Ile Phe Ser
50                  55                  60

Ala Gly Lys Gln Tyr Pro Val Leu Leu Arg His Ala Asn Ile Lys Gly
65                  70                  75                  80

Phe Arg Asp Asp Ala Ile Leu Asp Gly Arg Gly Ala Thr Val Arg Val
                85                  90                  95

Leu Ala Gly Asp Ala Gln Ala Pro Leu Ser Asp Leu Asn Leu Asp Glu
            100                 105                 110

Gly Ile Val Asp Ile Leu Met Ser Thr Gly Arg Ser Phe Ile Leu Ala
            115                 120                 125

Glu Ala Leu Ser Phe Ala Arg Trp Ala Ala Gly Pro Met Lys Ser Arg
130                 135                 140

Ala Ala Met Leu Gln Glu Phe Pro Lys Ile Ala Pro Ile Phe His Glu
145                 150                 155                 160

Ile Ile Arg Asp Pro Asp Ser Tyr Thr Gln Leu His Tyr Tyr Ser Glu
                165                 170                 175

Thr Thr Tyr Ser Phe Thr Ser Leu Asn Gln Gln Ser Phe Phe Leu Arg
            180                 185                 190

Tyr Arg Leu Val Asn Arg Gln Asn Pro Ser Ala Asp Thr Gly Trp Leu
        195                 200                 205

Lys Pro Glu Glu Val Lys Leu Pro Leu Asp Tyr Leu Pro Arg Val Ala
    210                 215                 220

Ser Asp Thr Arg Pro Glu Thr Tyr Leu Gln Asp Asp Phe Arg Gln Gln
225                 230                 235                 240

Val Arg Ser Thr Gly Val Ser Tyr Leu Leu Gln Ile Gln Leu Gln Pro
                245                 250                 255

Val Ser Asp Asp Ala Ala Met Asn Glu Thr Ala Lys Asp Cys Thr Ile
            260                 265                 270
```

```
Pro Trp Glu Glu Asp His Pro Phe His Asp Val Ala Val Leu Asp
        275                 280                 285
Leu Gly Ser Ile Leu Pro Asp Glu Leu Ala Glu Ala Leu Glu Phe Asn
    290                 295                 300
Pro Tyr Asn Ala Pro Glu Leu Ser Leu Ile Leu Ala Lys Thr Ala
305                 310                 315                 320
Arg Glu Thr Ala Ser Val Asn His Leu Arg Ser Val Val Tyr Gln Ile
                325                 330                 335
Ser Ala Asn Met Arg Lys Tyr Gln Thr Pro Ser Ser Ser Leu Val Asp
            340                 345                 350
Trp Gly Ser Gly His Gln Pro Ser Leu Pro Glu Gln Tyr Pro Tyr Gly
        355                 360                 365
Thr Gly Lys Thr Pro Ser Phe Asp Asn Thr Lys Pro Leu Pro Ala Arg
    370                 375                 380
Val Lys Pro Lys Pro Arg Tyr Trp Ala Asn Phe Gly Leu Lys Leu Ile
385                 390                 395                 400
Pro Asn Gln Gln Leu Asp Pro Asp Leu Pro Glu Leu Gly Ile Thr Gly
                405                 410                 415
Ala Leu Asp Leu Met Gly Thr Ser Val Val Ser Tyr Met Pro Pro Asn
            420                 425                 430
Leu Thr Arg Thr Arg Leu Asp Lys Phe Ser Asp Asp Phe Phe Val Glu
        435                 440                 445
Arg Arg Leu Asn Gly Phe Asn Pro Gly Lys Leu Asn Arg Val Thr Gly
    450                 455                 460
His Ala Trp Gln Tyr Gln Val Cys Tyr Asp Cys Ser Lys His Gln Val
465                 470                 475                 480
Glu Pro Ala Gly Ile Leu Pro Thr Lys Ile Thr Ala Arg Phe Asn Phe
                485                 490                 495
Cys Gly Gln Tyr Leu His Pro His Ser Ile Gln Phe Thr Leu Asn Gly
            500                 505                 510
Gln Thr Glu Thr Gln Gln Pro Gly Asp Glu Asn Trp Glu Trp Ser Lys
        515                 520                 525
Arg Leu Phe Arg Cys Ala Glu Phe Val Phe Gln Glu Ala Gln Ser His
    530                 535                 540
Leu Gly Arg Thr His Met Asn Leu Asp Gln Tyr Ala Met Ala Tyr Tyr
545                 550                 555                 560
Arg Asn Val Val Asn Asn Pro Ile Arg Leu Leu Glu Pro His Leu
                565                 570                 575
Glu Gly Leu Leu Ser Ile Asn Lys Leu Gly Ala Asn Leu Ile Ser Gly
            580                 585                 590
Pro Thr Gly Phe Ile Pro Glu Ala Ser Ser Leu Thr Pro Glu Ser Val
        595                 600                 605
Asp Asp Val Leu Lys Asp Glu Ile Ser His Leu Ser Tyr His Trp Thr
    610                 615                 620
Pro His Arg Gln Thr Leu Pro Asp Arg Val Leu Asn Asn His Tyr Asp
625                 630                 635                 640
Pro Ala Ala Ile Ala Met Trp Asn Leu Leu Thr Gln Tyr Val Arg Glu
                645                 650                 655
Phe Phe Glu Asp His Gln Ala Gly Met Glu Glu Tyr Trp Ser Glu Ile
            660                 665                 670
Gln Ala Met Ser His Asp Leu Val Thr His Ser Ile Leu Lys Pro Glu
        675                 680                 685
Leu Gly Thr Leu Ala Val Gln Asn Asn Ala Asp Leu Gln Gln Leu Cys
```

```
                690                 695                 700
Val Tyr Val Ile Phe Leu Ser Ser Phe Phe His Ser Trp Val Asn Asn
705                 710                 715                 720

Lys Gln Tyr Glu Asp Gly Gly Asp Val Ser Tyr Ser Thr Ile Gly Leu
                725                 730                 735

Trp Asp Thr Arg His Pro Lys Tyr Asp Pro Leu Arg Val Ala Glu Arg
                740                 745                 750

Glu Ala Lys Gln Val Thr Leu Leu Trp Thr Leu Ser His Val Arg Tyr
                755                 760                 765

Asn Pro Ile Met Asp Val Gly Pro Thr Ala Leu Lys Asn Leu Leu Trp
770                 775                 780

Gln Gln Arg Gln His Ile Glu Pro Gly Ile Pro Leu Ala Asn Leu Met
785                 790                 795                 800

Met Ser Thr Asn Ile
                805

<210> SEQ ID NO 4
<211> LENGTH: 862
<212> TYPE: PRT
<213> ORGANISM: Avena sativa

<400> SEQUENCE: 4

Met Leu Leu Gly Gly Leu Ile Asp Asn Leu Thr Gly Ala Asn Lys His
1               5                   10                  15

Ala Arg Leu Lys Gly Thr Val Val Leu Met Arg Lys Asn Val Leu Asp
                20                  25                  30

Leu Asn Asp Phe Gly Ala Thr Ile Ile Asp Gly Val Ser Glu Phe Leu
            35                  40                  45

Gly Lys Gly Val Thr Cys Gln Leu Ile Ser Ser Thr Val Val Asp Asn
50                  55                  60

Asn Asn Gly Asn Arg Gly Lys Val Gly Ala Glu Ala Gly Leu Glu Gln
65                  70                  75                  80

Trp Leu Thr Ser Leu Pro Ser Leu Thr Thr Gly Glu Ser Lys Phe Gly
                85                  90                  95

Leu Thr Phe Asp Trp Glu Val Asp Lys Leu Gly Val Pro Gly Ala Ile
            100                 105                 110

Val Val Asn Asn Tyr His Ser Ala Gln Phe Phe Leu Lys Thr Ile Thr
            115                 120                 125

Leu Asp Asp Val Pro Gly Arg Ala Gly Lys Leu Thr Phe Val Ala Asn
            130                 135                 140

Ser Trp Ile Tyr Pro Ala Glu Lys Tyr Arg Tyr Asn Arg Val Phe Phe
145                 150                 155                 160

Ala Asn Asp Thr Tyr Leu Pro Ser Gln Met Pro Ala Ala Leu Lys Pro
                165                 170                 175

Tyr Arg Asp Asp Glu Leu Arg Asn Leu Arg Gly Asp Gln Gln Gly
                180                 185                 190

Pro Tyr Glu Glu His Asp Arg Val Tyr Arg Tyr Asp Val Tyr Asn Asp
            195                 200                 205

Leu Gly Glu Asp Arg Pro Val Leu Gly Gly Thr Ala Asp His Pro Tyr
            210                 215                 220

Pro Arg Arg Gly Arg Thr Gly Arg Lys Pro Asn Pro Asn Asp Pro Ser
225                 230                 235                 240

Leu Glu Ser Arg Leu Ser Leu Leu Glu Gln Ile Tyr Val Pro Arg Asp
                245                 250                 255
```

```
Glu Lys Phe Gly His Leu Lys Met Ser Asp Phe Leu Gly Tyr Ser Ile
            260                 265                 270

Lys Ala Ile Thr Gln Gly Ile Leu Pro Ala Val Arg Thr Tyr Val Asp
        275                 280                 285

Cys Thr Pro Gly Glu Phe Asp Ser Phe Gln Asp Ile Ile Asn Leu Tyr
    290                 295                 300

Glu Gly Gly Ile Lys Leu Pro Lys Ile Ala Ala Leu Glu Glu Leu Arg
305                 310                 315                 320

Lys Arg Phe Pro Phe Gln Leu Leu Lys Asp Leu Leu Pro Val Gly Gly
                325                 330                 335

Asp Phe Leu Leu Lys Leu Pro Leu Pro His Ile Ile Lys Glu Asp Lys
            340                 345                 350

Gln Ala Trp Arg Thr Asp Glu Glu Phe Ala Arg Glu Val Leu Ala Gly
        355                 360                 365

Val Asn Pro Val Met Ile Thr Arg Leu Thr Glu Phe Pro Pro Lys Ser
    370                 375                 380

Thr Leu Asp Pro Ser Lys Tyr Gly Asp His Thr Ser Thr Ile Thr Ala
385                 390                 395                 400

Ala His Ile Glu Lys Asn Leu Glu Gly Leu Thr Val Gln Gln Ala Leu
                405                 410                 415

Glu Gly Asn Lys Leu Tyr Ile Leu Asp His His Asp Arg Phe Met Pro
            420                 425                 430

Phe Leu Ile Asp Val Asn Asn Leu Asp Gly Asn Phe Ile Tyr Ala Thr
        435                 440                 445

Arg Thr Leu Phe Phe Leu Arg Gly Asp Gly Arg Leu Thr Pro Leu Ala
    450                 455                 460

Ile Glu Leu Ser Glu Pro Phe Ile Gln Asp Gly Leu Thr Thr Ala Lys
465                 470                 475                 480

Ser Lys Val Tyr Thr Pro Val Pro Ser Gly Ser Val Glu Gly Trp Val
                485                 490                 495

Trp Glu Leu Ala Lys Ala Tyr Val Ala Val Gly Asp Ser Gly Trp His
            500                 505                 510

Gln Leu Val Ser His Trp Leu Asn Thr His Ala Val Met Glu Pro Phe
        515                 520                 525

Val Ile Ala Thr Asn Arg Gln Leu Ser Val Thr His Pro Val His Lys
    530                 535                 540

Leu Leu Ser Pro His Tyr Arg Asp Thr Met Thr Ile Asn Ala Leu Ala
545                 550                 555                 560

Arg Gln Thr Leu Ile Asn Ala Gly Gly Ile Phe Glu Met Thr Val Phe
                565                 570                 575

Pro Gly Lys Phe Ala Leu Gly Met Ser Ser Val Val Tyr Lys Asp Trp
            580                 585                 590

Asn Phe Ala Glu Gln Gly Leu Pro Asp Asp Leu Leu Arg Arg Gly Val
        595                 600                 605

Ala Val Pro Asp Pro Ser Ser Pro Tyr Lys Val Arg Leu Leu Ile Glu
    610                 615                 620

Asp Tyr Pro Tyr Ala Ala Asp Gly Leu Ala Ile Trp His Ala Ile Glu
625                 630                 635                 640

Gln Tyr Val Thr Glu Tyr Leu Ala Ile Tyr Tyr Pro Asp Asp Ala Val
                645                 650                 655

Leu Gln Asp Asp Val Glu Leu Gln Ala Trp Trp Lys Glu Ala Arg Glu
            660                 665                 670

Val Gly His Gly Asp Leu Lys Asp Ala Pro Trp Trp Pro Ser Met Gln
```

```
                  675                 680                 685
Thr Val Ala Glu Leu Ala Lys Ser Cys Ala Thr Ile Ile Trp Ile Ala
690                 695                 700

Ser Ala Leu His Ala Ala Val Asn Phe Gly Gln Tyr Pro Tyr Ala Gly
705                 710                 715                 720

Tyr Leu Pro Asn Arg Pro Thr Val Ser Arg Arg Met Pro Glu Pro
                725                 730                 735

Gly Thr Gln Glu Tyr Ala Glu Leu Glu Arg Asp Pro Glu Arg Ala Phe
                740                 745                 750

Ile His Thr Ile Thr Ser Gln Ile Gln Thr Ile Ile Gly Ile Ser Leu
                755                 760                 765

Leu Glu Val Leu Ser Lys His Ser Ser Asp Glu Leu Tyr Leu Gly Gln
770                 775                 780

Arg Asp Thr Pro Glu Trp Thr Ser Asp Pro Lys Ala Leu Ala Val Phe
785                 790                 795                 800

Gln Arg Phe Ser Asp Arg Leu Val Asp Ile Glu Ser Lys Val Val Gly
                805                 810                 815

Met Asn His Asp Pro Gln Leu Lys Asn Arg Asn Gly Pro Ala Lys Leu
                820                 825                 830

Pro Tyr Met Leu Leu Tyr Pro Asn Thr Ser Asp Arg Lys Gly Asp Ala
                835                 840                 845

Ala Gly Leu Thr Ala Lys Gly Ile Pro Asn Ser Ile Ser Ile
850                 855                 860

<210> SEQ ID NO 5
<211> LENGTH: 863
<212> TYPE: PRT
<213> ORGANISM: Oryza sativa

<400> SEQUENCE: 5

Met Leu Gly Gly Leu Lys Asp Lys Leu Thr Gly Lys Asn Gly Asn Lys
1               5                   10                  15

Ile Lys Gly Leu Ala Val Leu Met Ser Arg Lys Leu Leu Asp Pro Arg
                20                  25                  30

Asp Phe Thr Ala Ser Leu Leu Asp Asn Val His Glu Val Phe Gly Asn
                35                  40                  45

Ser Ile Thr Cys Gln Leu Val Ser Ala Thr Val Ala Asp Gln Asn Asn
                50                  55                  60

Glu Gly Arg Gly Ile Val Gly Ser Glu Ala Asn Leu Glu Gln Gly Leu
65              70                  75                  80

Thr Asp Leu Pro Ser Val Ser Gln Gly Glu Ser Lys Leu Thr Val Arg
                85                  90                  95

Phe Asn Trp Glu Met Asp Lys His Gly Val Pro Gly Ala Ile Ile Ile
                100                 105                 110

Lys Asn His His Ser Thr Lys Phe Phe Leu Lys Thr Ile Thr Leu His
                115                 120                 125

Asp Val Pro Gly Cys Asp Thr Ile Val Phe Val Ala Asn Ser Trp Ile
                130                 135                 140

Tyr Pro Val Gly Lys Tyr His Tyr Asn Arg Ile Phe Phe Ala Asn Asn
145                 150                 155                 160

Ser Tyr Leu Pro Ser Gln Met Pro Glu Ala Leu Arg Pro Tyr Arg Glu
                165                 170                 175

Asp Glu Leu Arg Tyr Leu Arg Gly Glu Asp Arg Gln Gly Pro Tyr Gln
                180                 185                 190
```

```
Glu His Asp Arg Ile Tyr Arg Tyr Asp Val Tyr Asn Asp Leu Gly Glu
            195                 200                 205

Pro Asp Arg Asp Asn Pro Arg Pro Val Leu Gly Gly Ser Gln Lys His
210                 215                 220

Pro Tyr Pro Arg Arg Gly Arg Thr Gly Arg Ile Pro Thr Lys Lys Asp
225                 230                 235                 240

Pro Asn Ser Glu Ser Arg Leu Ser Leu Leu Glu Gln Ile Tyr Val Pro
                245                 250                 255

Ser Asp Glu Arg Phe Ala His Leu Lys Met Ser Asp Phe Ala Gly Tyr
                260                 265                 270

Ser Ile Lys Ala Ile Val Gln Gly Ile Leu Pro Ala Ile Arg Thr Tyr
            275                 280                 285

Val Asp Leu Thr Pro Gly Glu Phe Asp Ser Phe Glu Asp Ile Leu Lys
            290                 295                 300

Leu Tyr Arg Gly Gly Leu Lys Leu Pro Ser Ile Pro Ala Leu Glu Glu
305                 310                 315                 320

Leu Arg Lys Ser Phe Pro Val Gln Leu Ile Lys Asp Leu Leu Pro Val
                325                 330                 335

Gly Gly Ser Tyr Leu Leu Lys Phe Pro Lys Pro Asp Ile Ile Lys Glu
                340                 345                 350

Asn Glu Val Ala Trp Arg Thr Asp Glu Glu Phe Ala Arg Glu Ile Leu
            355                 360                 365

Ala Gly Leu Asn Pro Met Val Ile Arg Arg Leu Thr Glu Phe Pro Pro
            370                 375                 380

Lys Ser Thr Leu Asp Pro Ser Lys Tyr Gly Asp Gln Thr Ser Thr Ile
385                 390                 395                 400

Thr Pro Ala His Ile Glu Lys Asn Leu Glu Gly Leu Ser Val Gln Gln
                405                 410                 415

Ala Leu Asp Ser Asn Arg Leu Tyr Ile Leu Asp His His Asp His Phe
                420                 425                 430

Met Pro Phe Leu Ile Asp Ile Asn Ser Leu Asp Gly Ile Phe Thr Tyr
            435                 440                 445

Ala Thr Arg Thr Leu Leu Phe Leu Arg Asp Asp Thr Leu Lys Pro
            450                 455                 460

Leu Ala Ile Glu Leu Ser Leu Pro His Ile Glu Gly Asn Leu Thr Ser
465                 470                 475                 480

Ala Lys Ser Lys Val His Thr Pro Ala Ser Gly Ile Glu Ser Trp
                485                 490                 495

Val Trp Gln Leu Ala Lys Ala Tyr Val Ala Val Asn Asp Ser Gly Trp
                500                 505                 510

His Gln Leu Ile Ser His Trp Leu Asn Thr His Ala Val Met Glu Pro
                515                 520                 525

Phe Val Ile Ala Thr Asn Arg Gln Leu Ser Val Thr His Pro Val Tyr
530                 535                 540

Lys Leu Leu Gln Pro His Tyr Arg Asp Thr Met Thr Ile Asn Ala Leu
545                 550                 555                 560

Ala Arg Gln Thr Leu Ile Asn Gly Gly Gly Ile Phe Glu Gln Thr Val
                565                 570                 575

Phe Pro Gly Lys His Ala Leu Ala Met Ser Ser Ala Val Tyr Lys Asn
                580                 585                 590

Trp Asn Phe Thr Glu Gln Gly Leu Pro Asp Asp Leu Ile Lys Arg Gly
                595                 600                 605

Ile Ala Ile Lys Asp Pro Ser Ser Pro Ser Lys Val Lys Leu Leu Ile
```

610 615 620

Lys Asp Tyr Pro Tyr Ala Thr Asp Gly Leu Ala Ile Trp Gln Ala Ile
625 630 635 640

Glu Gln Trp Val Thr Glu Tyr Cys Ala Ile Tyr Tyr Pro Asn Asp Gly
645 650 655

Val Leu Gln Gly Asp Val Glu Leu Gln Ala Trp Trp Lys Glu Val Arg
660 665 670

Glu Val Gly His Gly Asp Leu Lys Asp Ala Asp Trp Trp Pro Lys Met
675 680 685

Gln Ser Leu Pro Glu Leu Thr Lys Ala Cys Thr Thr Ile Ile Trp Ile
690 695 700

Ala Ser Ala Leu His Ala Ala Val Asn Phe Gly Gln Tyr Pro Tyr Ala
705 710 715 720

Gly Tyr Leu Pro Asn Arg Pro Thr Ile Ser Arg Arg Pro Met Pro Glu
725 730 735

Pro Gly Ser Lys Glu Tyr Thr Glu Leu Asp Glu Asn Pro Glu Lys Phe
740 745 750

Phe Ile Arg Thr Ile Thr Ser Gln Phe Gln Thr Ile Leu Gly Val Ser
755 760 765

Leu Ile Glu Ile Leu Ser Lys His Ser Ala Asp Glu Ile Tyr Leu Gly
770 775 780

Gln Arg Asp Thr Pro Glu Trp Thr Ser Asp Pro Lys Ala Leu Glu Ala
785 790 795 800

Phe Lys Arg Phe Ser Arg Gln Leu Val Glu Ile Glu Ser Lys Val Leu
805 810 815

Asn Met Asn Lys Asp Pro Leu Leu Lys Asn Arg Val Gly Pro Ala Asn
820 825 830

Phe Pro Tyr Thr Leu Met Phe Pro Asn Thr Ser Asp Asn Lys Gly Ala
835 840 845

Ala Glu Gly Ile Thr Ala Arg Gly Ile Pro Asn Ser Ile Ser Ile
850 855 860

<210> SEQ ID NO 6
<211> LENGTH: 619
<212> TYPE: PRT
<213> ORGANISM: Magnaporthe oryzae

<400> SEQUENCE: 6

Met Arg Val Leu Val Trp Ile Ala Gly Leu Ala Pro Leu Ala Val Ala
1 5 10 15

Val Pro Ser Ser Ser Tyr Arg Val Ala Val Ala Ala Arg Ala Asp Asn
20 25 30

Thr Ser Ala Ser Val Ala Pro Ser Gln Asn Val Ser Gly Ala Ala Pro
35 40 45

Pro Glu Leu Val Val Tyr Thr Leu Pro Cys Glu Asp Gly Asn Ser Thr
50 55 60

Ala Arg Thr Ala Glu Ile Arg Leu Lys Gln Ala Thr Leu Leu Tyr Gly
65 70 75 80

Pro Ser Leu Leu Gly Asn Ala Ser Tyr Phe Pro Gly Gly Pro Leu Gly
85 90 95

Asp Ala Ile Ser Leu Arg Asp Gln Thr Val Trp Glu Gly Ala Ala Val
100 105 110

Val Gln Ser Leu Arg Ala Phe Thr Asp Ala Ala Lys Val Ala Ala Asn
115 120 125

```
Ile Lys Gln Asn Gly Gly Leu Asn Ser Leu Asp Asp Phe Lys Val Leu
130                 135                 140

Tyr Gln Asp Gly Trp Lys Gly Ser Val Pro Gln Gly Ile Ala Arg Gly
145                 150                 155                 160

Gln Ser Glu Asn Tyr Thr Ser Asp Leu Leu Phe Ser Met Glu Arg Leu
                165                 170                 175

Ser Val Asn Pro Tyr Ile Leu Lys Arg Leu His Pro Thr Glu Asp Ala
            180                 185                 190

Leu Pro Phe Gln Val Asp Arg Ala Thr Val Lys Gln Leu Thr Lys Thr
        195                 200                 205

Ser Leu Lys Ala Leu His Ala Ala Gly Arg Leu Phe Val Ala Asp His
210                 215                 220

Ser Tyr Gln Arg Asn Tyr Thr Arg Leu Ala Asn Arg Tyr Ser Ala Ala
225                 230                 235                 240

Cys Thr Ala Leu Phe Tyr Leu Asp Pro Arg Ser Asn Gln Phe Leu Pro
                245                 250                 255

Leu Ala Ile Lys Thr Asn Val Gly Ala Asp Leu Thr Tyr Thr Pro Leu
            260                 265                 270

Asp Thr Asp Asn Asn Asn Trp Leu Leu Ala Lys Ile Met Phe Asn Asn
        275                 280                 285

Asn Asp Leu Phe His Gly Gln Ile Phe His Val Ala Tyr Pro His Ala
290                 295                 300

Ile Ala Glu Ile Val His Leu Ala Ala Leu Arg Thr Met Ser Ala Arg
305                 310                 315                 320

His Pro Val Leu Ala Leu Met Glu Arg Leu Met Tyr Gln Ala Tyr Ala
                325                 330                 335

Val Arg Pro Leu Gly Glu Arg Val Leu Phe Asn Lys Gly Gly Leu Phe
            340                 345                 350

Glu Gln Asn Phe Ala Tyr Pro Gln Asp Met Val Tyr Lys Phe Val Gly
        355                 360                 365

Asp Ser Tyr Pro Thr Thr Gly Arg Trp Arg Ala Gly Tyr Leu Asp Thr
370                 375                 380

Asp Val Arg Ala Arg Gly Leu Val Asp Ala Asp Tyr Gly Pro Glu Leu
385                 390                 395                 400

Pro His Phe Pro Phe Tyr Glu Asp Gly Ser Arg Leu Val Glu Val Ile
                405                 410                 415

Arg Arg Phe Val Arg Ser Phe Val Asp Ala Thr Tyr His Glu Ser Asp
            420                 425                 430

Glu Met Val Ala Lys Asp Ala Glu Leu Gln Ala Trp Val Ala Glu Ala
        435                 440                 445

Asn Gly Pro Ala Gly Val Glu Asp Phe Glu Pro Gly Pro Leu Asp Thr
450                 455                 460

Arg Glu Arg Leu Val Glu Val Leu Thr His Met Ala Trp Leu Thr Gly
465                 470                 475                 480

Cys Ala His His Val Leu Asn Gln Gly Glu Pro Val Thr Ala Ser Gly
                485                 490                 495

Val Leu Pro Met His Pro Thr Ala Leu Tyr Ala Pro Val Pro Thr Ser
            500                 505                 510

Lys Ala Asn Thr Thr Ala Asp Leu Leu Gly Tyr Leu Pro Ser Ala Gln
        515                 520                 525

Lys Ser Val Asp Gln Val Thr Leu Leu Ala Arg Phe Asn Arg Pro Asp
530                 535                 540

Val Val Pro Thr Asn Gln Thr Leu Arg Tyr Met Phe Ala Ala Pro Gln
```

```
                545                 550                 555                 560
Leu Leu Leu Gly Asn Gly Glu Ala Tyr Arg Arg Ala Asn Gln Arg Phe
                    565                 570                 575

Val Arg Ala Met Gly Arg Ile Ser Asp Glu Val Lys Ala Arg Arg Phe
                    580                 585                 590

Asp Asp Arg Gly Leu Ser Gln Gly Met Pro Phe Ile Trp Gln Ala Leu
                    595                 600                 605

Asp Pro Gly Asn Ile Pro Phe Tyr Leu Ser Val
                    610                 615

<210> SEQ ID NO 7
<211> LENGTH: 1121
<212> TYPE: PRT
<213> ORGANISM: Aspergillus fumigatus

<400> SEQUENCE: 7

Met Leu Arg Arg Phe Ser Ser Thr Phe Lys Lys Gly Asp Arg Glu
1               5                   10                  15

Ser Lys Gln Asn Gly Thr Ala Ser Ser Ser Ala Ala Val Ala Asn
                20                  25                  30

Thr Asn Asn Asp Asn Lys Arg His Ser Lys Ile Ser Ala Ala Arg
            35                  40                  45

Lys Ser Ser Ser Asp Asp Arg Asn Glu Lys Lys Gly Asn Ser Val
50                  55                  60

Ser Pro Phe Glu Lys Tyr Ala Ser Val Leu His Ala Ser Arg Ser Pro
65                  70                  75                  80

Ile Pro Asn Gln Thr Gly Asp Gly Ala Tyr Leu Glu His Glu His Thr
                85                  90                  95

Thr Ser Leu Leu Gln Asp Ala Arg His Leu Gly Phe Lys Asp Phe Lys
            100                 105                 110

Thr Leu Lys Glu Val Ile Glu Ser Lys Leu Pro Gly Gly Gln Leu Ile
        115                 120                 125

Asp Asp Lys Thr Met Leu Met Glu Arg Ile Ile Gln Leu Val Ser Arg
    130                 135                 140

Leu Pro His Asn Ser Lys His Arg Glu Glu Leu Thr Asn Ala Phe Leu
145                 150                 155                 160

Thr Glu Leu Trp Asp Ser Leu Pro His Pro Leu Ser Tyr Met Gly
                165                 170                 175

Asn Asp Tyr Ala Tyr Arg Ser Ala Asp Gly Ser Asn Asn Pro Thr
            180                 185                 190

Leu Pro Arg Leu Gly Ala Ala Asn Thr Leu Tyr Ala Arg Thr Ile Pro
        195                 200                 205

Pro Leu Ile Ile Gln Pro Gly Gly Leu Pro Asp Pro Gly Leu Val Phe
    210                 215                 220

Asp Thr Leu Phe Ala Arg Gln Thr Phe Lys Pro His Pro Asn Lys Val
225                 230                 235                 240

Ser Ser Val Phe Phe Tyr Trp Ala Ser Leu Ile Ile His Asp Ile Phe
                245                 250                 255

Gln Thr Asp Tyr Lys Asn Pro Asn Met Asn Lys Thr Ser Gly Tyr Leu
            260                 265                 270

Asp Leu Ser Ile Leu Tyr Gly Asp Val Gln Glu Gln Asn Leu Ile
        275                 280                 285

Arg Thr Phe Lys Asp Gly Lys Leu Lys Pro Asp Ser Phe Ser Glu Pro
    290                 295                 300
```

```
Arg Leu Gln Ala Phe Pro Ala Thr Cys Cys Val Leu Met Val Met Leu
305                 310                 315                 320

Asn Arg Phe His Asn Tyr Ala Val Glu Gln Leu Ala Ala Ile Asn Glu
            325                 330                 335

Asn Gly Arg Phe Thr Lys Pro Ala Asp Asn Leu Ser Glu Glu Glu Ala
        340                 345                 350

Lys Lys Ala Trp Ala Lys Tyr Asp Glu Asp Leu Phe Gln Thr Gly Arg
            355                 360                 365

Leu Ile Thr Cys Gly Leu Tyr Ile Asn Ile Thr Leu Tyr Asp Tyr Leu
        370                 375                 380

Arg Thr Ile Val Asn Leu Asn Arg Thr Asn Ser Thr Trp Cys Leu Asp
385                 390                 395                 400

Pro Arg Ala Gln Met Glu Gly Ser His Thr Ala Pro Ser Gly Leu Gly
                405                 410                 415

Asn Gln Cys Ser Val Glu Phe Asn Leu Ala Tyr Arg Trp His Ser Ala
            420                 425                 430

Thr Ser Ala Thr Asp Glu Lys Trp Thr Glu Asp Val Tyr Glu Arg Leu
        435                 440                 445

Met Gly Lys Pro Ala Ser Glu Val Ser Met Thr Glu Leu Leu Met Gly
450                 455                 460

Leu Gly Lys Tyr Gln Ala Glu Leu Pro Lys Asp Pro Ser Lys Arg Thr
465                 470                 475                 480

Phe Ala Asp Leu Glu Arg Gln Ala Asp Gly Arg Phe Lys Asp Glu Asp
                485                 490                 495

Leu Val Asn Leu Leu Val Asn Ala Val Glu Asp Val Ala Gly Ser Phe
            500                 505                 510

Gly Ala Arg Asn Val Pro Lys Val Leu Lys Asn Val Glu Ile Leu Gly
            515                 520                 525

Ile Ile Gln Ser Arg Lys Trp Asn Val Gly Ser Leu Asn Glu Phe Arg
530                 535                 540

Lys Phe Phe Gly Leu Lys Pro Tyr Glu Thr Phe Glu Glu Ile Asn Ser
545                 550                 555                 560

Asp Pro Asp Val Ala Glu Ser Leu Arg Ser Leu Tyr Asp His Pro Asp
                565                 570                 575

Phe Val Glu Leu Tyr Pro Gly Ile Val Ala Glu Glu Ala Lys Gln Pro
            580                 585                 590

Met Val Pro Gly Val Gly Ile Ala Pro Thr Tyr Thr Ile Ser Arg Ala
            595                 600                 605

Val Leu Ser Asp Ala Val Ala Leu Val Arg Gly Asp Arg Phe Tyr Thr
610                 615                 620

Ile Asp Tyr Asn Pro Arg Asn Leu Thr Asn Trp Gly Tyr Ser Glu Val
625                 630                 635                 640

Arg Tyr Asp Leu Ser Ile Asn Gln Gly Cys Ile Phe Tyr Lys Leu Ala
                645                 650                 655

Thr Arg Ala Phe Pro Asn Trp Phe Lys Pro Asp Ser Ile Tyr Ala His
            660                 665                 670

Tyr Pro Met Thr Ile Pro Ser Glu Asn Arg Lys Ile Met Lys Asp Leu
            675                 680                 685

Gly Arg Glu Ile His Tyr Ser Trp Asp Arg Pro Gln Tyr Thr Pro Pro
            690                 695                 700

Arg Val Asp Leu Val Ser Tyr Ser Asn Ala Lys Leu Val Ala Glu Gln
705                 710                 715                 720

Gln Asn Gln Phe Arg Ala Ala Trp Gly Asp Thr Val Glu Phe Val Phe
```

725                 730                 735
Gly Lys Ala Ser Lys Glu Phe Lys Leu Tyr Gln Asp Ser Ala Phe Ile
                740                 745                 750

Gln Lys His Ala Asp Val Met Ser Lys Leu Leu Asn Lys Glu Glu Trp
            755                 760                 765

His Arg Ser Val Lys Glu Phe Tyr Glu Asp Ile Thr Ala Lys Leu Leu
        770                 775                 780

Glu Asp Lys Thr Arg Arg Phe Gly Gly Ile Asn Gln Val Asp Ile Thr
785                 790                 795                 800

Asn Asp Val Gly Asn Leu Thr Pro Val Ile Phe Ala Ala Asn Val Phe
                805                 810                 815

Ser Leu Pro Leu Lys Ser Lys Glu Asn Pro Arg Gly Ile Tyr Thr Glu
                820                 825                 830

His Glu Met Phe Lys Val Leu Ala Ala Leu Tyr Asn Cys Leu Tyr Phe
            835                 840                 845

Asp Ile Asp Lys Thr Lys Ser Tyr Pro Leu His His Ala Ser Gln Ala
        850                 855                 860

Val Gly Glu Pro Leu Gly Lys Ala Leu Glu Ala Asn Val Lys Ala Leu
865                 870                 875                 880

Gly Gly Ser Ser Leu Leu Ser Gly Ile Phe Arg Ser Phe Arg Glu Asn
                885                 890                 895

Lys Asn Ala Leu Lys Glu Tyr Gly Val His Leu Thr Lys Gln Leu Leu
                900                 905                 910

Glu Asn Gly Leu Gly Ala His Glu Ile Ala Trp Ala Gln Phe Leu Pro
            915                 920                 925

Thr Val Ile Ala Met Val Pro Ala Gln Ala Gln Ala Phe Thr Gln Ile
        930                 935                 940

Val Asp Phe Tyr Leu Ser Lys Glu Gly Ser Lys His Leu Pro Ala Ile
945                 950                 955                 960

Gln Arg Leu Ala Lys Gln Asp Thr Lys Lys Ser Asp Glu Gln Leu Leu
                965                 970                 975

His Tyr Cys Leu Glu Ala Val Arg Leu Asn Asp Met Ser Gly Leu Tyr
            980                 985                 990

Arg Gln Ser Glu Thr Thr Leu Ala Val Thr Asp Glu Ala Val Glu Val
        995                 1000                1005

Thr Ile Gln Pro Gly Asp Lys Val Phe Val Ser Phe Ala Lys Ala
        1010                1015                1020

Asn Arg Asp Ala Ser Val Phe Pro Asp Pro Ala Glu Val Arg Leu
        1025                1030                1035

Asp Arg Pro Met Asn Ser Tyr Ile Asn Pro Thr Leu Gly Pro His
        1040                1045                1050

Gly Phe Leu Ser Lys Glu Thr Ser His Ile Ala Leu Thr Ala Met
        1055                1060                1065

Leu Arg Ala Val Gly Arg Leu Asn Asn Leu Arg Val Ala Pro Gly
        1070                1075                1080

Val Gln Gly Gln Leu Lys Lys Ile Pro Gln Pro Gly Gly Tyr Ser
        1085                1090                1095

Ala Tyr Leu Arg Glu Asp His Gly Ser Tyr Ser Ile Phe Pro Thr
        1100                1105                1110

Thr Phe Arg Val Gln Tyr Asp Ala
        1115                1120

<210> SEQ ID NO 8

<211> LENGTH: 1117
<212> TYPE: PRT
<213> ORGANISM: Aspergillus nidulans

<400> SEQUENCE: 8

```
Met Leu Arg Arg Phe Ser Thr Phe Arg Lys Ser Lys Gly Asp Lys Thr
1               5                   10                  15

Glu Lys Ala Asp Arg Asp Ser Lys Ala Asn Gly Ser Asn Ala Asn Ser
            20                  25                  30

Ala Ala Ala Ser Asn Ser Ser Lys Arg Gln Ser Lys Val Pro Pro
        35                  40                  45

Pro Arg Arg Pro Ser Ser Asp Ser Gly Ser Ser Ala Glu Ser Glu Asp
50                  55                  60

Val Pro Ala Val Phe Glu Lys Tyr Ala Gln Val Leu His Ala Ser Ser
65                  70                  75                  80

Arg Pro Ile Pro His Gln Gly Gly Glu Ala Ala Tyr Leu Glu Lys Glu
                85                  90                  95

His Pro Ser Gly Leu Phe Asn Asp Leu Lys Ser Leu Gly Phe Lys Asp
            100                 105                 110

Phe Ala Ser Leu Lys Asp Val Ile Lys Thr Lys Ile Asn Gly Glu Leu
        115                 120                 125

Thr Asp Asp Lys Thr Met Ile Met Glu Arg Ile Ile Gln Ile Val Ser
130                 135                 140

Ser Leu Pro Ser Asn Ser Lys Met Arg Val Asp Leu Thr Asn Met Phe
145                 150                 155                 160

Leu Asp Glu Leu Trp Gly Ser Leu Pro His Pro Pro Leu Ser Tyr Met
                165                 170                 175

Gly Asn Asp Tyr Gln Tyr Arg Ser Ala Asp Gly Ser Asn Asn Asn Pro
            180                 185                 190

Thr Leu Pro Trp Leu Gly Ala Ala Asn Thr Ala Tyr Ala Arg Ser Ile
        195                 200                 205

Glu Pro Leu Thr Val Gln Pro Gly Gly Leu Pro Asp Ala Gly Leu Val
210                 215                 220

Phe Asp Thr Leu Phe Ala Arg Gln Lys Phe Thr Pro His Pro Asn Lys
225                 230                 235                 240

Val Ser Ser Leu Phe Phe Asp Trp Ala Ser Leu Ile Ile His Asp Ile
                245                 250                 255

Phe Gln Thr Asp Tyr Arg Asp Tyr Asn Lys Asn Lys Thr Ser Ala Tyr
            260                 265                 270

Leu Asp Leu Ala Ile Leu Tyr Gly Asp Val Gln Glu Glu Gln Asp Leu
        275                 280                 285

Val Arg Thr His Lys Asp Gly Lys Leu Lys Pro Asp Ser Phe Ser Glu
290                 295                 300

Pro Arg Leu Gln Ala Phe Pro Ala Ala Cys Cys Val Leu Leu Val Met
305                 310                 315                 320

Leu Asn Arg Phe His Asn Tyr Val Val Glu Leu Ala Ala Ile Asn
                325                 330                 335

Glu Asn Gly Arg Phe Thr Lys Pro Ser Pro Asp Leu Pro Glu Glu Gln
            340                 345                 350

Ala Lys Lys Ala Trp Ala Lys Tyr Asp Glu Asp Leu Phe Gln Thr Gly
        355                 360                 365

Arg Leu Ile Thr Cys Gly Leu Phe Ile Asn Ile Thr Leu Tyr Asp Tyr
370                 375                 380

Leu Arg Thr Ile Val Asn Leu Asn Arg Val Asn Ser Thr Trp Cys Leu
```

-continued

```
            385                 390                 395                 400
Asp Pro Arg Ala Gln Met Glu Gly Ser Ala Thr Pro Ala Gly Leu Gly
                    405                 410                 415

Asn Gln Cys Ser Val Glu Phe Asn Leu Ala Tyr Arg Trp His Ser Ala
            420                 425                 430

Ile Ser Ala Asn Asp Glu Lys Trp Thr Glu Lys Val Tyr Glu Glu Leu
            435                 440                 445

Ile Gly Lys Pro Gly Ser Glu Ile Ser Thr Gln Glu Leu Leu Met Gly
        450                 455                 460

Leu Gly Lys Tyr Gly Ala Ser Leu Pro Lys Asp Pro Ser Gln Arg Thr
465                 470                 475                 480

Phe Ala Gly Leu Lys Arg Gln Glu Asp Gly Thr Phe Lys Asp Glu Glu
                485                 490                 495

Leu Val Asn Ile Leu Thr Ser Ala Ile Glu Asp Val Ala Gly Ser Phe
                500                 505                 510

Gly Ala Arg Asn Val Pro Lys Val Leu Lys Ala Val Glu Val Leu Gly
            515                 520                 525

Ile Glu Gln Gly Arg Lys Trp Asn Val Gly Ser Leu Asn Glu Phe Arg
        530                 535                 540

Lys Phe Phe Gly Leu Lys Asn Tyr Glu Thr Phe Glu Glu Ile Asn Ser
545                 550                 555                 560

Asp Pro Glu Val Ala Glu Ser Leu Arg Ala Leu Tyr Gly His Pro Asp
                565                 570                 575

Tyr Val Glu Leu Tyr Pro Gly Ile Val Ser Glu Glu Ala Lys Glu Pro
                580                 585                 590

Met Ile Pro Gly Val Gly Ile Ala Pro Thr Tyr Thr Ile Ser Arg Ala
            595                 600                 605

Val Leu Ser Asp Ala Val Ala Leu Val Arg Gly Asp Arg His Tyr Thr
        610                 615                 620

Val Asp Tyr Asn Pro Arg Asn Leu Thr Asn Trp Gly Tyr Asn Glu Val
625                 630                 635                 640

Arg Tyr Asp Leu Asn Ile Asn Gln Gly Cys Val Phe Tyr Lys Leu Ala
                645                 650                 655

Thr Arg Ala Phe Pro Asn Trp Phe Lys Pro Asp Ser Ile Tyr Ala His
                660                 665                 670

Tyr Pro Met Thr Ile Pro Ser Glu Asn Lys Val Ile Met Lys Asn Leu
            675                 680                 685

Gly Arg Glu Ala Asp Tyr Ser Trp Asp Arg Pro Gln Tyr Gln Ala Pro
        690                 695                 700

Arg Ala Ser Leu Thr Ser Tyr Ser Asn Val Lys Leu Ile Leu Asp Gln
705                 710                 715                 720

Gln Lys Asp Phe Arg Val Val Trp Gly Asp Cys Thr Pro Leu His Ser
                725                 730                 735

Gly Lys Gly Gly Glu Asp Phe Trp Ser Lys Thr Leu Ser Asp Pro Gln
            740                 745                 750

Phe Lys Lys Ser Ile Lys Glu Phe Tyr Glu Lys Thr Thr Leu Glu Leu
        755                 760                 765

Phe Ala Asp Lys Ser Val Asn Leu Ala Gly Arg Lys Gln Ile Asp Ile
        770                 775                 780

Val Lys Asp Val Gly Asn Ile Val Pro Ala Arg Phe Ala Ser Lys Leu
785                 790                 795                 800

Leu Ser Leu Pro Leu Arg Ser Lys Glu Asn Ser Lys Gly Val Phe Thr
                805                 810                 815
```

```
Asp His Glu Ile Phe Met Ala Leu Ala Val Ile Tyr Asn Ala Ile Phe
                820                 825                 830

Phe Asp Val Asp Thr Thr Lys Ser Phe Pro Leu Arg Lys Ala Ala Asp
                835                 840                 845

Ala Val Ser Lys Glu Leu Gly Lys His Val Glu Ser His Val Lys Ser
            850                 855                 860

Val Ser Ser Pro Gly Phe Leu Ser Arg Val Ile Asp Asn Phe Arg Asp
865                 870                 875                 880

Asp His Asn Ala Leu Lys Asp Leu Gly Asp Gln Leu Ile Lys Arg Leu
                885                 890                 895

Ala Glu Gly Gly Leu Ser Val Ser Asp Ile Thr Tyr Gly Gln Ile Leu
            900                 905                 910

Pro Thr Ala Val Glu Leu Val His Gly Gln Ala Gln Met Phe Thr Arg
            915                 920                 925

Val Val Glu Tyr Tyr Leu Asn Glu Gly Lys Gln His Leu Pro Glu Leu
            930                 935                 940

Ser Leu Leu Ala Lys Gln Asp Ser Ala Glu Thr Asp Ala Lys Leu Thr
945                 950                 955                 960

Arg Tyr Ala Leu Glu Ala Ile Arg Leu Asn Ala Gly Ser Gly Ala Tyr
                965                 970                 975

Arg Lys Ala Glu Thr Asn Phe Tyr Phe Lys Glu Gly Asp Ala Asp Ile
                980                 985                 990

Asn Leu Lys Pro Gly Asp Glu Ile Phe Ile Ser Ser Thr Gln Ala Asn
            995                 1000                1005

Arg Asp Pro Thr Ala Phe Pro Asp Pro Asp Glu Val Arg Leu Asp
        1010                1015                1020

Arg Pro Asp Glu Ser Tyr Leu Asn Tyr Gly Ile Gly Ser Gln Ile
        1025                1030                1035

Gly Leu Gly Lys Asp Ala Thr Leu Thr Ala Val Thr Ala Met Val
        1040                1045                1050

Arg Ala Ala Phe Ser Leu Glu Gly Leu Arg Pro Ala Pro Gly Val
        1055                1060                1065

Gln Gly Val Leu Lys Lys Val Val Arg Pro Glu Gly Tyr Thr Leu
        1070                1075                1080

Tyr Met Arg Glu Asp His Gly Ala Phe Ser Pro Phe Pro Thr Thr
        1085                1090                1095

Phe Arg Val His Phe Asp Gly Glu Val Val Thr Pro Lys Lys Gln
        1100                1105                1110

Ile Asp Ser Ala
        1115

<210> SEQ ID NO 9
<211> LENGTH: 1113
<212> TYPE: PRT
<213> ORGANISM: Aspergillus terreus

<400> SEQUENCE: 9

Met Leu Arg Arg Phe Ser Thr Gln Phe Lys Lys Ser Lys Gly Asp Arg
1               5                   10                  15

Glu Ser Lys Gln Asn Gly Thr Pro Gly Pro Ala Asn Asn Ser Ser Lys
                20                  25                  30

Arg Gln Ser Lys Leu Ala Gln Pro Arg Lys Ser Ser Ser Ser Ser Ser
            35                  40                  45

Asp Gly Glu Arg Ser Ser Lys Asn Glu Asp Gly Val Pro Ala Phe Glu
```

-continued

```
            50                  55                  60
Lys Tyr Ala Gln Val Leu His Ala Ser Arg Ser Pro Leu Pro Asn Gln
 65                  70                  75                  80

Thr Gly Asp Gly Ala Thr Ser Ala His Asp His Gln Thr Thr Leu Phe
                 85                  90                  95

Gln Asp Leu Arg Ser Phe Gly Phe Lys Asp Phe Gly Thr Leu Lys Glu
            100                 105                 110

Val Ile Ala Thr Lys Ala Lys Gly Glu His Val Asp Asp Lys Thr Met
            115                 120                 125

Val Met Glu Arg Ile Ile Gln Leu Val Ser Gly Leu Pro Ala Asn Ser
130                 135                 140

Lys Ser Arg Thr Glu Leu Thr His Leu Phe Leu Asp Gln Leu Trp Asp
145                 150                 155                 160

Ser Leu Pro His Pro Pro Leu Ser Tyr Met Gly Ser Asp Tyr Ala Tyr
                165                 170                 175

Arg Ser Ala Asp Gly Ser Asn Asn Pro Thr Leu Pro Trp Leu Gly
            180                 185                 190

Ala Ala Asn Thr Pro Tyr Ala Arg Ser Ile Ala Pro Leu Thr Ile Gln
            195                 200                 205

Pro Gly Gly Leu Pro Asp Ala Gly Leu Val Phe Asp Ser Leu Phe Ala
210                 215                 220

Arg Asp Lys Phe Arg Pro His Pro Asn Lys Val Ser Ser Val Phe Phe
225                 230                 235                 240

Asp Trp Ala Ser Leu Ile Ile His Asp Ile Phe Gln Thr Asp His Gln
                245                 250                 255

Asn Pro Asn Ile Asn Lys Thr Ser Gly Tyr Leu Asp Leu Ser Ile Leu
            260                 265                 270

Tyr Gly Asp Val Lys Glu Glu Gln Asp Leu Val Arg Thr His Lys Asp
            275                 280                 285

Gly Lys Leu Lys Pro Asp Ala Phe Ser Glu Pro Arg Leu Gln Ala Phe
            290                 295                 300

Pro Ala Thr Cys Cys Val Leu Val Met Leu Asn Arg Phe His Asn
305                 310                 315                 320

His Val Val Glu Gln Leu Ala Glu Ile Asn Glu Asn Gly Arg Phe Thr
                325                 330                 335

Lys Pro Ser Pro Asp Leu Pro Glu Asp Lys Ala Lys Ala Ala Trp Glu
            340                 345                 350

Lys Tyr Asp Glu Asp Leu Phe Gln Thr Gly Arg Leu Ile Thr Cys Gly
            355                 360                 365

Leu Tyr Ile Asn Ile Thr Leu Tyr Asp Tyr Leu Arg Thr Ile Val Asn
            370                 375                 380

Leu Asn Arg Val Asn Ser Thr Trp Cys Leu Asp Pro Arg Ala Gln Met
385                 390                 395                 400

Glu Gly Ser Ser Ser Thr Pro Ser Gly Leu Gly Asn Gln Cys Ser Val
                405                 410                 415

Glu Phe Asn Leu Ala Tyr Arg Trp His Ser Ala Ile Ser Ala Asn Asp
            420                 425                 430

Glu Lys Trp Thr Glu Gln Val Tyr Gln Asp Leu Met Gly Lys Pro Ala
            435                 440                 445

Glu Glu Val Ser Val Glu Glu Leu Leu Gly Gly Leu Met Lys Tyr Gly
            450                 455                 460

Arg Ser Leu Glu Lys Asp Pro Ser Lys Arg Thr Phe Ala Gly Leu Gln
465                 470                 475                 480
```

```
Arg Gln Ala Asp Gly Thr Phe Lys Asp Glu Glu Leu Val Glu Ile Leu
                485                 490                 495

Thr Asn Ala Val Glu Asp Val Ala Gly Ser Phe Gly Ala Arg His Val
            500                 505                 510

Pro Lys Ala Leu Lys Ala Val Glu Val Leu Gly Ile Asn Gln Ala Arg
        515                 520                 525

Gln Trp Asn Val Gly Ser Leu Asn Glu Phe Arg Lys Phe Phe Asp Leu
    530                 535                 540

Lys Pro Tyr Glu Ser Phe Glu Glu Ile Asn Ser Asp Pro Asp Val Ala
545                 550                 555                 560

Asp Ala Leu Arg Asn Leu Tyr Glu His Pro Asp Tyr Val Glu Leu Tyr
                565                 570                 575

Pro Gly Ile Val Ala Glu Glu Ala Lys Glu Pro Met Ile Pro Gly Val
            580                 585                 590

Gly Ile Ala Pro Thr Tyr Thr Ile Ser Arg Ala Val Leu Ser Asp Ala
        595                 600                 605

Val Ala Leu Val Arg Gly Asp Arg His Tyr Thr Ile Asp Tyr Asn Pro
    610                 615                 620

Arg Asn Leu Thr Asn Trp Gly Tyr Asn Glu Cys Arg Tyr Asp Leu Ser
625                 630                 635                 640

Ile Asn Gln Gly Cys Val Phe Tyr Lys Leu Ala Thr Arg Ala Phe Pro
                645                 650                 655

Asn Trp Phe Lys Pro Asp Ser Ile Tyr Ala His Tyr Pro Met Thr Ile
            660                 665                 670

Pro Ser Glu Asn Arg Asn Ile Met Lys Asn Leu Gly Arg Glu Ser His
        675                 680                 685

Tyr Ser Trp Glu Arg Pro Lys Phe Thr Pro Pro Gln Val Asn Leu Val
    690                 695                 700

Ser Tyr Pro Asn Val Lys Leu Ala Leu Glu Gln Glu Lys Gln Leu Arg
705                 710                 715                 720

Val Ile Trp Ser Gly Asn Thr Pro Leu Arg Pro Ala Lys Gly Gly Asp
                725                 730                 735

Asp Phe Trp Ser Lys Ala Leu Asn Asn Asp Glu Trp Arg Lys Asn Ile
            740                 745                 750

Lys Glu Phe Tyr Glu Asp Met Thr Ile Lys Leu Leu Asn Glu Lys Ser
        755                 760                 765

Cys Lys Leu Gly Gly Ile Arg Gln Ile Asp Ile Thr Arg Asp Leu Gly
    770                 775                 780

Asn Leu Ala Pro Val His Phe Ala Ser Lys Val Phe Ser Leu Pro Leu
785                 790                 795                 800

Lys Thr Lys Gln Asn Ser Lys Gly Val Phe Thr Glu His Glu Met Phe
                805                 810                 815

Met Ile Met Ala Val Val Phe Thr Ser Val Phe Phe Asp Val Asp Pro
            820                 825                 830

Thr Lys Ser Phe Pro Leu His Phe Ala Ser Arg Ala Val Ser Gln Gln
        835                 840                 845

Leu Gly Ser Ala Ile Glu Ser His Val Lys Ser Ile Gly His Pro Gly
    850                 855                 860

Phe Leu Ser Ala Ile Ile Asp Ser Phe Arg Asp Asp Asn Val Leu
865                 870                 875                 880

Lys Glu Tyr Gly Asp Gln Leu Ile Lys Lys Leu Leu Asp Ser Gly Leu
                885                 890                 895
```

```
Gly Val Ser Asp Val Thr Tyr Ser Gln Ile Leu Pro Thr Ala Val Ser
            900                 905                 910

Met Val His Asn Gln Ala Arg Met Phe Thr His Ile Val Asp Tyr Tyr
        915                 920                 925

Val Thr Glu Gly Lys Lys His Leu Pro Glu Ile Asn Arg Leu Ala Lys
    930                 935                 940

Glu Ser Thr Pro Glu Ala Asp Glu Lys Leu Thr Arg Tyr Cys Leu Glu
945                 950                 955                 960

Ala Phe Arg Leu Phe Gly Thr Phe Gly Ser Tyr Arg Glu Ala Gln Thr
                965                 970                 975

Asp Phe Thr Val Asn Asp Glu Ser Gly Pro Val Asp Ile Lys Gln Gly
            980                 985                 990

Asp Lys Val Phe Val Gly Ala Val  Lys Ala Asn Arg Asp  Pro Ser Val
        995                 1000                1005

Phe Pro  Asp Pro Asp Glu Val  Arg Leu Asp Arg Pro  Leu Asp Ser
    1010                1015                1020

Tyr Ile  Gln Phe Gly Leu Gly  Pro His Ala Gly Leu  Gly Lys Glu
    1025                1030                1035

Ala Thr  Leu Leu Ala Leu Thr  Ala Met Leu Arg Val  Val Gly Arg
    1040                1045                1050

Leu Asp  Asn Leu Arg Pro Ala  Pro Gly Pro Gln Gly  Gln Leu Lys
    1055                1060                1065

Lys Ile  Pro Arg Glu Gly Gly  Tyr Tyr Val Tyr Leu  Arg Glu Asp
    1070                1075                1080

Trp Gly  Ser Tyr Ser Pro Phe  Pro Thr Thr Phe Lys  Val His Phe
    1085                1090                1095

Asp Gly  Glu Leu Pro Ala Pro  Lys Lys Arg Gly Ile  Ala Ser Ala
    1100                1105                1110

<210> SEQ ID NO 10
<211> LENGTH: 1117
<212> TYPE: PRT
<213> ORGANISM: Aspergillus clavatus

<400> SEQUENCE: 10

Met Leu Arg Arg Phe Ser Ser Thr Phe Asn Lys Lys Gly Asp Arg
1               5                   10                  15

Glu Pro Lys Gln Asn Gly Val Ala Thr Thr Thr Thr Thr Thr Pro
            20                  25                  30

Thr Thr Asn Lys Arg Tyr Ser Lys Val Pro Glu Gly His Lys Ser Ser
        35                  40                  45

Ser Glu Glu Glu Arg Asn Glu Lys Lys Gly Gly Ala Val Ser Pro Phe
50                  55                  60

Glu Lys Tyr Ala Ser Val Leu His Ala Ser Arg Thr Pro Ile Pro Asn
65                  70                  75                  80

Gln Thr Gly Asp Gly Ala Tyr Leu Glu His Glu His Thr Thr Ser Leu
                85                  90                  95

Leu Gln Asp Ala Arg His Leu Gly Phe Lys Asp Leu Ala Thr Leu Lys
            100                 105                 110

Glu Val Ile Lys Asn Lys Ala Thr Gly Gln Leu Val Asp Asp Lys Thr
        115                 120                 125

Met Leu Met Glu Arg Val Ile Gln Leu Val Ser Ser Leu Pro His Asn
    130                 135                 140

Ser Lys His Arg Glu Glu Leu Thr His Ser Phe Leu Asp Glu Leu Trp
145                 150                 155                 160
```

```
Gly Ser Leu Pro His Pro Pro Leu Ser Tyr Met Gly Ser Glu Tyr Ala
                165                 170                 175

Tyr Arg Ser Ala Asp Gly Ser Asn Asn Pro Thr Leu Pro Trp Leu
        180                 185                 190

Gly Ala Ala Asn Thr Ala Tyr Ala Arg Thr Ile Ala Pro Leu Ile Ile
            195                 200                 205

Gln Pro Gly Gly Leu Pro Asp Pro Gly Leu Val Phe Asp Thr Leu Phe
210                 215                 220

Ala Arg Gln Ser Phe Lys Pro His Pro Asn Asn Val Ser Ser Leu Phe
225                 230                 235                 240

Phe Asp Trp Ala Ser Leu Ile Ile His Asp Ile Phe Gln Thr Asp Tyr
                245                 250                 255

Arg Asn Pro His Val Asn Lys Thr Ser Gly Tyr Leu Asp Leu Ser Ile
                260                 265                 270

Leu Tyr Gly Asp Val Gln Glu Glu Gln Asn Leu Ile Arg Thr Phe Glu
        275                 280                 285

Gly Gly Arg Leu Lys Thr Asp Ser Phe Ser Glu Pro Arg Leu Gln Ala
        290                 295                 300

Phe Pro Ala Ala Cys Cys Val Leu Leu Val Met Leu Asn Arg Phe His
305                 310                 315                 320

Asn His Val Val Glu Gln Leu Ala Ala Ile Asn Glu Asn Gly Arg Phe
                325                 330                 335

Thr Gln Pro Arg Asp Gly Leu Pro Glu Asp Gln Ala Lys Lys Ala Trp
                340                 345                 350

Glu Lys Tyr Asp Glu Asp Leu Phe Gln Thr Gly Arg Leu Ile Thr Cys
        355                 360                 365

Gly Leu Tyr Ile Asn Ile Thr Leu Tyr Asp Tyr Leu Arg Thr Ile Val
        370                 375                 380

Asn Leu Asn Arg Thr Asn Ser Thr Trp Cys Leu Asp Pro Arg Ala Gln
385                 390                 395                 400

Met Glu Gly Asn Asn Thr Thr Pro Ser Gly Leu Gly Asn Gln Cys Ser
                405                 410                 415

Val Glu Phe Asn Leu Ala Tyr Arg Trp His Ser Ala Ile Ser Ala Asn
                420                 425                 430

Asp Glu Lys Trp Thr Glu Lys Ile Tyr Glu Asp Leu Met Gly Lys Pro
            435                 440                 445

Ala Ser Glu Val Ser Met Thr Glu Leu Leu Met Gly Leu Gly Lys Tyr
450                 455                 460

Glu Ala Gly Leu Ser Lys Asp Pro Ser Gln Arg Thr Phe Ala Gly Leu
465                 470                 475                 480

Glu Arg Gln Ala Asp Gly Arg Phe Arg Asp Glu Asp Leu Val Asn Ile
                485                 490                 495

Leu Thr Gly Ala Ile Glu Asp Val Ala Gly Ser Phe Gly Ala Arg Asn
            500                 505                 510

Val Pro Lys Val Leu Lys Asn Val Glu Val Leu Gly Ile Leu Gln Ser
            515                 520                 525

Arg Lys Trp Asn Val Gly Ser Leu Asn Glu Phe Arg Lys Phe Phe Gly
        530                 535                 540

Leu Lys Pro Tyr Glu Thr Phe Glu Glu Ile Asn Ser Asp Pro Asp Val
545                 550                 555                 560

Ala Glu Ser Leu Arg Ser Leu Tyr Asp His Pro Asp Phe Val Glu Leu
                565                 570                 575
```

```
Tyr Pro Gly Ile Val Ser Glu Glu Ala Lys Glu Pro Met Ile Pro Gly
            580                 585                 590

Val Gly Ile Ala Pro Thr Tyr Thr Ile Ser Arg Ala Val Leu Ser Asp
        595                 600                 605

Ala Val Ala Leu Val Arg Gly Asp Arg Tyr Tyr Thr Ile Asp Tyr Asn
    610                 615                 620

Ala Arg Asn Leu Thr Asn Trp Gly Tyr Ser Glu Val Arg Tyr Asp Leu
625                 630                 635                 640

Ser Ile Asn Gln Gly Cys Val Phe Tyr Lys Leu Ala Thr Arg Ala Phe
                645                 650                 655

Pro Asp Trp Phe Lys Ser Asp Ser Ile Tyr Ala His Tyr Pro Met Thr
            660                 665                 670

Ile Pro Ser Glu Asn Arg Lys Ile Met Lys Asn Leu Gly Arg Glu Ala
        675                 680                 685

His Tyr Ser Tyr Asp Arg Pro Gln Tyr Ile Pro Pro Val Asp Leu
    690                 695                 700

Leu Ser Tyr Pro Ser Ala Lys Leu Val Ala Gln Arg Lys Asp Phe
705                 710                 715                 720

His Thr Val Trp Ala Asp Thr Val Glu Phe Val Phe Gly Lys Ala Ser
                725                 730                 735

Lys Asn Phe Lys Leu Ser Glu Asp Thr Ala Phe Ile Glu Arg Gln Arg
            740                 745                 750

Glu Thr Ile Ser Lys Leu Leu Ser Gln Asp Glu Trp Gln Arg Asn Val
        755                 760                 765

Lys Glu Phe Tyr Glu Glu Ile Thr Thr Gly Leu Leu Glu Glu Lys Thr
    770                 775                 780

Arg Arg Phe Ala Gly Ile Asn Gln Val Asp Ile Thr Arg Asp Ile Gly
785                 790                 795                 800

Asn Leu Val Pro Val Ile Phe Ala Ser Asn Leu Phe Ser Leu Pro Leu
                805                 810                 815

Arg Ser Lys Glu Asn Ser Arg Gly Ile Phe Thr Glu His Glu Met Phe
            820                 825                 830

Asn Val Leu Ala Val Leu Tyr Asn Cys Ile Tyr Phe Asp Ile Asp Lys
        835                 840                 845

Thr Lys Ser Phe Pro Leu His His Ala Ser Gln Ala Val Gly Glu Gln
    850                 855                 860

Leu Gly Lys Ala Val Glu Ala Asn Val Lys Ser Leu Gly Gly Ser Ser
865                 870                 875                 880

Leu Leu Ser Gly Ile Leu Gly Gly Ser Arg Asp Asn Lys Asn Ala Leu
                885                 890                 895

Lys Glu Tyr Gly Ala His Met Thr Lys Gln Leu Leu Glu Asn Gly Leu
            900                 905                 910

Gly Ala Ser Glu Ile Thr Trp Ser Gln Ile Leu Pro Thr Val Ile Ala
        915                 920                 925

Met Val Pro Ser Gln Ala Gln Ala Phe Thr Gln Ile Ile Asp Phe Tyr
    930                 935                 940

Leu Ser Lys Glu Gly Ser Lys Tyr Leu Pro Glu Ile Gln Arg Leu Ala
945                 950                 955                 960

Arg Glu Glu Ser Lys Glu Ser Asp Glu Gln Leu Leu Arg Tyr Cys Met
                965                 970                 975

Glu Ala Ile Arg Leu Asn Lys Thr Ser Gly Ala Tyr Arg Glu Ala Arg
            980                 985                 990

Thr Ser Leu Thr Val Thr Glu Glu  Thr Gly Gln Val Thr  Leu Gln Pro
```

```
            995                 1000                1005
Gly Asp Lys Val Phe Val Gly Phe Ala Lys Ala Asn Arg Asp Pro
    1010                1015                1020

Ser Val Phe Pro Asp Pro Ser Glu Val Arg Leu Asp Arg Pro Leu
    1025                1030                1035

Asp Ala Tyr Ile Asn His Ser Leu Gly Pro His Gly Phe Leu Ser
    1040                1045                1050

Lys Glu Thr Ser Gln Ile Ala Leu Thr Ala Met Leu Arg Ala Val
    1055                1060                1065

Gly Arg Leu Asn Asn Leu Arg Arg Ala Pro Gly Ala Gln Gly Glu
    1070                1075                1080

Val Lys Lys Val Pro Ile Ala Asp Gly Tyr Ser Ala Tyr Leu Arg
    1085                1090                1095

Glu Asp His Gly Ser Tyr Ser Val Phe Pro Thr Thr Phe Arg Val
    1100                1105                1110

His Tyr Asp Val
    1115

<210> SEQ ID NO 11
<211> LENGTH: 1125
<212> TYPE: PRT
<213> ORGANISM: Penicillium marneffei

<400> SEQUENCE: 11

Met Arg Arg Phe Ser Ser Val Phe Lys Lys Glu Glu Ser Lys Ala
1               5                   10                  15

Lys Glu Asn Gly His Ile Ser Glu Lys Val Asn Gly Lys Arg Gln Ser
                20                  25                  30

Lys Ala Val Ser Thr Ser Gln Pro Pro Ala Glu Pro Glu Asp His Ser
        35                  40                  45

Lys Ala Arg His Glu Val Ser Ala Ile Phe Glu Arg Tyr Ala Gln Val
    50                  55                  60

Ile His Ala Ser Arg Gln Pro Leu Pro Thr Gln Ser Gly Asp Gly Thr
65                  70                  75                  80

Tyr Leu Glu His Gly His Asp His Ser Ser Leu Phe Ser Asp Leu
                85                  90                  95

Arg Ser Leu Gly Phe Lys Asp Tyr Gly Thr Leu Val Glu Val Met Lys
                100                 105                 110

Asn Lys Ala Ser Gly Ser Tyr Val Asp Asp Lys Thr Met Leu Met Glu
            115                 120                 125

Arg Ile Ile Gln Leu Val Ser Gly Leu Pro Ser Asn Ser Glu Arg Arg
    130                 135                 140

Thr Glu Leu Thr Asn Ala Phe Leu Asp Glu Leu Trp Asp Ser Leu Pro
145                 150                 155                 160

His Pro Pro Leu Ser Phe Val Gly Pro Lys Phe Glu Tyr Arg Ser Ala
                165                 170                 175

Asp Gly Ser Trp Asn Asn Pro Thr Ile Pro Trp Leu Gly Ala Ala Asn
            180                 185                 190

Thr Glu Tyr Ser Arg Ser Ile Pro Pro Leu Thr Ile Gln Pro Ser Gly
        195                 200                 205

Leu Pro Asp Ala Gly Leu Val Phe Asp Ser Ile Met Ala Arg Glu Lys
    210                 215                 220

Phe Thr Pro His Pro Asn Lys Val Ser Ser Val Phe Phe Ala Trp Ala
225                 230                 235                 240
```

```
Ser Leu Ile Ile His Asp Ile Phe Gln Thr Asp Tyr Arg Asn Pro His
            245                 250                 255

Ile Ser Gln Thr Ser Ser Tyr Leu Asp Leu Ser Ile Leu Tyr Gly Asp
        260                 265                 270

Asn Gln Asp Asp Gln Asn Gln Met Arg Thr Phe Lys Asp Gly Lys Ile
    275                 280                 285

Lys Pro Asp Ser Phe Ser Glu Pro Arg Leu Gln Ala Phe Pro Ala Met
290                 295                 300

Cys Asn Val Leu Met Val Met Leu Asn Arg Phe His Asn Asn Val Val
305                 310                 315                 320

Glu Gln Ile Ala Gln Ile Asn Glu Asn Gly Arg Phe Asn Lys Pro Arg
                325                 330                 335

Pro Gly Leu Ser Pro Glu Gln Thr Glu Ala Ala Trp Lys Lys Tyr Asp
            340                 345                 350

Glu Asp Leu Phe Gln Thr Gly Arg Leu Ile Thr Cys Gly Leu Tyr Ile
        355                 360                 365

Asn Ile Thr Leu Tyr Asp Tyr Leu Arg Thr Ile Val Asn Leu Asn Arg
    370                 375                 380

Thr Asn Ser Thr Trp Cys Leu Asp Pro Arg Ala Arg Met Gln Gly Thr
385                 390                 395                 400

His Thr Thr Pro Ser Gly Leu Gly Asn Gln Cys Ser Val Glu Phe Asn
                405                 410                 415

Leu Ala Tyr Arg Trp His Ser Ala Thr Ser Tyr Asn Asp Glu Lys Trp
            420                 425                 430

Thr Glu Glu Val Tyr Arg Asp Leu Phe Gly Lys Pro Ala Glu Ile
        435                 440                 445

Ser Met Pro Glu Leu Leu Met Gly Leu His Lys Tyr Glu Gln Ser Ile
    450                 455                 460

Asp Lys Asp Pro Ser Lys Arg Thr Phe Ala Asn Leu Gln Arg Gln Ala
465                 470                 475                 480

Asp Gly Thr Phe Lys Asp Asp Leu Val Lys Ile Met Thr Ser Ala
                485                 490                 495

Val Glu Asp Val Ala Gly Ser Phe Gly Ala Arg Asn Val Pro Lys Val
            500                 505                 510

Met Arg Ser Ile Glu Ile Leu Gly Ile Glu Gln Ala Arg Lys Trp Asn
        515                 520                 525

Val Gly Ser Leu Asn Glu Phe Arg Lys Phe Asn Leu Lys Pro Tyr
    530                 535                 540

Glu Thr Phe Glu Glu Ile Asn Ser Asp Pro Tyr Val Ala Asp Gln Leu
545                 550                 555                 560

Arg His Leu Tyr Glu His Pro Asp Tyr Val Glu Leu Tyr Pro Gly Ile
                565                 570                 575

Val Ala Glu Glu Ala Lys Ala Pro Met Val Pro Gly Val Gly Ile Ala
            580                 585                 590

Pro Thr Tyr Thr Ile Ser Arg Ala Val Leu Ser Asp Ala Val Ala Leu
        595                 600                 605

Val Arg Gly Asp Arg Phe Tyr Thr Thr Asp Gln Thr Pro Arg Asn Leu
    610                 615                 620

Thr Asn Trp Gly Trp Gln Glu Ser Gly His Asp Leu Asn Ile Asn Gln
625                 630                 635                 640

Gly Cys Val Phe Tyr Lys Leu Ala Phe Arg Ala Phe Pro Asn His Phe
                645                 650                 655

Lys Pro Asp Ser Ile Tyr Ala His Tyr Pro Met Thr Ile Pro Glu Glu
```

-continued

```
                660                 665                 670
Asn Lys Val Ile Met Lys Asp Leu Gly Arg Glu Asp Tyr Ser Trp
                675                 680                 685

Asp Gln Pro Thr Phe Asn Ala Pro Arg Val Glu Leu Lys Thr Tyr Gln
                690                 695                 700

Ala Ala Gln Thr Val Leu Asn Asp Thr Arg Asn Phe Arg Val Thr Trp
705                 710                 715                 720

Gly Asp Ala Ser Ala Trp Val Phe Gly Glu Lys Thr Gly Phe Asp Tyr
                725                 730                 735

Met Leu Ser Gly Asp Thr Pro Phe His Gly Gln Gln Arg Glu Leu Leu
                740                 745                 750

Glu Arg Ser Leu Tyr Gln Glu Gly Trp Asp Ser Arg Leu Lys Glu Phe
                755                 760                 765

Tyr Glu Gln Ile Thr Leu Gln Leu Leu His Asp Lys Ser Tyr Thr Leu
                770                 775                 780

Ala Gly Thr Lys Gln Val Asp Leu Thr Arg Asp Val Gly Asn Leu Ala
785                 790                 795                 800

Thr Val His Phe Ala Ala His Leu Phe Gly Leu Pro Leu Lys Thr Lys
                805                 810                 815

Gly Asn Pro Arg Gly Ile Phe Thr Glu His Glu Leu Tyr Met Ala Asn
                820                 825                 830

Ala Val Ile Phe Gln Ala Val Phe Phe Asp Tyr Asp Leu Met Arg Ser
                835                 840                 845

Tyr Pro Leu Arg Gln Ala Ala Arg Ala Val Ala Lys Lys Ile Gly Glu
                850                 855                 860

Met Val Glu Leu Asn Val Lys Ser Ile Gly Ser Asn Gly Ile Ile Ser
865                 870                 875                 880

His Phe Ile Asp Gly Leu Arg Lys Gln Asp Asn Pro Leu Ser Asp Tyr
                885                 890                 895

Gly Glu Asn Leu Val Lys Lys Leu Leu Asp Ser Gly Leu Asn Ala His
                900                 905                 910

Glu Val Thr Trp Thr Gln Ile Leu Pro Ala Val Val Ser Met Val Pro
                915                 920                 925

Lys Leu Gly Gln Val Phe Thr Gln Ile Ile Asp Phe Tyr Leu Ser Asp
                930                 935                 940

Ala Gly Lys Ala Tyr Leu Pro Gly Ile Asn Arg Leu Thr Lys Leu Asn
945                 950                 955                 960

Thr Pro Glu Ser Asp Gln Ala Leu Thr His Tyr Val Leu Glu Ala Ile
                965                 970                 975

Arg Leu Asn Gly Thr Tyr Gly Ala Tyr Arg Glu Ala Gln Arg Asp Val
                980                 985                 990

Thr Val Asn Asp Gly Gly Asn Glu Ile Gln Val Asn Lys Gly Ala Lys
                995                1000                1005

Val Phe Val Ser Phe Ile Ser Ala Ser Arg Asp Pro Ala Ala Phe
                1010                1015                1020

Pro Glu Pro Glu Lys Val Val Leu Asp Arg Pro Val Glu Ser Tyr
                1025                1030                1035

Val His Tyr Gly Ile Gly Pro His Ser Cys Leu Gly Gln Asp Ala
                1040                1045                1050

Ser Leu Ile Ala Leu Thr Ser Met Leu Arg Val Val Gly Arg Leu
                1055                1060                1065

Glu Asn Leu Arg Arg Ala Arg Gly Thr Gln Gly Leu Leu Lys Lys
                1070                1075                1080
```

```
Ile Pro Arg Glu Gly Gly Ser Tyr His Tyr Leu Arg Glu Asp Gly
1085                1090                1095

Gly Ser Phe Thr Pro Phe Pro Ala Thr Phe Lys Val Glu Trp Asp
    1100            1105                1110

Ser Glu Leu Pro Pro Leu Lys Asn Arg Gly Thr Trp
    1115            1120                1125

<210> SEQ ID NO 12
<211> LENGTH: 1117
<212> TYPE: PRT
<213> ORGANISM: Penicillium decumbens

<400> SEQUENCE: 12

Met Leu Arg Arg Phe Ser Thr Gln Phe Arg Lys Asn Lys Glu Ser Asn
1               5                   10                  15

Ser Asp Ala Asp Ser Ser Lys Asn Ser Lys Glu Asn Gly Lys Arg His
            20                  25                  30

Ser Lys Pro Ile Gln Pro Ser Arg Lys Ala Ser Ser His Asp Glu Lys
        35                  40                  45

Gln His Ser Val Asn Arg Ala Glu Val Val Ala Val Phe Glu Lys His
50                  55                  60

Ala Gln Ala Ile His Ala Ser Arg Glu Pro Leu Pro Ser Gln Gly Gly
65                  70                  75                  80

Asp Gly Ala Tyr Leu Lys His Asp Gln Ser Gly Leu Phe Glu Asp
                85                  90                  95

Ile Lys Ser Leu Gly Phe Arg Asp Leu Ser Thr Val Lys Ser Leu Ile
            100                 105                 110

Lys Ser Lys Ala Ser Gly Glu Leu Ile Asp Asp Lys Thr Tyr Leu Met
        115                 120                 125

Glu Arg Ile Ile Gln Leu Val Ala Asp Met Pro Gly His Ser Lys Asn
130                 135                 140

Arg Val Glu Leu Thr Asn Gln Phe Leu Asp Glu Leu Trp Asp Ser Leu
145                 150                 155                 160

Pro His Pro Pro Leu Ser Tyr Met Gly Asp Glu Tyr Lys Tyr Arg Ser
                165                 170                 175

Ala Asp Gly Ser Arg Asn Asn Pro Thr Leu Pro Gln Leu Gly Ala Ala
            180                 185                 190

Asn Thr Pro Tyr Cys Arg Thr Ile Pro Pro Leu Thr Ile Gln Pro Ser
        195                 200                 205

Gly Leu Pro Asp Ala Gly Leu Leu Phe Asp Ser Leu Phe Ala Arg Gln
    210                 215                 220

Lys Phe Thr Pro His Pro Asn Lys Val Ser Ser Ile Phe Phe Asp Trp
225                 230                 235                 240

Ala Ser Leu Ile Ile His Asp Ile Phe Gln Thr Asp Tyr Arg Gln Gln
                245                 250                 255

His Val Asn Lys Thr Ser Ser Tyr Leu Asp Leu Ser Ile Leu Tyr Gly
            260                 265                 270

Asp Val Lys Glu Gln Gln Asp Leu Ile Arg Ser His Gln Asp Gly Lys
        275                 280                 285

Leu Lys Pro Asp Cys Phe Ser Glu Gly Arg Leu Gln Ala Leu Pro Ala
    290                 295                 300

Ala Cys Gly Val Leu Leu Val Met Leu Asn Arg Phe His Asn His Val
305                 310                 315                 320

Val Glu Gln Leu Ala Ala Ile Asn Glu Asn Gly Arg Phe Thr Lys Pro
```

```
                    325                 330                 335
Leu Asp Gly Leu Pro Glu Asp Ala Ala Lys Lys Ala Trp Ala Lys Tyr
                340                 345                 350

Asp Glu Asp Leu Phe Gln Thr Gly Arg Leu Ile Thr Cys Gly Leu Tyr
                355                 360                 365

Ile Asn Ile Thr Leu Tyr Asp Tyr Leu Arg Thr Ile Val Asn Leu Asn
                370                 375                 380

Arg Thr Asn Ser Thr Trp Cys Leu Asp Pro Arg Ala Gln Met Glu Lys
385                 390                 395                 400

Thr Gly Ala Thr Pro Ser Gly Leu Gly Asn Gln Cys Ser Val Glu Phe
                405                 410                 415

Asn Leu Ala Tyr Arg Trp His Ser Thr Ile Ala Gln Gly Asp Glu Lys
                420                 425                 430

Trp Ile Glu Gln Ile Tyr Tyr Asp Leu Met Gly Lys Pro Ala Glu Glu
                435                 440                 445

Val Ser Met His Glu Leu Leu Met Gly Met Lys Lys Val Glu Gly Ser
                450                 455                 460

Leu Asp Pro Asp Pro Ser Lys Arg Thr Phe Ala Arg Leu Glu Arg Gln
465                 470                 475                 480

Ala Asp Gly Thr Phe Lys Asp Glu Glu Leu Val Ala Ile Leu Thr Ser
                485                 490                 495

Ala Cys Glu Asp Val Ala Ser Ser Phe Gly Pro Arg Asn Val Pro Lys
                500                 505                 510

Ala Leu Arg Ser Ile Glu Ile Leu Gly Ile Glu Ala Ala Arg Arg Trp
                515                 520                 525

His Val Gly Ser Leu Asn Glu Phe Arg Lys His Phe Gly Leu Lys Pro
                530                 535                 540

Tyr Asp Thr Phe Glu Glu Ile Asn Ser Asn Pro Glu Ile Ala Asn Cys
545                 550                 555                 560

Leu Arg His Leu Tyr Glu His Pro Asp Tyr Val Glu Leu Tyr Pro Gly
                565                 570                 575

Ile Val Ser Glu Glu Pro Lys Glu Pro Met Val Pro Gly Val Gly Ile
                580                 585                 590

Ala Pro Thr Tyr Thr Ile Ser Arg Ala Ile Leu Ser Asp Ala Val Ala
                595                 600                 605

Leu Val Arg Gly Asp Arg His Tyr Thr Ile Asp Tyr Asn Ala Arg Asn
                610                 615                 620

Leu Thr Asn Trp Gly Tyr Asn Glu Cys Arg Tyr Asp Leu Asn Ile Asn
625                 630                 635                 640

Gln Gly Cys Val Phe Tyr Lys Leu Ala Leu Arg Ala Phe Pro Asn Trp
                645                 650                 655

Tyr Lys Pro Asp Ser Ile Tyr Ala His Tyr Pro Met Thr Ile Pro Ser
                660                 665                 670

Glu Asn Arg Asn Ile Met Lys Ser Leu Gly Arg Glu Gln Asp Tyr Ser
                675                 680                 685

Trp Glu Arg Pro Ser Phe Thr Pro Ser Arg Ile Asn Leu Ser Ser His
                690                 695                 700

Asn Asn Ala Arg Leu Val Leu Glu Asn Ser Thr Asp Phe Thr Pro Val
705                 710                 715                 720

Trp Ser Glu Ala Met Thr Glu Leu Phe Gly Lys Gly Glu Phe Gly Ala
                725                 730                 735

Gln Gln Arg Glu Ala Met Ser Ala Ala Phe Ala Thr Glu Asp Phe Leu
                740                 745                 750
```

```
Thr Leu Val Lys Asn Phe Tyr Glu Glu Val Thr Leu Arg Leu Ile Lys
        755                 760                 765

Glu Lys Gly Ala Asn Leu Val Gly Thr Asn Gln Val Asp Ile Thr Arg
770                 775                 780

Asp Val Gly Asn Leu Ala His Val His Phe Ala Ser Ala Leu Phe Gly
785                 790                 795                 800

Leu Pro Leu Lys Thr Asp Glu Asn Pro Arg Gly Leu Phe Thr Glu His
            805                 810                 815

Glu Met Tyr Met Ile Leu Ala Thr Ile Tyr Ser Ala Leu Phe Tyr Asp
            820                 825                 830

Val Asp Pro Ala Lys Ser Leu Pro Leu Asn Ser Ala Ala Ser Ala Val
            835                 840                 845

Ala Arg Gln Leu Gly Ser Val Val Glu Ala Thr Val Lys Thr Asp Thr
850                 855                 860

His Ser Gly Leu Phe Ser Gly Leu Ile Asn Ser Phe Arg Pro His Asp
865                 870                 875                 880

Asn Ala Ile Arg Glu His Gly Thr Ala Ala Leu Arg Arg Val Glu Glu
                885                 890                 895

Ser Gly Gln Ser Ala Ser Gln Ile Thr Trp Ser His Ile Ile Pro Thr
            900                 905                 910

Val Val Gly Met Val Pro Ser Gln Gly Gln Val Phe Thr Gln Val Ile
            915                 920                 925

Glu Tyr Tyr Thr Ser Pro Glu Gly Lys His His Trp Ser Glu Ile Ser
    930                 935                 940

Arg Leu Ala Arg Gln Asp Ser Lys Glu Ser Asp Glu Met Leu His Arg
945                 950                 955                 960

Tyr Cys Leu Glu Ala Ile Arg Ile Asn Gly Thr Phe Gly Glu Tyr Arg
                965                 970                 975

Glu Ala Lys Asn Pro Val Ile Leu Glu Glu Asn Glu Glu Val Ile Asn
            980                 985                 990

Val Gln Pro Gly Asn Lys Ile Phe Ala Ser Phe Ile Gln Ala Asn Leu
    995                 1000                1005

Asp Pro Ser Val Phe Pro Glu Pro Asn Ser Val Asn Leu Ser Arg
    1010                1015                1020

Pro Leu Ser Ser Tyr Ile His Gln Gly Gln Gly Pro Ala Asn Gly
    1025                1030                1035

Leu Gly Gln Glu Thr Thr Lys Ile Ala Leu Val Ser Met Leu Arg
    1040                1045                1050

Val Val Ala Arg Leu Pro Asn Leu Arg Arg Ala Pro Gly Ala Gln
    1055                1060                1065

Gly Gln Leu Lys Arg Ile Pro Gln Lys Gly Gly His Tyr Val Tyr
    1070                1075                1080

Leu Arg Gln Asp Gly Thr Ser Tyr Phe Pro Phe Pro Thr Thr Leu
    1085                1090                1095

Lys Leu His Trp Asp Gly Asp Phe Glu Phe Gln Thr Ser Gln Thr
    1100                1105                1110

Ser Lys Lys His
    1115

<210> SEQ ID NO 13
<211> LENGTH: 1118
<212> TYPE: PRT
<213> ORGANISM: Penicillium chrysogenum
```

```
<400> SEQUENCE: 13

Met Leu Lys Arg Phe Ser Thr Gln Phe Lys Arg Ser Lys Asp Ser Lys
1               5                   10                  15

Asp Pro Lys Glu Ser Asn Gly Asp Ala Glu Pro Lys Ser Thr Asp Lys
            20                  25                  30

Ser Ser Lys Arg Ala Ser Lys Val Ser Pro Ser Pro Lys Ser Thr His
        35                  40                  45

Lys Glu Glu Asn His Val Val Lys Arg Ser Glu Val Val Ala Val Phe
    50                  55                  60

Asp Lys Tyr Ala Gln Ala Ile His Ala Ser Gln Glu Pro Leu Pro Asn
65                  70                  75                  80

Gln Thr Ser Asp Gly Ala Tyr Leu Lys His Asp Lys Ser Ser Gly Leu
                85                  90                  95

Ile Asn Asp Ile Lys Ala Leu Gly Phe Arg Asp Val Gly Val Thr Val Lys
            100                 105                 110

Asp Leu Ile Ala Ser Lys Ala Ser Gly Gly Ile Ile Asp Asp Lys Thr
            115                 120                 125

Tyr Leu Met Glu Arg Ile Ile Gln Met Val Ala Asp Leu Pro Gly Asn
130                 135                 140

Ser Lys Asn Arg Thr Asp Leu Thr Gly Leu Phe Leu Asp Asp Leu Trp
145                 150                 155                 160

Asn Ser Ile Pro His Pro Pro Leu Ser Tyr Met Gly Asp Asp Tyr Lys
                165                 170                 175

Tyr Arg Ser Ala Asp Gly Ser Asn Asn Asn Pro Thr Leu Pro Trp Leu
            180                 185                 190

Gly Ala Ala Asn Thr Pro Tyr Cys Arg Thr Ile Ala Pro Leu Thr Ile
            195                 200                 205

Gln Pro Ser Gly Leu Pro Asp Ala Gly Leu Ile Phe Asp Thr Leu Tyr
        210                 215                 220

Ala Arg Gln Glu Phe Thr Pro His Pro Asn Lys Val Ser Ser Val Phe
225                 230                 235                 240

Phe Asp Trp Ala Ser Leu Ile Ile His Asp Ile Phe Gln Thr Asp Tyr
                245                 250                 255

Ser Gln Gln His Leu Asn Gln Thr Ser Ala Tyr Leu Asp Leu Ser Ile
            260                 265                 270

Leu Tyr Gly Asp Val Lys Glu Gln Gln Asp Lys Ile Arg Ser His Glu
            275                 280                 285

Asn Gly Lys Leu Lys Pro Asp Cys Phe Ser Glu Gly Arg Leu Gln Ala
290                 295                 300

Leu Pro Pro Ala Cys Gly Val Leu Leu Val Met Leu Asn Arg Phe His
305                 310                 315                 320

Asn His Ile Val Thr Gln Leu Ala Ala Ile Asn Glu Asn Gly Arg Phe
                325                 330                 335

Ser Ala Pro Arg Pro Gly Leu Ser Glu Glu Thr Lys Ala Ala Trp
            340                 345                 350

Ala Lys Arg Asp Glu Asp Leu Phe Gln Thr Gly Arg Leu Ile Thr Cys
            355                 360                 365

Gly Leu Tyr Ile Asn Ile Thr Leu Tyr Asp Tyr Leu Arg Thr Ile Val
        370                 375                 380

Asn Leu Asn Arg Thr Asn Ser Thr Trp Cys Leu Asp Pro Arg Ala Gln
385                 390                 395                 400

Ala Glu Lys Ala Asp Ala Thr Pro Ser Gly Leu Gly Asn Gln Cys Ser
                405                 410                 415
```

```
Val Glu Phe Asn Leu Ala Tyr Arg Trp His Ser Thr Ile Ser Gln Gly
                420                 425                 430

Asp Glu Lys Trp Ile Glu Gln Ile Tyr Tyr Asp Leu Met Gly Lys Pro
            435                 440                 445

Ala Glu Gln Val Ser Met Pro Glu Leu Leu Met Gly Met Lys Lys Val
        450                 455                 460

Lys Gly Met Leu Glu Ala Asp Pro Ala Lys Arg Thr Phe Gly His Leu
465                 470                 475                 480

Gln Arg Asn Ala Asp Gly Tyr Phe Asp Asp Gly Glu Leu Val Asn Ile
                485                 490                 495

Leu Thr Arg Ala Thr Glu Asp Val Ala Ser Ser Phe Gly Pro Arg Asn
            500                 505                 510

Val Pro Lys Ala Met Arg Ser Ile Glu Ile Leu Gly Ile Glu Ala Ser
        515                 520                 525

Arg Arg Trp Asn Val Gly Ser Leu Asn Glu Phe Arg Lys His Phe Gly
530                 535                 540

Leu Lys Pro Tyr Glu Thr Phe Glu Asp Val Asn Ser Asn Pro Glu Ile
545                 550                 555                 560

Ala Asn Thr Leu Arg His Leu Tyr Glu His Pro Asp Tyr Ile Glu Leu
                565                 570                 575

Tyr Pro Gly Ile Val Ser Glu Glu Ala Lys Glu Pro Met Ile Pro Gly
            580                 585                 590

Val Gly Ile Ala Pro Thr Tyr Thr Ile Ser Arg Ala Val Leu Ser Asp
        595                 600                 605

Ala Val Ala Leu Val Arg Gly Asp Arg His Tyr Thr Ile Asp Tyr Asn
610                 615                 620

Pro Arg Asn Leu Thr Asn Trp Gly Tyr Asn Glu Cys Arg Tyr Asp Leu
625                 630                 635                 640

Asn Ile Asn Gln Gly Cys Ile Phe Tyr Lys Leu Ala Thr Arg Ala Phe
                645                 650                 655

Pro Asn His Tyr Lys Pro Asp Ser Ile Tyr Ala His Tyr Pro Met Thr
            660                 665                 670

Ile Pro Ser Glu Asn Arg Asn Ile Met Lys Asp Leu Gly Arg Glu Gln
        675                 680                 685

Asp Tyr Ser Trp Asp Lys Pro Ala Phe Met Glu Pro Arg Val Asn Leu
690                 695                 700

Thr Ser His Gln Asn Ala Lys Leu Leu Leu Glu Asn Gln Lys Asp Phe
705                 710                 715                 720

Arg Pro Ser Trp Ala Arg Ser Met Ser Glu Leu Phe Lys Gly Gly Glu
                725                 730                 735

Phe Asp Thr Lys Gln Arg Glu Ala Ile Gly Lys Ala Leu Asn Thr Glu
            740                 745                 750

Glu Phe Pro Lys Leu Val Lys Thr Phe Tyr Glu Asp Ile Thr Glu Arg
        755                 760                 765

Leu Ile Ala Glu Lys Gly Gly Gln Leu Gly Lys Ile Asn Gln Ile Asp
770                 775                 780

Ile Thr Arg Asp Val Gly Asn Leu Ala His Val His Phe Ala Ser Thr
785                 790                 795                 800

Ile Phe Gly Val Pro Leu Lys Thr Glu Asp Asn Pro Arg Gly Leu Phe
                805                 810                 815

Thr Glu His Glu Met Tyr Met Ile Leu Ser Thr Ile Phe Ser Ala Leu
            820                 825                 830
```

```
Phe Phe Asp Val Asp Ala Pro Arg Ser Tyr Ala Leu Asn Arg Ala Ala
            835                 840                 845

Ser Ala Val Ser Asn Gln Leu Gly Gln Val Val Glu Ala Thr Val Lys
850                 855                 860

Ala Asp Thr Asn Ser Gly Leu Phe Ala Gly Ile Met Asp Asn Phe Arg
865                 870                 875                 880

Pro His Asp Asn Ala Leu Arg Glu Phe Gly Thr Glu Ala Ile Arg Arg
            885                 890                 895

Met Lys Glu Ala Gly Ser Ser Ala Ser Asp Ile Thr Trp Ser Ala Ile
                900                 905                 910

Val Pro Thr Ile Val Gly Leu Val Pro Asn Gln Ala Gln Val Phe Thr
            915                 920                 925

Gln Ile Ile Glu Phe Tyr Thr Ala Pro Glu Asn Lys Ala His Leu Ala
930                 935                 940

Glu Ile Asn Arg Phe Ala Lys Thr Asp Ser Ala Glu Ser Asp Glu Lys
945                 950                 955                 960

Leu Tyr Arg Tyr Cys Leu Glu Ala Val Arg Leu Asn Gly Thr Phe Gly
            965                 970                 975

Ala Phe Arg Glu Ala Lys Glu Thr Val Thr Val Glu Glu Asp Gly Lys
                980                 985                 990

Thr Tyr Thr Val Gln Pro Gly Gln Gln Val Phe Ala Ser Phe Asp Gln
            995                 1000                1005

Ala Asn His Asp Pro Ser Val Phe Pro Glu Pro Asn Glu Val Asn
        1010                1015                1020

Leu Asp Arg Pro Leu Asp Ser Tyr Ile Asn His Gly Gln Gly Pro
        1025                1030                1035

Thr Thr Gly Phe Gly Glu Val Thr Lys Ile Ala Leu Ile Ala
        1040                1045                1050

Met Leu Arg Val Val Gly Arg Leu Gln Gly Leu Arg Arg Ala Pro
        1055                1060                1065

Gly Ala Gln Gly Gln Leu Lys Lys Ile Pro Gln Glu Gly Gly Tyr
        1070                1075                1080

Gln Val Tyr Leu Arg Gly Asp Gly Thr Ala Tyr Cys Pro Phe Pro
        1085                1090                1095

Met Ser Leu Lys Leu His Trp Asp Gly Pro Phe Glu Gln Lys Lys
        1100                1105                1110

Lys Val Thr Ser Ser
        1115

<210> SEQ ID NO 14
<211> LENGTH: 1110
<212> TYPE: PRT
<213> ORGANISM: Aspergillus niger

<400> SEQUENCE: 14

Met Leu Arg Arg Phe Ser Ser Thr Phe Lys Arg Ser Ser Lys Gly Asp
1               5                   10                  15

Arg Asp Ser Lys Pro Asn Gly Thr Gln Val Asn Gly Gln Lys Arg Gln
            20                  25                  30

Ser Lys Val Pro Ala Pro Arg Lys Ser Ser Asp Glu Ser His Ser
        35                  40                  45

Asp His Gly Val Glu Ser Asp Asp Gly Val Ser Val Phe Glu Lys Tyr
    50                  55                  60

Ala Gln Val Leu His Ala Ser Arg Arg Pro Leu Pro Asn Gln Asn Gly
65                  70                  75                  80
```

```
Asp Gly Thr Tyr Leu Glu Gln Glu His Ser Gly Ser Leu Phe Lys Asp
                85                  90                  95

Leu Arg Ala Leu Gly Phe Lys Asp Ile Gly Thr Leu Lys Asp Leu Ile
            100                 105                 110

Lys Thr Lys Ala Lys Gly Glu Tyr Ile Asp Asp Lys Thr Met Leu Met
        115                 120                 125

Glu Arg Ile Ile Gln Leu Val Ser Ser Leu Pro Gly Asn Ser Lys Thr
    130                 135                 140

Arg Val Asp Leu Thr Asn Ala Phe Leu Asp Glu Leu Trp Gly Ser Leu
145                 150                 155                 160

Pro His Pro Pro Leu Ser Tyr Met Gly Glu Tyr Ala Tyr Arg Ser
                165                 170                 175

Ala Asp Gly Ser Asn Asn Pro Thr Leu Pro Trp Leu Gly Ala Ala
            180                 185                 190

Gly Thr Pro Tyr Ala Arg Ser Ile Ala Pro Leu Thr Ile Gln Pro Gly
        195                 200                 205

Gly Leu Pro Asp Ala Gly Leu Val Phe Asp Cys Leu Phe Ala Arg Glu
    210                 215                 220

Lys Phe Thr Pro His Pro Asn Lys Val Ser Ser Leu Phe Phe Asp Trp
225                 230                 235                 240

Ala Ser Leu Val Ile His Asp Ile Phe Gln Thr Asp Tyr Thr Asn Ser
                245                 250                 255

His Val Asn Lys Thr Ser Ala Tyr Leu Asp Leu Ser Ile Leu Tyr Gly
            260                 265                 270

Asp Asp Gln Glu Asp Gln Asn Leu Val Arg Thr Phe Lys Asp Gly Lys
        275                 280                 285

Leu Lys Pro Asp Thr Phe Ser Glu Gln Arg Leu Gln Ala Phe Pro Pro
    290                 295                 300

Ala Cys Ser Val Leu Met Val Met Leu Ser Arg Phe His Asn Trp Val
305                 310                 315                 320

Val Glu Glu Leu Ala Ala Ile Asn Glu Asn Gly Arg Phe Asn Lys Pro
                325                 330                 335

Asp Pro Arg Leu Asp Glu Glu Lys Ala Arg Lys Ala Trp Glu Lys Tyr
            340                 345                 350

Asp Asn Asp Leu Phe Gln Thr Gly Arg Leu Val Thr Cys Gly Leu Phe
        355                 360                 365

Ile Asn Ile Thr Leu Tyr Asp Tyr Leu Arg Thr Ile Val Asn Leu Asn
    370                 375                 380

Arg Ser Asn Ser Thr Trp Cys Leu Asp Pro Arg Val Gln Met Glu Gly
385                 390                 395                 400

Thr Lys Ser Thr Pro Ser Gly Leu Gly Asn Gln Cys Ser Val Glu Phe
                405                 410                 415

Asn Leu Ala Tyr Arg Trp His Ser Ala Ile Ser Ala Asn Asp Glu Lys
            420                 425                 430

Trp Thr Glu Glu Ile Tyr Glu Glu Leu Met Gly Lys Pro Ala Ser Glu
        435                 440                 445

Val Ser Met Arg Glu Leu Leu Val Gly Leu Gly Lys Tyr Glu Arg Glu
    450                 455                 460

Ile Pro Lys Asp Pro Ser Lys Arg Thr Phe Ala Gly Leu Lys Arg Gln
465                 470                 475                 480

Glu Asp Gly Thr Phe Lys Asp Glu Asp Leu Val Arg Ile Leu Ala Asn
                485                 490                 495
```

```
Ala Ile Glu Asp Val Ala Ser Ser Phe Gly Ala Arg Asn Val Pro Lys
            500                 505                 510

Val Leu Arg Ser Val Glu Ile Leu Gly Ile Glu Gln Gly Arg Lys Trp
        515                 520                 525

Asn Val Gly Ser Leu Asn Glu Phe Arg Lys Phe Phe Asp Leu Lys Pro
    530                 535                 540

Tyr Glu Thr Phe Glu Glu Ile Asn Ser Asp Pro Asp Val Ala Asp Ser
545                 550                 555                 560

Leu Arg His Leu Tyr Glu His Pro Asp Tyr Val Glu Leu Tyr Pro Gly
                565                 570                 575

Ile Val Ala Glu Glu Ala Lys Glu Pro Met Ile Pro Gly Val Gly Ile
            580                 585                 590

Ala Pro Thr Tyr Thr Ile Ser Arg Ala Val Leu Ser Asp Ala Val Ala
        595                 600                 605

Leu Val Arg Gly Asp Arg Tyr Tyr Thr Ile Asp Tyr Asn Pro Arg Asn
    610                 615                 620

Leu Thr Asn Trp Gly Tyr Asn Glu Val Arg Tyr Asp Leu Asn Ile Asn
625                 630                 635                 640

Gln Gly Cys Val Phe Tyr Lys Leu Ala Met Arg Ala Phe Pro Asn Tyr
                645                 650                 655

Phe Lys Pro Asp Ser Ile Tyr Ala His Tyr Pro Met Thr Ile Pro Ser
            660                 665                 670

Glu Asn Arg Asn Ile Met Lys Asn Leu Gly Arg Glu Ser His Tyr Ser
        675                 680                 685

Tyr Asp Arg Pro Arg Tyr Thr Glu Pro Val Pro Asn Leu Leu Ser Tyr
    690                 695                 700

Ala Asn Ala Lys Leu Val Leu Asn Asn Gln Lys Asp Phe Thr Val Pro
705                 710                 715                 720

Trp Gly Gly Leu Ser Ser Ile His Ala Gly Lys Gly Ala Asp Phe
                725                 730                 735

Trp Ser Lys Ser Phe Asp Asn Glu Gln Trp Arg Asn Ser Val Lys Glu
            740                 745                 750

Phe Tyr Glu Asp Ala Thr Leu Lys Leu Leu Asn Glu Lys Ser Cys Lys
        755                 760                 765

Leu Ala Gly Asn Lys Gln Val Asp Ile Ala Arg Asp Val Gly Asn Leu
    770                 775                 780

Val Pro Val His Phe Val Ser Lys Val Phe Ser Leu Pro Leu Lys Thr
785                 790                 795                 800

Lys Ser Asn Pro Arg Gly Ile Phe Thr Glu His Glu Met Phe Met Ile
                805                 810                 815

Met Ala Val Val Phe Asn Ser Thr Phe Phe Asp Val Asp Pro Thr Lys
            820                 825                 830

Ser Phe Pro Leu Gln His Ala Ala Arg Ala Val Ser Gln Glu Leu Gly
        835                 840                 845

Lys Val Val Glu Ala His Val Lys Ser Ile Asn His Pro Gly Phe Leu
    850                 855                 860

His Gly Ile Ile Asp Ser Phe Arg Asp His Asn Ala Leu Lys Asp
865                 870                 875                 880

Tyr Gly Asp Gln Leu Ile Lys Arg Leu Leu Glu Ser Gly Leu Gly Val
                885                 890                 895

Ser Asp Val Thr Trp Gly Gln Ile Leu Pro Ala Ala Val Glu Met Val
            900                 905                 910

His Thr Gln Ser Gln Met Phe Thr Gln Ile Ile His Phe Tyr Leu Thr
```

```
                915                 920                 925
Glu Gly Gln Lys Tyr Leu Pro Glu Ile Asn Arg Leu Ala Asn Glu Asn
            930                 935                 940
Thr Ala Glu Ala Asn Asp Arg Leu Thr Arg Phe Cys Leu Glu Ala Val
945                 950                 955                 960
Arg Leu Asn Gly Asn Leu Gly Ile Tyr Arg Glu Ala Gln Ala Asp Ile
                965                 970                 975
Asn Val Ser Asp Glu Thr Gly Gln Tyr Ser Val Lys Ser Gly Glu Lys
            980                 985                 990
Val Phe Val Gly Ser Ser Lys Ala Asn Arg Asp Pro Gln Ala Phe Pro
                995                1000                1005
Ser Pro Asp Glu Val Arg Leu Asp Arg Pro Leu Asp Ser Tyr Leu
       1010                1015                1020
His Tyr Gly Leu Gly Pro Gln Ser Gly Leu Gly Lys Asp Ala Thr
       1025                1030                1035
Leu Ala Ala Val Thr Ala Met Val Arg Val Val Ala Arg Leu Asp
       1040                1045                1050
Thr Leu Arg Pro Ala Pro Gly Ala Gln Gly Gln Leu Lys Lys Ile
       1055                1060                1065
Pro Gln Glu Ala Gly Phe Ser Val Tyr Met Arg Glu Asp Tyr Gly
       1070                1075                1080
Ser Tyr Ser Pro Phe Pro Thr Thr Tyr Lys Val His Tyr Asn Gly
       1085                1090                1095
Asp Val Pro Ala Pro Lys Arg Gln Val Thr Thr Ala
       1100                1105                1110

<210> SEQ ID NO 15
<211> LENGTH: 542
<212> TYPE: PRT
<213> ORGANISM: Nostoc punctiforme

<400> SEQUENCE: 15

Met Ala Gly Lys Arg Asp Thr Ser Lys Asp Gly Leu Gly Asn Lys Ile
1               5                   10                  15

Gln Thr Leu Val Leu Thr Asn Phe Lys Gly Leu Trp Gln Leu Leu Gln
            20                  25                  30

Ser Asn Glu Phe Ile Lys Arg Lys Val Asn Lys Thr Leu Leu Asn Ser
        35                  40                  45

Leu Ile Tyr Lys Ile Pro Thr Arg Pro Asn Ala Tyr Ser Met Met Thr
    50                  55                  60

Leu Asp Glu His Ile Pro Asp Thr Asn Ile Pro Lys Lys Thr Asp Thr
65                  70                  75                  80

Tyr Thr Ser Trp Glu Ser Leu Asn Asp Arg Thr Tyr Thr Gly Arg His
                85                  90                  95

Leu Pro Pro Asp Pro Lys Leu Asn Ala Glu Gly Asn Leu Pro Lys Val
            100                 105                 110

Glu Asp Leu Ala Ile Leu Phe Arg Lys Arg Asp Gly Lys Thr Ile Tyr
        115                 120                 125

Ser Gly Lys Ser Thr Met Leu Phe Pro Tyr Trp Val Gln Trp Phe Thr
    130                 135                 140

Asp Ser Phe Leu Arg Leu Asn His Tyr Asn Lys Leu Lys Asn Thr Ser
145                 150                 155                 160

Asn His Glu Ile Asp Leu Cys Asn Val Tyr Gly Leu Thr Arg Lys Gln
                165                 170                 175
```

```
Thr His Leu Leu Arg Ser Phe Gln Gly Gly Lys Leu Lys Thr Gln Lys
            180                 185                 190

Leu Lys Arg Gln Asp Gly Val Glu Glu Tyr Pro Leu Phe Tyr Tyr
        195                 200                 205

Ala Asp Pro Ala Gln Asp Lys Val Lys Pro Glu Phe Glu Gly Leu Tyr
        210                 215                 220

Glu Pro Ile Asn Asp Glu Lys Arg Gln Pro Ile Asp Lys Lys Gln Tyr
225                 230                 235                 240

Met Phe Ala Met Gly Val Glu Arg Ala Asn Val Gln Ile Gly Tyr Val
                245                 250                 255

Met Leu Asn Thr Leu Cys Phe Arg Glu His Asn Arg Leu Cys Asp Glu
            260                 265                 270

Leu Ala Arg Asn Tyr Pro Asp Trp Asp Asp Glu Arg Leu Phe Gln Thr
        275                 280                 285

Ser Arg Asn Ile Leu Met Ala Ile Ile Leu Lys Ile Ile Met Glu Glu
        290                 295                 300

Tyr Ile Asn His Ile Thr Pro Tyr His Phe Lys Leu Phe Ala Asp Pro
305                 310                 315                 320

Glu Ala Phe Thr Lys Glu Ser Trp His Arg Pro Asn Tyr Met Ala Ile
                325                 330                 335

Glu Phe Asp Phe Val Tyr Arg Trp His Ser Ala Ile Pro Glu Thr Phe
            340                 345                 350

Asn Tyr Asn Gly Lys Pro Thr His Ile Val Thr Ser Leu Trp Asn Asn
        355                 360                 365

Lys Met Phe Ile Asp Gln Gly Leu Gly Ala Leu Met Glu Glu Thr Cys
        370                 375                 380

Ser Gln Pro Gly Thr Lys Ile Gly Leu Phe Asn Thr Pro Asp Ile Leu
385                 390                 395                 400

Val Glu Leu Thr Glu Leu Pro Ser Ile Arg Leu Gly Arg Gln Leu Gln
                405                 410                 415

Leu Ala Ser Tyr Asn Asp Tyr Arg Glu Leu Cys Gly Phe Pro Arg Val
            420                 425                 430

Thr Arg Phe Glu Gln Val Thr Gly Asn Glu Phe Ala Gln Glu Lys Leu
        435                 440                 445

Lys Glu Leu Tyr Gly His Val Asp Lys Ile Glu Phe Phe Val Gly Leu
        450                 455                 460

Tyr Ala Glu Asp Gly Arg Glu Asn Ser Thr Ile Pro Ala Leu Val Ala
465                 470                 475                 480

Arg Leu Ile Gly Ile Asp Ala Phe Ser Gln Ala Leu Thr Asn Pro Leu
                485                 490                 495

Leu Ser Pro Asn Ile Phe Asn Lys Glu Thr Phe Ser Pro Val Gly Trp
            500                 505                 510

Glu Ile Leu Gln Asn Thr Lys Thr Val Ser Asp Leu Val Asn Arg Asn
        515                 520                 525

Val Pro Pro Ser Gly Lys Lys Tyr Lys Val Thr Phe Asp Leu
        530                 535                 540

<210> SEQ ID NO 16
<211> LENGTH: 634
<212> TYPE: PRT
<213> ORGANISM: Pseudomonas aeruginosa

<400> SEQUENCE: 16

Met Thr Leu Ser Arg Leu Ser Leu Ala Ile Leu Ser Val Leu Ala Gly
1               5                   10                  15
```

Ala Pro Ala Phe Ala Asp Asp Ser Gly Val Asp Leu Asp Gln Gly Trp
            20                  25                  30

Asn Gln Thr Gln Lys Thr Ala Trp Leu Glu Ala Gly Gln Gly Ser Arg
            35                  40                  45

Met Leu Pro Leu Ala Trp Leu Val Ala Leu Glu Gln Arg Ala Ser Glu
50                  55                  60

Glu Pro Leu Met Ser Asp Ala Leu Ile Arg Gln Tyr Gly Tyr Val Pro
65                  70                  75                  80

His Thr Leu Gly Gly Ser Ser Val Lys Val Gln Gly Tyr Ala Val
                85                  90                  95

Asp Arg Ser Asp Asp Ser Asp Leu Thr Phe Thr Lys Leu Arg Trp Lys
            100                 105                 110

Ala Leu Gln Gly Ser Arg Glu Pro Trp Val Gly Pro Thr Cys Ser Met
            115                 120                 125

Cys His Thr Ser His Ile Ser Tyr Gln Gly Thr Gln Leu Thr Val Tyr
    130                 135                 140

Gly Gly Gln Thr Met Gly Asp Leu Ala Gly Phe Gln Leu Glu Ile Leu
145                 150                 155                 160

Gly Ala Leu Gln Ser Thr Arg Ala Asp Thr Ala Lys Phe Glu Arg Phe
                165                 170                 175

Ala Arg Lys Val Leu Gly Ala Asp Gly Leu Val Ser Gly Tyr Asn Asp
            180                 185                 190

Ala Asn Lys Ala Arg Leu Gln Ala Ala Leu Asp Ala Thr Ile Val Arg
            195                 200                 205

Leu Arg Asp Gly Ser His Phe Asn Leu Pro His Asp Pro Glu Phe Gly
210                 215                 220

Pro Gly Arg Leu Asp Ala Ile Gly Ser Ile Phe Asn Ser Val Gly Tyr
225                 230                 235                 240

Glu Leu His Ala Asp Glu Gln Ile Tyr Gly Ala Glu Asp Ala Pro Val
            245                 250                 255

Ser Tyr Pro Phe Leu Trp Asn Val Pro Gln Leu Asp Arg Val Gln Trp
            260                 265                 270

Thr Gly Phe Asn Pro Asn His Ile Asn Val Val Asp Ile Asp Asn Arg
            275                 280                 285

Lys Phe Asp Val Gly Ala Leu Ala Arg Asn Ala Gly Glu Ala Val Gly
            290                 295                 300

Val Phe Ala Asp Val Lys Val Leu Ser Pro Ile Gln Ser Ala Leu His
305                 310                 315                 320

Ile Gly Tyr Pro Ser Ser Ile Asn Val Asp Asn Leu Ile Arg Ile Glu
                325                 330                 335

Asp Gln Leu Gly Gln Leu Lys Pro Pro Ala Trp Pro Asn Gln Leu Phe
            340                 345                 350

Gly Ala Pro Glu Pro Thr Arg Val Ala Glu Gly Arg Glu Leu Tyr Arg
            355                 360                 365

Gln His Cys Ser Ser Cys His Thr Pro Leu Asp Arg Asn Asp Leu Arg
            370                 375                 380

Thr Pro Val Lys Thr Val Leu Thr His Leu Gln Ala Arg Gly Glu Val
385                 390                 395                 400

Ala Pro Ile Gly Thr Asp Pro Trp Thr Ala Cys Asn Ser Ile Ala Gln
            405                 410                 415

Leu Lys Thr Gly Tyr Val Arg Gly Lys Pro Tyr Leu Ser Phe Val Gly
            420                 425                 430

```
Thr Gly Gln Arg Gly Phe Tyr Gly Lys Gln Ala Tyr Ala Val Asp Val
            435                 440                 445

Leu Gln Glu Val Val Gln Ala Leu Ala Ala Arg Gly Leu Ser Val
450                 455                 460

Ala Leu Gly Ala Phe Gln Thr Ala Leu Gly Ile Phe Asp Gly Gln
465                 470                 475                 480

Leu Pro Pro Leu Ile Ser Pro Val Pro Asp Ser Pro Ala Asp Ser
                485                 490                 495

Ala Glu Ala Thr Ala Ala Asp Ala Pro Gly Ala Leu Leu Ala Glu
            500                 505                 510

Asn Val Ala Ala Asp Ser Asp Lys Ala Arg Arg Leu Glu Gln Cys Leu
            515                 520                 525

Ala Met Thr Ser Asp Leu Met Ala Tyr Lys Ala Arg Pro Leu Asn Gly
            530                 535                 540

Ile Trp Ala Ser Pro Pro Tyr Leu His Asn Gly Ser Val Ala Thr Leu
545                 550                 555                 560

Tyr Asp Leu Leu Leu Pro Pro Asp Leu Arg Pro Arg Thr Phe Tyr Thr
                565                 570                 575

Gly Ser Val Glu Phe Asp Pro Val Asn Val Gly Tyr Ile Thr Asp Ala
            580                 585                 590

Gly Gly Ala Asn Arg Phe Leu Phe Asp Ser Gly Lys Pro Gly Asn Ala
            595                 600                 605

Asn Gly Gly His Asp Tyr Gly Asn Ala Gln Phe Asn Glu Gln Gln Arg
            610                 615                 620

Arg Ala Leu Val Glu Tyr Met Lys Thr Leu
625                 630

<210> SEQ ID NO 17
<211> LENGTH: 634
<212> TYPE: PRT
<213> ORGANISM: Pseudomonas aeruginosa

<400> SEQUENCE: 17

Met Thr Leu Ser Arg Leu Ser Leu Ala Ile Leu Ser Val Leu Ala Gly
1               5                   10                  15

Ala Pro Ala Phe Ala Asp Asp Ser Gly Val Asp Leu Asp Gln Gly Trp
            20                  25                  30

Asn Gln Thr Gln Lys Thr Ala Trp Leu Glu Ala Gly Gln Gly Ser Arg
        35                  40                  45

Met Leu Pro Leu Ala Trp Leu Val Ala Leu Glu Gln Arg Ala Ser Glu
    50                  55                  60

Glu Pro Leu Met Ser Asp Ala Leu Ile Arg Gln Tyr Gly Tyr Val Pro
65                  70                  75                  80

His Thr Leu Gly Gly Ser Ser Val Lys Val Val Gln Gly Tyr Ala Val
                85                  90                  95

Asp Arg Ser Asp Asp Ser Asp Leu Thr Phe Thr Lys Leu Arg Trp Lys
            100                 105                 110

Ala Leu Gln Gly Ser Arg Glu Pro Trp Val Gly Pro Thr Cys Ser Met
        115                 120                 125

Cys His Thr Ser His Ile Ser Tyr Gln Gly Thr Gln Leu Thr Val Tyr
    130                 135                 140

Gly Gly Gln Thr Met Gly Asp Leu Ala Gly Phe Gln Leu Glu Ile Leu
145                 150                 155                 160

Gly Ala Leu Gln Ser Thr Arg Ala Asp Thr Ala Lys Phe Glu Arg Phe
                165                 170                 175
```

```
Ala Arg Lys Val Leu Gly Ala Asp Gly Leu Val Ser Gly Tyr Asn Asp
            180                 185                 190

Ala Asn Lys Ala Arg Leu Gln Ala Leu Asp Ala Thr Ile Val Arg
        195                 200                 205

Leu Arg Asp Gly Ser His Phe Asn Leu Pro His Asp Pro Glu Phe Gly
210                 215                 220

Pro Gly Arg Leu Asp Ala Ile Gly Ser Ile Phe Asn Ser Val Gly Tyr
225                 230                 235                 240

Glu Leu His Ala Asp Glu Gln Ile Tyr Gly Ala Glu Asp Ala Pro Val
                245                 250                 255

Ser Tyr Pro Phe Leu Trp Asn Val Pro Gln Leu Asp Arg Val Gln Trp
            260                 265                 270

Thr Gly Phe Asn Pro Asn His Ile Asn Val Val Asp Ile Asp Asn Arg
            275                 280                 285

Lys Phe Asp Val Gly Ala Leu Ala Arg Asn Ala Gly Glu Ala Val Gly
        290                 295                 300

Val Phe Ala Asp Val Lys Val Leu Ser Pro Ile Gln Ser Ala Leu His
305                 310                 315                 320

Ile Gly Tyr Pro Ser Ser Ile Lys Val Asp Asn Leu Ile Arg Ile Glu
                325                 330                 335

Asp Gln Phe Gly Gln Leu Lys Pro Pro Ala Trp Pro Asn Gln Leu Phe
            340                 345                 350

Gly Ala Pro Glu Pro Thr Arg Val Ala Glu Gly Arg Glu Leu Tyr Arg
            355                 360                 365

Gln His Cys Ser Ser Cys His Thr Pro Leu Asp Arg Asn Asp Leu Arg
        370                 375                 380

Thr Pro Val Lys Thr Val Leu Thr His Leu Gln Ala Arg Gly Glu Val
385                 390                 395                 400

Ala Pro Ile Gly Thr Asp Pro Trp Thr Ala Cys Asn Ser Ile Ala Gln
                405                 410                 415

Leu Lys Thr Gly Tyr Val Arg Gly Lys Pro Tyr Leu Ser Phe Val Gly
            420                 425                 430

Thr Gly Gln Arg Gly Phe Tyr Gly Lys Gln Ala Tyr Ala Val Asp Val
            435                 440                 445

Leu Gln Glu Val Val Val Gln Ala Leu Ala Ala Arg Gly Leu Ser Val
450                 455                 460

Ala Leu Gly Ala Phe Gln Thr Ala Ala Leu Gly Ile Phe Asp Gly Gln
465                 470                 475                 480

Leu Pro Pro Leu Ile Ser Pro Val Pro Asp Ser Pro Asp Ala Asp Ser
                485                 490                 495

Val Glu Ala Thr Ala Ala Asp Ala Pro Gly Ala Leu Leu Leu Ala Glu
            500                 505                 510

Asn Val Ala Ala Asp Ser Asp Lys Ala Arg Arg Leu Glu Gln Cys Leu
        515                 520                 525

Ala Met Thr Ser Asp Leu Met Ala Tyr Lys Ala Arg Pro Leu Asn Gly
        530                 535                 540

Ile Trp Ala Ser Pro Pro Tyr Leu His Asn Gly Ser Val Ala Thr Leu
545                 550                 555                 560

Tyr Asp Leu Leu Leu Pro Pro Asp Leu Arg Pro Arg Thr Phe Tyr Thr
                565                 570                 575

Gly Ser Val Glu Phe Asp Pro Val Asn Val Gly Tyr Ile Thr Asp Ala
            580                 585                 590
```

```
Gly Gly Ala Asn Arg Phe Leu Phe Asp Ser Gly Lys Pro Gly Asn Ala
            595                 600                 605

Asn Gly Gly His Asp Tyr Gly Asn Ala Gln Phe Asn Glu Gln Gln Arg
610                 615                 620

Arg Ala Leu Val Glu Tyr Met Lys Thr Leu
625                 630
```

<210> SEQ ID NO 18
<211> LENGTH: 610
<212> TYPE: PRT
<213> ORGANISM: Fusarium oxysporum

<400> SEQUENCE: 18

```
Met Val Ala Leu Leu Ile Phe Leu Gly Ile Phe Thr Cys Val Glu Thr
1               5                   10                  15

Leu Pro Leu Ser Asp Ser Pro Ser Ser Tyr Ile Pro Glu Glu Val Pro
            20                  25                  30

Ser Ser Gln Thr Ala Asp Ile Gly Leu Pro Pro Thr Glu Phe Thr
        35                  40                  45

Leu Pro Asn Glu Asp Asp Glu Ile Leu Ile Arg Lys Leu Asn Ile Gln
50                  55                  60

Lys Thr Arg Lys Glu Ile Leu Tyr Gly Pro Ser Leu Ile Gly Lys Thr
65                  70                  75                  80

Ser Phe Phe Ile Ser Gly Pro Leu Gly Asp Gln Ile Ser Gln Arg Asp
                85                  90                  95

Gln Thr Leu Trp Ser Arg Asp Ala Ala Pro Val Val Gln Ala Val Ser
            100                 105                 110

His Asp Ala Ala Ala Leu His Asp Ile Gln Ile His Gly Gly Leu
        115                 120                 125

Gln Asn Leu Asp Asp Tyr Lys Ile Leu Tyr Gln Gly His Trp Ser Ser
130                 135                 140

Ser Val Pro Gly Gly Ile Ala Lys Gly Gln Phe Ser Asn Phe Thr Ser
145                 150                 155                 160

Asp Leu Leu Phe Ser Met Glu Arg Leu Ser Thr Asn Pro Tyr Ile Leu
                165                 170                 175

Arg Arg Leu His Pro His Ala Asp Glu Leu Pro Phe Ala Val Asp Ser
            180                 185                 190

Lys Ile Val Gln Lys Leu Thr Gly Ser Thr Leu Pro Ser Leu His Lys
        195                 200                 205

Ala Gly Arg Leu Phe Leu Ala Asp His Ser Tyr Gln Lys Asp Tyr Val
210                 215                 220

Ala Gln Glu Gly Arg Tyr Ala Ala Ala Cys Gln Ala Leu Phe Tyr Leu
225                 230                 235                 240

Asp Asp Arg Cys His Gln Phe Leu Pro Leu Ala Ile Lys Thr Asn Val
                245                 250                 255

Gly Ser Asn Leu Thr Tyr Thr Pro Leu Asp Glu Pro Asn Asp Trp Leu
            260                 265                 270

Leu Ala Lys Val Met Phe Asn Val Asn Asp Leu Phe His Gly Gln Met
        275                 280                 285

Tyr His Leu Ala Ser Thr His Ala Val Ala Glu Ile Val His Leu Ala
290                 295                 300

Ala Leu Arg Thr Met Ser Ser Arg His Pro Val Leu Ala Leu Leu Gln
305                 310                 315                 320

Arg Leu Met Tyr Gln Ala Tyr Ala Ile Arg Pro Ile Gly Asn Asn Ile
                325                 330                 335
```

```
Leu Phe Asn Pro Gly Gly Leu Ile Asp Gln Asn Ser Val Phe Ser Asn
                340                 345                 350

Val Ala Val Arg Lys Phe Ala Thr Asp Phe Tyr Pro Thr Val Ala Gly
            355                 360                 365

Pro Val Arg Ser Asn Tyr Phe Glu Ala Asn Leu Arg Ser Arg Gly Leu
        370                 375                 380

Leu Asn Ala Thr His Gly Pro Asp Leu Pro His Phe Pro Phe Tyr Glu
385                 390                 395                 400

Asp Gly Ala Arg Ile Ile Lys Val Ile Arg Thr Phe Ile Gln Ser Phe
                405                 410                 415

Val Lys Ser Ile Tyr Lys Ser Asp Lys Val Leu Ala Lys Asp Trp Glu
            420                 425                 430

Leu Gln Ala Trp Ile Ala Glu Ala Asn Gly Ala Ala Glu Val Ile Asp
        435                 440                 445

Phe Pro Pro Thr Pro Leu Lys Lys Arg Lys His Leu Val Asp Ile Leu
    450                 455                 460

Thr His Met Ala Trp Leu Thr Gly Val Ser His His Val Leu Asn Gln
465                 470                 475                 480

Gly Glu Pro Val Thr Thr Ser Gly Val Leu Pro Leu His Pro Gly Ser
                485                 490                 495

Leu Tyr Ala Pro Val Pro Gly Glu Lys Gly Val Val Asp Ser Leu Leu
            500                 505                 510

Pro Trp Leu Pro Asn Glu Gln Lys Ser Val Asp Gln Ile Ser Phe Leu
        515                 520                 525

Ala Leu Phe Asn Arg Pro Gln Ile Val Glu Asn Asn Arg Thr Leu Arg
    530                 535                 540

Tyr Met Phe Asn Ser Glu Ser Leu Leu Ala Gly Thr Val Arg Ala Val
545                 550                 555                 560

Ala Ala Ala Asn Glu Arg Phe Met Glu Met Gly His Ile Ser Gln
                565                 570                 575

Glu Ile Ser Asn Arg Lys Phe Asp Asp Asp Gly Leu Ser Gln Gly Met
            580                 585                 590

Pro Phe Ile Trp Thr Gly Met Asp Pro Gly Val Ile Pro Phe Tyr Leu
        595                 600                 605

Ser Val
    610

<210> SEQ ID NO 19
<211> LENGTH: 618
<212> TYPE: PRT
<213> ORGANISM: Gaeumannomyces graminis

<400> SEQUENCE: 19

Met Arg Ser Arg Ile Leu Ala Ile Val Phe Ala Ala Arg His Val Ala
1               5                   10                  15

Ala Leu Pro Leu Ala Ala Glu Asp Ala Ala Thr Leu Ser Leu Thr
            20                  25                  30

Ser Ser Ala Ser Ser Thr Thr Val Leu Pro Ser Pro Thr Gln Tyr Thr
        35                  40                  45

Leu Pro Asn Asn Asp Pro Asn Gln Gly Ala Arg Asn Ala Ser Ile Ala
    50                  55                  60

Arg Lys Arg Glu Leu Phe Leu Tyr Gly Pro Ser Thr Leu Gly Gln Thr
65                  70                  75                  80

Thr Phe Tyr Pro Thr Gly Glu Leu Gly Asn Asn Ile Ser Ala Arg Asp
```

-continued

```
                85                  90                  95
Val Leu Leu Trp Arg Gln Asp Ala Ala Asn Gln Thr Ala Thr Ala Tyr
            100                 105                 110

Arg Glu Ala Asn Glu Thr Phe Ala Asp Ile Thr Ser Arg Gly Gly Phe
            115                 120                 125

Lys Thr Leu Asp Asp Phe Ala Leu Leu Tyr Asn Gly His Trp Lys Glu
    130                 135                 140

Ser Val Pro Glu Gly Ile Ser Lys Gly Met Leu Ser Asn Cys Thr Ser
145                 150                 155                 160

Asp Leu Leu Phe Ser Met Glu Arg Leu Ser Ser Asn Pro Tyr Val Leu
                165                 170                 175

Lys Arg Leu His Pro Thr Lys Asp Lys Leu Pro Phe Ser Val Glu Ser
                180                 185                 190

Lys Val Val Lys Lys Leu Thr Ala Thr Thr Leu Glu Ala Leu His Lys
                195                 200                 205

Gly Gly Arg Leu Phe Leu Val Asp His Ser Tyr Gln Lys Lys Tyr Thr
    210                 215                 220

Pro Gln Pro Gly Arg Tyr Ala Ala Ala Cys Gln Gly Leu Phe Tyr Leu
225                 230                 235                 240

Asp Ala Arg Ser Asn Gln Phe Leu Pro Leu Ala Ile Lys Thr Asn Val
                245                 250                 255

Gly Val Asp Leu Thr Tyr Thr Pro Leu Asp Asp Lys Asp Asp Trp Leu
                260                 265                 270

Leu Ala Lys Ile Met Phe Asn Asn Asp Leu Phe Tyr Ser Gln Met
                275                 280                 285

Tyr His Val Leu Phe His Thr Ile Pro Glu Ile Val His Glu Ala Ala
    290                 295                 300

Phe Arg Thr Leu Ser Asp Arg His Pro Val Met Gly Val Leu Asn Arg
305                 310                 315                 320

Leu Met Tyr Gln Ala Tyr Ala Ile Arg Pro Val Gly Gly Ala Val Leu
                325                 330                 335

Phe Asn Pro Gly Gly Phe Trp Asp Gln Asn Phe Gly Leu Pro Ala Ser
                340                 345                 350

Ala Ala Ile Asp Phe Pro Gly Ser Val Tyr Ala Gln Gly Gly Gly
            355                 360                 365

Phe Gln Ala Gly Tyr Leu Glu Lys Asp Leu Arg Ser Arg Gly Leu Ile
    370                 375                 380

Gly Glu Asp Ser Gly Pro Arg Leu Pro His Phe Pro Phe Tyr Glu Asp
385                 390                 395                 400

Ala His Arg Leu Ile Gly Ala Ile Arg Phe Met Gln Ala Phe Val
                405                 410                 415

Asp Ser Thr Tyr Gly Ala Asp Asp Gly Asp Gly Ala Leu Leu Arg
            420                 425                 430

Asp Tyr Glu Leu Gln Asn Trp Ile Ala Glu Ala Asn Gly Pro Ala Gln
            435                 440                 445

Val Arg Asp Phe Pro Ala Ala Pro Leu Arg Arg Ala Gln Leu Val
    450                 455                 460

Asp Val Leu Thr His Val Ala Trp Ile Thr Gly Gly Ala His His Val
465                 470                 475                 480

Met Asn Gln Gly Ser Pro Val Lys Phe Ser Gly Val Leu Pro Leu His
                485                 490                 495

Pro Ala Ala Leu Tyr Ala Pro Ile Pro Thr Ala Lys Gly Ala Thr Gly
                500                 505                 510
```

```
Asn Gly Thr Arg Ala Gly Leu Leu Ala Trp Leu Pro Asn Glu Arg Gln
        515                 520                 525

Ala Val Glu Gln Val Ser Leu Leu Ala Arg Phe Asn Arg Ala Gln Val
        530                 535                 540

Gly Asp Arg Lys Gln Thr Val Arg Asp Ala Phe Ala Ala Pro Asp Leu
545                 550                 555                 560

Leu Ala Gly Asn Gly Pro Gly Tyr Ala Ala Asn Ala Arg Phe Val
        565                 570                 575

Glu Asp Thr Gly Arg Ile Ser Arg Glu Ile Ala Gly Arg Gly Phe Asp
        580                 585                 590

Gly Lys Gly Leu Ser Gln Gly Met Pro Phe Val Trp Thr Ala Leu Asn
        595                 600                 605

Pro Ala Val Asn Pro Phe Phe Leu Ser Val
        610                 615

<210> SEQ ID NO 20
<211> LENGTH: 609
<212> TYPE: PRT
<213> ORGANISM: Colletotrichum gloeosporioides

<400> SEQUENCE: 20

Met Arg Leu Leu Leu Ser Ile Ala Gly Leu Thr Thr Val Val Asn Ala
1               5                   10                  15

Leu Ala Val Arg Ala Asp Gly Asn Val Thr Ser Ser Thr Ala Val Ala
                20                  25                  30

Thr Pro Thr Ala Trp Thr Gly Phe Pro Val Pro Thr Glu Tyr Thr Leu
            35                  40                  45

Pro Gln Asp Asp His Asp Phe Gln Glu Arg Lys Glu Glu Ile Lys Leu
        50                  55                  60

Lys Arg Asp Thr Ile Thr Tyr Val Pro Ser Ile Ile Gly Glu Thr Ser
65                  70                  75                  80

Leu Phe Ile Gly Gly Ser Val Gly Thr Gln Ile Val Arg Gln Glu Gln
                85                  90                  95

Ala Lys Trp Ile Gln Asp Leu Thr Pro Val Gln Gln Asp Ala Phe Arg
            100                 105                 110

Glu Gly Asn Ala Ser Leu Lys Ala Ile Gln Asp His Gly Gly Leu Lys
        115                 120                 125

Thr Leu Glu Asp Tyr Lys Ile Leu Tyr Asp Gly His Trp Ser Gly Ser
    130                 135                 140

Val Pro Gly Gly Ile Ala Gln Gly Gln Phe Asn Asn Phe Thr Ser Asp
145                 150                 155                 160

Leu Leu Phe Ala Met Glu Arg Leu Ser Thr Asn Pro Tyr Val Val Arg
                165                 170                 175

Arg Leu Asn Pro Glu Ser Asp Lys Ile Pro Phe Ser Val Asp Ala Asn
            180                 185                 190

Asn Val Thr His Leu Thr Gly Thr Thr Leu Asp Thr Leu Phe Lys Ser
        195                 200                 205

Gly Ser Leu Phe Leu Ala Asp His Ser Tyr Gln Ala Glu Tyr Thr Ala
    210                 215                 220

Gln Asp Gly Arg Tyr Ser Ala Ala Cys Gln Ala Leu Phe Phe Leu Asp
225                 230                 235                 240

Gln Arg Ser Gly Gln Phe Leu Pro Leu Ala Ile Lys Thr Asn Val Gly
                245                 250                 255

Ser Asp Leu Val Tyr Thr Pro Leu Asp Asp Pro Asn Asp Trp Leu Leu
```

```
              260                 265                 270
Ala Lys Ile Met Tyr Asn Val Asn Asp Phe Phe His Gly Gln Ile Tyr
            275                 280                 285

His Leu Ala Asn Ser His Ala Val Ala Glu Ile Val Asn Leu Ala Ala
        290                 295                 300

Ile Arg Thr Leu Ser Ser Arg His Pro Val Phe Gly Leu Leu Gln Arg
305                 310                 315                 320

Leu Met Phe Gln Ala Tyr Ala Ile Arg Ala Thr Gly Glu Ile Ala Leu
                325                 330                 335

Phe Asn Pro Gly Gly Leu Phe Asp Gln Ser Phe Ala Phe Ser Asn Val
            340                 345                 350

Tyr Ala Arg Lys Phe Ala Thr Asp Phe Tyr Pro Thr Val Ala Gly Pro
        355                 360                 365

Phe Gln Ala Asn Tyr Phe Glu Glu Asp Leu Arg Ala Arg Gly Leu Leu
    370                 375                 380

Asn Ala Ser Tyr Gly Pro Glu Leu Pro His Leu Pro Phe His Glu Asp
385                 390                 395                 400

Gly His Lys Ile Ile Asn Ala Ile Arg Thr Phe Ile Gly Thr Phe Val
                405                 410                 415

Asp Thr Val Tyr Glu Ser Asp Lys Val Leu Ala Glu Asp Ser Glu Leu
            420                 425                 430

Gln Ala Trp Ile Ala Glu Ala Asn Gly Pro Ala Lys Val Ile Asn Phe
        435                 440                 445

Pro Ser Ala Pro Leu Asn Thr Arg Lys Gln Leu Ala Glu Ile Leu Thr
    450                 455                 460

His Met Ala Trp Leu Thr Gly Val Ser His His Val Leu Asn Gln Gly
465                 470                 475                 480

Glu Pro Phe Thr Thr Ser Gly Val Leu Pro Leu His Pro Ala Ser Leu
                485                 490                 495

Tyr Ala Pro Val Pro Thr Ala Lys Gly Gly Ile Lys Asp Leu Leu Pro
            500                 505                 510

Trp Leu Pro Asn Glu Gln Lys Ser Val Glu Gln Ile Ser Leu Leu Ala
        515                 520                 525

Arg Phe Asn Arg Pro Lys Ile Val Glu Asn Asn Glu Thr Leu Leu His
    530                 535                 540

Met Phe Asp Val Lys Thr Leu Leu Ser Gly Thr Gly Glu Ala Val Lys
545                 550                 555                 560

Ala Ala Asn Glu Gln Phe Met Ile Ala Met Gly Thr Ile Ser Lys Glu
                565                 570                 575

Ile Ser Thr Arg Lys Phe Asp Asp Gln Gly Leu Ser Gln Gly Met Pro
            580                 585                 590

Phe Ile Trp Thr Gly Met Asp Pro Gly Val Ile Pro Tyr Leu Ser
        595                 600                 605

Val

<210> SEQ ID NO 21
<211> LENGTH: 896
<212> TYPE: PRT
<213> ORGANISM: Arabidopsis thaliana

<400> SEQUENCE: 21

Met Tyr Cys Arg Glu Ser Leu Ser Ser Leu Gln Thr Leu Asn Val Ala
1               5                   10                  15

Lys Ser Leu Ser Ser Leu Phe Pro Lys Gln Ser Ala Leu Ile Asn Pro
```

```
                 20                  25                  30
Ile Ser Ala Gly Arg Arg Asn Asn Leu Pro Arg Pro Asn Leu Arg Arg
             35                  40                  45

Arg Cys Lys Val Thr Ala Ser Arg Ala Asn Ile Glu Gln Glu Gly Asn
             50                  55                  60

Thr Val Lys Glu Pro Ile Gln Asn Ile Lys Val Lys Gly Tyr Ile Thr
 65                  70                  75                  80

Ala Gln Glu Glu Phe Leu Glu Gly Ile Thr Trp Ser Arg Gly Leu Asp
                 85                  90                  95

Asp Ile Ala Asp Ile Arg Gly Arg Ser Leu Leu Val Glu Leu Ile Ser
                100                 105                 110

Ala Lys Thr Asp Gln Arg Ile Thr Val Glu Asp Tyr Ala Gln Arg Val
            115                 120                 125

Trp Ala Glu Ala Pro Asp Glu Lys Tyr Glu Cys Glu Phe Glu Met Pro
        130                 135                 140

Glu Asp Phe Gly Pro Val Gly Ala Ile Lys Ile Gln Asn Gln Tyr His
145                 150                 155                 160

Arg Gln Leu Phe Leu Lys Gly Val Glu Leu Lys Leu Pro Gly Gly Ser
                165                 170                 175

Ile Thr Phe Thr Cys Glu Ser Trp Val Ala Pro Lys Ser Val Asp Pro
                180                 185                 190

Thr Lys Arg Ile Phe Phe Ser Asp Lys Ser Tyr Leu Pro Ser Gln Thr
            195                 200                 205

Pro Glu Pro Leu Lys Lys Tyr Arg Lys Glu Glu Leu Glu Thr Leu Gln
        210                 215                 220

Gly Lys Asn Arg Glu Glu Val Gly Glu Phe Thr Lys Phe Glu Arg Ile
225                 230                 235                 240

Tyr Asp Tyr Asp Val Tyr Asn Asp Val Gly Asp Pro Asp Asn Asp Pro
                245                 250                 255

Glu Leu Ala Arg Pro Val Ile Gly Gly Leu Thr His Pro Tyr Pro Arg
                260                 265                 270

Arg Cys Lys Thr Gly Arg Lys Pro Cys Glu Thr Asp Pro Ser Ser Glu
            275                 280                 285

Gln Arg Tyr Gly Gly Glu Phe Tyr Val Pro Arg Asp Glu Glu Phe Ser
        290                 295                 300

Thr Ala Lys Gly Thr Ser Phe Thr Gly Lys Ala Val Leu Ala Ala Leu
305                 310                 315                 320

Pro Ser Ile Phe Pro Gln Ile Glu Ser Val Leu Leu Ser Pro Gln Glu
                325                 330                 335

Pro Phe Pro His Phe Lys Ala Ile Gln Asn Leu Phe Glu Glu Gly Ile
            340                 345                 350

Gln Leu Pro Lys Asp Ala Gly Leu Leu Pro Leu Leu Pro Arg Ile Ile
        355                 360                 365

Lys Ala Leu Gly Glu Ala Gln Asp Asp Ile Leu Gln Phe Asp Ala Pro
        370                 375                 380

Val Leu Ile Asn Arg Asp Arg Phe Ser Trp Leu Arg Asp Asp Glu Phe
385                 390                 395                 400

Ala Arg Gln Thr Leu Ala Gly Leu Asn Pro Tyr Ser Ile Gln Leu Val
                405                 410                 415

Glu Glu Trp Pro Leu Ile Ser Lys Leu Asp Pro Ala Val Tyr Gly Asp
            420                 425                 430

Pro Thr Ser Leu Ile Thr Trp Glu Ile Val Glu Arg Glu Val Lys Gly
        435                 440                 445
```

```
Asn Met Thr Val Asp Glu Ala Leu Lys Asn Lys Arg Leu Phe Val Leu
    450                 455                 460

Asp Tyr His Asp Leu Leu Pro Tyr Val Asn Lys Val Arg Glu Leu
465                 470                 475                 480

Asn Asn Thr Thr Leu Tyr Ala Ser Arg Thr Leu Phe Phe Leu Ser Asp
                485                 490                 495

Asp Ser Thr Leu Arg Pro Val Ala Ile Glu Leu Thr Cys Pro Pro Asn
            500                 505                 510

Ile Asn Lys Pro Gln Trp Lys Gln Val Phe Thr Pro Gly Tyr Asp Ala
        515                 520                 525

Thr Ser Cys Trp Leu Trp Asn Leu Ala Lys Thr His Ala Ile Ser His
    530                 535                 540

Asp Ala Gly Tyr His Gln Leu Ile Ser His Trp Leu Arg Thr His Ala
545                 550                 555                 560

Cys Thr Glu Pro Tyr Ile Ile Ala Ala Asn Arg Gln Leu Ser Ala Met
                565                 570                 575

His Pro Ile Tyr Arg Leu Leu His Pro His Phe Arg Tyr Thr Met Glu
            580                 585                 590

Ile Asn Ala Arg Ala Arg Gln Ser Leu Val Asn Gly Gly Ile Ile
        595                 600                 605

Glu Thr Cys Phe Trp Pro Gly Lys Tyr Ala Leu Glu Leu Ser Ser Ala
    610                 615                 620

Val Tyr Gly Lys Leu Trp Arg Phe Asp Gln Glu Gly Leu Pro Ala Asp
625                 630                 635                 640

Leu Ile Lys Arg Gly Leu Ala Glu Glu Asp Lys Thr Ala Glu His Gly
                645                 650                 655

Val Arg Leu Thr Ile Pro Asp Tyr Pro Phe Ala Asn Asp Gly Leu Ile
            660                 665                 670

Leu Trp Asp Ala Ile Lys Glu Trp Val Thr Asp Tyr Val Lys His Tyr
        675                 680                 685

Tyr Pro Asp Glu Glu Leu Ile Thr Ser Asp Glu Glu Leu Gln Gly Trp
    690                 695                 700

Trp Ser Glu Val Arg Asn Ile Gly His Gly Asp Lys Lys Asp Glu Pro
705                 710                 715                 720

Trp Trp Pro Val Leu Lys Thr Gln Asp Asp Leu Ile Gly Val Val Thr
                725                 730                 735

Thr Ile Ala Trp Val Thr Ser Gly His His Ala Ala Val Asn Phe Gly
            740                 745                 750

Gln Tyr Gly Tyr Gly Gly Tyr Phe Pro Asn Arg Pro Thr Thr Thr Arg
        755                 760                 765

Ile Arg Met Pro Thr Glu Asp Pro Thr Asp Glu Ala Leu Lys Glu Phe
    770                 775                 780

Tyr Glu Ser Pro Glu Lys Val Leu Leu Lys Thr Tyr Pro Ser Gln Lys
785                 790                 795                 800

Gln Ala Thr Leu Val Met Val Thr Leu Asp Leu Leu Ser Thr His Ser
                805                 810                 815

Pro Asp Glu Glu Tyr Ile Gly Glu Gln Gln Glu Ala Ser Trp Ala Asn
            820                 825                 830

Glu Pro Val Ile Asn Ala Ala Phe Glu Arg Phe Lys Gly Lys Leu Gln
        835                 840                 845

Tyr Leu Glu Gly Val Ile Asp Glu Arg Asn Val Asn Ile Thr Leu Lys
    850                 855                 860
```

```
Asn Arg Ala Gly Ala Gly Val Val Lys Tyr Glu Leu Leu Lys Pro Thr
865                 870                 875                 880

Ser Glu His Gly Val Thr Gly Met Gly Val Pro Tyr Ser Ile Ser Ile
            885                 890                 895
```

<210> SEQ ID NO 22
<211> LENGTH: 941
<212> TYPE: PRT
<213> ORGANISM: Oryza sativa

<400> SEQUENCE: 22

```
Met Leu Arg Pro Gln Leu Asn Pro Ser Ser His His Thr Thr
1               5                   10                  15

Thr Thr Ser Ser Ser Ser Thr Gln Leu Tyr Phe Ala Ser Ser Ser
                20                  25                  30

Cys Ile Ala Ser Leu Arg Arg Pro Ser Pro Ser Leu Ile Ala Gly
                35                  40                  45

Ala Gly Cys Arg Thr Thr Arg Arg Gln Gln Gly Arg Gln Arg Val
    50                  55                  60

Val Val Arg Cys Ala Ser Ser Ala Ala Ser Ser Ala Ser Glu Ala
65                  70                  75                  80

Ala Arg Arg Gly Thr Gly Ser Ser Asp Met Ala Pro Ala Ala Val Val
                85                  90                  95

Lys Val Lys Ala Val Ala Thr Ile Lys Val Thr Val Glu Gly Leu Leu
                100                 105                 110

Asn Ser Leu Arg Pro Ser Lys Ala Ile Asp Asn Ile Arg Asp Leu Ile
                115                 120                 125

Gly Arg Ser Leu Phe Leu Glu Leu Val Ser Ser Glu Leu Glu Ala Lys
    130                 135                 140

Thr Gly Lys Lys Lys Ala Thr Val His Ser Tyr Ala His Lys Val Asp
145                 150                 155                 160

Asp Asp Asp His Gly Val Val Thr Tyr Glu Ala Asp Phe Asp Val Pro
                165                 170                 175

Thr Gly Phe Gly Pro Ile Gly Ala Val Val Val Thr Asn Glu Leu Gly
                180                 185                 190

Gln Glu Met Phe Leu Glu Asp Leu Asn Leu Thr Ala Gly Asp Gly Ala
            195                 200                 205

Gly Asn Ser Thr Val Leu Pro Ile Arg Cys Asn Ser Trp Val Gln Pro
    210                 215                 220

Lys Ser Ser Ile Asp Glu Gly Thr Pro Gly Lys Arg Ile Phe Phe Ala
225                 230                 235                 240

Lys Ala Tyr Leu Pro Gly Gln Thr Pro Ala Gly Leu Arg Ser Tyr Arg
                245                 250                 255

Glu Glu Asp Leu Lys Gln Lys Arg Gly Asn Gly Ala Gly Gln Arg Glu
                260                 265                 270

Ala Asp Asp Arg Val Tyr Asp Tyr Asp Val Tyr Asn Asp Leu Gly Asn
            275                 280                 285

Pro Asp Ser Asn Gly Asp Leu Ala Arg Pro Val Leu Gly Gly Ser Lys
    290                 295                 300

Gln Phe Pro Tyr Pro Arg Arg Cys Arg Thr Gly Arg Pro Pro Ser Lys
305                 310                 315                 320

Lys Asp Pro Lys Ser Glu Thr Arg Lys Gly Asn Val Tyr Val Pro Arg
                325                 330                 335

Asp Glu Glu Phe Ser Glu Val Lys Asn Ala Gln Phe Leu Leu Lys Thr
                340                 345                 350
```

```
Leu Gln Ser Val Leu His Ala Ala Val Pro Ala Ala Gln Ser Ala Leu
            355                 360                 365

Ile Asp Asn Leu Ser Leu Asn Leu Pro Phe Pro Ser Phe Phe Val Ile
        370                 375                 380

Asp Lys Leu Phe Glu Asp Gly Val Glu Leu Pro Gly Val Glu Lys Leu
385                 390                 395                 400

Gly Phe Leu His Ser Ile Val Pro Arg Leu Leu Glu Leu Leu Arg Asp
                405                 410                 415

Ser Pro Gly Asp Lys Ile Leu Leu Phe Asp Thr Pro Ala Asn Val Gln
                420                 425                 430

Lys Asp Lys Phe Ala Trp Leu Arg Asp Glu Glu Phe Ala Arg Glu Thr
            435                 440                 445

Leu Ala Gly Ile Asn Pro Tyr Ala Ile Glu Leu Val Arg Glu Phe Pro
        450                 455                 460

Leu Lys Ser Lys Leu Asp Pro Ala Val Tyr Gly Pro Ala Glu Ser Ala
465                 470                 475                 480

Ile Thr Ala Asp Leu Leu Glu Glu Gln Met Arg Arg Val Met Thr Val
                485                 490                 495

Glu Glu Ala Ile Ser Gln Lys Arg Leu Phe Met Leu Asp Phe His Asp
                500                 505                 510

Leu Phe Leu Pro Tyr Val His Lys Ile Arg Ser Leu Lys His Thr Thr
            515                 520                 525

Met Tyr Gly Ser Arg Thr Ile Phe Phe Leu Thr Asp Asp Gly Thr Leu
        530                 535                 540

Arg Leu Leu Ala Ile Glu Leu Thr Arg Pro Ala Ser Pro Ser Gln Pro
545                 550                 555                 560

Gln Trp Arg Gln Val Phe Thr Pro Ser Thr Asp Thr Thr Lys Ser Trp
                565                 570                 575

Leu Trp Arg Met Ala Lys Ala His Val Arg Ala His Asp Ala Gly His
            580                 585                 590

His Glu Leu Ile Thr His Trp Leu Arg Thr His Cys Ala Val Glu Pro
        595                 600                 605

Tyr Ile Ile Ala Ala Asn Arg Gln Leu Ser Glu Met His Pro Ile Tyr
610                 615                 620

Gln Leu Leu His Pro His Phe Arg Tyr Thr Met Arg Ile Asn Ala Leu
625                 630                 635                 640

Ala Arg Ser Arg Leu Ile Ser Ala Ala Gly Ile Ile Glu Leu Ser Phe
            645                 650                 655

Ser Pro Gln Lys Tyr Ser Met Glu Leu Ser Ser Val Ala Tyr Asp Lys
        660                 665                 670

Leu Trp Arg Phe Asp Met Glu Ala Leu Pro Ala Asp Leu Val Arg Arg
        675                 680                 685

Gly Met Ala Glu Glu Asp Pro Thr Ala Glu His Gly Leu Arg Leu Ala
        690                 695                 700

Ile Glu Asp Tyr Pro Phe Ala Asn Asp Gly Leu Leu Ile Trp Asp Ala
705                 710                 715                 720

Ile Lys Thr Trp Val Gln Ala Tyr Val Ala Arg Phe Tyr Pro Asp Ala
                725                 730                 735

Asp Ser Val Ala Gly Asp Glu Glu Leu Gln Ala Phe Trp Thr Glu Val
            740                 745                 750

Arg Thr Lys Gly His Gly Asp Lys Lys Asp Ala Pro Trp Trp Pro Lys
        755                 760                 765
```

```
Leu Asp Ser Pro Glu Ser Leu Ala His Thr Leu Thr Thr Ile Val Trp
770                 775                 780

Val Ala Ala Ala His His Ala Ala Val Asn Phe Gly Gln Tyr Asp Phe
785                 790                 795                 800

Gly Gly Tyr Phe Pro Asn Arg Pro Ser Ile Ala Arg Thr Val Met Pro
                805                 810                 815

Val Glu Glu Pro Val Asp Gly Ala Ala Met Glu Arg Phe Leu Asp Asn
                820                 825                 830

Pro Asp Gln Ala Leu Arg Glu Cys Phe Pro Ser Gln Val Gln Ala Thr
            835                 840                 845

Val Val Met Ala Val Leu Asp Val Leu Ser Thr His Ser Thr Asp Glu
850                 855                 860

Glu Tyr Leu Gly Gly Glu Gln Thr Arg Pro Trp Asn Ser Asp Ala Ala
865                 870                 875                 880

Val Gln Ala Ala Tyr Ala Gly Phe Thr Ala Arg Leu Lys Glu Ile Glu
                885                 890                 895

Gly Val Ile Asp Gly Arg Asn Lys Asp Arg Lys Leu Lys Asn Arg Cys
                900                 905                 910

Gly Ala Gly Ile Leu Pro Tyr Gln Leu Met Lys Pro Phe Ser Asp Ala
            915                 920                 925

Gly Val Thr Gly Met Gly Ile Pro Asn Ser Thr Ser Ile
930                 935                 940

<210> SEQ ID NO 23
<211> LENGTH: 685
<212> TYPE: PRT
<213> ORGANISM: Pseudomonas aeruginosa

<400> SEQUENCE: 23

Met Lys Arg Arg Ser Val Leu Leu Ser Gly Val Ala Leu Ser Gly Thr
1               5                   10                  15

Ala Leu Ala Asn Asp Ser Ile Phe Phe Ser Pro Leu Lys Tyr Leu Gly
                20                  25                  30

Ala Glu Gln Gln Arg Ser Ile Asp Ala Ser Arg Ser Leu Leu Asp Asn
            35                  40                  45

Leu Ile Pro Pro Ser Leu Pro Gln Tyr Asp Asn Leu Ala Gly Lys Leu
50                  55                  60

Ala Arg Arg Ala Val Leu Thr Ser Lys Lys Leu Val Tyr Val Trp Thr
65                  70                  75                  80

Glu Asn Phe Ala Asn Val Lys Gly Val Pro Met Ala Arg Ser Val Pro
                85                  90                  95

Leu Gly Glu Leu Pro Asn Val Asp Trp Leu Leu Lys Thr Ala Gly Val
                100                 105                 110

Ile Val Glu Leu Ile Val Asn Phe Val Ala Ser Leu Pro Ala Ser Ala
            115                 120                 125

Ala Ala Gln Phe Glu Arg Ile Ala Ala Gly Leu Ser Gly Asp Leu Glu
            130                 135                 140

Ala Ala Arg Gln Val His Glu Ala Leu Leu Glu Ala Lys Asn Asp
145                 150                 155                 160

Pro Ala Ala Ala Gly Ser Leu Leu Arg Phe Thr Glu Leu Gln Thr
                165                 170                 175

Arg Val Ile Ala Leu Leu Thr Arg Val Gly Leu Leu Val Asp Asp Ile
            180                 185                 190

Leu Lys Ser Ala Ser Asn Leu Val Thr Gln Gly Gly Gln Gly Asp Gly
            195                 200                 205
```

```
Leu Asn Arg Phe Arg Ala Val Phe Gly Thr Leu Arg Leu Pro Glu Val
    210                 215                 220

Ala Asp Ser Phe Arg Asp Asp Glu Ala Phe Ala Tyr Trp Arg Val Ala
225                 230                 235                 240

Gly Pro Asn Pro Leu Leu Ile Arg Arg Val Asp Ala Leu Pro Ala Asn
                245                 250                 255

Phe Pro Leu Gly Glu Glu Gln Phe Arg Arg Val Met Gly Ala Asp Asp
            260                 265                 270

Ser Leu Leu Glu Ala Ala Ser Arg Arg Leu Tyr Leu Leu Asp Tyr
        275                 280                 285

Ala Glu Leu Gly Lys Leu Ala Pro Ser Gly Ala Val Asp Lys Leu Leu
290                 295                 300

Thr Gly Thr Gly Phe Ala Tyr Ala Pro Ile Ala Leu Phe Ala Leu Gly
305                 310                 315                 320

Lys Asp Arg Ala Gly Leu Leu Pro Val Ala Ile Gln Cys Gly Gln Asp
                325                 330                 335

Pro Ala Thr His Pro Met Phe Val Arg Pro Ala Glu Ser Glu Ser Asp
                340                 345                 350

Leu Tyr Trp Gly Trp Gln Met Ala Lys Thr Val Val Gln Val Ala Glu
            355                 360                 365

Glu Asn Tyr His Glu Met Phe Val His Leu Ala Gln Thr His Leu Val
370                 375                 380

Ser Glu Ala Phe Cys Leu Ala Thr Gln Arg Thr Leu Ala Pro Ser His
385                 390                 395                 400

Pro Leu His Val Leu Leu Ala Pro His Phe Glu Gly Thr Leu Phe Ile
                405                 410                 415

Asn Glu Gly Ala Ala Arg Ile Leu Leu Pro Ser Ala Gly Phe Ile Asp
            420                 425                 430

Val Met Phe Ala Ala Pro Ile Gln Asp Thr Gln Ala Thr Ala Gly Gly
            435                 440                 445

Asn Arg Leu Gly Phe Asp Phe Tyr Arg Gly Met Leu Pro Glu Ser Leu
    450                 455                 460

Lys Ala Arg Asn Val Asp Asp Pro Ala Ala Leu Pro Asp Tyr Pro Tyr
465                 470                 475                 480

Arg Asp Asp Gly Leu Leu Val Trp Asn Ala Ile Arg Gln Trp Ala Ala
                485                 490                 495

Asp Tyr Val Ala Val Tyr Tyr Ala Ser Asp Gly Asp Val Thr Ala Asp
                500                 505                 510

Val Glu Leu Ala Ala Trp Val Gly Glu Val Ile Gly Ser Gly Lys Val
            515                 520                 525

Ala Gly Phe Arg Pro Ile Thr Gly Arg Ser Gln Leu Val Glu Val Leu
            530                 535                 540

Thr Met Val Ile Phe Thr Ala Ser Ala Gln His Ala Ala Val Asn Phe
545                 550                 555                 560

Pro Gln Pro Ser Met Met Thr Tyr Ala Pro Ala Ile Cys Ala Met Ser
                565                 570                 575

Ala Ala Pro Ala Pro Asp Ser Pro Ser Gly Lys Ser Glu Ala Asp Trp
            580                 585                 590

Leu Lys Met Met Pro Pro Thr Leu Val Ala Leu Glu Lys Val Asn Ile
        595                 600                 605

Tyr His Leu Leu Gly Ser Val Tyr His Gly Arg Leu Gly Asp Tyr Arg
    610                 615                 620
```

```
Gln Thr Gly Phe Pro Tyr Ala Pro Val Phe Ser Asp Arg Arg Val Thr
625                 630                 635                 640

Ala Ser Gly Gly Pro Leu Glu Arg Phe Gln Ala Arg Leu Lys Glu Val
                645                 650                 655

Glu Ala Thr Ile Arg Thr Arg Asn Gln Ala Arg Arg Lys Pro Tyr Glu
            660                 665                 670

Tyr Leu Leu Pro Ser Arg Ile Pro Ala Ser Thr Asn Ile
            675                 680                 685

<210> SEQ ID NO 24
<211> LENGTH: 880
<212> TYPE: PRT
<213> ORGANISM: Momordica charantia

<400> SEQUENCE: 24

Met Phe Gly Ile Gly Lys Ser Ile Ile Glu Gly Ala Val Asn Thr Thr
1               5                   10                  15

Gly Asp Leu Ala Gly Ser Val Ile Asn Ala Gly Gly Asn Ile Val Gly
                20                  25                  30

Arg Val Thr Asn Ile Gly Gly Lys Lys Ile Lys Gly Thr Val Val Leu
            35                  40                  45

Met Arg Ser Asn Val Leu Asp Phe Thr Glu Phe His Ser Ser Leu Leu
50                  55                  60

Asp Gly Val Thr Glu Leu Leu Gly Gly Ile Ser Leu Gln Leu Ile
65                  70                  75                  80

Ser Ala Thr His Ala Ser Asn Asp Ser Arg Gly Lys Val Gly Lys Gly
                85                  90                  95

Ala Phe Leu Glu Arg Trp Leu Thr Ser Val Pro Pro Leu Phe Ala Gly
                100                 105                 110

Glu Ser Val Phe Gln Val Asn Phe Asp Trp Glu Glu Asn Phe Gly Phe
            115                 120                 125

Pro Gly Ala Phe Phe Ile Lys Asn Gly His Thr Ser Glu Phe Phe Leu
130                 135                 140

Lys Ser Val Thr Leu Glu Asp Val Pro Gly Phe Gly Arg Val His Phe
145                 150                 155                 160

Asp Cys Asn Ser Trp Val Tyr Pro Ser Arg Arg Tyr Lys Lys Asp Arg
                165                 170                 175

Ile Phe Phe Ala Asn His Thr Cys Leu Pro Ile Asp Thr Pro Asp Ser
            180                 185                 190

Leu Arg Lys Tyr Arg Glu Glu Leu Leu Asn Leu Arg Gly Asp Gly
            195                 200                 205

Thr Gly Glu Arg Lys Glu Trp Asp Arg Ile Tyr Asp Tyr Asp Val Tyr
210                 215                 220

Asn Asp Leu Cys Asp Pro Asn Gly Gly Pro Asn Leu Val Arg Pro Ile
225                 230                 235                 240

Leu Gly Gly Ser Asp Gln Tyr Pro Tyr Pro Arg Arg Gly Arg Thr Gly
                245                 250                 255

Arg Pro Pro Ala Arg Lys Asp His Lys Tyr Glu Ser Arg Leu Ser Asp
            260                 265                 270

Val Met Ser Leu Asn Ile Tyr Val Pro Arg Asp Glu Asn Phe Gly His
            275                 280                 285

Leu Lys Met Ala Asp Phe Leu Gly Asn Thr Leu Lys Val Leu Ser Thr
            290                 295                 300

Ser Ile Gln Pro Gly Leu Glu Ile Phe Asp Ser Thr Pro Gly Glu
305                 310                 315                 320
```

```
Phe Asp Lys Phe Lys Glu Val Asp Asp Leu Phe Glu Arg Gly Phe Pro
            325                 330                 335

Ile Pro Leu Asn Ile Phe Lys Asn Leu Thr Glu Asp Leu Ala Pro Pro
            340                 345                 350

Leu Phe Lys Ala Phe Leu Arg Ser Asp Gly Arg Phe Leu Lys Tyr
            355                 360                 365

Pro Thr Pro Gln Val Ile Lys Asp Asn Lys Leu Gly Trp Arg Thr Asp
            370                 375                 380

Glu Glu Phe Ala Arg Glu Met Ile Ala Gly Val Asn Pro Leu Ile Ile
385                     390                 395                 400

Arg Arg Leu Glu Val Phe Pro Pro Leu Ser Lys Leu Asp Pro His Val
                405                 410                 415

Tyr Gly Asn Gln Asn Ser Thr Met Thr Glu Glu Gln Ile Lys His Gly
            420                 425                 430

Leu Asp Gly Leu Thr Val Asp Glu Ala Ile Lys Glu Asn Lys Leu Tyr
            435                 440                 445

Ile Leu Asp His His Asp Ala Leu Met Pro Tyr Leu Arg Arg Ile Asn
    450                 455                 460

Ser Thr Ser Thr Lys Thr Tyr Ala Thr Arg Thr Leu Leu Phe Leu Lys
465                 470                 475                 480

Asp Asp Ser Thr Leu Lys Pro Leu Ala Ile Glu Leu Ser Leu Pro His
                485                 490                 495

Pro Gln Gly Asp Glu His Gly Ala Ile Ser Lys Leu Tyr Phe Pro Ala
                500                 505                 510

Glu Gly Arg Val Glu Ser Ala Ile Trp Gln Leu Ala Lys Ala Tyr Val
                515                 520                 525

Ala Val Asn Asp Ser Gly Tyr His Gln Leu Asn Ser His Trp Leu His
    530                 535                 540

Thr His Ala Val Leu Glu Pro Phe Val Ile Thr His Arg Arg Leu
545                 550                 555                 560

Ser Val Leu His Pro Ile His Lys Leu Leu Ala Pro His Tyr Lys Asp
                565                 570                 575

Thr Met Phe Ile Asn Ala Ser Ala Arg Gln Val Leu Ile Asn Ala Gly
            580                 585                 590

Gly Leu Ile Glu Ser Thr Gln Phe Pro Ala Lys Tyr Ala Met Glu Leu
            595                 600                 605

Ser Ser Tyr Ile Tyr Lys Glu Trp Lys Phe Pro Asp Glu Ala Leu Pro
            610                 615                 620

Thr Asn Leu Ile Lys Arg Gly Val Ala Ile Glu Asp Ser Gly Ser Pro
625                 630                 635                 640

His Gly Val Arg Leu Leu Ile Asn Asp Tyr Pro Phe Ala Val Asp Gly
                645                 650                 655

Leu Glu Ile Trp Ser Ala Ile Lys Thr Trp Val Thr Asp Tyr Cys Ser
                660                 665                 670

Leu Tyr Tyr Lys Asp Asp Ala Ile Arg Asn Asp Val Glu Leu Gln
            675                 680                 685

Ser Trp Trp Lys Glu Leu Arg Glu Lys Gly His Thr Asp Lys Lys Asp
690                 695                 700

Glu Pro Trp Trp Pro Lys Met Gln Thr Phe Ser Glu Leu Ile Glu Ser
705                 710                 715                 720

Cys Thr Ile Ile Ile Trp Ile Ser Ser Ala Leu His Ala Ala Val Asn
                725                 730                 735
```

-continued

Phe Gly Gln Tyr Pro Tyr Gly Gly Tyr Val Pro Asn Arg Pro Thr Thr
                740                 745                 750

Ser Arg Arg Phe Met Pro Glu Val Gly Thr Ala Glu Tyr Lys Glu Val
        755                 760                 765

Glu Ser Asn Pro Glu Lys Ala Phe Leu Arg Thr Ile Ser Ser Gln Ile
    770                 775                 780

Val Ala Leu Leu Gly Leu Ser Ile Ile Glu Ile Leu Ser Lys His Ala
785                 790                 795                 800

Ser Asp Glu Val Tyr Leu Gly Gln Arg Ala Ser Ile Glu Trp Thr Ser
                805                 810                 815

Asp Lys Ser Ala Ile Glu Ala Phe Glu Lys Phe Gly Lys Glu Leu Phe
        820                 825                 830

Glu Val Glu Asp Arg Ile Met Arg Arg Asn Gln Asp Val Asn Leu Lys
    835                 840                 845

Asn Arg Ala Gly Pro Val Asn Met Pro Tyr Thr Leu Leu Val Pro Ser
850                 855                 860

Ser Thr Glu Gly Leu Thr Gly Arg Gly Ile Pro Asn Ser Ile Ser Ile
865                 870                 875                 880

<210> SEQ ID NO 25
<211> LENGTH: 674
<212> TYPE: PRT
<213> ORGANISM: Homo sapiens

<400> SEQUENCE: 25

Met Pro Ser Tyr Thr Val Thr Val Ala Thr Gly Ser Gln Trp Phe Ala
1               5                   10                  15

Gly Thr Asp Asp Tyr Ile Tyr Leu Ser Leu Val Gly Ser Ala Gly Cys
                20                  25                  30

Ser Glu Lys His Leu Leu Asp Lys Pro Phe Tyr Asn Asp Phe Glu Arg
            35                  40                  45

Gly Ala Val Asp Ser Tyr Asp Val Thr Val Asp Glu Glu Leu Gly Glu
        50                  55                  60

Ile Gln Leu Val Arg Ile Glu Lys Arg Lys Tyr Trp Leu Asn Asp Asp
65                  70                  75                  80

Trp Tyr Leu Lys Tyr Ile Thr Leu Lys Thr Pro His Gly Asp Tyr Ile
                85                  90                  95

Glu Phe Pro Cys Tyr Arg Trp Ile Thr Gly Asp Val Glu Val Val Leu
            100                 105                 110

Arg Asp Gly Arg Ala Lys Leu Ala Arg Asp Asp Gln Ile His Ile Leu
        115                 120                 125

Lys Gln His Arg Arg Lys Glu Leu Glu Thr Arg Gln Lys Gln Tyr Arg
    130                 135                 140

Trp Met Glu Trp Asn Pro Gly Phe Pro Leu Ser Ile Asp Ala Lys Cys
145                 150                 155                 160

His Lys Asp Leu Pro Arg Asp Ile Gln Phe Asp Ser Glu Lys Gly Val
                165                 170                 175

Asp Phe Val Leu Asn Tyr Ser Lys Ala Met Glu Asn Leu Phe Ile Asn
            180                 185                 190

Arg Phe Met His Met Phe Gln Ser Ser Trp Asn Asp Phe Ala Asp Phe
        195                 200                 205

Glu Lys Ile Phe Val Lys Ile Ser Asn Thr Ile Ser Glu Arg Val Met
    210                 215                 220

Asn His Trp Gln Glu Asp Leu Met Phe Gly Tyr Gln Phe Leu Asn Gly
225                 230                 235                 240

```
Cys Asn Pro Val Leu Ile Arg Arg Cys Thr Glu Leu Pro Glu Lys Leu
            245                 250                 255
Pro Val Thr Thr Glu Met Val Glu Cys Ser Leu Glu Arg Gln Leu Ser
            260                 265                 270
Leu Glu Gln Glu Val Gln Gln Gly Asn Ile Phe Ile Val Asp Phe Glu
            275                 280                 285
Leu Leu Asp Gly Ile Asp Ala Asn Lys Thr Asp Pro Cys Thr Leu Gln
            290                 295                 300
Phe Leu Ala Ala Pro Ile Cys Leu Leu Tyr Lys Asn Leu Ala Asn Lys
305                 310                 315                 320
Ile Val Pro Ile Ala Ile Gln Leu Asn Gln Ile Pro Gly Asp Glu Asn
            325                 330                 335
Pro Ile Phe Leu Pro Ser Asp Ala Lys Tyr Asp Trp Leu Leu Ala Lys
            340                 345                 350
Ile Trp Val Arg Ser Ser Asp Phe His Val His Gln Thr Ile Thr His
            355                 360                 365
Leu Leu Arg Thr His Leu Val Ser Glu Val Phe Gly Ile Ala Met Tyr
            370                 375                 380
Arg Gln Leu Pro Ala Val His Pro Ile Phe Lys Leu Leu Val Ala His
385                 390                 395                 400
Val Arg Phe Thr Ile Ala Ile Asn Thr Lys Ala Arg Glu Gln Leu Ile
            405                 410                 415
Cys Glu Cys Gly Leu Phe Asp Lys Ala Asn Ala Thr Gly Gly Gly Gly
            420                 425                 430
His Val Gln Met Val Gln Arg Ala Met Lys Asp Leu Thr Tyr Ala Ser
            435                 440                 445
Leu Cys Phe Pro Glu Ala Ile Lys Ala Arg Gly Met Glu Ser Lys Glu
            450                 455                 460
Asp Ile Pro Tyr Tyr Phe Tyr Arg Asp Asp Gly Leu Leu Val Trp Glu
465                 470                 475                 480
Ala Ile Arg Thr Phe Thr Ala Glu Val Val Asp Ile Tyr Tyr Glu Gly
            485                 490                 495
Asp Gln Val Val Glu Glu Asp Pro Glu Leu Gln Asp Phe Val Asn Asp
            500                 505                 510
Val Tyr Val Tyr Gly Met Arg Gly Arg Lys Ser Ser Gly Phe Pro Lys
            515                 520                 525
Ser Val Lys Ser Arg Glu Gln Leu Ser Glu Tyr Leu Thr Val Val Ile
            530                 535                 540
Phe Thr Ala Ser Ala Gln His Ala Ala Val Asn Phe Gly Gln Tyr Asp
545                 550                 555                 560
Trp Cys Ser Trp Ile Pro Asn Ala Pro Pro Thr Met Arg Ala Pro Pro
            565                 570                 575
Pro Thr Ala Lys Gly Val Val Thr Ile Glu Gln Ile Val Asp Thr Leu
            580                 585                 590
Pro Asp Arg Gly Arg Ser Cys Trp His Leu Gly Ala Val Trp Ala Leu
            595                 600                 605
Ser Gln Phe Gln Glu Asn Glu Leu Phe Leu Gly Met Tyr Pro Glu Glu
            610                 615                 620
His Phe Ile Glu Lys Pro Val Lys Glu Ala Met Ala Arg Phe Arg Lys
625                 630                 635                 640
Asn Leu Glu Ala Ile Val Ser Val Ile Ala Glu Arg Asn Lys Lys Lys
            645                 650                 655
```

```
Gln Leu Pro Tyr Tyr Leu Ser Pro Asp Arg Ile Pro Asn Ser Val
            660                 665                 670

Ala Ile

<210> SEQ ID NO 26
<211> LENGTH: 1066
<212> TYPE: PRT
<213> ORGANISM: Plexaura homomalla

<400> SEQUENCE: 26

Met Thr Trp Lys Asn Phe Gly Phe Glu Ile Phe Gly Glu Lys Tyr Gly
  1               5                  10                  15

Gln Glu Glu Leu Glu Lys Arg Ile Lys Asp Glu His Thr Pro Pro
             20                  25                  30

Asp Ser Pro Val Phe Gly Gly Leu Lys Leu Lys Leu Lys Glu Lys
         35                  40                  45

Phe Lys Thr Leu Phe Thr Leu Gly Thr Thr Leu Lys Gly Phe Arg Arg
 50                  55                  60

Ala Thr His Thr Val Gly Thr Gly Gly Ile Gly Glu Ile Thr Ile Val
 65                  70                  75                  80

Asn Asp Pro Lys Phe Pro Glu His Glu Phe Thr Ala Gly Arg Thr
                 85                  90                  95

Phe Pro Ala Arg Leu Arg His Ala Asn Leu Lys Tyr Pro Asp Asp Ala
                100                 105                 110

Gly Ala Asp Ala Arg Ser Phe Ser Ile Lys Phe Ala Asp Ser Asp Ser
            115                 120                 125

Asp Gly Pro Leu Asp Ile Val Met Asn Thr Gly Glu Ala Asn Ile Phe
130                 135                 140

Trp Asn Ser Pro Ser Leu Glu Asp Phe Val Pro Val Glu Glu Gly Asp
145                 150                 155                 160

Ala Ala Glu Glu Tyr Val Tyr Lys Asn Pro Tyr Tyr Tyr Asn Leu
                165                 170                 175

Val Glu Ala Leu Arg Arg Ala Pro Asp Thr Phe Ala His Leu Tyr Tyr
                180                 185                 190

Tyr Ser Gln Val Thr Met Pro Phe Lys Ala Lys Asp Gly Lys Val Arg
            195                 200                 205

Tyr Cys Arg Tyr Arg Ala Leu Pro Gly Asp Val Asp Ile Lys Glu Glu
210                 215                 220

Asp Glu Ser Gly Arg Leu Thr Glu Glu Gln Arg Lys Ile Trp Ile
225                 230                 235                 240

Phe Ser Arg His Glu Asn Glu Lys Arg Pro Asp Asp Tyr Leu Arg Lys
                245                 250                 255

Glu Tyr Val Glu Arg Leu Gln Lys Gly Pro Val Asn Tyr Arg Leu Gln
                260                 265                 270

Ile Gln Ile His Glu Ala Ser Pro Asp Asp Thr Ala Thr Ile Phe His
            275                 280                 285

Ala Gly Ile Leu Trp Asp Lys Glu Thr His Pro Trp Phe Asp Leu Ala
        290                 295                 300

Lys Val Ser Ile Lys Thr Pro Leu Ser Pro Asp Val Leu Glu Lys Thr
305                 310                 315                 320

Ala Phe Asn Ile Ala Asn Gln Pro Ala Ser Leu Gly Leu Leu Glu Ala
                325                 330                 335

Lys Ser Pro Glu Asp Tyr Asn Ser Ile Gly Glu Leu Arg Val Ala Val
                340                 345                 350
```

-continued

```
Tyr Thr Trp Val Gln His Leu Arg Lys Leu Lys Ile Gly Ser Leu Val
        355                 360                 365

Pro Ala Gly Gln Asn Ala Ile Tyr Asn Val Glu Val Glu Thr Gly Asp
370                 375                 380

Arg Glu His Ala Gly Thr Asp Ala Thr Ile Thr Ile Arg Ile Thr Gly
385                 390                 395                 400

Ala Lys Gly Arg Thr Asp Tyr Leu Lys Leu Asp Lys Trp Phe His Asn
                405                 410                 415

Asp Phe Glu Ala Gly Ser Lys Glu Gln Tyr Thr Val Gln Gly Phe Asp
                420                 425                 430

Val Gly Asp Ile Gln Leu Ile Glu Leu His Ser Asp Gly Gly Gly Tyr
            435                 440                 445

Trp Ser Gly Asp Pro Asp Trp Phe Val Asn Arg Val Ile Ile Ser
    450                 455                 460

Ser Thr Gln Asp Arg Val Tyr Ser Phe Pro Cys Phe Arg Trp Val Ile
465                 470                 475                 480

Lys Asp Met Val Leu Phe Pro Gly Glu Ala Thr Leu Pro Phe Asn Glu
                485                 490                 495

Val Pro Ala Ile Val Ser Glu Gln Arg Gln Lys Glu Leu Glu Gln Arg
                500                 505                 510

Lys Leu Thr Tyr Gln Trp Asp Tyr Val Ser Asp Asp Met Pro Gly Asn
            515                 520                 525

Ile Lys Ala Lys Thr His Asp Asp Leu Pro Arg Asp Val Gln Phe Thr
            530                 535                 540

Asp Glu Lys Ser Arg Ser Tyr Gln Glu Ser Arg Lys Ala Ala Leu Val
545                 550                 555                 560

Asn Leu Gly Ile Gly Ser Leu Phe Thr Met Phe Glu Asn Trp Asp Ser
                565                 570                 575

Tyr Asp Asp Tyr His Ile Leu Tyr Arg Asn Trp Ile Leu Gly Gly Thr
                580                 585                 590

Pro Asn Met Ala Asp Arg Trp His Glu Asp Arg Trp Phe Gly Tyr Gln
            595                 600                 605

Phe Leu Asn Gly Ala Asn Pro Val Ile Leu Thr Arg Cys Asp Ala Leu
610                 615                 620

Pro Ser Asn Phe Pro Val Thr Asn Glu His Val Asn Ala Ser Leu Asp
625                 630                 635                 640

Arg Gly Lys Asn Leu Asp Glu Glu Ile Lys Asp Gly His Ile Tyr Ile
                645                 650                 655

Val Asp Phe Lys Val Leu Val Gly Ala Lys Ser Tyr Gly Gly Pro Val
                660                 665                 670

Leu Glu Asp Ile Gly Tyr Lys Val Pro Asp His Leu Lys His Asp Glu
            675                 680                 685

Ala Asp Ile Arg Tyr Cys Ala Ala Pro Leu Ala Leu Phe Tyr Val Asn
690                 695                 700

Lys Leu Gly His Leu Met Pro Ile Ala Ile Gln Ile Asn Gln Glu Pro
705                 710                 715                 720

Gly Pro Glu Asn Pro Ile Trp Thr Pro His Glu Glu Asn Glu His Asp
                725                 730                 735

Trp Met Met Ala Lys Phe Trp Leu Gly Val Ala Glu Ser Asn Phe His
            740                 745                 750

Gln Leu Asn Thr His Leu Leu Arg Thr His Leu Thr Thr Glu Ser Phe
        755                 760                 765

Ala Leu Ser Thr Trp Arg Asn Leu Ala Ser Ala His Pro Val Phe Lys
```

```
             770                 775                 780
Leu Leu Gln Pro His Ile Tyr Gly Val Leu Ala Ile Asp Thr Ile Gly
785                 790                 795                 800

Arg Lys Glu Leu Ile Gly Ser Gly Gly Ile Val Asp Gln Ser Leu Ser
                805                 810                 815

Leu Gly Gly Gly Gly His Val Thr Phe Met Glu Lys Cys Phe Lys Glu
                820                 825                 830

Val Asn Leu Gln Asp Tyr His Leu Pro Asn Ala Leu Lys Lys Arg Gly
                835                 840                 845

Val Asp Asp Pro Ser Lys Leu Pro Gly Phe Tyr Tyr Arg Asp Asp Gly
                850                 855                 860

Leu Ala Leu Trp Glu Ala Ile Glu Thr Phe Ile Gly Glu Ile Ile Ala
865                 870                 875                 880

Ile Phe Tyr Lys Asn Asp Asp Val Lys Arg Asp Asn Glu Ile Gln
                885                 890                 895

Ser Trp Ile Tyr Asp Val His Lys Asn Gly Trp Arg Val Asn Pro Gly
                900                 905                 910

His Gln Asp His Gly Val Pro Ala Ser Phe Glu Ser Arg Glu Gln Leu
                915                 920                 925

Lys Glu Val Leu Thr Ser Leu Val Phe Thr Phe Ser Cys Gln His Ala
                930                 935                 940

Ala Val Asn Phe Ser Gln Lys Asp His Tyr Gly Phe Thr Pro Asn Ala
945                 950                 955                 960

Pro Ala Val Leu Arg His Pro Pro Lys Lys Lys Gly Glu Ala Thr
                965                 970                 975

Leu Gln Ser Ile Leu Ser Thr Leu Pro Ser Lys Ser Gln Ala Ala Lys
                980                 985                 990

Ala Ile Ala Thr Val Tyr Ile Leu Thr Lys Phe Ser Glu Asp Glu Arg
                995                 1000                1005

Tyr Leu Gly Asn Tyr Ser Ala Thr Ala Trp Glu Asp Lys Asp Ala
                1010                1015                1020

Leu Asp Ala Ile Asn Arg Phe Gln Asp Lys Leu Glu Asp Ile Ser
                1025                1030                1035

Lys Lys Ile Lys Gln Arg Asn Glu Asn Leu Glu Val Pro Tyr Ile
                1040                1045                1050

Tyr Leu Leu Pro Glu Arg Ile Pro Asn Gly Thr Ala Ile
                1055                1060                1065

<210> SEQ ID NO 27
<211> LENGTH: 663
<212> TYPE: PRT
<213> ORGANISM: Homo sapiens

<400> SEQUENCE: 27

Met Gly Arg Tyr Arg Ile Arg Val Ala Thr Gly Ala Trp Leu Phe Ser
1               5                   10                  15

Gly Ser Tyr Asn Arg Val Gln Leu Trp Leu Val Gly Thr Arg Gly Glu
                20                  25                  30

Ala Glu Leu Glu Leu Gln Leu Arg Pro Ala Arg Gly Glu Glu Glu Glu
            35                  40                  45

Phe Asp His Asp Val Ala Glu Asp Leu Gly Leu Leu Gln Phe Val Arg
        50                  55                  60

Leu Arg Lys His His Trp Leu Val Asp Asp Ala Trp Phe Cys Asp Arg
65              70                  75                  80
```

-continued

```
Ile Thr Val Gln Gly Pro Gly Ala Cys Ala Glu Val Ala Phe Pro Cys
                 85                  90                  95
Tyr Arg Trp Val Gln Gly Glu Asp Ile Leu Ser Leu Pro Glu Gly Thr
            100                 105                 110
Ala Arg Leu Pro Gly Asp Asn Ala Leu Asp Met Phe Gln Lys His Arg
        115                 120                 125
Glu Lys Glu Leu Lys Asp Arg Gln Ile Tyr Cys Trp Ala Thr Trp
    130                 135                 140
Lys Glu Gly Leu Pro Leu Thr Ile Ala Ala Asp Arg Lys Asp Asp Leu
145                 150                 155                 160
Pro Pro Asn Met Arg Phe His Glu Glu Lys Arg Leu Asp Phe Glu Trp
                165                 170                 175
Thr Leu Lys Ala Gly Ala Leu Glu Met Ala Leu Lys Arg Val Tyr Thr
            180                 185                 190
Leu Leu Ser Ser Trp Asn Cys Leu Glu Asp Phe Asp Gln Ile Phe Trp
        195                 200                 205
Gly Gln Lys Ser Ala Leu Ala Glu Lys Val Arg Gln Cys Trp Gln Asp
    210                 215                 220
Asp Glu Leu Phe Ser Tyr Gln Phe Leu Asn Gly Ala Asn Pro Met Leu
225                 230                 235                 240
Leu Arg Arg Ser Thr Ser Leu Pro Ser Arg Leu Val Leu Pro Ser Gly
                245                 250                 255
Met Glu Glu Leu Gln Ala Gln Leu Glu Lys Glu Leu Gln Asn Gly Ser
            260                 265                 270
Leu Phe Glu Ala Asp Phe Ile Leu Leu Asp Gly Ile Pro Ala Asn Val
        275                 280                 285
Ile Arg Gly Glu Lys Gln Tyr Leu Ala Ala Pro Leu Val Met Leu Lys
    290                 295                 300
Met Glu Pro Asn Gly Lys Leu Gln Pro Met Val Ile Gln Ile Gln Pro
305                 310                 315                 320
Pro Asn Pro Ser Ser Pro Thr Pro Thr Leu Phe Leu Pro Ser Asp Pro
                325                 330                 335
Pro Leu Ala Trp Leu Leu Ala Lys Ser Trp Val Arg Asn Ser Asp Phe
            340                 345                 350
Gln Leu His Glu Ile Gln Tyr His Leu Leu Asn Thr His Leu Val Ala
        355                 360                 365
Glu Val Ile Ala Val Ala Thr Met Arg Cys Leu Pro Gly Leu His Pro
    370                 375                 380
Ile Phe Lys Phe Leu Ile Pro His Ile Arg Tyr Thr Met Glu Ile Asn
385                 390                 395                 400
Thr Arg Ala Arg Thr Gln Leu Ile Ser Asp Gly Gly Ile Phe Asp Lys
                405                 410                 415
Ala Val Ser Thr Gly Gly Gly His Val Gln Leu Leu Arg Arg Ala
            420                 425                 430
Ala Ala Gln Leu Thr Tyr Cys Ser Leu Cys Pro Pro Asp Asp Leu Ala
        435                 440                 445
Asp Arg Gly Leu Leu Gly Leu Pro Gly Ala Leu Tyr Ala His Asp Ala
    450                 455                 460
Leu Arg Leu Trp Glu Ile Ile Ala Arg Tyr Val Glu Gly Ile Val His
465                 470                 475                 480
Leu Phe Tyr Gln Arg Asp Asp Ile Val Lys Gly Asp Pro Glu Leu Gln
                485                 490                 495
Ala Trp Cys Arg Glu Ile Thr Glu Val Gly Leu Cys Gln Ala Gln Asp
```

```
                    500                 505                 510
Arg Gly Phe Pro Val Ser Phe Gln Ser Gln Ser Gln Leu Cys His Phe
            515                 520                 525

Leu Thr Met Cys Val Phe Thr Cys Thr Ala Gln His Ala Ala Ile Asn
        530                 535                 540

Gln Gly Gln Leu Asp Trp Tyr Ala Trp Val Pro Asn Ala Pro Cys Thr
545                 550                 555                 560

Met Arg Met Pro Pro Thr Thr Lys Glu Asp Val Thr Met Ala Thr
                565                 570                 575

Val Met Gly Ser Leu Pro Asp Val Arg Gln Ala Cys Leu Gln Met Ala
            580                 585                 590

Ile Ser Trp His Leu Ser Arg Arg Gln Pro Asp Met Val Pro Leu Gly
        595                 600                 605

His His Lys Glu Lys Tyr Phe Ser Gly Pro Lys Pro Lys Ala Val Leu
            610                 615                 620

Asn Gln Phe Arg Thr Asp Leu Glu Lys Leu Glu Lys Glu Ile Thr Ala
625                 630                 635                 640

Arg Asn Glu Gln Leu Asp Trp Pro Tyr Glu Tyr Leu Lys Pro Ser Cys
                645                 650                 655

Ile Glu Asn Ser Val Thr Ile
            660

<210> SEQ ID NO 28
<211> LENGTH: 701
<212> TYPE: PRT
<213> ORGANISM: Homo sapiens

<400> SEQUENCE: 28

Met Ala Thr Tyr Lys Val Arg Val Ala Thr Gly Thr Asp Leu Leu Ser
1               5                   10                  15

Gly Thr Arg Asp Ser Ile Ser Leu Thr Ile Val Gly Thr Gln Gly Glu
            20                  25                  30

Ser His Lys Gln Leu Leu Asn His Phe Gly Arg Asp Phe Ala Thr Gly
        35                  40                  45

Ala Val Gly Gln Tyr Thr Val Gln Cys Pro Gln Asp Leu Gly Glu Leu
    50                  55                  60

Ile Ile Ile Arg Leu His Lys Glu Arg Tyr Ala Phe Phe Pro Lys Asp
65                  70                  75                  80

Pro Trp Tyr Cys Asn Tyr Val Gln Ile Cys Ala Pro Asn Gly Arg Ile
                85                  90                  95

Tyr His Phe Pro Ala Tyr Gln Trp Met Asp Gly Tyr Glu Thr Leu Ala
            100                 105                 110

Leu Arg Glu Ala Thr Gly Lys Thr Thr Ala Asp Ser Leu Pro Val
        115                 120                 125

Leu Leu Glu His Arg Lys Glu Glu Ile Arg Ala Lys Gln Asp Phe Tyr
    130                 135                 140

His Trp Arg Val Phe Leu Pro Gly Leu Pro Ser Tyr Val His Ile Pro
145                 150                 155                 160

Ser Tyr Arg Pro Pro Val Arg Arg His Arg Asn Pro Asn Arg Pro Glu
                165                 170                 175

Trp Asn Gly Tyr Ile Pro Gly Phe Pro Ile Leu Ile Asn Phe Lys Ala
            180                 185                 190

Thr Lys Phe Leu Asn Leu Asn Leu Arg Tyr Ser Phe Leu Lys Thr Ala
        195                 200                 205
```

Ser Phe Phe Val Arg Leu Gly Pro Met Ala Leu Ala Phe Lys Val Arg
210                 215                 220

Gly Leu Leu Asp Cys Lys His Ser Trp Lys Arg Leu Lys Asp Ile Arg
225                 230                 235                 240

Lys Ile Phe Pro Gly Lys Lys Ser Val Val Ser Glu Tyr Val Ala Glu
            245                 250                 255

His Trp Ala Glu Asp Thr Phe Phe Gly Tyr Gln Tyr Leu Asn Gly Val
            260                 265                 270

Asn Pro Gly Leu Ile Arg Arg Cys Thr Arg Ile Pro Asp Lys Phe Pro
        275                 280                 285

Val Thr Asp Asp Met Val Ala Pro Phe Leu Gly Glu Gly Thr Cys Leu
        290                 295                 300

Gln Ala Glu Leu Glu Lys Gly Asn Ile Tyr Leu Ala Asp Tyr Arg Ile
305                 310                 315                 320

Met Glu Gly Ile Pro Thr Val Glu Leu Ser Gly Arg Lys Gln His His
                325                 330                 335

Cys Ala Pro Leu Cys Leu Leu His Phe Gly Pro Glu Gly Lys Met Met
            340                 345                 350

Pro Ile Ala Ile Gln Leu Ser Gln Thr Pro Gly Pro Asp Cys Pro Ile
        355                 360                 365

Phe Leu Pro Ser Asp Ser Glu Trp Asp Trp Leu Leu Ala Lys Thr Trp
370                 375                 380

Val Arg Tyr Ala Glu Phe Tyr Ser His Glu Ala Ile Ala His Leu Leu
385                 390                 395                 400

Glu Thr His Leu Ile Ala Glu Ala Phe Cys Leu Ala Leu Leu Arg Asn
                405                 410                 415

Leu Pro Met Cys His Pro Leu Tyr Lys Leu Leu Ile Pro His Thr Arg
            420                 425                 430

Tyr Thr Val Gln Ile Asn Ser Ile Gly Arg Ala Val Leu Leu Asn Glu
        435                 440                 445

Gly Gly Leu Ser Ala Lys Gly Met Ser Leu Gly Val Glu Gly Phe Ala
450                 455                 460

Gly Val Met Val Arg Ala Leu Ser Glu Leu Thr Tyr Asp Ser Leu Tyr
465                 470                 475                 480

Leu Pro Asn Asp Phe Val Glu Arg Gly Val Gln Asp Leu Pro Gly Tyr
                485                 490                 495

Tyr Tyr Arg Asp Asp Ser Leu Ala Val Trp Asn Ala Leu Glu Lys Tyr
            500                 505                 510

Val Thr Glu Ile Ile Thr Tyr Tyr Pro Ser Asp Ala Ala Val Glu
        515                 520                 525

Gly Asp Pro Glu Leu Gln Ser Trp Val Gln Glu Ile Phe Lys Glu Cys
530                 535                 540

Leu Leu Gly Arg Glu Ser Ser Gly Phe Pro Arg Cys Leu Arg Thr Val
545                 550                 555                 560

Pro Glu Leu Ile Arg Tyr Val Thr Ile Val Ile Tyr Thr Cys Ser Ala
                565                 570                 575

Lys His Ala Ala Val Asn Thr Gly Gln Met Glu Phe Thr Ala Trp Met
            580                 585                 590

Pro Asn Phe Pro Ala Ser Met Arg Asn Pro Ile Gln Thr Lys Gly
        595                 600                 605

Leu Thr Thr Leu Glu Thr Phe Met Asp Thr Leu Pro Asp Val Lys Thr
610                 615                 620

Thr Cys Ile Thr Leu Leu Val Leu Trp Thr Leu Ser Arg Glu Pro Asp

```
                625                 630                 635                 640
Asp Arg Arg Pro Leu Gly His Phe Pro Asp Ile His Phe Val Glu Glu
                    645                 650                 655

Ala Pro Arg Arg Ser Ile Glu Ala Phe Arg Gln Arg Leu Asn Gln Ile
                    660                 665                 670

Ser His Asp Ile Arg Gln Arg Asn Lys Cys Leu Pro Ile Pro Tyr Tyr
                    675                 680                 685

Tyr Leu Asp Pro Val Leu Ile Glu Asn Ser Ile Ser Ile
                    690                 695                 700

<210> SEQ ID NO 29
<211> LENGTH: 662
<212> TYPE: PRT
<213> ORGANISM: Homo sapiens

<400> SEQUENCE: 29

Met Gly Leu Tyr Arg Ile Arg Val Ser Thr Gly Ala Ser Leu Tyr Ala
1               5                   10                  15

Gly Ser Asn Asn Gln Val Gln Leu Trp Leu Val Gly Gln His Gly Glu
            20                  25                  30

Ala Ala Leu Gly Lys Arg Leu Trp Pro Ala Arg Gly Lys Glu Thr Glu
        35                  40                  45

Leu Lys Val Glu Val Pro Glu Tyr Leu Gly Pro Leu Leu Phe Val Lys
    50                  55                  60

Leu Arg Lys Arg His Leu Leu Lys Asp Asp Ala Trp Phe Cys Asn Trp
65                  70                  75                  80

Ile Ser Val Gln Gly Pro Gly Ala Gly Asp Glu Val Arg Phe Pro Cys
                85                  90                  95

Tyr Arg Trp Val Glu Gly Asn Gly Val Leu Ser Leu Pro Glu Gly Thr
            100                 105                 110

Gly Arg Thr Val Gly Glu Asp Pro Gln Gly Leu Phe Gln Lys His Arg
        115                 120                 125

Glu Glu Glu Leu Glu Glu Arg Arg Lys Leu Tyr Arg Trp Gly Asn Trp
    130                 135                 140

Lys Asp Gly Leu Ile Leu Asn Met Ala Gly Ala Lys Leu Tyr Asp Leu
145                 150                 155                 160

Pro Val Asp Glu Arg Phe Leu Glu Asp Lys Arg Val Asp Phe Glu Val
                165                 170                 175

Ser Leu Ala Lys Gly Leu Ala Asp Leu Ala Ile Lys Asp Ser Leu Asn
            180                 185                 190

Val Leu Thr Cys Trp Lys Asp Leu Asp Asp Phe Asn Arg Ile Phe Trp
        195                 200                 205

Cys Gly Gln Ser Lys Leu Ala Glu Arg Val Arg Asp Ser Trp Lys Glu
    210                 215                 220

Asp Ala Leu Phe Gly Tyr Gln Phe Leu Asn Gly Ala Asn Pro Val Val
225                 230                 235                 240

Leu Arg Arg Ser Ala His Leu Pro Ala Arg Leu Val Phe Pro Pro Gly
                245                 250                 255

Met Glu Glu Leu Gln Ala Gln Leu Glu Lys Glu Leu Glu Gly Gly Thr
            260                 265                 270

Leu Phe Glu Ala Asp Phe Ser Leu Leu Asp Gly Ile Lys Ala Asn Val
        275                 280                 285

Ile Leu Cys Ser Gln Gln His Leu Ala Ala Pro Leu Val Met Leu Lys
    290                 295                 300
```

```
Leu Gln Pro Asp Gly Lys Leu Leu Pro Met Val Ile Gln Leu Gln Leu
305                 310                 315                 320

Pro Arg Thr Gly Ser Pro Pro Pro Leu Phe Leu Pro Thr Asp Pro
            325                 330                 335

Pro Met Ala Trp Leu Leu Ala Lys Cys Trp Val Arg Ser Ser Asp Phe
            340                 345                 350

Gln Leu His Glu Leu Gln Ser His Leu Leu Arg Gly His Leu Met Ala
            355                 360                 365

Glu Val Ile Val Ala Thr Met Arg Cys Leu Pro Ser Ile His Pro
            370                 375                 380

Ile Phe Lys Leu Ile Ile Pro His Leu Arg Tyr Thr Leu Glu Ile Asn
385                 390                 395                 400

Val Arg Ala Arg Thr Gly Leu Val Ser Asp Met Gly Ile Phe Asp Gln
                405                 410                 415

Ile Met Ser Thr Gly Gly Gly His Val Gln Leu Leu Lys Gln Ala
            420                 425                 430

Gly Ala Phe Leu Thr Tyr Ser Ser Phe Cys Pro Pro Asp Asp Leu Ala
            435                 440                 445

Asp Arg Gly Leu Leu Gly Val Lys Ser Ser Phe Tyr Ala Gln Asp Ala
450                 455                 460

Leu Arg Leu Trp Glu Ile Ile Tyr Arg Tyr Val Glu Gly Ile Val Ser
465                 470                 475                 480

Leu His Tyr Lys Thr Asp Val Ala Val Lys Asp Pro Glu Leu Gln
            485                 490                 495

Thr Trp Cys Arg Glu Ile Thr Glu Ile Gly Leu Gln Gly Ala Gln Asp
            500                 505                 510

Arg Gly Phe Pro Val Ser Leu Gln Ala Arg Asp Gln Val Cys His Phe
            515                 520                 525

Val Thr Met Cys Ile Phe Thr Cys Thr Gly Gln His Ala Ser Val His
530                 535                 540

Leu Gly Gln Leu Asp Trp Tyr Ser Trp Val Pro Asn Ala Pro Cys Thr
545                 550                 555                 560

Met Arg Leu Pro Pro Thr Thr Lys Asp Ala Thr Leu Glu Thr Val
            565                 570                 575

Met Ala Thr Leu Pro Asn Phe His Gln Ala Ser Leu Gln Met Ser Ile
            580                 585                 590

Thr Trp Gln Leu Gly Arg Arg Gln Pro Val Met Val Ala Val Gly Gln
            595                 600                 605

His Glu Glu Glu Tyr Phe Ser Gly Pro Glu Pro Lys Ala Val Leu Lys
            610                 615                 620

Lys Phe Arg Glu Glu Leu Ala Ala Leu Asp Lys Glu Ile Glu Ile Arg
625                 630                 635                 640

Asn Ala Lys Leu Asp Met Pro Tyr Glu Tyr Leu Arg Pro Ser Val Val
                645                 650                 655

Glu Asn Ser Val Ala Ile
            660

<210> SEQ ID NO 30
<211> LENGTH: 937
<212> TYPE: PRT
<213> ORGANISM: Physcomitrella patens

<400> SEQUENCE: 30

Met Met Leu Asn Arg Leu Glu Thr Gly Ser Leu Ala Ser Ala Phe Arg
1               5                   10                  15
```

```
Gly Ser Arg Glu Glu Phe Val Ser Arg Gly Arg Ser Pro Gly Arg
            20                  25                  30

Ser Gln Ser Ile Gln Val Arg Ala Ser Ser Gly Gly Asp Pro Ala Gly
        35                  40                  45

Trp Leu Gln Thr Ala Ser Lys Gln Leu Gly Lys Leu Ser Ser Phe Gly
50                  55                  60

Glu Lys Arg Lys Thr Ala Thr Ser Thr Ser Thr Arg Gly Pro Ser Gly
65                  70                  75                  80

Asp Asn Val Gln Tyr Thr Gly Val Ala Thr Met Lys Lys Leu Lys
                85                  90                  95

Val Leu Asp Leu Ile Asp Arg Val Ala Asp Ile Gln Asp Asp Thr Ser
            100                 105                 110

Glu Ile Val Gly Gly Lys Arg Val Thr Val Gln Leu Val Ser Lys Asp
            115                 120                 125

Val Asp Pro Lys Thr Gly Glu Ser Met Lys Ser Ser Glu Val Ile Phe
130                 135                 140

Pro Asn Trp Ala Gly Leu Glu Gly Pro Ala Ala Ser Leu Ile Asp Phe
145                 150                 155                 160

Val Leu Glu Phe Thr Val Pro Lys Ser Phe Gly Val Pro Gly Ala Ile
                165                 170                 175

Leu Val Lys Asn Ala His Pro Asn Glu Phe Leu Leu Val Ser Phe Glu
            180                 185                 190

Leu Glu Leu His Asp Lys Ser Lys Ala His Tyr Val Thr Asn Ser Trp
            195                 200                 205

Val Tyr Asn Thr Glu Lys Thr Gly Ala Arg Ile Phe Phe Gln Asn Thr
210                 215                 220

Ala Tyr Leu Pro Asp Glu Thr Pro Ala Ser Leu Lys Ala Leu Arg Glu
225                 230                 235                 240

Gln Glu Leu Ile Asn Leu Arg Gly Asp Gly Thr Gly Glu Arg Gln Ile
                245                 250                 255

Gly Asp Arg Ile Tyr Asp Tyr Ala Val Tyr Asn Asp Leu Gly Asn Ile
            260                 265                 270

Glu Gln Asn Glu Lys Phe Glu Arg Pro Asn Leu Gly Gly Asn Asp Met
            275                 280                 285

Tyr His Phe Pro Arg Arg Met Arg Thr Gly Arg Arg Asn Thr Thr Val
290                 295                 300

Glu Ala Lys Lys Phe Pro Gly Met Val Tyr Glu Thr Arg Lys Thr Lys
305                 310                 315                 320

Gly Asp Phe Tyr Ile Pro Arg Asp Glu Ala Phe Glu Arg Ala Lys Met
                325                 330                 335

Ser Asp Phe Leu Ala Asp Gly Phe Arg Ser Ile Gly His Ser Val Ser
            340                 345                 350

Ser Lys Val Thr Gly Phe Val Thr Arg Lys Gln Glu Phe Asp Thr Val
            355                 360                 365

Glu Glu Ile Lys Lys Leu Tyr Ala Lys Lys Gly Glu Lys Val Gly Gly
            370                 375                 380

Ile Asn Asn Val Leu Pro Asp Lys Glu Asp Ile Pro Glu Gln Glu Gln
385                 390                 395                 400

Tyr Pro Leu Val Phe Leu Gln Glu Val Leu Lys Pro Asp Gly Lys Met
                405                 410                 415

Glu His Pro Leu Leu Tyr Pro Leu Pro Gln Leu Leu Gln Ala Asp Asp
            420                 425                 430
```

```
Thr Ser Trp Arg Ser Asn Asp Glu Phe Ala Arg Glu Phe Leu Ala Gly
        435                 440                 445

Leu Asn Pro Val Met Ile Thr Arg Val Lys Phe Pro Ile Arg Ser Ser
450                 455                 460

Leu Asp Pro Ala Glu Phe Gly Asp Pro Thr Ser Ala Ile Thr Lys Asp
465                 470                 475                 480

His Ile Glu Gly Ser Leu Glu Gly Leu Ser Val Glu Ala Val Thr
                485                 490                 495

Ser Asn Arg Leu Phe Val Val Asp Tyr His Asp Ala Phe Leu Pro Phe
            500                 505                 510

Val Ala Lys Ile Asn Ala Gln Gln Asn Ser Ala Thr Tyr Ala Thr Arg
        515                 520                 525

Thr Leu Leu Phe Leu Ser Lys Asp Gly Ile Leu Lys Leu Leu Ala Ile
    530                 535                 540

Glu Leu Ala Leu Pro Pro Lys Thr Val Gly Glu Arg Ile Thr Arg
545                 550                 555                 560

Val Leu Thr Thr Arg Lys Asp Asp Gln Leu Trp Lys Val Asn Trp Glu
            565                 570                 575

Trp Glu Leu Ala Lys Ala His Val Ser Asn Asn Asp Ile Thr Ala His
        580                 585                 590

Gln Val Phe Ser His Phe Ser Arg Cys His Ala Val Thr Glu Ala Val
    595                 600                 605

Ile Ile Cys Ser Asn Arg Asn Leu Ser Lys Leu His Pro Leu Met Gln
610                 615                 620

Leu Leu Ala Pro His Phe Lys Ser Thr Leu Glu Ile Asn Arg Gln Ala
625                 630                 635                 640

Arg Ala Thr Leu Ile Ala Ala Gly Gly Ser Ile Glu Thr His Phe Thr
            645                 650                 655

Thr Arg Ala Tyr Ser Leu Glu Met Ala Ala Val Asn Tyr Lys Asp Thr
        660                 665                 670

Trp Thr Phe Glu Ser Gln Ala Leu Pro Thr Asp Leu Val Ala Arg Gly
    675                 680                 685

Met Ala Val Pro Asp Pro Asp Ser Pro His Gly Val Arg Leu Val Val
690                 695                 700

Glu Asp Tyr Pro Tyr Ala Ala Asp Gly Leu Glu Leu Trp Gly Ala Leu
705                 710                 715                 720

Lys Ala Trp His Lys Glu Tyr Val Asp Ile Tyr Tyr Lys Asp Asp Ala
            725                 730                 735

Ala Val Leu Gln Asp Ser Glu Leu Met Thr Trp Trp Thr Glu Met Arg
        740                 745                 750

Glu Lys Ala His Glu Asp Lys Lys Asp Ser His Gly Trp Pro Glu Leu
    755                 760                 765

Asn Ser Lys Glu Ala Leu Val Asp Ile Leu Thr Thr Val Ile Trp Ile
770                 775                 780

Pro Ser Cys Leu His Ala Ala Val Asn Phe Gly Gln Tyr Asp Phe Ala
785                 790                 795                 800

Gly Phe Met Pro His His Pro Thr Leu Thr Arg Arg Leu Leu Pro Glu
            805                 810                 815

His Gly Asn Glu Lys Asp Lys Ala Asp Phe Asn Lys Asn Pro Glu Lys
        820                 825                 830

Tyr Tyr Leu Thr Ser Ile Ser Asn Ile Asp Ser Thr Thr Thr Ala Met
    835                 840                 845

Ser Val Tyr Glu Val Leu Ser Ala His Cys Pro Ile Glu Glu Tyr Ile
```

```
                850                 855                 860
Gly Glu Arg Arg Gly Asn Trp Thr Asn Asn Glu Lys Val Leu Ala Ala
865                 870                 875                 880

Phe Lys Gly Phe Lys Glu Ser Val Asn Glu Ala Asp Ala Val Met Arg
                885                 890                 895

Ala Arg Asn Ala Asp Pro Lys Leu Arg Asn Arg Gly Gly Pro Val Lys
            900                 905                 910

Met Pro Tyr Gln Leu Leu Arg Pro His Ser Lys Pro Gly Val Thr Ser
        915                 920                 925

Met Gly Val Pro Asn Ser Ile Thr Ile
    930                 935

<210> SEQ ID NO 31
<211> LENGTH: 676
<212> TYPE: PRT
<213> ORGANISM: Homo sapiens

<400> SEQUENCE: 31

Met Ala Glu Phe Arg Val Arg Val Ser Thr Gly Glu Ala Phe Gly Ala
1               5                   10                  15

Gly Thr Trp Asp Lys Val Ser Val Ser Ile Val Gly Arg Gly Gly Glu
            20                  25                  30

Ser Pro Pro Leu Pro Leu Asp Asn Leu Gly Lys Glu Phe Thr Ala Gly
        35                  40                  45

Ala Glu Glu Asp Phe Gln Val Thr Leu Pro Glu Asp Val Gly Arg Val
    50                  55                  60

Leu Leu Leu Arg Val His Lys Ala Pro Pro Val Leu Pro Leu Leu Gly
65                  70                  75                  80

Pro Leu Ala Pro Asp Ala Trp Phe Cys Arg Trp Phe Gln Leu Thr Pro
                85                  90                  95

Pro Arg Gly Gly His Leu Leu Phe Pro Cys Tyr Gln Trp Leu Glu Gly
            100                 105                 110

Ala Gly Thr Leu Val Leu Gln Glu Gly Thr Ala Lys Val Ser Trp Ala
        115                 120                 125

Asp His His Pro Val Leu Gln Gln Gln Arg Gln Glu Glu Leu Gln Ala
    130                 135                 140

Arg Gln Glu Met Tyr Gln Trp Lys Ala Tyr Asn Pro Gly Trp Pro His
145                 150                 155                 160

Cys Leu Asp Glu Lys Thr Val Glu Asp Leu Glu Leu Asn Ile Lys Tyr
                165                 170                 175

Ser Thr Ala Lys Asn Ala Asn Phe Tyr Leu Gln Ala Gly Ser Ala Phe
            180                 185                 190

Ala Glu Met Lys Ile Lys Gly Leu Leu Asp Arg Lys Gly Leu Trp Arg
        195                 200                 205

Ser Leu Asn Glu Met Lys Arg Ile Phe Asn Phe Arg Arg Thr Pro Ala
    210                 215                 220

Ala Glu His Ala Phe Glu His Trp Gln Glu Asp Ala Phe Phe Ala Ser
225                 230                 235                 240

Gln Phe Leu Asn Gly Leu Asn Pro Val Leu Ile Arg Arg Cys His Tyr
                245                 250                 255

Leu Pro Lys Asn Phe Pro Val Thr Asp Ala Met Val Ala Ser Val Leu
            260                 265                 270

Gly Pro Gly Thr Ser Leu Gln Ala Glu Leu Glu Lys Gly Ser Leu Phe
        275                 280                 285
```

```
Leu Val Asp His Gly Ile Leu Ser Gly Ile Gln Thr Asn Val Ile Asn
290                 295                 300

Gly Lys Pro Gln Phe Ser Ala Ala Pro Met Thr Leu Leu Tyr Gln Ser
305                 310                 315                 320

Pro Gly Cys Gly Pro Leu Leu Pro Leu Ala Ile Gln Leu Ser Gln Thr
            325                 330                 335

Pro Gly Pro Asn Ser Pro Ile Phe Leu Pro Thr Asp Lys Trp Asp
            340                 345                 350

Trp Leu Leu Ala Lys Thr Trp Val Arg Asn Ala Glu Phe Ser Phe His
            355                 360                 365

Glu Ala Leu Thr His Leu Leu His Ser His Leu Leu Pro Glu Val Phe
370                 375                 380

Thr Leu Ala Thr Leu Arg Gln Leu Pro His Cys His Pro Leu Phe Lys
385                 390                 395                 400

Leu Leu Ile Pro His Thr Arg Tyr Thr Leu His Ile Asn Thr Leu Ala
                405                 410                 415

Arg Glu Leu Leu Ile Val Pro Gly Gln Val Val Asp Arg Ser Thr Gly
            420                 425                 430

Ile Gly Ile Glu Gly Phe Ser Glu Leu Ile Gln Arg Asn Met Lys Gln
            435                 440                 445

Leu Asn Tyr Ser Leu Leu Cys Leu Pro Glu Asp Ile Arg Thr Arg Gly
450                 455                 460

Val Glu Asp Ile Pro Gly Tyr Tyr Tyr Arg Asp Asp Gly Met Gln Ile
465                 470                 475                 480

Trp Gly Ala Val Glu Arg Phe Val Ser Glu Ile Ile Gly Ile Tyr Tyr
            485                 490                 495

Pro Ser Asp Glu Ser Val Gln Asp Arg Glu Leu Gln Ala Trp Val
            500                 505                 510

Arg Glu Ile Phe Ser Lys Gly Phe Leu Asn Gln Glu Ser Ser Gly Ile
            515                 520                 525

Pro Ser Ser Leu Glu Thr Arg Glu Ala Leu Val Gln Tyr Val Thr Met
            530                 535                 540

Val Ile Phe Thr Cys Ser Ala Lys His Ala Ala Val Ser Ala Gly Gln
545                 550                 555                 560

Phe Asp Ser Cys Ala Trp Met Pro Asn Leu Pro Ser Met Gln Leu
            565                 570                 575

Pro Pro Pro Thr Ser Lys Gly Leu Ala Thr Cys Glu Gly Phe Ile Ala
            580                 585                 590

Thr Leu Pro Pro Val Asn Ala Thr Cys Asp Val Ile Leu Ala Leu Trp
            595                 600                 605

Leu Leu Ser Lys Glu Pro Gly Asp Gln Arg Pro Leu Gly Thr Tyr Pro
610                 615                 620

Asp Glu His Phe Thr Glu Glu Ala Pro Arg Arg Ser Ile Ala Thr Phe
625                 630                 635                 640

Gln Ser Arg Leu Ala Gln Ile Ser Arg Gly Ile Gln Glu Arg Asn Gln
            645                 650                 655

Gly Leu Val Leu Pro Tyr Thr Tyr Leu Asp Pro Pro Leu Ile Glu Asn
            660                 665                 670

Ser Val Ser Ile
            675

<210> SEQ ID NO 32
<211> LENGTH: 685
<212> TYPE: PRT
```

<213> ORGANISM: Pseudomonas aeruginosa

<400> SEQUENCE: 32

```
Met Lys Arg Arg Ser Val Leu Leu Ser Gly Val Ala Leu Ser Gly Thr
1               5                   10                  15

Ala Leu Ala Asn Asp Ser Ile Phe Phe Ser Pro Leu Lys Tyr Leu Gly
            20                  25                  30

Ala Glu Gln Gln Arg Ser Ile Asp Ala Ser Arg Ser Leu Leu Asp Asn
        35                  40                  45

Leu Ile Pro Pro Ser Leu Pro Gln Tyr Asp Asn Leu Ala Gly Lys Leu
    50                  55                  60

Ala Arg Arg Ala Val Leu Thr Ser Lys Lys Leu Val Tyr Val Trp Thr
65                  70                  75                  80

Glu Asn Phe Gly Asn Val Lys Gly Val Pro Met Ala Arg Ser Val Pro
                85                  90                  95

Leu Gly Glu Leu Pro Asn Val Asp Trp Leu Leu Lys Thr Ala Gly Val
            100                 105                 110

Ile Val Glu Leu Ile Val Asn Phe Val Ala Ser Leu Pro Ala Ser Ala
        115                 120                 125

Ala Ala Gln Phe Glu Arg Ile Ala Thr Gly Leu Ser Gly Asp Leu Glu
    130                 135                 140

Ala Ala Arg Gln Val His Glu Ala Leu Leu Glu Glu Ala Lys Asn Asp
145                 150                 155                 160

Pro Ala Ala Gly Ser Leu Leu Arg Phe Thr Glu Leu Gln Thr
                165                 170                 175

Arg Val Ile Ala Ile Leu Thr Arg Val Gly Leu Leu Val Asp Asp Ile
        180                 185                 190

Leu Lys Ser Ala Ser Asn Leu Val Thr Gln Arg Gly Gln Gly Asp Gly
    195                 200                 205

Leu Asn Arg Phe Arg Ala Val Phe Gly Thr Leu Arg Leu Pro Glu Val
210                 215                 220

Ala Asp Ser Phe Arg Asp Asp Glu Ala Phe Ala Tyr Trp Arg Val Ala
225                 230                 235                 240

Gly Pro Asn Pro Leu Leu Ile Arg Arg Val Asp Ala Leu Pro Ala Asn
                245                 250                 255

Phe Pro Leu Gly Glu Glu Gln Phe Arg Arg Val Met Gly Ala Asp Asp
            260                 265                 270

Ser Leu Leu Glu Ala Ala Ala Ser Arg Arg Leu Tyr Leu Leu Asp Tyr
        275                 280                 285

Ala Glu Leu Gly Lys Leu Ala Pro Ser Gly Ala Val Asp Lys Leu Leu
    290                 295                 300

Thr Gly Thr Gly Phe Ala Tyr Ala Pro Ile Ala Leu Phe Ala Leu Gly
305                 310                 315                 320

Lys Asp Arg Ala Arg Leu Leu Pro Val Ala Ile Gln Cys Gly Gln Asp
                325                 330                 335

Pro Ala Thr His Pro Met Phe Val Arg Pro Ala Glu Ser Glu Ser Asp
            340                 345                 350

Leu Tyr Trp Gly Trp Gln Met Ala Lys Thr Val Val Gln Val Ala Glu
        355                 360                 365

Glu Asn Tyr His Glu Met Phe Val His Leu Ala Gln Thr His Leu Val
    370                 375                 380

Ser Glu Ala Phe Cys Leu Ala Thr Gln Arg Thr Leu Ala Pro Ser His
385                 390                 395                 400
```

```
Pro Leu His Val Leu Leu Ala Pro His Phe Glu Gly Thr Leu Phe Ile
            405                 410                 415

Asn Glu Gly Ala Ala Arg Ile Leu Leu Pro Ser Ala Gly Phe Ile Asp
        420                 425                 430

Val Met Phe Ala Ala Pro Ile Gln Asp Thr Gln Ala Thr Ala Gly Gly
        435                 440                 445

Asn Arg Leu Gly Phe Asp Phe Tyr Arg Gly Met Leu Pro Glu Ser Leu
        450                 455                 460

Lys Ala Arg Asn Val Asp Asp Pro Leu Ala Leu Pro Asp Tyr Pro Tyr
465                 470                 475                 480

Arg Asp Asp Gly Leu Leu Val Trp Asn Ala Ile Arg Gln Trp Ala Ala
            485                 490                 495

Asp Tyr Val Ala Val Tyr Tyr Ala Ser Asp Gly Asp Val Thr Ala Asp
            500                 505                 510

Val Glu Leu Ala Ala Trp Val Gly Glu Val Ile Gly Ser Gly Lys Val
            515                 520                 525

Ala Gly Phe Arg Pro Ile Thr Gly Arg Ser Gln Leu Val Glu Val Leu
            530                 535                 540

Thr Met Val Ile Phe Thr Ala Ser Ala Gln His Ala Ala Val Asn Phe
545                 550                 555                 560

Pro Gln Pro Ser Met Met Thr Tyr Ala Pro Ala Ile Cys Ala Met Ser
                565                 570                 575

Ala Ala Pro Ala Pro Asp Ser Pro Ser Gly Lys Ser Glu Ala Asp Trp
            580                 585                 590

Leu Lys Met Met Pro Pro Thr Leu Val Ala Leu Glu Lys Val Asn Ile
            595                 600                 605

Tyr His Leu Leu Gly Ser Val Tyr His Gly Arg Leu Gly Asp Tyr Arg
            610                 615                 620

Gln Thr Gly Phe Pro Tyr Ala Pro Val Phe Ser Asp Arg Arg Val Thr
625                 630                 635                 640

Ala Ser Gly Gly Pro Leu Glu Arg Phe Gln Ala Arg Leu Lys Glu Val
                645                 650                 655

Glu Ala Thr Ile Arg Thr Arg Asn Gln Ala Arg Arg Pro Tyr Glu
            660                 665                 670

Tyr Leu Leu Pro Ser Arg Ile Pro Ala Ser Thr Asn Ile
            675                 680                 685

<210> SEQ ID NO 33
<211> LENGTH: 569
<212> TYPE: PRT
<213> ORGANISM: Cyanothece sp.

<400> SEQUENCE: 33

Met Val Gln Pro Ser Leu Pro Gln Asp Asp Thr Pro Asp Gln Gln Glu
1               5                   10                  15

Gln Arg Asn Arg Ala Ile Ala Gln Gln Arg Glu Ala Tyr Gln Tyr Ser
            20                  25                  30

Glu Thr Ala Gly Ile Leu Leu Ile Lys Thr Leu Pro Gln Ser Glu Met
        35                  40                  45

Phe Ser Leu Lys Tyr Leu Ile Glu Arg Asp Lys Gly Leu Val Ser Leu
    50                  55                  60

Ile Ala Asn Thr Leu Ala Ser Asn Ile Glu Asn Ile Phe Asp Pro Phe
65                  70                  75                  80

Asp Lys Leu Glu Asp Phe Glu Glu Met Phe Pro Leu Leu Pro Lys Pro
                85                  90                  95
```

```
Leu Val Met Asn Thr Phe Arg Asn Asp Arg Val Phe Ala Arg Gln Arg
            100                 105                 110

Ile Ala Gly Pro Asn Pro Met Val Ile Glu Arg Val Asp Lys Leu
        115                 120                 125

Pro Asp Asn Phe Pro Val Thr Asp Ala Met Phe Gln Lys Ile Met Phe
    130                 135                 140

Thr Lys Lys Thr Leu Ala Glu Ala Ile Ala Gln Gly Lys Leu Phe Ile
145                 150                 155                 160

Thr Asn Tyr Lys Gly Leu Ala Glu Leu Ser Pro Gly Arg Tyr Glu Tyr
            165                 170                 175

Gln Lys Asn Gly Thr Leu Val Gln Lys Thr Lys Thr Ile Ala Ala Pro
        180                 185                 190

Leu Val Leu Tyr Ala Trp Lys Pro Glu Gly Phe Gly Asp Tyr Arg Gly
        195                 200                 205

Ser Leu Ala Pro Ile Ala Ile Gln Ile Asn Gln Gln Pro Asp Pro Ile
        210                 215                 220

Thr Asn Pro Ile Tyr Thr Pro Arg Asp Gly Lys His Trp Phe Ile Ala
225                 230                 235                 240

Lys Ile Phe Ala Gln Met Ala Asp Gly Asn Cys His Glu Ala Ile Ser
            245                 250                 255

His Leu Ala Arg Thr His Leu Ile Leu Glu Pro Phe Val Leu Ala Thr
            260                 265                 270

Ala Asn Glu Leu Ala Pro Asn His Pro Leu Ser Val Leu Leu Lys Pro
        275                 280                 285

His Phe Gln Phe Thr Leu Ala Ile Asn Glu Leu Ala Arg Glu Gln Leu
        290                 295                 300

Ile Ser Ala Gly Gly Tyr Ala Asp Asp Leu Leu Ala Gly Thr Leu Glu
305                 310                 315                 320

Ala Ser Ile Ala Val Ile Lys Ala Ala Ile Lys Glu Tyr Met Asp Asn
            325                 330                 335

Phe Thr Glu Phe Ala Leu Pro Arg Glu Leu Ala Arg Arg Gly Val Gly
            340                 345                 350

Ile Gly Asp Val Asp Gln Arg Gly Glu Asn Phe Leu Pro Asp Tyr Pro
        355                 360                 365

Tyr Arg Asp Asp Ala Met Leu Leu Trp Asn Ala Ile Glu Val Tyr Val
        370                 375                 380

Arg Asp Tyr Leu Ser Leu Tyr Tyr Gln Ser Pro Val Gln Ile Arg Gln
385                 390                 395                 400

Asp Thr Glu Leu Gln Asn Trp Val Arg Arg Leu Val Ser Pro Glu Gly
            405                 410                 415

Gly Arg Val Thr Gly Leu Val Ser Asn Gly Glu Leu Asn Thr Ile Glu
            420                 425                 430

Ala Leu Val Ala Ile Ala Thr Gln Val Ile Phe Val Ser Gly Pro Gln
        435                 440                 445

His Ala Ala Val Asn Tyr Pro Gln Tyr Asp Tyr Met Ala Phe Ile Pro
        450                 455                 460

Asn Met Pro Leu Ala Thr Tyr Ala Thr Pro Asn Lys Glu Ser Asn
465                 470                 475                 480

Ile Ser Glu Ala Thr Ile Leu Asn Ile Leu Pro Pro Gln Lys Leu Ala
            485                 490                 495

Ala Arg Gln Leu Glu Leu Met Arg Thr Leu Cys Val Phe Tyr Pro Asn
            500                 505                 510
```

```
Arg Leu Gly Tyr Pro Asp Thr Glu Phe Val Asp Val Arg Ala Gln Gln
            515                 520                 525

Val Leu His Gln Phe Gln Glu Arg Leu Gln Glu Ile Glu Gln Arg Ile
            530                 535                 540

Val Leu Cys Asn Glu Lys Arg Leu Glu Pro Tyr Thr Tyr Leu Leu Pro
545                 550                 555                 560

Ser Asn Val Pro Asn Ser Thr Ser Ile
                565

<210> SEQ ID NO 34
<211> LENGTH: 630
<212> TYPE: PRT
<213> ORGANISM: Nostoc punctiforme

<400> SEQUENCE: 34

Met Thr Ala Leu Ser Pro Asp His Ser Ile Ser Ser Ser Thr His
1               5                   10                  15

Thr Leu Asp Ile Ala Arg Gln Glu Tyr Gln Tyr Asn Tyr Asn His Ile
            20                  25                  30

Pro Ser Ile Ala Met Val Asp Arg Leu Ser Ile Thr Glu Glu Phe Thr
            35                  40                  45

Thr Asn Trp Tyr Phe Leu Leu Ala Gln Gln Leu Arg Val Leu Phe Ile
50                  55                  60

Asn Thr Leu Ile Val Asn Arg Gly Asn Gln Asp Ser Lys Ser Ile Arg
65                  70                  75                  80

Asp Asp Val Glu Arg Phe Ile Leu Glu Ala Leu Leu Lys Gly Ala Val
            85                  90                  95

Pro Ala Arg Ile Ser Ile Leu Ala Arg Ile Leu Gln Ile Ile Pro Gln
            100                 105                 110

Leu Leu Leu Lys Glu Ile Ser Lys Asp Phe Arg Glu Leu Asp Asp Leu
            115                 120                 125

Phe His Ser Ile Leu Lys Glu Asn Gly Leu Ala Ile Leu Arg Asp Ala
            130                 135                 140

Leu Lys Arg Ile Ile Thr Leu Leu Tyr Glu Gly Gln Pro Thr Gly His
145                 150                 155                 160

Ala Thr Ser Leu Lys Asp Tyr Glu Asn Leu Phe Pro Val Ile Ser Leu
                165                 170                 175

Pro Ala Ile Ala Lys Thr Tyr Gln Glu Asp Glu Val Phe Ala Tyr Met
            180                 185                 190

Arg Val Ala Gly Tyr Asn Pro Val Thr Ile Lys Arg Val Thr Thr Leu
            195                 200                 205

Ser Asp Arg Phe Pro Val Thr Asp Glu His Tyr Gln Ala Val Met Gly
            210                 215                 220

Thr Asp Asp Ser Leu Ala Ala Gly Ile Glu Gly Arg Leu Tyr Leu
225                 230                 235                 240

Ala Asp Tyr Lys Ile Leu Asp Gly Ala Ile Asn Gly Thr Phe Pro His
                245                 250                 255

Glu Gln Lys Tyr Leu Tyr Ala Pro Leu Ala Leu Phe Ala Leu Pro Lys
            260                 265                 270

Gly Ser Asp Pro Thr Arg Leu Leu Arg Pro Val Ala Ile Gln Cys Gly
            275                 280                 285

Gln Thr Pro Gly Pro Asp Tyr Pro Ile Val Thr Pro Asn Ser Gly Lys
            290                 295                 300

Tyr Ala Trp Leu Phe Ala Lys Thr Ile Val Gln Ile Ala Asp Ala Asn
305                 310                 315                 320
```

-continued

```
Ile His Glu Ala Val Thr His Leu Ala Arg Thr His Leu Leu Val Gly
            325                 330                 335

Val Phe Ala Ile Ala Thr Ala Arg Gln Leu Pro Leu Thr His Pro Leu
            340                 345                 350

Arg Ile Leu Leu Arg Pro His Phe Asp Ser Thr Leu Ala Ile Asn Asp
            355                 360                 365

Ala Ala Gln Arg Ile Leu Ile Ala Pro Gly Gly Val Asp Arg Leu
            370                 375                 380

Leu Ser Ser Ser Ile Asp Asn Ser Arg Val Leu Ala Val Leu Gly Leu
385                 390                 395                 400

Gln Ser Tyr Ser Phe Asn Ser Thr Ile Leu Pro Asn Gln Phe Gln Gln
            405                 410                 415

Arg Gly Val Asp Asp Pro Asn Leu Leu Pro Ile Tyr Pro Tyr Arg Asp
            420                 425                 430

Asp Ala Leu Leu Ile Trp Asn Ala Ile His Gln Trp Val Trp Asp Tyr
            435                 440                 445

Leu Asn Leu Tyr Tyr Thr Thr Asp Glu Asp Ile Gln Lys Asp Arg Ala
    450                 455                 460

Leu Gln Ala Trp Ala Ala Glu Ile Pro Ala Tyr Asp Gly Gly Arg Ile
465                 470                 475                 480

Pro Asp Phe Gly Glu Asp Gly Gly Ile Lys Thr Leu Asn Tyr Leu Ile
            485                 490                 495

Asp Ala Thr Thr Leu Ile Ile Phe Thr Ala Ser Ala Gln His Ala Ala
            500                 505                 510

Val Asn Phe Pro Gln Lys Asp Leu Met Gly Tyr Ala Ala Ala Ile Pro
            515                 520                 525

Leu Ala Gly Tyr Leu Pro Ala Ser Thr Leu Lys Arg Glu Val Thr Glu
            530                 535                 540

Gln Asp Tyr Leu Asn Leu Leu Pro Pro Leu Asp Gln Ala Gln Arg Gln
545                 550                 555                 560

Tyr Asn Leu Leu Ser Leu Leu Gly Ser Val Tyr Tyr Asn Lys Leu Gly
                565                 570                 575

Glu Tyr Glu Gln Gly Tyr Phe Thr Asp Glu Lys Val Lys Pro Leu Leu
            580                 585                 590

Gln Ala Phe Gln Ser His Leu Gln Gln Val Glu Asn Thr Ile Lys Gln
            595                 600                 605

Arg Asn Leu His Arg Pro Pro Tyr Glu Tyr Leu Leu Pro Ser Lys Ile
            610                 615                 620

Pro Gln Ser Ile Asn Ile
625                 630

<210> SEQ ID NO 35
<211> LENGTH: 936
<212> TYPE: PRT
<213> ORGANISM: Hordeum vulgare

<400> SEQUENCE: 35

Met Leu Thr Ala Thr Lys Pro Leu Val Gly Gly Ala Cys Ala Ala Pro
1               5                   10                  15

Ser Ser Ser Ala Arg Arg Arg Thr Phe Val Val Pro Glu Ala Arg Arg
            20                  25                  30

Lys Pro Gly Asn Gly Arg Arg Thr Ser Val Ser Lys Val Gly Ser Thr
            35                  40                  45

Ser Thr Ser Thr Thr Thr Thr Thr Thr Thr Thr Leu Ser Ala Asp Ser
```

```
                50                  55                  60
Asn Gly Ala Ala Val Gly Thr Val Thr Arg Pro Asp Val His Val Gln
 65                  70                  75                  80

Asp Arg Thr His Ala Thr Glu Met Lys Ala Thr Val Thr Val His Met
                     85                  90                  95

Ser Lys Ala Ala Gly Val Arg Asp Phe Leu Tyr Asp Leu Ile Leu Lys
                100                 105                 110

Thr Trp Leu His Val Asp Leu Val Ser Ser Glu Leu Asp Pro Gln Thr
                115                 120                 125

Gly Gln Glu Arg Glu Pro Ile Ser Gly Ala Val Lys His Ser Gly Arg
130                 135                 140

Val Asp Asp Glu Trp Asp Met Tyr Glu Ala Thr Phe Lys Val Pro Ala
145                 150                 155                 160

Ser Phe Gly Pro Ile Gly Ala Val Gln Val Thr Asn Tyr His His Ser
                165                 170                 175

Glu Met Leu Leu Gly Asp Ile Glu Val Phe Pro Thr Gly Gln Glu Glu
                180                 185                 190

Ser Ala Val Thr Phe His Cys Lys Ser Trp Ile Asp Pro Ser His Cys
                195                 200                 205

Thr Pro Asp Lys Arg Val Phe Phe Pro Ala His Ser Tyr Leu Pro Ser
210                 215                 220

Gln Thr Pro Lys Gly Val Glu Gly Leu Arg Lys Arg Glu Leu Glu Ile
225                 230                 235                 240

Leu Arg Gly Thr Gly Cys Gly Glu Arg Lys Glu His Asp Arg Ile Tyr
                245                 250                 255

Asp Tyr Asp Val Tyr Asn Asp Leu Gly Asn Pro Asp Asp Asn Asn
                260                 265                 270

Pro Thr Thr Arg Pro Val Leu Gly Gly Lys Glu His Pro Tyr Pro Arg
                275                 280                 285

Arg Cys Arg Thr Gly Arg Pro Arg Ser Lys Lys Asp Pro Phe Ser Glu
                290                 295                 300

Glu Arg Ser His Lys Glu His Ile Tyr Val Pro Arg Asp Glu Ala Phe
305                 310                 315                 320

Thr Glu Arg Lys Met Gly Ala Phe Asp Thr Lys Lys Phe Met Ser Gln
                325                 330                 335

Leu His Ala Leu Thr Thr Gly Leu Lys Thr Ala Lys His Lys Ser Gln
                340                 345                 350

Ser Phe Pro Ser Leu Ser Ala Ile Asp Gln Leu Tyr Asp Asp Asn Phe
                355                 360                 365

Arg Asn Gln Pro Val Gln Pro Glu Gly Gly Lys Leu Arg Phe Val Ile
                370                 375                 380

Asp Leu Leu Glu Thr Glu Leu Leu His Leu Phe Lys Leu Glu Gly Ala
385                 390                 395                 400

Ala Phe Leu Glu Gly Ile Arg Arg Val Phe Lys Phe Glu Thr Pro Glu
                405                 410                 415

Ile His Asp Arg Asp Lys Phe Ala Trp Phe Arg Asp Glu Glu Phe Ala
                420                 425                 430

Arg Gln Thr Ile Ala Gly Met Asn Pro Met Ser Ile Gln Leu Val Thr
                435                 440                 445

Glu Phe Pro Ile Lys Ser Asn Leu Asp Glu Ala Thr Tyr Gly Pro Ala
                450                 455                 460

Asp Ser Leu Ile Thr Lys Glu Val Val Glu Glu Gln Ile Arg Arg Val
465                 470                 475                 480
```

```
Met Thr Ala Asp Glu Ala Val Gln Asn Lys Lys Leu Phe Met Leu Asp
                485                 490                 495
Tyr His Asp Leu Leu Pro Tyr Val His Lys Val Arg Lys Leu Asp
            500                 505                 510
Gly Thr Thr Leu Tyr Gly Ser Arg Ala Leu Phe Phe Leu Thr Ala Asp
            515                 520                 525
Gly Thr Leu Arg Pro Ile Ala Ile Glu Leu Thr Arg Pro Lys Ser Lys
        530                 535                 540
Lys Lys Pro Gln Trp Arg Gln Val Phe Thr Pro Gly Cys Asp Gly Ser
545                 550                 555                 560
Val Thr Gly Ser Trp Leu Trp Gln Leu Ala Lys Ala His Ile Leu Ala
                565                 570                 575
His Asp Ala Gly Val His Gln Leu Val Ser His Trp Leu Arg Thr His
            580                 585                 590
Ala Cys Thr Glu Pro Tyr Ile Ile Ala Ala Asn Arg Gln Leu Ser Gln
            595                 600                 605
Met His Pro Val Tyr Arg Leu Leu His Pro His Phe Arg Phe Thr Met
        610                 615                 620
Glu Ile Asn Ala Gln Ala Arg Ala Met Leu Ile Asn Ala Gly Gly Ile
625                 630                 635                 640
Ile Glu Gly Ser Phe Val Pro Gly Glu Tyr Ser Leu Glu Leu Ser Ser
                645                 650                 655
Val Ala Tyr Asp Gln Gln Trp Arg Phe Asp Met Glu Ala Leu Pro Glu
            660                 665                 670
Asp Leu Ile Arg Arg Gly Met Ala Val Arg Asn Pro Asn Gly Glu Leu
            675                 680                 685
Glu Leu Ala Ile Glu Asp Tyr Pro Tyr Ala Asn Asp Gly Leu Leu Val
        690                 695                 700
Trp Asp Ala Ile Lys Gln Trp Ala Leu Thr Tyr Val Gln His Tyr Tyr
705                 710                 715                 720
Pro Cys Ala Ala Asp Ile Val Asp Asp Glu Glu Leu Gln Ala Trp Trp
                725                 730                 735
Thr Glu Val Arg Thr Lys Gly His Ala Asp Lys Gln Asp Glu Pro Trp
            740                 745                 750
Trp Pro Glu Leu Asp Ser His Glu Asn Leu Ala Gln Thr Leu Ala Thr
            755                 760                 765
Ile Met Trp Val Thr Ser Gly His His Ala Ala Val Asn Phe Gly Gln
        770                 775                 780
Tyr Pro Met Ala Gly Tyr Ile Pro Asn Arg Pro Thr Met Ala Arg Arg
785                 790                 795                 800
Asn Met Pro Thr Glu Ile Gly Gly Asp Asp Met Arg Asp Phe Val Glu
                805                 810                 815
Ala Pro Glu Lys Val Leu Leu Asp Thr Phe Pro Ser Gln Tyr Gln Ser
            820                 825                 830
Ala Ile Val Leu Ala Ile Leu Asp Leu Leu Ser Thr His Ser Ser Asp
            835                 840                 845
Glu Glu Tyr Met Gly Thr His Glu Glu Pro Ala Trp Thr Lys Asp Gly
        850                 855                 860
Val Ile Asn Gln Ala Phe Glu Glu Phe Lys Glu Ser Thr Arg Lys Ile
865                 870                 875                 880
Val Glu Gln Val Asp Glu Trp Asn Asn Asp Pro Asp Arg Lys Asn Arg
                885                 890                 895
```

-continued

```
His Gly Ala Gly Met Val Pro Tyr Val Leu Leu Arg Pro Ser Asp Gly
                900                 905                 910

Asp Pro Thr Asp Gly Pro Thr Asp Glu Lys Met Val Met Glu Met
            915                 920                 925

Gly Ile Pro Asn Ser Ile Ser Ile
            930                 935

<210> SEQ ID NO 36
<211> LENGTH: 639
<212> TYPE: PRT
<213> ORGANISM: Arabidopsis thaliana

<400> SEQUENCE: 36

Met Lys Val Ile Thr Ser Leu Ile Ser Ser Ile Leu Leu Lys Phe Ile
1               5                   10                  15

His Lys Asp Phe His Glu Ile Tyr Ala Arg Met Ser Leu Leu Asp Arg
            20                  25                  30

Phe Leu Leu Leu Ile Val His Gly Val Asp Lys Met Val Pro Trp His
        35                  40                  45

Lys Leu Pro Val Phe Leu Gly Leu Thr Tyr Leu Glu Val Arg Arg His
    50                  55                  60

Leu His Gln Gln Tyr Asn Leu Leu Asn Val Gly Gln Thr Pro Thr Gly
65                  70                  75                  80

Ile Arg Phe Asp Pro Ala Asn Tyr Pro Tyr Arg Thr Ala Asp Gly Lys
                85                  90                  95

Phe Asn Asp Pro Phe Asn Glu Gly Val Gly Ser Gln Asn Ser Phe Phe
            100                 105                 110

Gly Arg Asn Cys Pro Pro Val Asp Gln Lys Ser Lys Leu Arg Arg Pro
        115                 120                 125

Asp Pro Met Val Val Ala Thr Lys Leu Leu Gly Arg Lys Lys Phe Ile
    130                 135                 140

Asp Thr Gly Lys Gln Phe Asn Met Ile Ala Ala Ser Trp Ile Gln Phe
145                 150                 155                 160

Met Ile His Asp Trp Ile Asp His Leu Glu Asp Thr His Gln Ile Glu
                165                 170                 175

Leu Val Ala Pro Lys Glu Val Ala Ser Lys Cys Pro Leu Ser Ser Phe
            180                 185                 190

Arg Phe Leu Lys Thr Lys Glu Val Pro Thr Gly Phe Phe Glu Ile Lys
        195                 200                 205

Thr Gly Ser Gln Asn Ile Arg Thr Pro Trp Trp Asp Ser Ser Val Ile
    210                 215                 220

Tyr Gly Ser Asn Ser Lys Thr Leu Asp Arg Val Arg Thr Tyr Lys Asp
225                 230                 235                 240

Gly Lys Leu Lys Ile Ser Glu Glu Thr Gly Leu Leu Leu His Asp Glu
                245                 250                 255

Asp Gly Leu Ala Ile Ser Gly Asp Ile Arg Asn Ser Trp Ala Gly Val
            260                 265                 270

Ser Ala Leu Gln Ala Leu Phe Ile Lys Glu His Asn Ala Val Cys Asp
        275                 280                 285

Ala Leu Lys Asp Glu Asp Asp Leu Glu Asp Glu Asp Leu Tyr Arg
    290                 295                 300

Tyr Ala Arg Leu Val Thr Ser Ala Val Val Ala Lys Ile His Thr Ile
305                 310                 315                 320

Asp Trp Thr Val Gln Leu Leu Lys Thr Asp Thr Leu Leu Ala Gly Met
                325                 330                 335
```

```
Arg Ala Asn Trp Tyr Gly Leu Leu Gly Lys Lys Phe Lys Asp Ser Phe
            340                 345                 350

Gly His Ala Gly Ser Ser Ile Leu Gly Gly Val Val Gly Met Lys Lys
            355                 360                 365

Pro Gln Asn His Gly Val Pro Tyr Ser Leu Thr Glu Asp Phe Thr Ser
370                 375                 380

Val Tyr Arg Met His Ser Leu Leu Pro Asp Gln Leu His Ile Leu Asp
385                 390                 395                 400

Ile Asp Asp Val Pro Gly Thr Asn Lys Ser Leu Pro Leu Ile Gln Glu
                405                 410                 415

Ile Ser Met Arg Asp Leu Ile Gly Arg Lys Gly Glu Glu Thr Met Ser
                420                 425                 430

His Ile Gly Phe Thr Lys Leu Met Val Ser Met Gly His Gln Ala Ser
            435                 440                 445

Gly Ala Leu Glu Leu Met Asn Tyr Pro Met Trp Leu Arg Asp Ile Val
        450                 455                 460

Pro His Asp Pro Asn Gly Gln Ala Arg Pro Asp His Val Asp Leu Ala
465                 470                 475                 480

Ala Leu Glu Ile Tyr Arg Asp Arg Glu Arg Ser Val Pro Arg Tyr Asn
                485                 490                 495

Glu Phe Arg Arg Ser Met Phe Met Ile Pro Ile Thr Lys Trp Glu Asp
            500                 505                 510

Leu Thr Glu Asp Glu Glu Ala Ile Glu Val Leu Asp Asp Val Tyr Asp
        515                 520                 525

Gly Asp Val Glu Glu Leu Asp Leu Leu Val Gly Leu Met Ala Glu Lys
    530                 535                 540

Lys Ile Lys Gly Phe Ala Ile Ser Glu Thr Ala Phe Tyr Ile Phe Leu
545                 550                 555                 560

Ile Met Ala Thr Arg Arg Leu Glu Ala Asp Arg Phe Thr Ser Asp
                565                 570                 575

Phe Asn Glu Thr Ile Tyr Thr Lys Lys Gly Leu Glu Trp Val Asn Thr
            580                 585                 590

Thr Glu Ser Leu Lys Asp Val Ile Asp Arg His Tyr Pro Asp Met Thr
        595                 600                 605

Asp Lys Trp Met Asn Ser Glu Ser Ala Phe Ser Val Trp Asp Ser Pro
610                 615                 620

Pro Leu Thr Lys Asn Pro Ile Pro Leu Tyr Leu Arg Ile Pro Ser
625                 630                 635

<210> SEQ ID NO 37
<211> LENGTH: 631
<212> TYPE: PRT
<213> ORGANISM: Arabidopsis thaliana

<400> SEQUENCE: 37

Met Gly Phe Ser Pro Ser Ser Ser Trp Phe Leu His Pro Gln Leu His
1               5                   10                  15

His Val Val Ser Lys Met Ser Tyr Phe Asp Ala Phe Leu Phe Tyr Ile
            20                  25                  30

Val His Leu Val Asp Lys Leu Gly Leu Trp His Arg Phe Pro Val Leu
        35                  40                  45

Leu Gly Val Ala Tyr Leu Gly Leu Arg Arg His Leu His Gln Arg Tyr
    50                  55                  60

Asn Leu Val His Val Gly Pro Ile Asn Gly Gln Gly Tyr Asp Thr Asp
```

```
                65                  70                  75                  80
Glu Phe Cys Tyr Arg Thr Ala Asp Gly Lys Cys Asn His Pro Ser Asp
                    85                  90                  95
Asn Thr Ile Gly Ser Gln Gly Ser Phe Ile Gly Arg Asn Met Pro Pro
                100                 105                 110
Ser Thr Ser Gln Tyr Gly Ile Leu Asp Pro His Pro Ser Val Val Ala
                115                 120                 125
Thr Lys Leu Leu Ala Arg Lys Arg Phe Ile Asp Asn Gly Asp Gln Phe
            130                 135                 140
Asn Val Ile Ala Cys Ser Trp Ile Gln Phe Met Ile His Asp Trp Val
145                 150                 155                 160
Asp His Leu Glu Asp Thr His Gln Ile Glu Leu Ala Pro Glu Glu
                165                 170                 175
Val Ala Ser Gly Cys Pro Leu Lys Ser Phe Lys Phe Leu Arg Thr Lys
                180                 185                 190
Lys Val Pro Thr Asp Asp His His Lys Ser Gly Ala Val Asn Thr Arg
                195                 200                 205
Thr Pro Trp Trp Asp Gly Ser Val Ile Tyr Gly Asn Asp Glu Thr Gly
            210                 215                 220
Met Arg Arg Val Arg Val Phe Lys Asp Gly Lys Leu Lys Ile Ser Gly
225                 230                 235                 240
Asp Gly Leu Leu Glu Arg Asp Glu Arg Gly Val Pro Ile Ser Gly Asp
                245                 250                 255
Ile Arg Asn Ser Trp Ser Gly Phe Ser Leu Leu Gln Ala Leu Phe Val
                260                 265                 270
Lys Glu His Asn Ser Val Cys Asp Met Leu Lys Glu Arg Tyr Pro Asp
                275                 280                 285
Phe Asp Asp Glu Lys Leu Tyr Arg Thr Ala Arg Leu Val Thr Ala Ala
            290                 295                 300
Val Ile Ala Lys Val His Thr Ile Asp Trp Thr Ile Glu Leu Leu Lys
305                 310                 315                 320
Thr Asp Thr Leu Thr Ala Gly Met Arg Ile Asn Trp Tyr Gly Phe Phe
                325                 330                 335
Gly Lys Lys Val Lys Asp Met Val Gly Ala Arg Phe Gly Pro Leu Phe
                340                 345                 350
Ser Gly Leu Val Gly Leu Lys Lys Pro Asn Asp His Gly Val Pro Tyr
                355                 360                 365
Ser Leu Thr Glu Glu Phe Val Ser Val Tyr Arg Met His Cys Leu Leu
            370                 375                 380
Pro Glu Thr Leu Ile Leu Arg Asp Met Asn Ser Glu Asn Val Asp Lys
385                 390                 395                 400
Glu Asn Pro Ala Ile Glu Arg Glu Ile Pro Met Thr Glu Leu Ile Gly
                405                 410                 415
Lys Lys Ala Gly Glu Lys Ala Ser Lys Leu Gly Phe Glu Gln Leu Leu
                420                 425                 430
Val Ser Met Gly His Gln Ser Cys Gly Ala Leu Thr Leu Trp Asn Tyr
            435                 440                 445
Pro Asn Trp Met Arg Asn Leu Val Ala Gln Ile Asp Gly Glu Asp
450                 455                 460
Arg Pro His Leu Ile Asp Met Ala Ala Leu Glu Ile Tyr Arg Asp Arg
465                 470                 475                 480
Glu Arg Gly Val Pro Arg Tyr Asn Glu Phe Arg Lys Asn Leu Leu Met
                485                 490                 495
```

```
Ser Pro Ile Ser Lys Trp Glu Glu Leu Thr Asp Asp Glu Ala Ile
            500                 505                 510

Lys Val Leu Arg Glu Val Tyr Glu Asp Ile Glu Lys Leu Asp Leu
            515                 520                 525

Asn Val Gly Leu His Ala Glu Lys Lys Ile Lys Gly Phe Ala Ile Ser
            530                 535                 540

Glu Thr Ala Phe Phe Ile Phe Leu Leu Val Ala Ser Arg Arg Leu Glu
545                 550                 555                 560

Ala Asp Arg Phe Phe Thr Thr Asn Phe Asn Glu Lys Thr Tyr Thr Lys
                565                 570                 575

Glu Gly Leu Glu Trp Val Asn Thr Thr Glu Thr Leu Lys Asp Val Ile
            580                 585                 590

Asp Arg His Phe Pro Arg Leu Thr Asp Gln Trp Met Arg Cys Ser Ser
            595                 600                 605

Ala Phe Ser Val Trp Gly Ser Asp Pro Asn Pro Lys Asn Trp Val Pro
            610                 615                 620

Leu Tyr Leu Arg Ser Ala Pro
625                 630

<210> SEQ ID NO 38
<211> LENGTH: 613
<212> TYPE: PRT
<213> ORGANISM: Fusarium graminearum

<400> SEQUENCE: 38

Met Ala Ser Val Thr Ser Ile Ile Phe Val Ala Leu Val Ala Gly Val
1               5                   10                  15

Leu Tyr Ala Ala Arg Met Ser Leu Val Pro Ile Leu Lys Ser Leu Tyr
            20                  25                  30

Ile Arg Leu Trp Lys Gly Val Asn His Phe Ile Glu Trp His Lys Leu
        35                  40                  45

Pro Thr Trp Phe Ala Val Phe Asn Leu Leu Ala Leu Arg Tyr Glu Leu
    50                  55                  60

Arg Glu Gly Asn Leu His Asp Thr Ser Pro Asn Ala Glu Phe Gln Gly
65              70                  75                  80

Thr Asp Lys Cys Pro Met Ser Asp Ser Lys Phe Val Ser Ser Arg Asp
                85                  90                  95

Ser Asp Gly Leu Tyr Asn Asp Leu Lys Gln Pro Lys Met Gly Cys Ala
            100                 105                 110

Gly Met Arg Phe Gly Arg Asn Val Pro Arg Lys Tyr Thr Lys Pro Pro
        115                 120                 125

Thr Glu Gln Glu Leu Leu Thr Pro Asn Pro Arg Val Ile Ser Glu Lys
    130                 135                 140

Ile Leu Ala Arg Pro Glu Gly Gln Phe Lys Pro Ala Glu Ile Val Asn
145                 150                 155                 160

Leu Leu Ala Ala Ala Trp Ile Gln Phe Gln Val His Asp Trp Ala Gln
                165                 170                 175

His Phe Leu Val Thr Asn Gly Asp Lys Asp Ile Asp Ile Pro Leu His
            180                 185                 190

Asn Lys Asp Lys Trp Thr Glu Gln Ser Met Lys Ile Pro Arg Thr Lys
        195                 200                 205

Lys Ala Asp Ile Leu Ser Lys Gln Asp Ala Glu Thr Pro Ala Tyr Asp
    210                 215                 220

Asn Glu Asn Thr His Trp Trp Asp Ala Ser Gln Ile Tyr Gly Ser Ser
```

-continued

```
225                 230                 235                 240

Glu Ala Glu Thr Gln Ala Leu Arg Ala Lys Cys His Lys Ser Lys Pro
                245                 250                 255

Gly Gln Leu Glu Leu His Leu Ser Asn Pro Ser Trp Ser Ser Asp His
            260                 265                 270

Ile Phe Asp Thr Ala Arg Leu Ile Asn Cys Ala Leu Met Ala Lys Ile
        275                 280                 285

His Thr Val Glu Trp Thr Pro Gly Ile Leu Gln His Pro Ala Leu Gln
    290                 295                 300

Ile Gly Met Asn Ala Asn Trp Trp Gly Leu Leu Gly Asp Lys Leu Trp
305                 310                 315                 320

His Ala Phe Gly Arg Val Phe Asp Asn Lys Ser Glu Val Ile Ser Gly
                325                 330                 335

Ile Pro Gly Ser Gly Val Asp His Asp Lys Ala Pro Tyr Cys Leu Thr
            340                 345                 350

Glu Glu Phe Val Ser Val Tyr Arg Leu His Ser Leu Ile Pro Asp Asn
        355                 360                 365

Val Ala Phe Phe Asn Ile Lys Asp Gly Gln His Glu Gly Thr Leu Pro
    370                 375                 380

Ile Val Asp Val Ser Phe Glu Ser Ala Arg Lys Pro Phe Asp Glu Gly
385                 390                 395                 400

Lys Ser Gly Leu Gly Leu Ser Phe Ala Asp Val Phe Tyr Ser Phe Gly
                405                 410                 415

Val Asn Tyr Pro Gly Ala Ile Arg Ala His Asn Met Pro Asn Phe Leu
            420                 425                 430

Arg Asp Leu Lys Ile Pro Ala Asp Lys Asp Phe Pro Glu Gly Arg His
        435                 440                 445

Leu Asp Leu Gly Thr Ile Asp Ile Leu Arg Asp Arg Glu Arg Gly Val
    450                 455                 460

Pro Arg Tyr Asn Ala Phe Arg Arg Leu Phe His Met Pro Ala Ala Lys
465                 470                 475                 480

Ser Phe Ile Asp Leu Thr Gly Gly Asp Asp Lys Leu Ala Ser Glu Leu
                485                 490                 495

Glu Glu Val Tyr Glu Gly Asp Leu Glu Ala Val Asp Leu Leu Val Gly
            500                 505                 510

Thr Leu Cys Glu Pro Leu Pro Lys Gly Phe Gly Phe Ser Asp Thr Ala
        515                 520                 525

Phe Arg Val Phe Ile Leu Met Ala Thr Arg Arg Ile Lys Ser Asp Arg
    530                 535                 540

Phe Ile Ala Gly Asp Gly Trp Cys Pro Glu Val Tyr Thr Arg Glu Gly
545                 550                 555                 560

Met Asp Trp Val Gln Lys Asn Thr Met Lys Asp Val Leu Cys Arg His
                565                 570                 575

Phe Pro Glu Leu Ala Ala Pro Leu His Asn Val Lys Asn Ala Phe Ala
            580                 585                 590

Pro Trp Thr Lys Leu Gly Gln Thr Ala Ala Tyr Ala Gly Pro Glu Thr
        595                 600                 605

Asn Lys Ala Lys Ser
    610
```

<210> SEQ ID NO 39
<211> LENGTH: 653
<212> TYPE: PRT
<213> ORGANISM: Fusarium verticillioides

<400> SEQUENCE: 39

```
Met Ala Ser Val Leu Ser Lys Glu Ser Leu Ala Ile Ile Leu Ser Val
1               5                   10                  15

Val Thr Leu Leu Ile Gly Leu Ser His Phe Asn Met Ile Ser Leu Lys
            20                  25                  30

Ser Ile Phe Lys Ser Val Tyr Ile Arg Leu Trp Lys Leu Val Asn Val
        35                  40                  45

Phe Val His Trp His Lys Leu Pro Thr Trp Leu Gly Val Phe Asn Leu
    50                  55                  60

Leu Ala Leu Arg Tyr Glu Leu Arg Glu Lys Asn Leu His Asp Thr Tyr
65                  70                  75                  80

Pro Asn Ala Glu Phe Gln Gly Thr Ala Ala Asp Cys Pro Met Lys Asn
                85                  90                  95

Ser Lys Phe Ile Ala Thr Arg Asn Ser Asp Gly Asp Phe Asn Asp Leu
            100                 105                 110

Ala Gln Pro Lys Met Gly Cys Ala Gly Met Arg Phe Gly Arg Asn Val
        115                 120                 125

Pro Arg Asn His Thr Thr Pro Pro Thr Gln Gln Glu Leu Leu Thr Pro
130                 135                 140

Asn Pro Arg Leu Ile Ser Glu Lys Ile Leu Ala Arg Pro Glu Gly Gln
145                 150                 155                 160

Phe Lys Pro Ala Glu Ile Val Asn Leu Leu Ala Ala Trp Ile Gln
                165                 170                 175

Phe Gln Val His Asp Trp Ala Gln His Ser Leu Val Thr Asn Gly Asp
            180                 185                 190

Lys Asp Val Glu Ile Leu Leu Asp Lys Ala Asp Arg Trp Ser Glu Arg
        195                 200                 205

Ile Met Lys Ile Pro Arg Thr Lys Lys Asp Asp Pro Leu Ser Gln Gln
        210                 215                 220

Asp Ile Glu Thr Pro Ala Tyr Thr Asn Glu Cys Thr His Trp Trp Asp
225                 230                 235                 240

Ala Ser Gln Ile Tyr Gly Ser Thr Glu Ala Glu Thr Lys Ala Leu Arg
                245                 250                 255

Ala Gln Cys Asp Lys Ser Tyr Pro Gly Gln Leu His Val Thr Arg Glu
            260                 265                 270

Asp Gly Val Gln Phe Leu Pro Arg Ser Asp Gly Ile Pro Lys Thr
        275                 280                 285

Gly Phe Arg Gln Asn Trp Trp Leu Gly Leu Glu Leu Leu His Thr Leu
        290                 295                 300

Phe Ala Leu Glu His Asn Ala Ile Ala Thr Gln Leu His Leu Ser Asn
305                 310                 315                 320

Pro Ser Trp Ser Ser Asp Gln Ile Phe Asp Thr Ala Arg Leu Ile Asn
                325                 330                 335

Cys Ala Leu Met Ala Lys Ile His Thr Val Glu Trp Thr Pro Gly Ile
            340                 345                 350

Leu Gln His Pro Ala Leu Gln Ile Gly Met Asn Ala Asn Trp Trp Gly
        355                 360                 365

Leu Leu Gly Asp Lys Leu Trp His Val Phe Gly Arg Val Phe Asp Asn
        370                 375                 380

Lys Ser Glu Val Ile Ser Gly Ile Pro Gly Ser Gly Val Asp His Asp
385                 390                 395                 400

Asn Val Pro Tyr Cys Leu Thr Glu Glu Phe Val Ser Val Tyr Arg Leu
```

405                 410                 415
His Pro Leu Ile Pro Asp Asn Val Ala Phe Ser Ile Lys Asp Gly
                420                 425                 430

Gln His Lys Gly Thr Leu Pro Ile Lys Glu Val Ala Phe Lys Ser Ala
                435                 440                 445

Arg Lys Pro Phe Asp Glu Asp Lys Ser Gly Leu Gly Leu Ser Phe Ala
            450                 455                 460

Asp Val Phe Tyr Ser Phe Gly Val Asn Tyr Pro Gly Ala Ile Arg Ala
465                 470                 475                 480

His Asn Met Pro Asn Phe Leu Arg Asp Leu Asn Ile Pro Gly Asp Lys
                485                 490                 495

Asp Phe Pro His Gly Arg His Leu Asp Leu Gly Thr Ile Asp Ile Leu
                500                 505                 510

Arg Asp Arg Glu Arg Gly Val Pro Arg Tyr Asn Ala Phe Arg Arg Leu
            515                 520                 525

Phe His Met Ala Pro Ala Lys Thr Phe Ile Asp Leu Thr Gly Gly Asp
        530                 535                 540

Ser Lys Leu Ala Ala Glu Leu Glu Glu Val Tyr Asp Gly Asp Leu Glu
545                 550                 555                 560

Ala Val Asp Leu Leu Val Gly Thr Leu Ser Glu Pro Leu Pro Lys Gly
                565                 570                 575

Phe Gly Phe Ser Asp Thr Ala Phe Arg Val Phe Ile Leu Met Ala Thr
                580                 585                 590

Arg Arg Ile Lys Ser Asp Arg Phe Leu Ala Gly Asp Gly Trp Cys Pro
            595                 600                 605

Glu Val Tyr Thr Arg Glu Gly Ile Asn Trp Val Gln Asn Asn Thr Met
        610                 615                 620

Lys Asp Val Leu Cys Arg His Phe Pro Glu Leu Ala Ala Thr Leu His
625                 630                 635                 640

Asn Val Lys Asn Leu Ser Val Ser Phe Ile Leu Ser Leu
                645                 650

<210> SEQ ID NO 40
<211> LENGTH: 668
<212> TYPE: PRT
<213> ORGANISM: Fusarium oxysporum

<400> SEQUENCE: 40

Met Ala Ser Val Leu Ser Lys Glu Ser Leu Ala Ile Ser Leu Ser Ile
1               5                   10                  15

Val Thr Leu Leu Ile Gly Leu Ser His Phe Asn Met Ile Ser Leu Lys
                20                  25                  30

Pro Ile Phe Lys Ser Val Tyr Ile Arg Leu Trp Lys Phe Val Asn Ile
            35                  40                  45

Phe Val His Trp His Lys Leu Pro Thr Trp Leu Gly Val Phe Asn Leu
        50                  55                  60

Leu Ala Leu Arg Tyr Glu Leu Arg Glu Lys Asn Leu His Asp Thr Tyr
65                  70                  75                  80

Pro Asn Ala Glu Phe Gln Gly Thr Thr Ala Asp Cys Pro Met Lys Asn
                85                  90                  95

Ser Lys Phe Ile Ala Asn Arg Asn Ser Asp Gly Asp Phe Asn Asp Leu
            100                 105                 110

Ala Gln Pro Lys Met Gly Cys Ala Gly Met Arg Phe Gly Arg Asn Val
        115                 120                 125

```
Pro Arg Lys Tyr Thr Thr Pro Pro Thr Gln Gln Glu Leu Leu Thr Pro
130                 135                 140

Asn Pro Arg Ile Ile Ser Glu Lys Ile Leu Ala Arg Pro Glu Gly Gln
145                 150                 155                 160

Phe Lys Pro Ala Glu Ile Val Asn Leu Leu Ala Ala Trp Ile Gln
        165                 170                 175

Phe Gln Val His Asp Trp Ala Gln His Phe Leu Val Thr Asn Gly Asp
            180                 185                 190

Lys Asp Val Glu Ile Pro Leu Asp Lys Ala Asp Arg Trp Ser Glu Arg
        195                 200                 205

Ile Met Lys Ile Pro Arg Thr Lys Lys Asp Asp Ala Leu Ser Gln Gln
210                 215                 220

Asp Ile Glu Thr Pro Ala Tyr Thr Asn Glu Cys Thr His Trp Trp Asp
225                 230                 235                 240

Ala Ser Gln Ile Tyr Gly Ser Thr Glu Ala Glu Thr Lys Ala Leu Arg
                245                 250                 255

Ala Gln Cys Asp Lys Ser Tyr Pro Gly Gln Leu His Val Thr Arg Glu
            260                 265                 270

Asp Gly Val Gln Phe Leu Pro Arg Ser Asp Asp Gly Ile Pro Lys Thr
        275                 280                 285

Gly Phe Arg Gln Asn Trp Trp Leu Gly Leu Glu Leu Leu His Thr Leu
290                 295                 300

Phe Ala Leu Glu His Asn Ala Ile Ala Thr Gln Leu His Leu Ser Asn
305                 310                 315                 320

Pro Ser Trp Ser Ser Asp Gln Ile Phe Asp Thr Ala Arg Leu Ile Asn
                325                 330                 335

Cys Ala Leu Met Ala Lys Ile His Thr Val Glu Trp Thr Pro Gly Ile
            340                 345                 350

Leu Gln His Pro Ala Leu Gln Ile Gly Met Asn Ala Asn Trp Trp Gly
        355                 360                 365

Leu Leu Gly Asp Lys Leu Trp His Val Phe Gly Arg Val Phe Asp Asn
370                 375                 380

Lys Ser Glu Val Ile Ser Gly Ile Pro Gly Ser Gly Val Asp His Asp
385                 390                 395                 400

Asn Val Pro Tyr Cys Leu Thr Glu Glu Phe Val Ser Val Tyr Arg Leu
                405                 410                 415

His Pro Leu Ile Pro Asp Asn Val Ala Phe Phe Ser Ile Lys Asp Gly
            420                 425                 430

Gln His Lys Gly Thr Leu Pro Ile Lys Asp Val Ala Phe Glu Ser Ala
        435                 440                 445

Arg Lys Pro Phe Asp Glu Asp Lys Ser Gly Leu Gly Leu Ser Phe Ala
450                 455                 460

Asp Val Phe Tyr Ser Phe Gly Val Asn Tyr Pro Gly Ala Ile Arg Ala
465                 470                 475                 480

His Asn Met Pro Asn Phe Leu Arg Asp Leu Asn Ile Pro Gly Asp Lys
                485                 490                 495

Asp Phe Pro Gln Gly Arg His Leu Asp Leu Gly Thr Ile Asp Ile Leu
            500                 505                 510

Arg Asp Arg Glu Arg Gly Val Pro Arg Tyr Asn Ala Phe Arg Arg Leu
        515                 520                 525

Phe His Met Ala Pro Ala Lys Ser Phe Leu Asp Leu Thr Gly Gly Asp
530                 535                 540

Ala Lys Leu Ala Ala Glu Leu Glu Asp Val Tyr Asp Gly Asp Leu Glu
```

```
545                 550                 555                 560
Ala Val Asp Leu Leu Val Gly Thr Leu Ser Glu Pro Leu Pro Lys Gly
                565                 570                 575

Phe Gly Phe Ser Asp Thr Ala Phe Arg Val Phe Ile Leu Met Ala Thr
                580                 585                 590

Arg Arg Ile Lys Ser Asp Arg Phe Leu Ala Gly Asp Gly Trp Cys Pro
                595                 600                 605

Glu Val Tyr Thr Arg Glu Gly Ile Asn Trp Val Gln Asn Asn Thr Met
                610                 615                 620

Lys Asp Val Leu Cys Arg His Phe Pro Glu Leu Ala Ala Thr Leu His
625                 630                 635                 640

Asn Val Lys Asn Ala Phe Ala Pro Trp Thr Lys Ile Gly Gln Thr Glu
                645                 650                 655

Ala Tyr Ala Gly Pro Glu Thr Asn Lys Ala Lys Asn
                660                 665

<210> SEQ ID NO 41
<211> LENGTH: 618
<212> TYPE: PRT
<213> ORGANISM: Oryza sative

<400> SEQUENCE: 41

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
                20                  25                  30

His Ala Phe Asp Lys Arg Asn Leu Trp His Lys Val Pro Val Pro Ile
                35                  40                  45

Gly Leu Leu Tyr Leu Asn Thr Arg Arg Thr Leu Leu Glu Lys Tyr Asn
            50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
                100                 105                 110

Val Asp Gln Gln Asp Glu Leu Met Ser Pro Asp Pro Phe Val Val Ala
            115                 120                 125

Thr Lys Leu Leu Ala Arg Arg Glu Tyr Lys Asp Thr Gly Lys Gln Phe
130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
                180                 185                 190

Glu Leu Pro Thr Asn Ser Asp Gly Ile Lys Ile Gly His Tyr Asn Ile
            195                 200                 205

Arg Thr Ala Trp Trp Asp Gly Ser Ala Val Tyr Gly Asn Asn Glu Glu
            210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255
```

```
Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
    450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Leu Phe
                485                 490                 495

Leu Ile Pro Ile Lys Ser Trp Glu Asp Leu Thr Ser Asp Lys Asp Ala
            500                 505                 510

Ile Glu Thr Ile Arg Ala Ile Tyr Gly Asp Asp Val Glu Lys Leu Asp
        515                 520                 525

Leu Leu Val Gly Leu Met Ala Glu Lys Lys Ile Lys Gly Phe Ala Ile
    530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Gly Thr Tyr Thr
                565                 570                 575

Lys Lys Gly Met Gln Trp Val Lys Thr Thr Glu Gly Leu Arg Asp Val
            580                 585                 590

Ile Asn Arg His Tyr Pro Glu Ile Thr Ala Lys Trp Met Lys Ser Ser
        595                 600                 605

Ser Ala Phe Ser Val Trp Asp Ala Asp Tyr
    610                 615

<210> SEQ ID NO 42
<211> LENGTH: 599
<212> TYPE: PRT
<213> ORGANISM: Homo sapiens

<400> SEQUENCE: 42

Met Ser Arg Ser Leu Leu Leu Trp Phe Leu Leu Phe Leu Leu Leu Leu
1               5                   10                  15
```

```
Pro Pro Leu Pro Val Leu Leu Ala Asp Pro Gly Ala Pro Thr Pro Val
            20                  25                  30

Asn Pro Cys Cys Tyr Tyr Pro Cys Gln His Gln Gly Ile Cys Val Arg
        35                  40                  45

Phe Gly Leu Asp Arg Tyr Gln Cys Asp Cys Thr Arg Thr Gly Tyr Ser
    50                  55                  60

Gly Pro Asn Cys Thr Ile Pro Gly Leu Trp Thr Trp Leu Arg Asn Ser
65                  70                  75                  80

Leu Arg Pro Ser Pro Ser Phe Thr His Phe Leu Leu Thr His Gly Arg
                85                  90                  95

Trp Phe Trp Glu Phe Val Asn Ala Thr Phe Ile Arg Glu Met Leu Met
                100                 105                 110

Arg Leu Val Leu Thr Val Arg Ser Asn Leu Ile Pro Ser Pro Pro Thr
            115                 120                 125

Tyr Asn Ser Ala His Asp Tyr Ile Ser Trp Glu Ser Phe Ser Asn Val
    130                 135                 140

Ser Tyr Tyr Thr Arg Ile Leu Pro Ser Val Pro Lys Asp Cys Pro Thr
145                 150                 155                 160

Pro Met Gly Thr Lys Gly Lys Lys Gln Leu Pro Asp Ala Gln Leu Leu
                165                 170                 175

Ala Arg Arg Phe Leu Leu Arg Arg Lys Phe Ile Pro Asp Pro Gln Gly
            180                 185                 190

Thr Asn Leu Met Phe Ala Phe Phe Ala Gln His Phe Thr His Gln Phe
            195                 200                 205

Phe Lys Thr Ser Gly Lys Met Gly Pro Gly Phe Thr Lys Ala Leu Gly
    210                 215                 220

His Gly Val Asp Leu Gly His Ile Tyr Gly Asp Asn Leu Glu Arg Gln
225                 230                 235                 240

Tyr Gln Leu Arg Leu Phe Lys Asp Gly Lys Leu Lys Tyr Gln Val Leu
                245                 250                 255

Asp Gly Glu Met Tyr Pro Pro Ser Val Glu Glu Ala Pro Val Leu Met
            260                 265                 270

His Tyr Pro Arg Gly Ile Pro Pro Gln Ser Gln Met Ala Val Gly Gln
            275                 280                 285

Glu Val Phe Gly Leu Leu Pro Gly Leu Met Leu Tyr Ala Thr Leu Trp
    290                 295                 300

Leu Arg Glu His Asn Arg Val Cys Asp Leu Leu Lys Ala Glu His Pro
305                 310                 315                 320

Thr Trp Gly Asp Glu Gln Leu Phe Gln Thr Thr Arg Leu Ile Leu Ile
                325                 330                 335

Gly Glu Thr Ile Lys Ile Val Ile Glu Glu Tyr Val Gln Gln Leu Ser
            340                 345                 350

Gly Tyr Phe Leu Gln Leu Lys Phe Asp Pro Glu Leu Leu Phe Gly Val
    355                 360                 365

Gln Phe Gln Tyr Arg Asn Arg Ile Ala Met Glu Phe Asn His Leu Tyr
    370                 375                 380

His Trp His Pro Leu Met Pro Asp Ser Phe Lys Val Gly Ser Gln Glu
385                 390                 395                 400

Tyr Ser Tyr Glu Gln Phe Leu Phe Asn Thr Ser Met Leu Val Asp Tyr
                405                 410                 415

Gly Val Glu Ala Leu Val Asp Ala Phe Ser Arg Gln Ile Ala Gly Arg
            420                 425                 430
```

```
Ile Gly Gly Gly Arg Asn Met Asp His His Ile Leu His Val Ala Val
            435                 440                 445

Asp Val Ile Arg Glu Ser Arg Glu Met Arg Leu Gln Pro Phe Asn Glu
450                 455                 460

Tyr Arg Lys Arg Phe Gly Met Lys Pro Tyr Thr Ser Phe Gln Glu Leu
465                 470                 475                 480

Val Gly Glu Lys Glu Met Ala Ala Glu Leu Glu Leu Tyr Gly Asp
                485                 490                 495

Ile Asp Ala Leu Glu Phe Tyr Pro Gly Leu Leu Leu Glu Lys Cys His
            500                 505                 510

Pro Asn Ser Ile Phe Gly Glu Ser Met Ile Glu Ile Gly Ala Pro Phe
            515                 520                 525

Ser Leu Lys Gly Leu Leu Gly Asn Pro Ile Cys Ser Pro Glu Tyr Trp
530                 535                 540

Lys Pro Ser Thr Phe Gly Gly Glu Val Gly Phe Asn Ile Val Lys Thr
545                 550                 555                 560

Ala Thr Leu Lys Lys Leu Val Cys Leu Asn Thr Lys Thr Cys Pro Tyr
            565                 570                 575

Val Ser Phe Arg Val Pro Asp Ala Ser Gln Asp Asp Gly Pro Ala Val
                580                 585                 590

Glu Arg Pro Ser Thr Glu Leu
            595

<210> SEQ ID NO 43
<211> LENGTH: 624
<212> TYPE: PRT
<213> ORGANISM: Pseudomonas aeruginosa

<400> SEQUENCE: 43

Met His Pro Thr Phe Ser Arg Val Leu Leu Ala Ala Leu Ala Ala
1               5                   10                  15

Ala Gly Ser Pro Ala Val Ala Thr Glu Ile Gln Leu Glu Gln Gly Trp
                20                  25                  30

Asn Ala Glu Gln Arg Ala Ser Trp Tyr Asp Ala Ser Leu Gly Ser Arg
            35                  40                  45

Leu Leu Pro Leu Ala Trp Ala Gln Ala Leu Glu Arg Pro Asp Ser Glu
50                  55                  60

Glu Arg Leu Phe Ser Glu Asp Asn Ala Arg Arg Leu Gly Phe Pro Leu
65                  70                  75                  80

Arg Asn Trp Gln Gly Gly Glu Leu Arg Leu Pro Arg Gly Phe Ala Leu
                85                  90                  95

Asp Gln Gln Asp Asp Ser Gln Phe Ser Asp Thr Arg Leu Arg Trp Lys
            100                 105                 110

Ala Arg Gln Ser Ser Glu Pro Trp Val Gly Leu Asn Cys Ala Gly
            115                 120                 125

Cys His Ser Thr Asp Ile Ser Tyr Arg Gly Ser Glu Leu Thr Val Asp
            130                 135                 140

Ala Gly Ala Thr Leu Ala Asn Val Gln Ala Ile Phe Asp Glu Val Leu
145                 150                 155                 160

Ala Ala Leu Arg Arg Thr Ser Asp Asp Gly Asp Lys Phe Ala Arg Phe
                165                 170                 175

Ala Gly Asn Val Leu Gly Ser Glu Asp Ser Pro Ala Asn Arg Glu Leu
            180                 185                 190

Leu Lys Ala Ala Leu Val Lys Arg Ala Ala Leu Ile Asp Thr Leu Leu
            195                 200                 205
```

```
Ser Met Ser Ala Thr Asp Leu Gln Pro Gly Pro Gly Arg Leu Asp Ala
    210                 215                 220

Thr Gly Gln Ser Leu Asn Arg Ala Ala Ile Asn Ser Gly Ala Arg His
225                 230                 235                 240

Leu Gln Ala Asn Pro Thr Asp Ala Pro Thr Ser Phe Pro Ala Leu Trp
                245                 250                 255

His Thr Leu Gln Met Asp Lys Leu Gln Ser Ser Gly Phe Val Pro Asn
            260                 265                 270

Val Lys Val Leu Asp Leu Asn Gly Gln Val Phe Asp Leu Gly Tyr Leu
        275                 280                 285

Ala Gly Asp Ile Gly Val Val Gln Gly Asp Tyr Gly Asp Val Val Ser
    290                 295                 300

His Pro Leu Ser Gly Leu Glu Gly Tyr Ile Ser Ser Ile Arg Val Asp
305                 310                 315                 320

Asn Leu Thr Arg Val Glu Gly Leu Ile His Lys Leu Lys Ala Pro Ala
                325                 330                 335

Trp Pro Ser Gln Leu Phe Gly Ala Pro Asp Ser Ala Arg Leu Ala Gln
            340                 345                 350

Gly Lys Arg Leu Tyr Glu Glu Asn Cys Ala Ala Cys His Ala Ser Ile
        355                 360                 365

Gly Arg Asp Asp Leu Gln Thr Pro Ile Lys Val Arg Gln Val Arg Leu
    370                 375                 380

Lys Ala His Gly Asp Asp Ala Pro Ile Gly Thr Asp Pro Trp Met Ala
385                 390                 395                 400

Cys Asn Thr Phe Thr Phe Ser Ser Pro Ser Gly Asn Tyr Phe Gly Leu
                405                 410                 415

Phe Arg Pro Ser Leu Gly Thr Pro Ser Gly Val Gly Ile Val Gly Arg
            420                 425                 430

Thr Ser Lys Ile Ala Asp Met Gln Val Pro Glu Val Phe Gln Ile Met
        435                 440                 445

Leu Gly Lys Lys Gly Gln Leu Ala Asp Gly Ile Ala Glu Ile Ile His
    450                 455                 460

Ala Ile Val Thr Gly Gln Gln Thr Leu Pro Gly Ser Asp Ser Leu Gln
465                 470                 475                 480

Ala Val Pro Ala Gly Gln Leu Leu Ala Gly Ala Ala Pro Ala Asp
                485                 490                 495

Ser Gln Ala Gln Ser Leu Ala Ala Gly Glu Val Pro Thr Asp Lys Ser
            500                 505                 510

Ala Arg Lys Asp Tyr Cys Leu Asn Thr Glu His Pro Phe Leu Gly Tyr
        515                 520                 525

Ile Ala Arg Pro Leu Asn Gly Ile Trp Ala Thr Ala Pro Tyr Leu His
    530                 535                 540

Asn Gly Ser Val Pro Ser Leu Tyr Asp Leu Leu Pro Gln Glu Gln
545                 550                 555                 560

Arg Pro Ala Thr Phe Tyr Thr Gly Ser His Glu Phe Asp Pro Ser Arg
                565                 570                 575

Val Gly Tyr Leu Thr Ala Pro Gly Pro Asp Asn Ala Phe Leu Phe Asp
            580                 585                 590

Thr His Leu Glu Gly Asn Ser Asn Ala Gly His Asp Phe Ala Arg Glu
        595                 600                 605

Tyr Asp Glu Ser Gln Arg Leu Ala Leu Leu Glu Tyr Leu Lys Thr Leu
    610                 615                 620
```

<210> SEQ ID NO 44
<211> LENGTH: 624
<212> TYPE: PRT
<213> ORGANISM: Pseudomonas aeruginosa

<400> SEQUENCE: 44

```
Met His Pro Thr Phe Ser Arg Ile Leu Leu Ala Ala Leu Ala Ser
1               5                   10                  15

Ala Gly Ser Pro Ala Val Ala Thr Glu Ile Gln Leu Glu Gln Gly Trp
            20                  25                  30

Asn Ala Glu Gln Arg Ala Ser Trp Tyr Asp Ala Ser Leu Gly Ser Arg
        35                  40                  45

Leu Leu Pro Leu Ala Trp Ala Gln Ala Leu Glu Arg Pro Asp Ser Glu
    50                  55                  60

Glu Arg Leu Phe Ser Glu Asp Asn Ala Arg Arg Leu Gly Phe Pro Leu
65                  70                  75                  80

Arg Asn Trp Gln Gly Gly Glu Leu Arg Leu Pro Arg Gly Phe Ala Leu
                85                  90                  95

Asp Gln Gln Asp Asp Ser Gln Phe Ser Asp Thr Arg Leu Arg Trp Lys
            100                 105                 110

Ala Arg Gln Ser Ser Ser Glu Pro Trp Val Gly Leu Asn Cys Ala Gly
        115                 120                 125

Cys His Ser Thr Asp Ile Ser Tyr Arg Gly Ser Glu Leu Thr Val Asp
    130                 135                 140

Ala Gly Ala Thr Leu Ala Asn Val Gln Ala Ile Phe Asp Glu Val Leu
145                 150                 155                 160

Ala Ala Leu Arg Arg Thr Ser Asp Asp Gly Asp Lys Phe Ala Arg Phe
                165                 170                 175

Ala Gly Asn Val Leu Gly Ser Glu Asp Ser Pro Ala Asn Arg Asp Leu
            180                 185                 190

Leu Lys Ala Ala Leu Ala Lys Cys Ala Ala Leu Ile Asp Thr Leu Leu
        195                 200                 205

Ser Met Ser Ala Thr Asp Leu Gln Pro Gly Pro Gly Arg Leu Asp Ala
    210                 215                 220

Thr Gly Gln Ser Leu Asn Arg Ala Ala Ile Asn Ser Gly Ala Arg His
225                 230                 235                 240

Leu Gln Ala Asn Pro Thr Asp Ala Pro Thr Ser Phe Pro Ala Leu Trp
                245                 250                 255

His Thr Leu Gln Met Asp Lys Leu Gln Ser Ser Gly Phe Val Pro Asn
            260                 265                 270

Val Lys Val Leu Asp Leu Asn Gly Gln Val Phe Asp Leu Gly Tyr Leu
        275                 280                 285

Ala Gly Asp Ile Gly Val Val Gln Gly Asp Tyr Gly Asp Val Val Ser
    290                 295                 300

His Pro Leu Ser Gly Leu Glu Gly Tyr Ile Ser Ser Ile Arg Val Asp
305                 310                 315                 320

Asn Leu Thr Arg Val Glu Gly Leu Ile His Lys Leu Lys Ala Pro Ala
                325                 330                 335

Trp Pro Ser Gln Leu Phe Gly Ala Pro Asp Ser Ala Arg Leu Ala Gln
            340                 345                 350

Gly Lys Arg Leu Tyr Glu Glu Asn Cys Ala Ala Cys His Ala Ser Ile
        355                 360                 365

Gly Arg Asp Asp Leu Gln Thr Pro Ile Lys Val Arg Gln Val Arg Leu
    370                 375                 380
```

Lys Ala His Gly Asp Asp Ala Pro Ile Gly Thr Asp Pro Trp Met Ala
385                 390                 395                 400

Cys Asn Thr Phe Thr Phe Ser Ser Pro Ser Gly Asn Tyr Phe Gly Leu
            405                 410                 415

Phe Arg Pro Ser Leu Gly Thr Pro Ser Gly Val Gly Ile Val Gly Arg
        420                 425                 430

Thr Ser Lys Ile Ala Asp Met Gln Val Pro Glu Val Phe Gln Ile Met
    435                 440                 445

Leu Gly Lys Lys Gly Gln Leu Ala Asp Gly Ile Ala Glu Ile Ile His
450                 455                 460

Ala Ile Val Thr Gly Gln Gln Thr Leu Pro Gly Ser Asp Ser Leu Gln
465                 470                 475                 480

Ala Leu Pro Thr Gly Gln Leu Leu Ala Gly Gly Asp Pro Ala Gly
                485                 490                 495

Ser Gln Ala Pro Ser Leu Ala Ala Gly Glu Val Pro Ala Asp Lys Ser
            500                 505                 510

Ala Arg Lys Asp Tyr Cys Leu Asn Thr Glu His Pro Phe Leu Gly Tyr
        515                 520                 525

Ile Ala Arg Pro Leu Asn Gly Ile Trp Ala Thr Ala Pro Tyr Leu His
    530                 535                 540

Asn Gly Ser Val Pro Ser Leu Tyr Asp Leu Leu Pro Gln Glu Gln
545                 550                 555                 560

Arg Pro Thr Thr Phe Tyr Thr Gly Ser His Glu Phe Asp Pro Ser Arg
                565                 570                 575

Val Gly Tyr Leu Thr Gly Pro Gly Pro Asp Asn Ala Phe Leu Phe Asp
            580                 585                 590

Thr His Leu Glu Gly Asn Ser Asn Ala Gly His Asp Phe Ala Arg Glu
        595                 600                 605

Tyr Asp Glu Ser Gln Arg Leu Ala Leu Leu Gly Tyr Leu Lys Thr Leu
    610                 615                 620

<210> SEQ ID NO 45
<211> LENGTH: 711
<212> TYPE: PRT
<213> ORGANISM: Homo sapiens

<400> SEQUENCE: 45

Met Ala Val Tyr Arg Leu Cys Val Thr Thr Gly Pro Tyr Leu Arg Ala
1               5                   10                  15

Gly Thr Leu Asp Asn Ile Ser Val Thr Leu Val Gly Thr Cys Gly Glu
            20                  25                  30

Ser Pro Lys Gln Arg Leu Asp Arg Met Gly Arg Asp Phe Ala Pro Gly
        35                  40                  45

Ser Val Gln Lys Tyr Lys Val Arg Cys Thr Ala Glu Leu Gly Glu Leu
    50                  55                  60

Leu Leu Leu Arg Val His Lys Glu Arg Tyr Ala Phe Phe Arg Lys Asp
65                  70                  75                  80

Ser Trp Tyr Cys Ser Arg Ile Cys Val Thr Glu Pro Asp Gly Ser Val
                85                  90                  95

Ser His Phe Pro Cys Tyr Gln Trp Ile Glu Gly Tyr Cys Thr Val Glu
            100                 105                 110

Leu Arg Pro Gly Thr Ala Arg Thr Ile Cys Gln Asp Ser Leu Pro Leu
        115                 120                 125

Leu Leu Asp His Arg Thr Arg Glu Leu Arg Ala Arg Gln Glu Cys Tyr

```
                130             135             140
Arg Trp Lys Ile Tyr Ala Pro Gly Phe Pro Cys Met Val Asp Val Asn
145                 150                 155                 160

Ser Phe Gln Glu Met Glu Ser Asp Lys Lys Phe Ala Leu Thr Lys Thr
                165                 170                 175

Thr Thr Cys Val Asp Gln Gly Asp Ser Ser Gly Asn Arg Tyr Leu Pro
                180                 185                 190

Gly Phe Pro Met Lys Ile Asp Ile Pro Ser Leu Met Tyr Met Glu Pro
                195                 200                 205

Asn Val Arg Tyr Ser Ala Thr Lys Thr Ile Ser Leu Leu Phe Asn Ala
                210                 215                 220

Ile Pro Ala Ser Leu Gly Met Lys Leu Arg Gly Leu Leu Asp Arg Lys
225                 230                 235                 240

Gly Ser Trp Lys Lys Leu Asp Asp Met Gln Asn Ile Phe Trp Cys His
                245                 250                 255

Lys Thr Phe Thr Thr Lys Tyr Val Thr Glu His Trp Cys Glu Asp His
                260                 265                 270

Phe Phe Gly Tyr Gln Tyr Leu Asn Gly Val Asn Pro Val Met Leu His
                275                 280                 285

Cys Ile Ser Ser Leu Pro Ser Lys Leu Pro Val Thr Asn Asp Met Val
                290                 295                 300

Ala Pro Leu Leu Gly Gln Asp Thr Cys Leu Gln Thr Glu Leu Glu Arg
305                 310                 315                 320

Gly Asn Ile Phe Leu Ala Asp Tyr Trp Ile Leu Ala Glu Ala Pro Thr
                325                 330                 335

His Cys Leu Asn Gly Arg Gln Gln Tyr Val Ala Ala Pro Leu Cys Leu
                340                 345                 350

Leu Trp Leu Ser Pro Gln Gly Ala Leu Val Pro Leu Ala Ile Gln Leu
                355                 360                 365

Ser Gln Thr Pro Gly Pro Asp Ser Pro Ile Phe Leu Pro Thr Asp Ser
                370                 375                 380

Glu Trp Asp Trp Leu Leu Ala Lys Thr Trp Val Arg Asn Ser Glu Phe
385                 390                 395                 400

Leu Val His Glu Asn Asn Thr His Phe Leu Cys Thr His Leu Leu Cys
                405                 410                 415

Glu Ala Phe Ala Met Ala Thr Leu Arg Gln Leu Pro Leu Cys His Pro
                420                 425                 430

Ile Tyr Lys Leu Leu Leu Pro His Thr Arg Tyr Thr Leu Gln Val Asn
                435                 440                 445

Thr Ile Ala Arg Ala Thr Leu Leu Asn Pro Glu Gly Leu Val Asp Gln
                450                 455                 460

Val Thr Ser Ile Gly Arg Gln Gly Leu Ile Tyr Leu Met Ser Thr Gly
465                 470                 475                 480

Leu Ala His Phe Thr Tyr Thr Asn Phe Cys Leu Pro Asp Ser Leu Arg
                485                 490                 495

Ala Arg Gly Val Leu Ala Ile Pro Asn Tyr His Tyr Arg Asp Asp Gly
                500                 505                 510

Leu Lys Ile Trp Ala Ala Ile Glu Ser Phe Val Ser Glu Ile Val Gly
                515                 520                 525

Tyr Tyr Tyr Pro Ser Asp Ala Ser Val Gln Gln Asp Ser Glu Leu Gln
                530                 535                 540

Ala Trp Thr Gly Glu Ile Phe Ala Gln Ala Phe Leu Gly Arg Glu Ser
545                 550                 555                 560
```

```
Ser Gly Phe Pro Ser Arg Leu Cys Thr Pro Gly Glu Met Val Lys Phe
            565                 570                 575

Leu Thr Ala Ile Ile Phe Asn Cys Ser Ala Gln His Ala Ala Val Asn
            580                 585                 590

Ser Gly Gln His Asp Phe Gly Ala Trp Met Pro Asn Ala Pro Ser Ser
            595                 600                 605

Met Arg Gln Pro Pro Pro Gln Thr Lys Gly Thr Thr Thr Leu Lys Thr
610                 615                 620

Tyr Leu Asp Thr Leu Pro Glu Val Asn Ile Ser Cys Asn Asn Leu Leu
625                 630                 635                 640

Leu Phe Trp Leu Val Ser Gln Glu Pro Lys Asp Gln Arg Pro Leu Gly
            645                 650                 655

Thr Tyr Pro Asp Glu His Phe Thr Glu Glu Ala Pro Arg Arg Ser Ile
            660                 665                 670

Ala Ala Phe Gln Ser Arg Leu Ala Gln Ile Ser Arg Asp Ile Gln Glu
            675                 680                 685

Arg Asn Gln Gly Leu Ala Leu Pro Tyr Thr Tyr Leu Asp Pro Pro Leu
690                 695                 700

Ile Glu Asn Ser Val Ser Ile
705                 710

<210> SEQ ID NO 46
<211> LENGTH: 393
<212> TYPE: PRT
<213> ORGANISM: Nostoc punctiforme

<400> SEQUENCE: 46

Met Lys Leu Phe Thr Glu Tyr Pro Glu Lys Asp Glu Leu Lys Tyr Cys
1               5                   10                  15

Asp Leu Met Ser Glu Leu Val Lys Lys Asn Met Glu Asn Leu Tyr Gly
            20                  25                  30

Gly Lys Lys Lys Lys Thr Ala Lys Arg Asp Thr His Ser Lys Thr His
            35                  40                  45

Ala Ala Val Gln Gly Thr Leu Glu Ile Phe Asp Phe Asp Glu Ala Ala
50                  55                  60

Ile Lys Gln Glu Leu Ser Lys Arg Thr Ser Leu Ser Glu Ala Glu Leu
65                  70                  75                  80

Ser Ala Ile Ser Leu Lys Gln Gly Leu Phe Ala Thr Pro Lys Gln Tyr
            85                  90                  95

Pro Val Trp Leu Arg Phe Ala Asn Gly Ala Phe Ser Val Lys Asn Asp
            100                 105                 110

Tyr Glu Gly Asp Thr Arg Ser Met Ala Val Lys Ala Ile Gly Val Glu
            115                 120                 125

Gly Glu Arg Leu Ser Gln Ser His Glu Leu Lys Thr Gln Asp Ile Ile
            130                 135                 140

Thr His Asn Thr Glu Phe Phe Val Arg Thr Ile Lys Asp Phe His
145                 150                 155                 160

Ser Phe Phe Leu Thr Val Tyr Arg Ala Gly Leu Phe Pro Leu Phe Lys
            165                 170                 175

Leu Leu Val Leu Phe Trp Leu Lys Leu His Pro Tyr Glu Ser Thr Leu
            180                 185                 190

Leu Gln Thr Ser Phe Lys Arg Phe Pro Lys Ser Leu Leu Lys Glu Arg
            195                 200                 205

Tyr Trp Ser Ala Ser Ala Phe Ser Val Gly Leu Lys Ser Gly Phe Asp
```

-continued

```
            210                 215                 220
Pro Ser Gln Pro Gly Arg Val Pro Val Glu Tyr Pro Ala Val Ile Lys
225                 230                 235                 240

Tyr Gly Phe Thr Pro Val Ser Ser Gln Pro His Gln Gln Phe Pro
                245                 250                 255

Leu Glu Ser Arg Ser Glu Ser Glu Leu Lys Leu Ala Lys Ala Ser Gly
                260                 265                 270

Ser Glu Asp Asn Tyr Tyr Arg Glu Asp Ile Ile Gln Ala Leu Ala Lys
                275                 280                 285

Pro Asp Ala Glu Tyr Tyr Trp Asp Phe Gln Ile Gln Phe Gln Thr Ser
290                 295                 300

Pro Glu Met Ser Ile Asp Asp Thr Thr Ile Val Trp Asn Glu Glu Glu
305                 310                 315                 320

Ser Pro Phe Phe Thr Val Gly Arg Leu Thr Ile Lys His Gln Lys Val
                325                 330                 335

Asn Tyr Pro Gln Ala Asn Asp Phe Gly Glu Asn Leu Ser Phe Ser Pro
                340                 345                 350

Gly Asn Gly Leu Ala Val His Arg Pro Val Gly Ala Ile Asn Arg Leu
                355                 360                 365

Arg Ser Ile Val Tyr Pro Ile Val Ala Asn Asp Arg His Gln Lys Arg
370                 375                 380

Gly Val Lys Tyr Gln Glu Pro Thr Val
385                 390

<210> SEQ ID NO 47
<211> LENGTH: 1143
<212> TYPE: PRT
<213> ORGANISM: Aspergillus terreus

<400> SEQUENCE: 47

Met Ser Ser Val Ile Val Ala Leu Ala Val Leu Val Leu Ser Leu Leu
1               5                   10                  15

Tyr Leu Thr Leu Phe Arg Asn Asp Leu Thr His Leu Ile Ile Glu Lys
                20                  25                  30

Leu Gln Ser Phe Arg Thr Gly Ser Gly Trp Glu Leu Ser Pro Arg Ser
            35                  40                  45

Arg Leu Leu Pro Arg Ala Thr Lys Ala Ala Leu Ser Ser Ile Thr Gly
        50                  55                  60

Thr Gly Val Gly Ile Trp Ser Arg Leu Tyr Ala Arg Ile Phe His Ser
65                  70                  75                  80

Asp Glu Leu Ala Glu Glu Asp Glu Lys Tyr Gln Ala Gly Glu
                85                  90                  95

Ala Tyr Gly Asp Pro Lys Val Leu Ala Thr Ser Leu Ile Lys Asp Leu
                100                 105                 110

Arg Ala Leu Gly Val Lys Gly Arg Arg Ser Asp Leu Arg Thr Leu Ile
            115                 120                 125

Glu Met Val Lys Asn Lys Gly Lys Pro Met Asp Asp Arg Gln Met His
130                 135                 140

Met Glu Lys Ile Ile Ala Ile Val Ala Met Leu Pro Arg Thr Ser Lys
145                 150                 155                 160

Ala Arg Gln Arg Leu Thr Gly Val Leu Ile Asp Gln Leu Trp Arg Ser
                165                 170                 175

Leu Gln His Pro Pro Leu Ser Tyr Phe Gly Asn Lys Tyr Gln Tyr Arg
                180                 185                 190
```

```
Thr Pro Asp Gly Ser Tyr Asn Asn Pro Leu Glu Pro Asn Leu Gly Lys
        195                 200                 205

Ala Gly Ser Pro Tyr Ala Arg Ser Ile Pro Arg Ile Lys Thr Met His
    210                 215                 220

Gly Val Arg Pro Asp Pro Gly Leu Leu Phe Asp Leu Leu Met Ala Arg
225                 230                 235                 240

Asp Asp Ser Thr Phe Lys Glu Asn Pro Ala Gly Ile Ser Ser Met Leu
                245                 250                 255

Phe Tyr His Ala Ser Ile Ile Ile His Asp Ile Phe Arg Thr Asn Arg
            260                 265                 270

Arg Asp Pro Asn Ile Ser Asp Thr Ser Ser Tyr Leu Asp Leu Ala Pro
        275                 280                 285

Leu Tyr Gly Ser Ser Leu Glu Asp Gln Leu Lys Val Arg Thr Met Glu
    290                 295                 300

Lys Gly Met Leu Lys Pro Asp Thr Phe His Glu Lys Arg Leu Leu Gly
305                 310                 315                 320

Gln Pro Ala Gly Val Asn Val Ile Leu Val Met Tyr Ser Arg Phe His
                325                 330                 335

Asn Tyr Val Ala Asp Met Leu Leu Lys Ile Asn Glu Asn Gly Arg Phe
            340                 345                 350

Thr Leu Pro Pro Thr Ser Ser Glu Glu Ala Arg Lys Lys Ala Leu Ala
        355                 360                 365

Lys Gln Asp Glu Asp Leu Phe Gln Val Ala Arg Leu Val Val Asn Gly
    370                 375                 380

Leu Tyr Val Asn Ile Ser Leu His Asp Tyr Leu Arg Gly Leu Thr Asn
385                 390                 395                 400

Thr His His Ser Ala Ser Asp Trp Thr Leu Asp Pro Arg Ile Ala Val
                405                 410                 415

Gly Arg Thr Phe Asp Pro Asp Gly Val Pro Arg Gly Ile Gly Asn Gln
            420                 425                 430

Ile Ser Ala Glu Phe Asn Leu Leu Tyr Arg Phe His Ser Val Ile Ser
        435                 440                 445

Arg Arg Asp Glu Lys Trp Thr Asn Glu Phe Leu Lys Ser Leu Phe Pro
    450                 455                 460

Asp Leu Asn Lys Pro Leu Asp Gln Leu Thr Pro Gln Glu Phe Met Met
465                 470                 475                 480

Gly Leu Met Arg Tyr Glu Gln Ser Ile Asp Lys Asp Pro Ser Lys Arg
                485                 490                 495

Glu Phe Gly Gly Leu Lys Arg Ser Pro Asp Gly Lys Phe Asn Asp Ala
            500                 505                 510

Asp Leu Val Gln Ile Leu Lys Asp Ser Met Glu Asp Pro Ala Gly Leu
        515                 520                 525

Phe Gly Pro Arg Asn Val Pro Lys Ala Leu Arg Met Ile Glu Ile Ala
    530                 535                 540

Gly Ile Met Ser Ala Arg Lys Trp Asp Leu Gly Ser Leu Asn Glu Met
545                 550                 555                 560

Arg Asp Phe Phe Lys Leu Lys Arg His Ala Thr Phe Glu Asp Ile Asn
                565                 570                 575

Pro Asp Pro Glu Ile Ala Asp Leu Leu Arg Lys Leu Tyr Asp His Pro
            580                 585                 590

Asp Met Val Glu Met Tyr Pro Gly Met Phe Leu Glu Asp Ala Lys Pro
        595                 600                 605

Arg Leu Asp Pro Gly Cys Gly Gly Cys Pro Pro Tyr Thr Val Gly Arg
```

```
            610                 615                 620
Ala Val Phe Ser Asp Ala Val Thr Leu Val Arg Ser Asp Arg Phe Leu
625                 630                 635                 640

Thr Leu Asp Tyr Thr Ala Ser Asn Leu Thr Asn Trp Gly Phe Arg Glu
                    645                 650                 655

Val Gln Gln Asp Tyr Asp Ile Leu Gly Gly Ser Met Phe His Lys Leu
                660                 665                 670

Ile Gln Arg Ala Leu Pro Gly Trp Phe Pro Tyr Asn Ser Leu His Ala
                675                 680                 685

Thr Gln Pro Met Phe Thr Arg Lys Met Asn Glu Gln Ile Ala Arg Glu
                690                 695                 700

Ile Gly Thr Ile Asp His Tyr Ser Leu Ala Asp Pro Ala Pro Pro Pro
705                 710                 715                 720

Arg Lys Ile Val Leu Thr Asp Tyr Ala Thr Asn Ile Lys Val Leu Lys
                    725                 730                 735

Asp Gln Ala Ser Phe Arg Val Pro Trp Ala Arg Tyr Leu Asn Asp Met
                740                 745                 750

Phe Pro Gly Lys Thr Tyr Asn Asp Tyr Met Leu Gly Gly Asp Asp Pro
                755                 760                 765

Ala Asn Ala Ala Gln Lys Lys Leu Val His Ser Ile Leu Phe Ser Pro
770                 775                 780

Asp Gln Phe Leu Asp Leu Leu Ser Glu Thr Thr Thr Lys Leu Gly Ser
785                 790                 795                 800

Glu Leu Leu Lys Ala Asn Thr Leu Trp Leu Thr Lys Asp Leu His Gln
                    805                 810                 815

Val Asp Ile Ile Arg Asp Val Ala Ile Pro Leu Asn Ala Arg Ile Met
                820                 825                 830

Ala Asp Leu Phe Cys Leu Asp Met Lys Thr Pro Glu Asn Pro Thr Gly
                835                 840                 845

Ser Met Asn Ala Ala Thr Val Tyr Arg His Leu Met Asn Val Arg Ile
                850                 855                 860

Trp Gly Phe Asn Asn Asn Asp Pro Ala Leu Met Leu Gln Arg Arg Lys
865                 870                 875                 880

Trp Ala Ile Glu Ser Ala Glu Ala Leu Ile Glu Thr Thr Arg Lys Leu
                    885                 890                 895

Val Asn Glu Gln Ala Gln Pro Ala Gln Ser Gly Val Leu Lys Asn Leu
                900                 905                 910

Met Thr Arg Arg Gln Ala Thr Gly Thr Leu Arg Trp Tyr Gly Asn Asn
                915                 920                 925

Val Ala Lys Glu Met Met Glu Met Gly Met Ser Ala Glu Glu Val Ala
930                 935                 940

Asp Ile Cys Trp Leu Thr Ala Ile Gly Gly Val Gly Thr Pro Ser Gly
945                 950                 955                 960

Val Val Ala Asn Val Leu Gln Tyr Tyr Phe Arg Tyr Glu Asn Ile Gly
                    965                 970                 975

His Trp Glu Glu Ile Gln Lys Leu Val Thr Gln Pro Asp Thr Pro Ala
                980                 985                 990

Ala Asp Arg Thr Leu Arg Gln Tyr  Val Leu Glu Ala Asn  Arg Leu Thr
                995                 1000                1005

Ser Met  Glu Cys Thr Val Arg  Val Cys Ala Arg Pro  Val Thr Val
        1010                1015                1020

Asp Gly  His Asp Phe Lys Pro  Gly Glu Val Ile Val  Asn His Leu
        1025                1030                1035
```

```
Gly Leu Ala Cys Arg Asp Pro His Asn Ile Pro Asp Ala Asp Lys
    1040                1045                1050

Phe Arg Leu Asp Arg Pro Ala Ser Ala Tyr Ile Gln Trp Gly Tyr
    1055                1060                1065

Gly Ala His Glu Cys Leu Gly Lys Glu Ile Ala Ile Thr Phe Ala
    1070                1075                1080

Val Ser Met Ile Arg Ile Leu Ala Gly Leu Lys Tyr Leu Arg Pro
    1085                1090                1095

Ala Pro Gly Glu Met Gly Val Leu Lys Ser Val Met Ala Asp Gly
    1100                1105                1110

Arg Gln Ala Phe Leu Asn Asp Ser Trp Ser Trp Leu Thr Gln Asp
    1115                1120                1125

Pro Thr Ser Lys Ser Asn Met His Gly Lys Ala Ser Ala Val Asp
    1130                1135                1140

<210> SEQ ID NO 48
<211> LENGTH: 518
<212> TYPE: PRT
<213> ORGANISM: Arabidopsis thaliana

<400> SEQUENCE: 48

Met Ala Ser Ile Ser Thr Pro Phe Pro Ile Ser Leu His Pro Lys Thr
1               5                   10                  15

Val Arg Ser Lys Pro Leu Lys Phe Arg Val Leu Thr Arg Pro Ile Lys
                20                  25                  30

Ala Ser Gly Ser Glu Thr Pro Asp Leu Thr Val Ala Thr Arg Thr Gly
            35                  40                  45

Ser Lys Asp Leu Pro Ile Arg Asn Ile Pro Gly Asn Tyr Gly Leu Pro
        50                  55                  60

Ile Val Gly Pro Ile Lys Asp Arg Trp Asp Tyr Phe Tyr Asp Gln Gly
65                  70                  75                  80

Ala Glu Glu Phe Phe Lys Ser Arg Ile Arg Lys Tyr Asn Ser Thr Val
                85                  90                  95

Tyr Arg Val Asn Met Pro Pro Gly Ala Phe Ile Ala Glu Asn Pro Gln
                100                 105                 110

Val Val Ala Leu Leu Asp Gly Lys Ser Phe Pro Val Leu Phe Asp Val
            115                 120                 125

Asp Lys Val Glu Lys Lys Asp Leu Phe Thr Gly Thr Tyr Met Pro Ser
        130                 135                 140

Thr Glu Leu Thr Gly Gly Tyr Arg Ile Leu Ser Tyr Leu Asp Pro Ser
145                 150                 155                 160

Glu Pro Lys His Glu Lys Leu Lys Asn Leu Leu Phe Phe Leu Leu Lys
                165                 170                 175

Ser Ser Arg Asn Arg Ile Phe Pro Glu Phe Gln Ala Thr Tyr Ser Glu
                180                 185                 190

Leu Phe Asp Ser Leu Glu Lys Glu Leu Ser Leu Lys Gly Lys Ala Asp
            195                 200                 205

Phe Gly Gly Ser Ser Asp Gly Thr Ala Phe Asn Phe Leu Ala Arg Ala
        210                 215                 220

Phe Tyr Gly Thr Asn Pro Ala Asp Thr Lys Leu Lys Ala Asp Ala Pro
225                 230                 235                 240

Gly Leu Ile Thr Lys Trp Val Leu Phe Asn Leu His Pro Leu Leu Ser
                245                 250                 255

Ile Gly Leu Pro Arg Val Ile Glu Glu Pro Leu Ile His Thr Phe Ser
```

```
        260                 265                 270
Leu Pro Pro Ala Leu Val Lys Ser Asp Tyr Gln Arg Leu Tyr Glu Phe
            275                 280                 285

Phe Leu Glu Ser Ala Gly Glu Ile Leu Val Glu Ala Asp Lys Leu Gly
            290                 295                 300

Ile Ser Arg Glu Glu Ala Thr His Asn Leu Leu Phe Ala Thr Cys Phe
305                 310                 315                 320

Asn Thr Trp Gly Gly Met Lys Ile Leu Phe Pro Asn Met Val Lys Arg
                325                 330                 335

Ile Gly Arg Ala Gly His Gln Val His Asn Arg Leu Ala Glu Glu Ile
            340                 345                 350

Arg Ser Val Ile Lys Ser Asn Gly Gly Glu Leu Thr Met Gly Ala Ile
            355                 360                 365

Glu Lys Met Glu Leu Thr Lys Ser Val Val Tyr Glu Cys Leu Arg Phe
            370                 375                 380

Glu Pro Pro Val Thr Ala Gln Tyr Gly Arg Ala Lys Lys Asp Leu Val
385                 390                 395                 400

Ile Glu Ser His Asp Ala Ala Phe Lys Val Lys Ala Gly Glu Met Leu
                405                 410                 415

Tyr Gly Tyr Gln Pro Leu Ala Thr Arg Asp Pro Lys Ile Phe Asp Arg
            420                 425                 430

Ala Asp Glu Phe Val Pro Glu Arg Phe Val Gly Glu Gly Glu Lys
            435                 440                 445

Leu Leu Arg His Val Leu Trp Ser Asn Gly Pro Glu Thr Glu Thr Pro
            450                 455                 460

Thr Val Gly Asn Lys Gln Cys Ala Gly Lys Asp Phe Val Val Leu Val
465                 470                 475                 480

Ala Arg Leu Phe Val Ile Glu Ile Phe Arg Arg Tyr Asp Ser Phe Asp
                485                 490                 495

Ile Glu Val Gly Thr Ser Pro Leu Gly Ser Ser Val Asn Phe Ser Ser
            500                 505                 510

Leu Arg Lys Ala Ser Phe
            515

<210> SEQ ID NO 49
<211> LENGTH: 1066
<212> TYPE: PRT
<213> ORGANISM: Plexaura homomalla

<400> SEQUENCE: 49

Met Thr Trp Lys Asn Phe Gly Phe Glu Ile Phe Gly Glu Lys Tyr Gly
1               5                   10                  15

Gln Glu Glu Leu Glu Lys Arg Ile Lys Asp Glu His Thr Pro Pro
            20                  25                  30

Asp Ser Pro Val Phe Gly Gly Leu Lys Leu Lys Leu Lys Glu Lys
            35                  40                  45

Phe Lys Thr Leu Phe Thr Leu Gly Thr Thr Leu Lys Gly Phe Arg Arg
    50                  55                  60

Ala Thr His Thr Val Gly Thr Gly Gly Ile Gly Glu Ile Thr Ile Val
65                  70                  75                  80

Asn Asp Pro Lys Phe Pro Glu His Glu Phe Thr Ala Gly Arg Thr
                85                  90                  95

Phe Pro Ala Arg Leu Arg His Ala Asn Leu Lys Tyr Pro Asp Asp Ala
            100                 105                 110
```

Gly Ala Asp Ala Arg Ser Phe Ser Ile Lys Phe Ala Asp Ser Asp Ser
                115                 120                 125

Asp Gly Pro Leu Asp Ile Val Met Asn Thr Gly Glu Ala Asn Ile Phe
            130                 135                 140

Trp Asn Ser Pro Ser Leu Glu Asp Phe Val Pro Val Glu Glu Gly Asp
145                 150                 155                 160

Ala Ala Glu Glu Tyr Val Tyr Lys Asn Pro Tyr Tyr Tyr Asn Leu
                165                 170                 175

Val Glu Ala Leu Arg Arg Ala Pro Asp Thr Phe Ala His Leu Tyr Tyr
                180                 185                 190

Tyr Ser Gln Val Thr Met Pro Phe Lys Ala Lys Asp Gly Lys Val Arg
            195                 200                 205

Tyr Cys Arg Tyr Arg Ala Leu Pro Gly Asp Val Asp Ile Lys Glu Glu
            210                 215                 220

Asp Glu Ser Gly Arg Leu Thr Glu Glu Glu Gln Arg Lys Ile Trp Ile
225                 230                 235                 240

Phe Ser Arg His Glu Asn Glu Lys Arg Pro Asp Asp Tyr Leu Arg Lys
                245                 250                 255

Glu Tyr Val Glu Arg Leu Gln Lys Gly Pro Val Asn Tyr Arg Leu Gln
            260                 265                 270

Ile Gln Ile His Glu Ala Ser Pro Asp Asp Thr Ala Thr Ile Phe His
        275                 280                 285

Ala Gly Ile Leu Trp Asp Lys Glu Thr His Pro Trp Phe Asp Leu Ala
        290                 295                 300

Lys Val Ser Ile Lys Thr Pro Leu Ser Pro Asp Val Leu Glu Lys Thr
305                 310                 315                 320

Ala Phe Asn Ile Ala Asn Gln Pro Ala Ser Leu Gly Leu Leu Glu Ala
                325                 330                 335

Lys Ser Pro Glu Asp Tyr Asn Ser Ile Gly Glu Leu Arg Val Ala Val
            340                 345                 350

Tyr Thr Trp Val Gln His Leu Arg Lys Leu Lys Ile Gly Ser Leu Val
            355                 360                 365

Pro Ala Gly Gln Asn Ala Ile Tyr Asn Val Glu Val Glu Thr Gly Asp
370                 375                 380

Arg Glu His Ala Gly Thr Asp Ala Thr Ile Thr Ile Arg Ile Thr Gly
385                 390                 395                 400

Ala Lys Gly Arg Thr Asp Tyr Leu Lys Leu Asp Lys Trp Phe His Asn
                405                 410                 415

Asp Phe Glu Ala Gly Ser Lys Gln Tyr Thr Val Gln Gly Phe Asp
            420                 425                 430

Val Gly Asp Ile Gln Leu Ile Glu Leu His Ser Asp Gly Gly Tyr
            435                 440                 445

Trp Ser Gly Asp Pro Asp Trp Phe Val Asn Arg Val Ile Ile Ser
450                 455                 460

Ser Thr Gln Asp Arg Val Tyr Ser Phe Pro Cys Phe Arg Trp Val Ile
465                 470                 475                 480

Lys Asp Met Val Leu Phe Pro Gly Glu Ala Thr Leu Pro Phe Asn Glu
            485                 490                 495

Val Pro Ala Ile Val Ser Glu Gln Arg Gln Lys Glu Leu Glu Gln Arg
            500                 505                 510

Lys Leu Thr Tyr Gln Trp Asp Tyr Val Ser Asp Met Pro Gly Asn
            515                 520                 525

Ile Lys Ala Lys Thr His Asp Asp Leu Pro Arg Asp Val Gln Phe Thr

```
                530             535             540
Asp Glu Lys Ser Arg Ser Tyr Gln Glu Ser Arg Lys Ala Ala Leu Val
545                 550                 555                 560

Asn Leu Gly Ile Gly Ser Leu Phe Thr Met Phe Glu Asn Trp Asp Ser
                565                 570                 575

Tyr Asp Asp Tyr His Ile Leu Tyr Arg Asn Trp Ile Leu Gly Gly Thr
                580                 585                 590

Pro Asn Met Ala Asp Arg Trp His Glu Asp Arg Trp Phe Gly Tyr Gln
            595                 600                 605

Phe Leu Asn Gly Ala Asn Pro Val Ile Leu Thr Arg Cys Asp Ala Leu
            610                 615                 620

Pro Ser Asn Phe Pro Val Thr Asn Glu His Val Asn Ala Ser Leu Asp
625                 630                 635                 640

Arg Gly Lys Asn Leu Asp Glu Glu Ile Lys Asp Gly His Ile Tyr Ile
                645                 650                 655

Val Asp Phe Lys Val Leu Val Gly Ala Lys Ser Tyr Gly Gly Pro Val
                660                 665                 670

Leu Glu Asp Ile Gly Tyr Lys Val Pro Asp His Leu Lys His Asp Glu
            675                 680                 685

Ala Asp Ile Arg Tyr Cys Ala Ala Pro Leu Ala Leu Phe Tyr Val Asn
690                 695                 700

Lys Leu Gly His Leu Met Pro Ile Ala Ile Gln Ile Asn Gln Glu Pro
705                 710                 715                 720

Gly Pro Glu Asn Pro Ile Trp Thr Pro His Glu Glu Asn Glu His Asp
                725                 730                 735

Trp Met Met Ala Lys Phe Trp Leu Gly Val Ala Glu Ser Asn Phe His
                740                 745                 750

Gln Leu Asn Thr His Leu Leu Arg Thr His Leu Thr Thr Glu Ser Phe
            755                 760                 765

Ala Leu Ser Thr Trp Arg Asn Leu Ala Ser Ala His Pro Val Phe Lys
            770                 775                 780

Leu Leu Gln Pro His Ile Tyr Gly Val Leu Ala Ile Asp Thr Ile Gly
785                 790                 795                 800

Arg Lys Glu Leu Ile Gly Ser Gly Gly Ile Val Asp Gln Ser Leu Ser
                805                 810                 815

Leu Gly Gly Gly Gly His Val Thr Phe Met Glu Lys Cys Phe Lys Glu
                820                 825                 830

Val Asn Leu Gln Asp Tyr His Leu Pro Asn Ala Leu Lys Lys Arg Gly
            835                 840                 845

Val Asp Asp Pro Ser Lys Leu Pro Gly Phe Tyr Tyr Arg Asp Asp Gly
850                 855                 860

Leu Ala Leu Trp Glu Ala Ile Glu Thr Phe Ile Gly Glu Ile Ile Ala
865                 870                 875                 880

Ile Phe Tyr Lys Asn Asp Asp Val Lys Arg Asp Asn Glu Ile Gln
                885                 890                 895

Ser Trp Ile Tyr Asp Val His Lys Asn Gly Trp Arg Val Asn Pro Gly
                900                 905                 910

His Gln Asp His Gly Val Pro Ala Ser Phe Glu Ser Arg Glu Gln Leu
            915                 920                 925

Lys Glu Val Leu Thr Ser Leu Val Phe Thr Phe Ser Cys Gln His Ala
            930                 935                 940

Ala Val Asn Phe Ser Gln Lys Asp His Tyr Gly Phe Thr Pro Asn Ala
945                 950                 955                 960
```

-continued

Pro Ala Val Leu Arg His Pro Pro Lys Lys Gly Glu Ala Thr
            965             970             975

Leu Gln Ser Ile Leu Ser Thr Leu Pro Ser Lys Ser Gln Ala Ala Lys
            980             985             990

Ala Ile Ala Thr Val Tyr Ile Leu Thr Lys Phe Ser Glu Asp Glu Arg
            995             1000            1005

Tyr Leu Gly Asn Tyr Ser Ala Thr Ala Trp Glu Asp Lys Asp Ala
            1010            1015            1020

Leu Asp Ala Ile Asn Arg Phe Gln Asp Lys Leu Glu Asp Ile Ser
            1025            1030            1035

Lys Lys Ile Lys Gln Arg Asn Glu Asn Leu Glu Val Pro Tyr Ile
            1040            1045            1050

Tyr Leu Leu Pro Glu Arg Ile Pro Asn Gly Thr Ala Ile
            1055            1060            1065

<210> SEQ ID NO 50
<211> LENGTH: 1151
<212> TYPE: PRT
<213> ORGANISM: Fusarium oxysporum

<400> SEQUENCE: 50

Met Ser Phe Asn Glu Lys Phe Gln Ala Gly Glu Ser Tyr Gly Asp Ser
1               5                   10                  15

Lys Glu Asp Pro Ser Ser Leu Leu Asn Asn Pro Glu Lys Leu Val Ala
            20                  25                  30

Asp Leu Met Lys Asp Phe Ala Gly Val Arg Ser Gln Ala Ser Pro Ala
        35                  40                  45

Gln Leu Leu Gly Leu Val Lys Glu Leu Leu Gln Lys Gly Gln Pro Leu
    50                  55                  60

Asp Asp Lys Lys Gly Thr Thr Glu Leu Leu Ile Gly Ile Leu Thr Ala
65                  70                  75                  80

Leu Pro Ala Thr Ser Lys Ala Arg Thr Ala Leu Thr Asn Lys Leu Ile
                85                  90                  95

Asp Thr Leu Trp Gly Asn Leu Gln His Pro Pro Leu Ser Tyr Met Gly
            100                 105                 110

Gly Asp Val Lys Tyr Asp Val Val Asn Ser Asp Lys Pro Ala His Lys
        115                 120                 125

His Asn Cys Glu Leu Tyr Asp Thr Ile Glu Phe Lys Val Pro Gly Thr
    130                 135                 140

Asp Val Leu Leu Arg Glu Gln Val Pro Gln Ala Pro Asp Gly Leu His
145                 150                 155                 160

Gln Tyr Arg Met Pro Asp Gly Ser Phe Asn Asn Ile Leu Glu Pro Asn
                165                 170                 175

Leu Gly Arg Ala Gly Thr Pro Tyr Ala Lys Ser Val Lys Ser Glu Lys
            180                 185                 190

Arg Leu His Gly Val Lys Pro Asp Pro Gly Leu Leu Phe Asp Leu Leu
        195                 200                 205

Met Ala Arg Asp Glu Thr Thr Phe Gln Glu Asn Pro Ala Gly Ile Ser
    210                 215                 220

Ser Met Leu Phe Tyr His Ala Ala Ile Ile His Asp Ile Phe Arg
225                 230                 235                 240

Thr Asn Arg Thr Asp Met Asn Lys Ser Asp Thr Ser Ser Tyr Leu Asp
                245                 250                 255

Leu Ala Pro Leu Tyr Gly Ser Ser Leu Lys Asp Gln His Glu Ile Arg

```
              260                 265                 270
Thr Met Lys Glu Gly Lys Leu Lys Pro Asp Thr Phe His Glu Lys Arg
        275                 280                 285
Leu Leu Gly Gln Pro Ala Gly Val Asn Val Met Leu Val Leu Tyr Ser
        290                 295                 300
Arg Phe His Asn Tyr Val Ala Asp Ile Leu Leu Lys Ile Asn Glu Asn
305                 310                 315                 320
Gly Arg Phe Ser Leu Ser Val Pro Pro Asn Ala Ser Glu Glu Asp Lys
                325                 330                 335
Ala Lys Ala Ile Ala Lys Gln Asp His Asp Leu Phe Asn Val Ala Arg
        340                 345                 350
Leu Ile Thr Gly Gly Leu Tyr Ile Asn Ile Cys Leu His Asp Tyr Leu
        355                 360                 365
Arg Ala Ile Thr Asn Thr His His Ser Ala Ser Asp Trp Thr Leu Asp
        370                 375                 380
Pro Arg Val Ala Ile Asp Lys Gln Phe Asp Gly Asp Val Pro Arg
385                 390                 395                 400
Gly Val Gly Asn Gln Val Ser Val Glu Phe Asn Leu Leu Tyr Arg Phe
                405                 410                 415
His Ser Cys Ile Ser Lys Arg Asp Glu Lys Trp Ile Asn Asn Phe Phe
                420                 425                 430
Leu Lys Leu Phe Pro Gly Arg Lys Ala Glu Asp Leu Gln Asp Val Ser
        435                 440                 445
Trp Thr Glu Leu Gly Gln Ala Leu Leu Ile Phe Glu Gln Asn Thr Pro
        450                 455                 460
Lys Asp Pro Ser Val Arg Thr Phe Asp Gly Leu Glu Arg Gln Ala Asp
465                 470                 475                 480
Gly Thr Phe Lys Asp Glu Asp Leu Val Arg Ile Leu Lys Asp Ala Met
                485                 490                 495
Glu Asp Pro Ala Gly Thr Phe Gly Ala Arg Met Val Pro Lys Ala Leu
                500                 505                 510
Lys Val Val Glu Val Leu Gly Ile Ile Gln Gly Arg Lys Trp Gln Cys
        515                 520                 525
Ala Ser Leu Asn Glu Phe Arg Glu Phe Gly Leu Lys Arg Tyr Asp
        530                 535                 540
Ser Phe Ser Glu Ile Asn Ser Asn Pro Asp Ile Ala Asn Ile Leu Glu
545                 550                 555                 560
Lys Leu Tyr Thr Asp Pro Asp Met Val Glu Leu Tyr Pro Gly Leu Met
                565                 570                 575
Ile Glu Asp Ile Lys Pro Gln Arg Asn Pro Gly Ser Gly Ile Met Pro
                580                 585                 590
Thr Tyr Ser Val Gly Arg Ala Val Leu Ser Asp Ala Val Thr Leu Val
        595                 600                 605
Arg Ser Asp Arg Phe Asn Thr Ile Asp Tyr Thr Val Ser Asn Leu Thr
        610                 615                 620
Ala Trp Gly Tyr Asn Glu Val Gln Gln Asp Tyr Lys Thr Leu Gly Gly
625                 630                 635                 640
Ser Met Leu Tyr Lys Leu Ile Gln Arg Gly Val Pro Asn Trp Phe Pro
                645                 650                 655
Phe Asn Ser Ile Ala Val Met Gln Pro Met Tyr Thr Lys Lys Ala Asn
                660                 665                 670
Glu Gln Ile Ala Lys Glu Ile Gly Thr Phe Asp Gln Tyr Thr Leu Asp
        675                 680                 685
```

```
Asp Pro Lys Ala Pro Pro Lys Val Ala Val Leu Thr Ser Gly Pro Ala
690                 695                 700

Ile Lys Gln Ile Leu Ser Asn Thr Lys Gln Tyr Val Val Pro Trp Leu
705                 710                 715                 720

Lys Pro Leu Asn Thr Leu Phe Pro Gly Lys Lys Asp Phe Gly Trp Phe
                725                 730                 735

Met Leu Ala Gly Asp Gln Pro Gln Asn Tyr Thr His Arg Ala Asn Phe
            740                 745                 750

Ser Lys Ala Met Ser Lys Ile Pro Asn Met His Asn Ala Val His Ala
        755                 760                 765

Phe Ile Glu Arg Glu Gly Thr Lys Leu Ile Asn Lys Glu Thr Phe Thr
770                 775                 780

Leu Lys Lys Gly Leu Asp Gln Ile Asp Ile Ile Arg Asp Val Ala Ile
785                 790                 795                 800

Pro Leu Asn Thr Gln Leu Leu Ala Asp Leu Phe Tyr Phe Asp Leu Arg
                805                 810                 815

Thr Glu Glu Asn Pro Asp Gly Lys Leu Gly Val Ala Glu Leu Tyr Arg
            820                 825                 830

Ser Leu Leu Asp Ile Arg Ile Trp Gly Val Asn Asn Asn Asp Pro Ala
        835                 840                 845

Gln Ala Trp Asn Arg Arg Arg Arg Ala Gln Glu Gly Ala Lys Arg Met
850                 855                 860

Ile Glu Thr Thr Lys Thr Ile Val Ala Glu Ala Asp Ala Gly Arg Pro
865                 870                 875                 880

Arg Gly Ile Gly Leu Val Ser Ala Val Ala Asn Arg Ile Gly Ala Arg
                885                 890                 895

Ser Tyr Leu Lys Lys Asp Ser Leu Arg Ser Cys Gly Leu Lys Leu Val
            900                 905                 910

Glu Glu Leu Leu Ala Gln Gly Asn Asn Val Asp Gln Val Thr Asp Asn
        915                 920                 925

Leu Trp Leu Thr Ala Phe Gly Ile Gly Val Pro Val Thr Ala Phe
930                 935                 940

Tyr Glu Val Leu Ser Phe Phe Leu Arg Pro Glu Asn Glu Ala Ile Trp
945                 950                 955                 960

Ala Glu Val Gln Ala Ile Ala Gln Lys Gly Asp Asp Ala Thr Leu His
                965                 970                 975

Ala Tyr Val Ala Glu Ala Gln Arg Met Thr Ser Ser Gln Arg Asn Val
            980                 985                 990

Arg Val Ala Thr Ala Pro Gly Glu Val Gln Gly Gln Ala Ile Gln Pro
        995                 1000                1005

Gly Thr Ala Val Val Leu Met Leu Gly Glu Ala Gly Arg Asn Pro
    1010                1015                1020

Lys Glu Val Pro Asp Ala Gly Lys Phe Asn Pro Gln Arg Lys Lys
    1025                1030                1035

Glu Asp Val Ser Ala Phe Ser Tyr Gly Gln His Glu Cys Ile Ala
    1040                1045                1050

Lys Asp Val Ala Leu Ala Phe Val Thr Gly Leu Ile Lys Leu Val
    1055                1060                1065

Ala Asp Leu Lys Glu Leu Arg Pro Ala Pro Gly Gln Met Gly Thr
    1070                1075                1080

Val Lys Thr Ile Gln Val Gly Thr Glu Lys Ala Tyr Leu Asn Asp
    1085                1090                1095
```

Ser Trp Ser Tyr Leu Gly Phe Asp Ala Ser Thr Trp Lys Val His
1100                1105                1110

Phe Asn Gly His Gly Lys Gly Lys Phe Glu Gly Glu Arg Val Pro
1115                1120                1125

Thr Lys Ser Thr Pro Ile Gln Glu Tyr Tyr Tyr Leu Leu Gln Lys
1130                1135                1140

Arg Lys Asp Glu Ile Leu Gly Asn
1145                1150

<210> SEQ ID NO 51
<211> LENGTH: 1162
<212> TYPE: PRT
<213> ORGANISM: Colletotrichum graminicola

<400> SEQUENCE: 51

Met Ser Phe Asp Gln Lys Phe Met Ala Gly Glu Thr Tyr Gly Asp Glu
1               5                   10                  15

Arg Lys Ser Ser Ala Asn Phe Phe Ser Asp Pro Thr Lys Val Ala Thr
                20                  25                  30

Asp Leu Leu Lys Asp Tyr Ala Gly Leu Arg Ser Gln Thr Ser Pro Ala
            35                  40                  45

Glu Leu Ala Gly Leu Ile Lys Glu Leu Leu Gln Lys Gly Gln Pro Leu
        50                  55                  60

Asp Asp Lys Lys Gly Thr Thr Glu Ile Leu Ile Gly Ile Leu Thr Ser
65                  70                  75                  80

Leu Pro Ser Thr Ser Ser Thr Arg Val Gln Leu Thr Asn Lys Leu Ile
                85                  90                  95

Asp Thr Leu Trp Gly Thr Leu Gln His Pro Pro Leu Ser Tyr Val Gly
            100                 105                 110

Gly Asp Val Lys Tyr Glu Val Val Asn Pro Asn Glu Thr Ala Ser Lys
        115                 120                 125

Asp Lys Gln Gln Thr Glu Asp Ser Ile Glu Phe Lys Ala Pro Asp Ser
    130                 135                 140

Asp Val Ile Leu Arg Glu Gln Val Pro Arg Pro Asp Gly Leu His
145                 150                 155                 160

His Tyr Arg Met Pro Asp Gly Ser Tyr Asn Asn Ile Leu Glu Pro Asn
                165                 170                 175

Leu Gly Lys Ala Gly Thr Pro Tyr Ala Lys Thr Val Arg Thr Ser Lys
            180                 185                 190

Arg Leu His Gly Val Lys Pro Asp Pro Gly Leu Leu Phe Asp Leu Leu
        195                 200                 205

Met Ala Arg Asp Asp Ser Thr Phe Lys Glu Asn Pro Ala Gly Ile Ser
    210                 215                 220

Ser Met Leu Phe Tyr His Ala Ser Ile Ile Ile His Asp Ile Phe Arg
225                 230                 235                 240

Thr Asn Arg Thr Asp Met Asn Lys Ser Asp Thr Ser Ser Tyr Leu Asp
                245                 250                 255

Leu Ala Pro Leu Tyr Gly Ser Ser Leu Lys Asp Gln Leu Glu Ile Arg
            260                 265                 270

Thr Met Lys Glu Gly Met Leu Pro Asp Thr Phe His Glu Arg Arg
        275                 280                 285

Leu Leu Gly Gln Pro Ala Gly Val Asn Ala Met Leu Val Leu Tyr Asn
    290                 295                 300

Arg Phe His Asn Tyr Val Cys Asp Ile Leu Leu Lys Ile Asn Glu Asn
305                 310                 315                 320

```
Gly Arg Phe Thr Leu Gln Cys Pro Ala Asp Ala Ser Pro Glu Asp Arg
            325                 330                 335

Ala Lys Ala Val Ala Lys Gln Asp His Asp Leu Phe Asn Thr Ala Arg
            340                 345                 350

Leu Ile Val Gly Gly Leu Tyr Ile Asn Ile Ser Leu His Asp Tyr Leu
            355                 360                 365

Arg Ala Ile Thr Asn Thr His His Ser Lys Ser Asp Trp Thr Leu Asp
            370                 375                 380

Pro Arg Val Glu Ile Gly Lys Gln Phe Asp Gly Glu Gly Val Pro Arg
385                 390                 395                 400

Gly Val Gly Asn Gln Val Ser Val Glu Phe Asn Leu Leu Tyr Arg Phe
            405                 410                 415

His Ser Cys Ile Ser Lys Lys Asp Glu Arg Trp Ile Asp Asn Phe Phe
            420                 425                 430

Ala Lys Leu Phe Pro Asp Arg Lys Pro Glu Asp Leu Gln Asn Val Gly
            435                 440                 445

Met Ala Glu Leu Gly Gln Ala Leu Met Thr Phe Glu Gln Ser Ile Pro
            450                 455                 460

Lys Asp Pro Ser Ala Arg Thr Phe Asp Asn Leu Glu Arg Gln Ala Asp
465                 470                 475                 480

Gly Lys Phe Lys Asp Glu Asp Leu Val Arg Val Leu Lys Glu Ala Met
            485                 490                 495

Asp Asp Pro Ala Gly Cys Phe Gly Ala Arg Met Val Pro Lys Ala Leu
            500                 505                 510

Lys Ile Val Glu Ile Leu Gly Ile Asn Gln Ala Arg Lys Trp Gln Val
            515                 520                 525

Ala Ser Leu Asn Glu Phe Arg Glu Phe Phe Gly Leu Lys Lys Tyr Asp
            530                 535                 540

Lys Phe Ala Glu Ile Asn Ser Asn Pro Glu Ile Ala Thr Leu Leu Glu
545                 550                 555                 560

Lys Leu Tyr Thr Asp Pro Asp Met Val Glu Leu Tyr Pro Gly Leu Met
            565                 570                 575

Ile Glu Asp Ile Lys Pro Ala Arg Asn Thr Gly Ser Gly Ile Cys Pro
            580                 585                 590

Thr Tyr Ser Val Gly Arg Ala Val Leu Ser Asp Ala Val Thr Leu Val
            595                 600                 605

Arg Ser Asp Arg Phe Asn Thr Leu Asp Tyr Thr Val Ser Asn Leu Thr
            610                 615                 620

Ala Trp Gly Tyr Asn Glu Val Gln Gln Asp Tyr Lys Thr Leu Gly Gly
625                 630                 635                 640

Ser Met Leu Tyr Lys Leu Ile Gln Arg Gly Leu Pro Asn Trp Phe Pro
            645                 650                 655

Tyr Asn Ser Val Ala Val Met Gln Pro Met Tyr Thr Lys Lys Ala Asn
            660                 665                 670

Glu Ser Ile Ala Lys Glu Leu Gly Thr Leu His Leu Tyr Thr Ser Asn
            675                 680                 685

Asp Pro Lys Pro Pro Lys Ile Val Val Ala Thr Ser Val Ala
            690                 695                 700

Ile Lys Gln Val Leu Gly Asn Ser Lys Gln Phe Val Val Pro Trp Leu
705                 710                 715                 720

Gln Pro Leu Asn Asp Leu Phe Thr Gly Thr Lys Lys Asp Ile Ser Trp
            725                 730                 735
```

-continued

```
Phe Met Leu Ala Gly Asp Glu Pro Lys Asn Tyr Gln His Arg Val Asn
                740                 745                 750

Leu Leu Lys Ala Met Gly Lys Ile Pro Asn Leu His Asn Ala Val His
            755                 760                 765

Glu Phe Val Asp Arg Val Gly Ala Lys Leu Ile Glu Lys Glu Thr Phe
    770                 775                 780

Lys Leu Lys Glu Gly Leu Cys Gln Met Asp Ile Ile Arg Asp Val Ala
785                 790                 795                 800

Ile Pro Leu Asn Ala Gln Leu Leu Ala Asp Leu Phe Tyr Phe Asp Met
                805                 810                 815

Arg Thr Asp Glu Asn Pro Asn Gly Thr Leu Ser Ala Ala Asp Leu Tyr
            820                 825                 830

Arg His Leu Leu Asn Ile Arg Val Trp Gly Val Asn Asn Asp Pro
        835                 840                 845

Ala Gln Ala Trp Asn Arg Arg Arg Ala Thr Glu Ser Val Asn Ala
    850                 855                 860

Ile Ile Asp Ser Thr Arg Gly Leu Val Asn Glu Val Val Gly Arg
865                 870                 875                 880

Gly Leu Gly Phe Gly Ile Ala Ser Thr Ile Ser Gly Val Val Gly Arg
                885                 890                 895

Lys Ser Asn Phe Lys Lys Asp Ser Leu Arg Ser Cys Gly His Lys Leu
            900                 905                 910

Val Glu Leu Leu Ala Gln Gly Asn Ser Ala Glu Gln Val Val Asp
        915                 920                 925

Asn Met Trp Leu Thr Ala Phe Gly Gly Ile Gly Ala Pro Val Thr Ala
    930                 935                 940

Phe Tyr Glu Val Leu Glu Tyr Phe Leu Arg Arg Glu Asn Ala Ser Ile
945                 950                 955                 960

Trp Ala Glu Val Gln Thr Leu Ala Gln Lys Asn Asp Asp Ala Gly Leu
                965                 970                 975

His Ala Tyr Val Lys Glu Ala Gln Arg Leu Thr Ser Ser Gln Arg Asn
            980                 985                 990

Val Arg Val Ala Thr Val Ala Ala Glu Val Asp Gly Lys Gln Val Gln
        995                 1000                1005

Pro Gly Asn Val Val Met Leu Leu Gly Asp Ala Gly Arg Asn
    1010                1015                1020

Pro Lys Glu Val Ala Asn Pro Asp Lys Phe Asp Ala Lys Arg Lys
    1025                1030                1035

Thr Asp Pro Val Ser Ala Phe Ser Tyr Gly Gln His Glu Cys Leu
    1040                1045                1050

Ala Lys Asp Ile Ala Thr Thr Phe Ile Val Gly Leu Val Lys Leu
    1055                1060                1065

Val Ala Asp Leu Lys Gln Leu Arg Pro Ala Pro Gly Gln Met Gly
    1070                1075                1080

Leu Val Lys Thr Ile Arg Val Gly Ser Glu Lys Ala Tyr Leu Asn
    1085                1090                1095

Asp Ser Trp Ser Tyr Leu Gly Phe Asp Ala Ser Thr Trp Lys Val
    1100                1105                1110

His Phe Asp Gly His Gly Lys Gly Asn Phe Glu Gly Asp Val Gln
    1115                1120                1125

Pro Asn Lys Pro Ile Asp Leu Gly Gln Tyr Tyr Tyr Leu Leu Gln
    1130                1135                1140

Lys Arg Lys Glu Lys Leu Leu Asn Gly Asn Ser Ser Asn Gly Thr
```

Asn Gly Ser Ser
        1160

<210> SEQ ID NO 52
<211> LENGTH: 1161
<212> TYPE: PRT
<213> ORGANISM: Glomerella cingulate

<400> SEQUENCE: 52

Met Ala Phe Asn Thr Lys Phe Gln Ala Gly Glu Ser Tyr Gly Asp Glu
1               5                   10                  15

Arg Lys Gly Ser Asn Asn Phe Phe Ala Asp Pro Lys Lys Val Ala Met
            20                  25                  30

Asp Ile Ile Lys Asp Leu Gly Gly Ala His Gly Gln Leu Asn Leu Leu
        35                  40                  45

Glu Val Thr Ala Leu Val Gln Gln Leu Leu Gln Lys Gly Glu Pro Leu
    50                  55                  60

Asp Asp Lys Lys Gly Thr Thr Glu Ala Leu Ile Gly Ile Leu Thr Ser
65                  70                  75                  80

Leu Pro Ser Gly Ser Asn Thr Arg Val Gln Leu Thr Asn Lys Leu Ile
                85                  90                  95

Asp Thr Leu Trp Gly Asn Leu Gln His Pro Leu Ser Tyr Val Gly
            100                 105                 110

Gly Asp Val Lys Tyr Glu Val Val Lys Thr Lys Glu Gln Leu Ala Lys
        115                 120                 125

Glu Gln Ala Asp Leu Ala Ala Gln Gly Lys Ala Pro Gln Ser Pro Glu
    130                 135                 140

Glu Ser His Ile Thr Phe Lys Ala Pro Asp Phe Pro Asp Ile Thr Leu
145                 150                 155                 160

Arg Glu His Leu Pro Thr Pro Pro Asp Asn Tyr Lys Met Pro Asp Gly
                165                 170                 175

Ser Tyr Asn Asn Ile Leu Glu Pro Asn Leu Gly Ala Ala Gly Thr Pro
            180                 185                 190

Tyr Ala Lys Thr Val Lys Thr Glu Lys Arg Leu Ala Gly Val Lys Pro
        195                 200                 205

Asp Pro Gly Leu Leu Phe Asp Leu Leu Leu Ala Arg Asp Asp Lys Lys
    210                 215                 220

Phe Thr Glu Asn Pro Ala Gly Ile Ser Ser Met Leu Phe Tyr His Ala
225                 230                 235                 240

Ser Ile Ile Ile His Asp Ile Phe Arg Thr Asn Arg His Asp Leu Asn
                245                 250                 255

Lys Ser Asp Thr Ser Ser Tyr Leu Asp Leu Ala Pro Leu Tyr Gly Ser
            260                 265                 270

Ser Phe Lys Asp Gln Leu Glu Ile Arg Thr Met Lys Glu Gly Lys Leu
        275                 280                 285

Lys Pro Asp Thr Phe His Glu Lys Arg Leu Leu Gly Gln Pro Ala Gly
    290                 295                 300

Val Asn Val Met Leu Val Leu Ser Ser Arg Phe His Asn Tyr Val Ala
305                 310                 315                 320

Asp Ile Leu Leu Lys Ile Asn Glu Asn Gly Arg Phe Thr Leu Gln Thr
                325                 330                 335

Ala Lys Asp Ala Ala Pro Glu Asp Gln Ala Lys Ala Val Ala Lys Gln
            340                 345                 350

```
Asp His Asp Leu Phe Asn Val Ala Arg Leu Val Thr Gly Gly Leu Tyr
            355                 360                 365
Ile Asn Ile Cys Leu His Asp Tyr Leu Arg Ala Ile Thr Asn Thr His
    370                 375                 380
His Ser Lys Ser Asp Trp Thr Leu Asp Pro Arg Val Glu Ile Gly Lys
385                 390                 395                 400
Gln Phe Asp Gly Glu Gly Val Pro Arg Gly Val Gly Asn Gln Val Ser
                405                 410                 415
Val Glu Phe Asn Leu Leu Tyr Arg Phe His Ser Cys Ile Ser Lys Lys
            420                 425                 430
Asp Glu Arg Trp Ile Asp Gly Phe Phe Ala Lys Leu Phe Pro Gly Arg
        435                 440                 445
Lys Pro Glu Asp Leu Gln Asn Val Gly Met Glu Glu Leu Gly Ala Ala
    450                 455                 460
Leu Met Lys Phe Glu Met Gly Ile Asp Lys Asp Pro Ser Lys Arg Thr
465                 470                 475                 480
Phe Asp Asp Leu Gln Arg Gly Glu Asp Gly Lys Phe Arg Asp Glu Asp
                485                 490                 495
Leu Val Arg Val Leu Lys Glu Ala Met Glu Asp Pro Ala Gly Thr Phe
            500                 505                 510
Gly Ala Arg Met Val Pro Lys Ala Leu Lys Ile Val Glu Ile Met Gly
        515                 520                 525
Ile Lys Gln Ala Arg Ala Trp Gln Val Ala Ser Leu Asn Glu Phe Arg
    530                 535                 540
Asp Phe Phe Gly Leu Lys Arg His Asp Thr Phe Lys Asp Ile Asn Ser
545                 550                 555                 560
Asn Glu Glu Ile Ala Thr Leu Leu Glu Lys Leu Tyr Thr Asp Pro Asp
                565                 570                 575
Met Val Glu Leu Tyr Pro Gly Leu Met Ile Glu Asp Ile Lys Pro Val
            580                 585                 590
Arg Asn Thr Gly Ser Gly Ile Cys Pro Thr Tyr Ser Val Gly Arg Ala
        595                 600                 605
Val Leu Ser Asp Ala Val Thr Leu Val Arg Ser Asp Arg Phe Asn Thr
    610                 615                 620
Ile Asp Tyr Thr Val Ser Asn Leu Thr Ala Trp Gly Tyr Asn Glu Val
625                 630                 635                 640
Gln Gln Asp Tyr Lys Thr Leu Gly Gly Ser Met Leu Tyr Lys Leu Ile
                645                 650                 655
Gln Arg Gly Leu Pro Gly Trp Phe Pro Phe Asn Ser Ile Ala Val Met
            660                 665                 670
Gln Pro Met Tyr Thr Lys Lys Ala Asn Glu Arg Ile Ala Arg Glu Ile
        675                 680                 685
Gly Thr Phe Asn Gln Phe Thr Leu Asp Asp Pro Lys Ala Pro Pro Lys
    690                 695                 700
Pro Val Val Val Ala Ser Ser Glu Gly Ile Lys Arg Val Leu Gly Ser
705                 710                 715                 720
Pro Asp Lys Phe Val Val Pro Trp Leu Thr Pro Leu Asn Ala Leu Tyr
                725                 730                 735
Thr Asp Thr Lys Lys Asp Ile Ser Trp Phe Met Leu Ala Gly Asp Gly
            740                 745                 750
Ser Thr Asn Lys Gln Glu Lys Val Asn Phe Val Asn Ala Met Lys Lys
        755                 760                 765
Val Pro Asn Leu His Asn Ala Val His Gln Phe Ile Glu Arg Val Gly
```

```
                770                 775                 780
Arg Gln Leu Ile Glu Lys Glu Thr Phe Lys Leu Lys Glu Gly Leu Cys
785                 790                 795                 800

Gln Met Asp Ile Ile Arg Asp Val Ala Ile Pro Leu Asn Ala Gln Leu
                805                 810                 815

Leu Ala Asp Leu Phe Tyr Phe Asp Leu Arg His Glu Glu Asn Pro Gly
                820                 825                 830

Gly Thr Leu Ser Ala Thr Asp Leu Tyr Arg His Leu Leu Asn Ile Arg
                835                 840                 845

Ile Trp Gly Val Asn Asn Asp Pro Gly Gln Ala Trp Asn Arg Arg
    850                 855                 860

Arg Arg Ala Ala Glu Ser Ala Lys Val Ile Thr Asp Ser Thr Arg Lys
865                 870                 875                 880

Leu Val Asp Glu Val Ser Arg Gly Arg Gly Leu Asn Leu Gly Phe Ile
                885                 890                 895

Ser Ala Ile Asn Glu Val Ala Ser Arg Lys Thr His Ile Lys Lys Asp
                900                 905                 910

Ser Leu Arg Ser Cys Gly Tyr Lys Leu Val Glu Glu Leu Leu Asn Gln
                915                 920                 925

Gly Gly Ser Pro Glu Lys Val Thr Asp Asn Val Trp Leu Thr Ala Phe
                930                 935                 940

Gly Gly Ile Gly Val Pro Val Thr Thr Phe Tyr Glu Val Met Glu Tyr
945                 950                 955                 960

Phe Leu Arg Pro Glu Asn Lys Ser Ile Trp Gly Glu Val Gln Ala Leu
                965                 970                 975

Ala Gln Lys Asn Asp Glu Ala Gly Leu His Ala Tyr Val Asn Glu Ala
                980                 985                 990

Met Arg Leu Thr Ser Gly Gln Arg Asn Val Arg Ile Ala Thr Val Lys
                995                 1000                1005

Asp Glu Ile Asp Gly Gln Lys Val Glu Pro Gly Asn Ala Val Val
    1010                1015                1020

Met Leu Leu Gly Ala Ala Gly Arg Asn Pro Lys Glu Val Pro Asn
    1025                1030                1035

Ala Asp Lys Phe Asp Ala Lys Arg Ser Thr Asp His Ile Lys Pro
    1040                1045                1050

Phe Ser Tyr Gly Gln His Glu Cys Val Gly Gln Asp Val Ala Arg
    1055                1060                1065

Ala Phe Val Thr Gly Leu Val Lys Leu Val Ala Asp Leu Arg Gln
    1070                1075                1080

Leu Arg Pro Ala Pro Gly Glu Met Gly Lys Val Lys Thr Ile Gln
    1085                1090                1095

Val Gly Thr Glu Arg Ala Tyr Leu Asn Asp Ser Trp Ser Tyr Leu
    1100                1105                1110

Gly Phe Asp Ala Ser Thr Trp Lys Val His Phe Asp Gly His Gly
    1115                1120                1125

Gln Gly Thr Tyr Glu Gly Asp Pro Glu Pro Asn Lys Pro Ile Asp
    1130                1135                1140

Met Gly Arg Tyr Tyr Tyr Ile Leu Gln Lys Arg Lys Glu Ser Leu
    1145                1150                1155

Leu Lys Gly
    1160

<210> SEQ ID NO 53
```

```
<211> LENGTH: 1251
<212> TYPE: PRT
<213> ORGANISM: Aspergillus niger

<400> SEQUENCE: 53

Met Gly Ser Ile Phe Ile Ala Leu Leu Cys Leu Leu Ser Tyr Leu
1               5                   10                  15

Tyr Leu Arg Val Phe Ala Asp Asp Leu Thr Arg Pro Leu Gln Ile Leu
            20                  25                  30

Ala Lys Phe Phe Ser Ser His Gln His Pro Thr Trp Lys Leu Arg Pro
        35                  40                  45

Arg Phe Leu Pro Lys Ala Thr Arg Ala Ala Leu Ser Ser Ile Ala Gly
    50                  55                  60

Thr Gly Glu Gly Leu Trp Gln Arg Leu Tyr Ala Arg Thr Phe His Ala
65                  70                  75                  80

Gln Glu Leu Ala Glu Val Asp Asp Leu Lys Tyr Gln Ala Gly Glu
                85                  90                  95

Pro Tyr Gly Asp Pro Asp Val Leu Ala Thr Gly Leu Val Lys Asp Leu
            100                 105                 110

Ser Ala Leu Gly Leu Lys Gly Lys Arg Ser Asp Leu Arg Thr Leu Ile
        115                 120                 125

Gln Leu Val Lys Ala Lys Gly Lys Pro Ile Asp Asp Arg Gln Met Leu
    130                 135                 140

Met Glu Lys Val Ile Ala Ile Val Ser Met Leu Pro Arg Thr Ser Lys
145                 150                 155                 160

Ser Arg Gln Arg Leu Thr Gly Ile Leu Val Asp Gln Leu Trp Gln Ser
                165                 170                 175

Leu Glu His Pro Pro Leu Ser Tyr Phe Gly Asn Lys Tyr Gln Tyr Arg
            180                 185                 190

Thr Pro Asp Gly Ser Tyr Asn Asn Pro Leu Glu Pro Asp Leu Gly Lys
        195                 200                 205

Ala Gly Ser Pro Tyr Ala Arg Ser Val Pro Arg Leu Lys Ala Leu His
    210                 215                 220

Gly Val Gln Pro Asp Pro Gly Leu Leu Phe Asp Leu Leu Met Ala Arg
225                 230                 235                 240

Asp Asp Thr Thr Phe Arg Glu Asn Pro Ala Gly Ile Ser Ser Val Leu
                245                 250                 255

Phe Tyr His Ala Ser Ile Ile Ile His Asp Val Phe Cys Thr Asn Arg
            260                 265                 270

Arg Asp Pro Asn Ile Ser Asp Thr Ser Ser Tyr Leu Asp Leu Ala Pro
        275                 280                 285

Leu Tyr Gly Ser Ser Tyr Glu Asp Gln Leu Arg Val Arg Thr Met Gln
    290                 295                 300

Arg Gly Met Leu Lys Pro Asp Thr Phe His Glu Lys Arg Leu Leu Gly
305                 310                 315                 320

Gln Pro Pro Gly Val Asn Val Ile Leu Val Met Tyr Asn Arg Phe His
                325                 330                 335

Asn Tyr Val Ala Asp Val Leu Leu Lys Ile Asn Glu Asn Gly Arg Phe
            340                 345                 350

Thr Leu Pro Pro Thr Thr Ser Glu Asp Ala Lys Arg Lys Ala Leu Ala
        355                 360                 365

Lys Gln Asp Glu Asp Leu Phe Gln Val Thr Arg Leu Ile Val Asn Gly
    370                 375                 380

Leu Tyr Val Asn Ile Ser Leu His Asp Tyr Leu Arg Gly Leu Thr Asn
```

```
        385                 390                 395                 400
Thr His His Ser Ala Ser Asp Trp Thr Leu Asp Pro Arg Val Ala Val
                    405                 410                 415
Ser Arg Ala Phe Asp Ala Asp Gly Val Pro Arg Gly Val Gly Asn Gln
                420                 425                 430
Val Ser Ala Glu Phe Asn Leu Leu Tyr Arg Phe His Ser Val Ile Ser
            435                 440                 445
Arg Arg Asp Glu Gln Trp Thr Asn Glu Phe Leu Lys Ser Leu Phe Pro
450                 455                 460
Asp Leu Lys Lys Pro Leu Glu Gln Leu Thr Pro Gln Glu Phe Met Gln
465                 470                 475                 480
Gly Leu Ile Asn Tyr Glu Arg Ser Ile Asp Lys Asp Pro Ser Lys Arg
                485                 490                 495
Glu Phe Gly Gly Leu Lys Arg Asn Gln Asp Gly Arg Phe Asn Asp Ala
                500                 505                 510
Glu Leu Val Gln Ile Leu Lys Asp Ser Met Glu Asp Pro Ala Gly Leu
            515                 520                 525
Phe Gly Ala Arg Met Val Pro Lys Ala Leu Arg Met Val Glu Ile Ala
530                 535                 540
Gly Ile Leu Thr Ala Arg Lys Trp Asn Leu Ala Ser Leu Asn Glu Met
545                 550                 555                 560
Arg Asp Phe Phe Lys Leu Lys Arg His Ser Ser Phe Glu Asp Ile Asn
                565                 570                 575
Pro Asp Pro Lys Ile Ala Asp Leu Leu Arg Lys Leu Tyr Asp His Pro
                580                 585                 590
Asp Met Val Glu Met Tyr Pro Gly Ile Phe Leu Glu Asp Ala Lys Pro
            595                 600                 605
Ala Met Asp Pro Gly Cys Gly Cys Pro Pro Tyr Thr Val Gly Arg
            610                 615                 620
Ala Val Phe Ser Asp Ala Val Thr Leu Val Arg Ser Asp Arg Phe Leu
625                 630                 635                 640
Thr Leu Asp Tyr Thr Ala Ser Asn Leu Thr Asn Trp Gly Ile Arg Glu
                645                 650                 655
Val Gln Gln Asp Tyr Asp Ile Leu Gly Gly Ser Met Phe His Lys Leu
                660                 665                 670
Ile Gln Arg Ala Leu Pro Gly Trp Phe Pro Tyr Asn Ser Leu His Ala
            675                 680                 685
Thr Gln Pro Met Phe Thr Arg Lys Met Asn Glu Gln Ile Ala Lys Glu
            690                 695                 700
Ile Gly Thr Ile Asp Arg Tyr Ser Gln Glu Asp Pro Lys Pro Pro
705                 710                 715                 720
Arg Thr Val Met Leu Ala Asn His Ala Thr Ile Glu Val Leu Lys
                725                 730                 735
Asp Gln Asp Thr Phe Arg Val Pro Trp Ala Arg Tyr Leu Asn Asp Met
                740                 745                 750
Ile Pro Gly Lys Arg Phe Asn Asp Tyr Met Leu Gly Gly Asp Gly Pro
            755                 760                 765
Val Asn Ala Ala Gln Lys Lys Leu Val Lys Ser Ile Leu Phe Ser Pro
            770                 775                 780
Asp Gln Phe Asn Gln Leu Leu Ser Gln Thr Thr Val Arg Leu Gly Lys
785                 790                 795                 800
Glu Leu Leu Glu Leu Asn Thr Leu Gln Leu Ser Lys Asp Leu Asn Gln
                805                 810                 815
```

-continued

Val Asp Ile Ile Arg Asp Val Ala Ile Pro Leu Asn Ala Arg Ile Met
              820                 825                 830

Ala Asp Leu Phe Cys Leu Asp Met Lys Thr Pro Glu Asn Glu Ser Gly
              835                 840                 845

Ser Met Asn Ala Ala Thr Val Tyr Lys His Leu Met Asn Val Arg Thr
850                 855                 860

Trp Gly Phe Asn Asn Thr Asp Pro Gly Leu Met Leu Gln Arg Arg Lys
865                 870                 875                 880

Trp Ala Ser Glu Ser Ala Glu Ala Leu Val Lys Thr Thr Leu Lys Val
              885                 890                 895

Val Asn Glu Gln Ala Gln Pro Gln Lys Thr His Met Leu Lys Lys Leu
              900                 905                 910

Thr Gly Tyr Gln Arg Ser Glu Val Ser Thr Leu Arg Trp Tyr Gly Asn
              915                 920                 925

Asn Val Val Lys Gln Met Met Glu Met Asp Thr Ala Ala Glu Thr
930                 935                 940

Ala Glu Val Cys Trp Leu Thr Ala Val Gly Gly Val Gly Ala Pro Val
945                 950                 955                 960

Gly Leu Val Ala Asp Val Leu Gln Tyr Tyr Leu Arg Pro Glu Asn Ile
              965                 970                 975

Asp His Trp Lys Arg Ile Gln Asn Leu Val Ser Gln Pro Asp Asn Ser
              980                 985                 990

Gly Ser Ile Asp Lys Leu Leu Arg Gln Tyr Val Leu Glu Ala Gln Arg
              995                1000                1005

Leu Thr Ser Met Glu Cys Thr Val Arg Val Cys Arg Ala His Arg
        1010                1015                1020

Thr Ile Asn Asp Gln Glu Phe Lys Pro Gly Asp Val Val Ile Thr
        1025                1030                1035

Leu Leu Gly Pro Ala Cys Arg Asp Pro Thr Ser Ile Pro Asp Ala
        1040                1045                1050

Glu Thr Phe Lys Leu Asp Arg Pro Ser Asn Ala Tyr Ile His Phe
        1055                1060                1065

Gly Tyr Gly Ala His Glu Cys Leu Gly Lys Glu Ile Gly Leu Thr
        1070                1075                1080

Phe Ala Val Ser Met Leu Arg Val Leu Ala Gly Leu Lys Tyr Leu
        1085                1090                1095

Arg Pro Ala Pro Gly Asp Met Gly Met Leu Lys Ser Ile Ile Val
        1100                1105                1110

Asp Gly Arg Arg Val Tyr Leu Asn Asp Ser Trp Ser Trp Met Ile
        1115                1120                1125

Gln Asp Pro Thr Thr Trp Lys Leu His Phe Ala Gly Tyr Gly Gln
        1130                1135                1140

Gly Ala Tyr Glu Ala Pro Ala Pro Pro Pro Ala Pro Thr Phe
        1145                1150                1155

Pro Val Ile Asp Gln Ser Pro Asp Thr Ser Asp Glu Asp Gly Val
        1160                1165                1170

Asp Asp Thr Ile Tyr Ser Thr Val Pro Thr Lys His His His
        1175                1180                1185

Gly Asp Pro Glu Tyr Thr Arg Gln Glu Ser Tyr Thr Met Thr Asp
        1190                1195                1200

Gly Gly Ile Gly Met Ser Thr Gln Tyr Ser Phe Gly Gln His His
        1205                1210                1215

His His Gln Tyr His Glu Ile Thr Arg Thr Ser Ser Ser Ser Leu
1220                    1225                1230

Pro Ser Met Leu Gly Asp Asp Glu Ser Tyr Gly Arg Phe Ser Gly
    1235                1240                1245

Thr Leu Asn
    1250

<210> SEQ ID NO 54
<211> LENGTH: 478
<212> TYPE: PRT
<213> ORGANISM: Solanum tuberosum

<400> SEQUENCE: 54

Met Ser Ser Tyr Ser Glu Leu Ser Asn Leu Pro Ile Arg Glu Ile Pro
1               5                   10                  15

Gly Asp Tyr Gly Phe Pro Ile Ile Ser Ala Ile Lys Asp Arg Tyr Asp
                20                  25                  30

Tyr Phe Tyr Asn Gln Gly Glu Asp Ala Trp Phe His Asn Lys Ala Glu
            35                  40                  45

Lys Tyr Lys Ser Thr Val Val Lys Ile Asn Met Ala Pro Gly Pro Phe
50                  55                  60

Thr Ser Asn Asp Tyr Lys Leu Val Ala Phe Leu Asp Ala Asn Ser Phe
65                  70                  75                  80

Val Cys Met Phe Asp Asn Ser Leu Ile Asp Lys Thr Asp Thr Leu Gly
                85                  90                  95

Gly Thr Phe Lys Pro Gly Lys Glu Tyr Tyr Ser Gly Tyr Arg Pro Val
                100                 105                 110

Ala Phe Ile Asp Thr Lys Asp Pro Asn His Ala Ala Leu Lys Gly Tyr
            115                 120                 125

Ile Leu Ser Ala Phe Ala Lys Arg His Asn Leu Phe Ile Pro Leu Phe
130                 135                 140

Arg Asn Ser Leu Ser Asp His Leu Phe Asn Asn Leu Glu Lys Gln Val
145                 150                 155                 160

Thr Glu Gln Gly Lys Ser Asp Phe Asn Ala Leu Leu Pro Thr Met Thr
                165                 170                 175

Phe Asn Phe Ile Phe Arg Leu Leu Cys Asp Gln Thr Asn Pro Ser Asp
            180                 185                 190

Thr Val Leu Gly Ala Gln Gly Pro Glu His Leu Arg Lys Trp Leu Phe
        195                 200                 205

Pro Gln Leu Ile Pro Ser Leu Ser Ala Lys Lys Leu Pro Asn Ile Ile
210                 215                 220

Glu Asp Thr Leu Phe His Asn Phe Leu Ile Pro Phe Gly Phe Ile Lys
225                 230                 235                 240

Ser Asp Tyr Asn Lys Leu Val Asp Ala Phe Ser Lys Ser Ala Val Ser
                245                 250                 255

Ile Leu Asp Glu Ala Glu Lys Leu Gly Ile Lys Arg Glu Glu Ala Val
            260                 265                 270

Gln Asn Ile Leu Phe Leu Val Gly Ile Asn Met Phe Ala Gly Leu Asn
        275                 280                 285

Ala Phe Ser Pro His Leu Phe Arg Phe Val Gly Glu Ala Gly Ala Ser
290                 295                 300

Leu His Thr Gln Leu Ala Lys Glu Ile Arg Thr Val Ile Lys Glu Glu
305                 310                 315                 320

Gly Gly Ala Ile Thr Leu Ser Ala Ile Asn Lys Met Ser Leu Val Lys
                325                 330                 335

```
Ser Val Val Tyr Glu Thr Leu Arg Leu Arg Pro Val Pro Leu Gln
            340                 345                 350

Tyr Gly Lys Ala Lys Asp Phe Met Val Gln Ser His Asp Ala Ser
            355                 360                 365

Tyr Lys Ile Asn Lys Gly Gln Phe Val Val Gly Tyr Gln Pro Met Ala
            370                 375                 380

Ser Arg Asp Pro Lys Ile Phe Ala Asn Pro Asp Glu Phe Val Pro Asp
385                 390                 395                 400

Arg Phe Met Asn Asp Gly Glu Lys Met Leu Lys His Val Leu Trp Ser
            405                 410                 415

Asn Gly Arg Glu Thr Glu Asn Pro Ala Pro Asp Asn Lys Gln Cys Pro
            420                 425                 430

Gly Lys Asp Leu Val His Leu Leu Gly Arg Leu Ile Leu Val Glu Phe
            435                 440                 445

Phe Met Arg Tyr Asp Thr Phe Thr Val Glu Ile Thr Pro Leu Phe Arg
            450                 455                 460

Ala Pro Asn Val Ala Phe Lys Thr Leu Thr Lys Ala Ser Lys
465                 470                 475

<210> SEQ ID NO 55
<211> LENGTH: 472
<212> TYPE: PRT
<213> ORGANISM: Allium sativum

<400> SEQUENCE: 55

Met Ser Thr Ser Asn Gly Ser Thr Glu Asn Ile Gln Lys Pro Leu Arg
1               5                   10                  15

Lys Ile Pro Asp Ile Thr Gly Thr Pro Ile Leu Thr Ala Ile Lys Asp
                20                  25                  30

Arg Leu Asp Phe Phe Tyr Asn Gln Gly Gln Tyr Glu Tyr Phe Gln Ser
            35                  40                  45

Arg Val Lys Lys Asn Asn Ser Thr Ile Leu Arg Met Asn Met Ile Pro
        50                  55                  60

Gly Pro Phe Ala Ser Asn Pro Lys Ile Val Ala Leu Cys Asp Ala Ala
65                  70                  75                  80

Ser Phe Pro Thr Leu Phe Asp Pro Ser Lys Val Ser Lys Val Asn Ser
                85                  90                  95

Leu Thr Gly Asn Tyr Met Pro Ala Leu Ser Phe Thr Gly Gly Tyr Arg
            100                 105                 110

Val Cys Ala Tyr Leu Asp Pro Ser Glu Pro Thr His Thr Lys Ile Lys
        115                 120                 125

Gln Val Phe Phe Asn Ala Gln Ala Ala Lys Lys Asp Thr Phe Ile Pro
    130                 135                 140

Thr Phe Val Ser Thr Phe Asn Ser Met Phe Asp Lys Met Asp Ala Glu
145                 150                 155                 160

Val Glu Ser Lys Lys Lys Ala Glu Phe Thr Lys Phe Asn Glu Ala Ala
                165                 170                 175

Val Phe Glu Phe Val Gly Leu Ala Leu Val Gly Pro Lys Pro Ala Arg
            180                 185                 190

Glu Val Phe Asp Ser Ala Lys Lys Ser Val Phe Gln Phe His Pro
        195                 200                 205

Phe Ile Thr Ala Gly Leu Pro Ala Leu Val Glu Glu Leu Ala Phe His
    210                 215                 220

Met Phe Pro Phe Pro Ser Phe Val Ala Lys Ser Ser Tyr Lys Ile Leu
```

```
                    225                 230                 235                 240
        Tyr Glu Tyr Phe Ser Thr Gly Gly Ser Trp Ile Leu Asp Asn Ala Glu
                        245                 250                 255

Glu Ile Gly Leu Ser Arg Glu Glu Ala Ile His His Leu Ile Phe Thr
                        260                 265                 270

Trp Ala Ile Asn Ala Tyr Leu Gly Ile Arg Thr Cys Leu Met Arg Leu
                        275                 280                 285

Phe Lys Trp Ile Val Ala Ser Gly Pro Asp Leu Gln Glu Lys Leu Ala
                        290                 295                 300

Arg Glu Val Arg Ser Val Val Arg Ser Glu Glu Gly Lys Ile Thr Phe
        305                 310                 315                 320

Ala Gly Ile Glu Lys Met Glu Leu Val Lys Ser Val Ala Tyr Glu Ser
                        325                 330                 335

Phe Arg Phe Asp Pro Pro Val Gln Val Gln Tyr Gly Thr Ala Lys Ser
                        340                 345                 350

Asp Leu Ile Ile Glu Ser His Asp Gly Lys Tyr Gln Val Lys Lys Gly
                        355                 360                 365

Glu Met Leu Cys Gly Phe Gln Pro Met Ala Thr Arg Asp Pro Lys Val
                        370                 375                 380

Phe Asp Arg Ala Asp Glu Phe Val Pro Asp Arg Phe Met Gly Asp Gly
        385                 390                 395                 400

Lys Lys Leu Val Lys His Val Leu Trp Ala Asn Gly Tyr Gly Thr Asp
                        405                 410                 415

Ala Pro Lys Ala Asp Asp Lys Ile Cys Ala Gly Lys Asp Leu Gly Val
                        420                 425                 430

Leu Val Gly Arg Leu Leu Ile Ala Val Met Phe Leu Arg Tyr Asp Lys
                        435                 440                 445

Ile Gly Gly Val Val Gly Lys Thr Met Glu Glu Val Asp Val Ile Val
                        450                 455                 460

Asn Glu Leu Thr Lys Val Ala Val
        465                 470

<210> SEQ ID NO 56
<211> LENGTH: 1081
<212> TYPE: PRT
<213> ORGANISM: Asperigullus nidalus

<400> SEQUENCE: 56

Met Gly Glu Asp Lys Glu Thr Asn Ile Leu Ala Gly Leu Gly Asn Thr
1               5                   10                  15

Ile Ser Gln Val Glu Asn Val Val Ala Ala Ser Leu Arg Pro Leu Pro
                20                  25                  30

Thr Ala Thr Gly Asp Gly Thr Tyr Val Ala Glu Ser Thr Gln Thr Gly
                35                  40                  45

Leu Ala Lys Asp Leu Ser His Val Asp Leu Lys Asp Val Arg Thr Leu
                50                  55                  60

Ala Glu Val Val Lys Ser Ala Ala Thr Gly Glu Pro Val Asp Asp Lys
65                  70                  75                  80

Gln Tyr Ile Met Glu Arg Val Ile Gln Leu Ala Ala Gly Leu Pro Ser
                85                  90                  95

Thr Ser Arg Asn Ala Ala Glu Leu Thr Lys Ser Phe Leu Asn Met Leu
                100                 105                 110

Trp Asn Asp Leu Glu His Pro Pro Val Ser Tyr Leu Gly Ala Asp Ser
                115                 120                 125
```

-continued

```
Met His Arg Lys Ala Asp Gly Ser Gly Asn Asn Arg Phe Trp Pro Gln
    130                 135                 140
Leu Gly Ala Ala Gly Ser Ala Tyr Ala Arg Ser Val Arg Pro Lys Thr
145                 150                 155                 160
Met Gln Ser Pro Ser Leu Pro Asp Pro Glu Thr Ile Phe Asp Cys Leu
                165                 170                 175
Leu Arg Arg Lys Glu Tyr Arg Glu His Pro Asn Lys Ile Ser Ser Val
            180                 185                 190
Leu Phe Tyr Leu Ala Ser Ile Ile Ile His Asp Leu Phe Gln Thr Asp
        195                 200                 205
Pro Lys Asp Asn Ser Val Ser Lys Thr Ser Ser Tyr Leu Asp Leu Ser
    210                 215                 220
Pro Leu Tyr Gly Asn Asn Gln Asp Glu Gln Asn Leu Val Arg Thr Phe
225                 230                 235                 240
Lys Asp Gly Lys Leu Lys Pro Asp Cys Phe Ala Thr Lys Arg Val Leu
                245                 250                 255
Gly Phe Pro Pro Gly Val Gly Val Leu Leu Ile Met Phe Asn Arg Phe
            260                 265                 270
His Asn Tyr Val Val Asp Gln Leu Ala Ala Ile Asn Glu Cys Gly Arg
        275                 280                 285
Phe Thr Lys Pro Asp Glu Ser Asn Val Asp Glu Tyr Ala Lys Tyr Asp
    290                 295                 300
Asn Asn Leu Phe Gln Thr Gly Arg Leu Val Thr Cys Gly Leu Tyr Ala
305                 310                 315                 320
Asn Ile Ile Leu Lys Asp Tyr Val Arg Thr Ile Leu Asn Ile Asn Arg
                325                 330                 335
Thr Asp Ser Thr Trp Ser Leu Asp Pro Arg Met Glu Met Lys Asp Gly
            340                 345                 350
Leu Leu Gly Glu Ala Ala Ala Met Ala Thr Gly Asn Gln Val Ser Ala
        355                 360                 365
Glu Phe Asn Val Val Tyr Arg Trp His Ala Cys Ile Ser Lys Arg Asp
    370                 375                 380
Glu Lys Trp Thr Glu Asp Phe His Arg Glu Ile Met Pro Gly Val Asp
385                 390                 395                 400
Pro Ser Thr Leu Ser Met Gln Asp Phe Val Ala Gly Leu Gly Arg Trp
                405                 410                 415
Gln Ala Gly Leu Pro Gln Glu Pro Leu Glu Arg Pro Phe Ser Gly Leu
            420                 425                 430
Gln Arg Lys Pro Asp Gly Ala Phe Asn Asp Asp Leu Val Asn Leu
        435                 440                 445
Phe Glu Lys Ser Val Glu Asp Cys Ala Gly Ala Phe Gly Ala Ser His
    450                 455                 460
Val Pro Ala Ile Phe Lys Ser Val Glu Ala Leu Gly Ile Met Gln Ala
465                 470                 475                 480
Arg Arg Trp Asn Leu Gly Thr Leu Asn Glu Phe Arg Gln Tyr Phe Asn
                485                 490                 495
Leu Ala Pro His Lys Thr Phe Glu Asp Ile Asn Ser Asp Pro Tyr Ile
            500                 505                 510
Ala Asp Gln Leu Lys Arg Leu Tyr Asp His Pro Asp Leu Val Glu Ile
        515                 520                 525
Tyr Pro Gly Val Val Glu Glu Ala Lys Asp Ser Met Val Pro Gly
    530                 535                 540
Ser Gly Leu Cys Thr Asn Phe Thr Ile Ser Arg Ala Ile Leu Ser Asp
```

```
       545                 550                 555                 560
   Ala Val Ala Leu Val Arg Gly Asp Arg Phe Tyr Thr Val Asp Tyr Thr
                       565                 570                 575
   Pro Lys His Leu Thr Asn Trp Ala Tyr Asn Glu Ile Gln Pro Asn Asn
                       580                 585                 590
   Ala Val Asp Gln Gly Gln Val Phe Tyr Lys Leu Val Leu Arg Ala Phe
                       595                 600                 605
   Pro Asn His Phe Asp Gly Asn Ser Ile Tyr Ala His Phe Pro Leu Val
                       610                 615                 620
   Val Pro Ser Glu Asn Glu Lys Ile Leu Lys Ser Leu Gly Val Ala Glu
   625                 630                 635                 640
   Lys Tyr Ser Trp Glu Lys Pro Ser Arg Ile Ser His Pro Ile Phe Ile
                       645                 650                 655
   Ser Ser His Ala Ala Cys Met Ser Ile Leu Glu Asn Gln Glu Thr Phe
                       660                 665                 670
   Lys Val Thr Trp Gly Arg Lys Ile Glu Phe Leu Met Gln Arg Asp Lys
                       675                 680                 685
   His Gln Tyr Gly Lys Asp Phe Met Leu Ser Gly Asp Arg Pro Pro Asn
                       690                 695                 700
   Ala Ala Ser Arg Lys Met Met Gly Ser Ala Leu Tyr Arg Asp Glu Trp
   705                 710                 715                 720
   Glu Ala Glu Val Lys Asn Phe Tyr Glu Gln Thr Thr Leu Lys Leu Leu
                       725                 730                 735
   His Lys Asn Ser Tyr Lys Leu Ala Gly Val Asn Gln Val Asp Ile Val
                       740                 745                 750
   Arg Asp Val Ala Asn Leu Ala Gln Val His Phe Cys Ser Ser Val Phe
                       755                 760                 765
   Ser Leu Pro Leu Lys Thr Asp Ser Asn Pro Arg Gly Ile Phe Ala Glu
                       770                 775                 780
   Ser Glu Leu Tyr Lys Ile Met Ala Ala Val Phe Thr Ala Ile Phe Tyr
   785                 790                 795                 800
   Asp Ala Asp Ile Gly Lys Ser Phe Glu Leu Asn Gln Ala Ala Arg Thr
                       805                 810                 815
   Val Thr Gln Gln Leu Gly Gln Leu Thr Met Ala Asn Val Glu Ile Ile
                       820                 825                 830
   Ala Lys Thr Gly Leu Ile Ala Asn Leu Val Asn Arg Leu His Arg Arg
                       835                 840                 845
   Asp Val Leu Ser Glu Tyr Gly Ile His Met Ile Gln Arg Leu Leu Asp
                       850                 855                 860
   Ser Gly Leu Pro Ala Thr Glu Ile Val Trp Thr His Ile Leu Pro Thr
   865                 870                 875                 880
   Ala Gly Gly Met Val Ala Asn Gln Ala Gln Leu Phe Ser Gln Cys Leu
                       885                 890                 895
   Asp Tyr Tyr Leu Ser Glu Glu Gly Ser Gly His Leu Pro Glu Ile Asn
                       900                 905                 910
   Arg Leu Ala Lys Glu Asn Thr Pro Glu Ala Asp Glu Leu Leu Thr Arg
                       915                 920                 925
   Tyr Phe Met Glu Gly Ala Arg Leu Arg Ser Ser Val Ala Leu Pro Arg
                       930                 935                 940
   Val Ala Ala Gln Pro Thr Val Glu Asp Asn Gly Glu Lys Leu Thr
   945                 950                 955                 960
   Ile Lys Ala Gly Gln Val Val Met Cys Asn Leu Val Ser Ala Cys Met
                       965                 970                 975
```

```
Asp Pro Thr Ala Phe Pro Asp Pro Glu Lys Val Lys Leu Asp Arg Asp
            980                 985                 990

Met Asn Leu Tyr Ala His Phe Gly Phe Gly Pro His Lys Cys Leu Gly
        995                 1000                1005

Leu Asp Leu Cys Lys Thr Gly Leu Ser Thr Met Leu Lys Val Leu
    1010                1015                1020

Gly Arg Leu Asp Asn Leu Arg Arg Ala Pro Gly Ala Gln Gly Gln
    1025                1030                1035

Leu Lys Lys Leu Ser Gly Pro Gly Gly Ile Ala Lys Tyr Met Asn
    1040                1045                1050

Glu Asp Gln Ser Gly Phe Thr Pro Phe Pro Ser Thr Met Lys Ile
    1055                1060                1065

Gln Trp Asp Gly Glu Leu Pro Gln Leu Lys Glu Asp Phe
    1070                1075                1080

<210> SEQ ID NO 57
<211> LENGTH: 1079
<212> TYPE: PRT
<213> ORGANISM: Aspergillus fumigatus

<400> SEQUENCE: 57

Met Ser Glu Lys Gln Thr Gly Ser Ala Asn Gly Gly Leu Gly Lys Thr
1               5                   10                  15

Leu Ala Gln Leu Glu Gln Val Val Ser Ala Ser Leu Arg Pro Leu Pro
            20                  25                  30

Cys Gln Thr Gly Asp Gly Thr Tyr Val Thr Glu Gln Val Lys Thr Gly
        35                  40                  45

Ile Leu Lys Asp Leu Ser His Val Asp Leu Gly Asp Leu Lys Thr Leu
    50                  55                  60

Val Asp Val Ser Lys Ser Ala Leu Thr Gly Glu Ala Leu Asp Asp Arg
65                  70                  75                  80

Lys Tyr Ile Met Glu Arg Val Ile Gln Leu Ser Ala Gly Leu Pro Ser
                85                  90                  95

Thr Ser Gln Ile Gly Lys Glu Leu Thr Asn Thr Phe Leu Thr Thr Leu
            100                 105                 110

Trp Asn Asp Leu Glu His Pro Pro Ile Ser Tyr Leu Gly Arg Asp Ala
        115                 120                 125

Met Tyr Arg Arg Ala Asp Gly Ser Gly Asn Asn Val Leu Trp Pro His
    130                 135                 140

Ile Gly Ala Ala Gly Thr Pro Tyr Ala Arg Ser Val Gln Pro Lys Thr
145                 150                 155                 160

Val Gln Ser Pro Asn Leu Pro Asp Pro Glu Thr Leu Phe Asp Cys Leu
                165                 170                 175

Leu Ala Arg Lys Glu Tyr Lys Glu His Pro Asn Lys Ile Ser Ser Val
            180                 185                 190

Leu Phe Tyr Ile Ala Ser Ile Ile His Asp Leu Phe Glu Thr Asp
        195                 200                 205

Arg Lys Asp Pro Ala Ile Ser Leu Thr Ser Ser Tyr Leu Asp Leu Ser
    210                 215                 220

Pro Leu Tyr Gly Asn Asn Gln Gln Glu Gln Asp Leu Ile Arg Thr Phe
225                 230                 235                 240

Lys Asp Gly Lys Leu Lys Pro Asp Cys Phe Ser Thr Lys Arg Val Leu
                245                 250                 255

Gly Phe Pro Pro Gly Val Gly Val Val Leu Ile Met Phe Asn Arg Phe
```

```
                260                 265                 270
His Asn Tyr Val Val Glu Lys Leu Ala Met Ile Asn Glu Gly Gly Arg
        275                 280                 285

Phe Thr Lys Pro Gln Glu Ser Asp Thr Ala Ala Tyr Ala Lys Tyr Asp
        290                 295                 300

Asn Asp Leu Phe Gln Thr Gly Arg Leu Val Thr Cys Gly Leu Tyr Val
305                 310                 315                 320

Asn Ile Ile Leu Lys Asp Tyr Val Arg Thr Ile Leu Asn Ile Asn Arg
                325                 330                 335

Thr Asp Ser Ile Trp Ser Leu Asp Pro Arg Ser Glu Met Lys Asp Gly
                340                 345                 350

Leu Leu Gly Arg Ala Ala Gln Ala Thr Gly Asn Gln Val Ala Ala
                355                 360                 365

Glu Phe Asn Leu Val Tyr Arg Trp His Ser Cys Ile Ser Gln Arg Asp
        370                 375                 380

Gln Lys Trp Thr Glu Asp Met Tyr Gln Glu Leu Phe Pro Gly Gln Asp
385                 390                 395                 400

Pro Ser Lys Ile Ser Leu Gln Asp Phe Leu Arg Gly Leu Gly Arg Trp
                405                 410                 415

Glu Ala Lys Leu Pro Gly Glu Pro Arg Glu Arg Pro Phe Ala Gly Leu
                420                 425                 430

Gln Arg Lys Ala Asp Gly Ser Tyr Asp Asp Asn Asp Leu Val Lys Ile
                435                 440                 445

Phe Glu Glu Ser Val Glu Asp Cys Ala Gly Ala Phe Gly Ala Leu His
        450                 455                 460

Val Pro Thr Val Phe Arg Ser Ile Glu Ala Leu Gly Ile Gln Gln Ala
465                 470                 475                 480

Arg Ser Trp Asn Leu Ala Thr Leu Asn Glu Phe Arg Lys Tyr Phe Asn
                485                 490                 495

Leu Ala Pro Tyr Lys Thr Phe Glu Glu Ile Asn Ser Asp Pro Tyr Val
                500                 505                 510

Ala Asp Gln Leu Lys Arg Leu Tyr Asp His Pro Asp Arg Val Glu Ile
        515                 520                 525

Tyr Pro Gly Ile Ile Val Glu Asp Ala Lys Glu Ser Met Ala Pro Gly
        530                 535                 540

Ser Gly Leu Cys Thr Asn Phe Thr Ile Ser Arg Ala Ile Leu Ser Asp
545                 550                 555                 560

Ala Val Ala Leu Val Arg Gly Asp Arg Phe His Thr Val Asp Phe Thr
                565                 570                 575

Pro Lys His Leu Thr Asn Trp Ala Tyr Asn Glu Ile Gln Pro Gln Asp
                580                 585                 590

Ser Val Asp Gln Thr His Val Phe Tyr Lys Leu Val Leu Arg Ala Phe
        595                 600                 605

Pro Asn His Phe Arg Gly Asp Ser Ile Tyr Ala His Phe Pro Leu Val
        610                 615                 620

Val Pro Ser Glu Asn Lys Lys Ile Leu Thr Lys Leu Gly Thr Ala Asp
625                 630                 635                 640

Lys Tyr Ser Trp Asp Arg Pro Asn Tyr Thr Pro Pro Gln Phe Ile
                645                 650                 655

Asn Ser His Ser Ala Cys Met Ser Ile Leu Ser Asp Gln Glu Thr Phe
                660                 665                 670

Lys Val Thr Trp Gly Ser Lys Ile Glu Phe Leu Met Arg His Asn Asn
                675                 680                 685
```

Gln Pro Tyr Gly Arg Asp Phe Met Leu Ser Gly Asp Arg Thr Pro Asn
690                 695                 700

Ala Met Ser Arg Gln Met Met Gly Lys Ala Leu Tyr Arg Asp Lys Trp
705                 710                 715                 720

Glu Thr Glu Val Lys Arg Phe Tyr Glu Asn Ile Thr Leu Lys Leu Leu
            725                 730                 735

His Arg Tyr Ser Tyr Lys Leu Ala Gly Val Asn Gln Val Asp Val Val
            740                 745                 750

Arg Asp Ile Ala Asn Leu Ala Gln Val His Phe Cys Ala Ser Val Phe
            755                 760                 765

Ser Leu Pro Leu Lys Thr Glu Ser Asn Pro Arg Gly Ile Phe Thr Glu
770                 775                 780

Ser Glu Leu Tyr Gln Ile Met Ala Val Val Phe Thr Ser Ile Phe Tyr
785                 790                 795                 800

Asp Ala Asp Ile Gly Lys Ser Phe Glu Leu Asn Gln Ala Ala Arg Ala
                805                 810                 815

Val Thr Gln Gln Leu Gly Gln Leu Thr Leu Ala Asn Val Glu Leu Ile
            820                 825                 830

Ala Lys Thr Gly Phe Ile Ala Asn Leu Val Asn Ser Leu His Arg His
            835                 840                 845

Asp Val Leu Ser Glu Tyr Gly Val His Met Ile Gln Arg Leu Leu Asp
850                 855                 860

Ser Gly Met Pro Ala Pro Glu Ile Val Trp Thr His Val Leu Pro Thr
865                 870                 875                 880

Ala Gly Gly Met Val Ala Asn Gln Ala Gln Leu Phe Ser Gln Ser Leu
                885                 890                 895

Asp Tyr Tyr Leu Ser Glu Glu Gly Ser Val His Leu Pro Glu Ile Asn
            900                 905                 910

Arg Leu Ala Lys Glu Asp Thr Thr Glu Ala Asp Asp Leu Leu Leu Arg
            915                 920                 925

Tyr Phe Met Glu Gly Ala Arg Ile Arg Ser Ser Val Ala Leu Pro Arg
930                 935                 940

Val Val Ala Gln Pro Thr Val Glu Asp Asn Gly Gln Lys Ile Thr
945                 950                 955                 960

Leu Lys Gln Gly Gln His Ile Ile Cys Asn Leu Val Ser Ala Ser Met
                965                 970                 975

Asp Pro Val Thr Phe Pro Glu Pro Asp Lys Val Lys Leu Asp Arg Asp
            980                 985                 990

Met Asn Leu Tyr Ala His Phe Gly  Phe Gly Pro His Gln Cys Leu Gly
            995                 1000                1005

Leu Gly Leu Cys Lys Thr Ala  Leu Thr Thr Met Leu Lys Val Ile
    1010                1015                1020

Gly Arg Leu Asp Asn Leu Arg  Arg Ala Pro Gly Gly Gln Gly Lys
    1025                1030                1035

Leu Lys Lys Leu Ser Gly Pro  Gly Gly Ile Ala Met  Tyr Met Thr
    1040                1045                1050

Pro Asp Gln Thr Ala Phe Phe  Pro Phe Pro Thr Thr  Met Lys Ile
    1055                1060                1065

Gln Trp Asp Gly Asp Leu Pro  Glu Val Lys Glu
    1070                1075

<210> SEQ ID NO 58
<211> LENGTH: 1153

<212> TYPE: PRT
<213> ORGANISM: Magnaporthe oryzae

<400> SEQUENCE: 58

Met Asp Gly Ala Val Arg Leu Asp Trp Thr Gly Leu Asp Leu Thr Gly
1               5                   10                  15

His Glu Ile His Asp Gly Val Pro Ile Ala Ser Arg Val Gln Val Met
            20                  25                  30

Val Ser Phe Pro Leu Phe Lys Asp Gln His Ile Ile Met Ser Ser Lys
        35                  40                  45

Glu Ser Pro Ser Arg Lys Ser Ser Thr Ile Gly Gln Ser Thr Arg Asn
    50                  55                  60

Gly Ser Cys Gln Ala Asp Thr Gln Lys Gly Gln Leu Pro Pro Val Gly
65                  70                  75                  80

Glu Lys Pro Lys Pro Val Lys Glu Asn Pro Met Lys Lys Leu Lys Glu
                85                  90                  95

Met Ser Gln Arg Pro Leu Pro Thr Gln His Gly Asp Gly Thr Tyr Pro
            100                 105                 110

Thr Glu Lys Lys Leu Thr Gly Ile Gly Glu Asp Leu Lys His Ile Arg
        115                 120                 125

Gly Tyr Asp Val Lys Thr Leu Leu Ala Met Val Lys Ser Lys Leu Lys
    130                 135                 140

Gly Glu Lys Leu Lys Asp Asp Lys Thr Met Leu Met Glu Arg Val Met
145                 150                 155                 160

Gln Leu Val Ala Arg Leu Pro Thr Glu Ser Lys Lys Arg Ala Glu Leu
                165                 170                 175

Thr Asp Ser Leu Ile Asn Glu Leu Trp Glu Ser Leu Asp His Pro Pro
            180                 185                 190

Leu Asn Tyr Leu Gly Pro Glu His Ser Tyr Arg Thr Pro Asp Gly Ser
        195                 200                 205

Tyr Asn His Pro Phe Asn Pro Gln Leu Gly Ala Ala Gly Ser Arg Tyr
    210                 215                 220

Ala Arg Ser Val Ile Pro Thr Val Thr Pro Pro Gly Ala Leu Pro Asp
225                 230                 235                 240

Pro Gly Leu Ile Phe Asp Ser Ile Met Gly Arg Thr Pro Asn Ser Tyr
                245                 250                 255

Arg Lys His Pro Asn Asn Val Ser Ser Ile Leu Trp Tyr Trp Ala Thr
            260                 265                 270

Ile Ile Ile His Asp Ile Phe Trp Thr Asp Pro Arg Asp Ile Asn Thr
        275                 280                 285

Asn Lys Ser Ser Ser Tyr Leu Asp Leu Ala Pro Leu Tyr Gly Asn Ser
    290                 295                 300

Gln Glu Met Gln Asp Ser Ile Arg Thr Phe Lys Asp Gly Arg Met Lys
305                 310                 315                 320

Pro Asp Cys Tyr Ala Asp Lys Arg Leu Ala Gly Met Pro Pro Gly Val
                325                 330                 335

Ser Val Leu Leu Ile Met Phe Asn Arg Phe His Asn His Val Ala Glu
            340                 345                 350

Asn Leu Ala Leu Ile Asn Glu Gly Gly Arg Phe Asn Lys Pro Ser Asp
        355                 360                 365

Leu Leu Glu Gly Glu Ala Arg Glu Ala Ala Trp Lys Lys Tyr Asp Asn
    370                 375                 380

Asp Leu Phe Gln Val Ala Arg Leu Val Thr Ser Gly Leu Tyr Ile Asn
385                 390                 395                 400

```
Ile Thr Leu Val Asp Tyr Val Arg Asn Ile Val Asn Leu Asn Arg Val
                405                 410                 415
Asp Thr Thr Trp Thr Leu Asp Pro Arg Gln Asp Ala Gly Ala His Val
            420                 425                 430
Gly Thr Ala Asp Gly Ala Glu Arg Gly Thr Gly Asn Ala Val Ser Ala
        435                 440                 445
Glu Phe Asn Leu Cys Tyr Arg Trp His Ser Cys Ile Ser Glu Lys Asp
    450                 455                 460
Ser Lys Phe Val Glu Ala Gln Phe Gln Asn Ile Phe Gly Lys Pro Ala
465                 470                 475                 480
Ser Glu Val Arg Pro Asp Glu Met Trp Lys Gly Phe Ala Lys Met Glu
                485                 490                 495
Gln Asn Thr Pro Ala Asp Pro Gly Gln Arg Thr Phe Gly Gly Phe Lys
            500                 505                 510
Arg Gly Pro Asp Gly Lys Phe Asp Asp Asp Leu Val Arg Cys Ile
        515                 520                 525
Ser Glu Ala Val Glu Asp Val Ala Gly Ala Phe Gly Ala Arg Asn Val
    530                 535                 540
Pro Gln Ala Met Lys Val Val Glu Thr Met Gly Ile Ile Gln Gly Arg
545                 550                 555                 560
Lys Trp Asn Val Ala Gly Leu Asn Glu Phe Arg Lys His Phe His Leu
                565                 570                 575
Lys Pro Tyr Ser Thr Phe Glu Asp Ile Asn Ser Asp Pro Gly Val Ala
            580                 585                 590
Glu Ala Leu Arg Arg Leu Tyr Asp His Pro Asp Asn Val Glu Leu Tyr
        595                 600                 605
Pro Gly Leu Val Ala Glu Glu Asp Lys Gln Pro Met Val Pro Gly Val
    610                 615                 620
Gly Ile Ala Pro Thr Tyr Thr Ile Ser Arg Val Val Leu Ser Asp Ala
625                 630                 635                 640
Val Cys Leu Val Arg Gly Asp Arg Phe Tyr Thr Thr Asp Phe Thr Pro
                645                 650                 655
Arg Asn Leu Thr Asn Trp Gly Tyr Lys Glu Val Asp Tyr Asp Leu Ser
            660                 665                 670
Val Asn His Gly Cys Val Phe Tyr Lys Leu Phe Ile Arg Ala Phe Pro
        675                 680                 685
Asn His Phe Lys Gln Asn Ser Val Tyr Ala His Tyr Pro Met Val Val
    690                 695                 700
Pro Ser Glu Asn Lys Arg Ile Leu Glu Ala Leu Gly Arg Ala Asp Leu
705                 710                 715                 720
Phe Asp Phe Glu Ala Pro Lys Tyr Ile Pro Pro Arg Val Asn Ile Thr
                725                 730                 735
Ser Tyr Gly Gly Ala Glu Tyr Ile Leu Glu Thr Gln Glu Lys Tyr Lys
            740                 745                 750
Val Thr Trp His Glu Gly Leu Gly Phe Leu Met Gly Glu Gly Gly Leu
        755                 760                 765
Lys Phe Met Leu Ser Gly Asp Asp Pro Leu His Ala Gln Gln Arg Lys
    770                 775                 780
Cys Met Ala Ala Gln Leu Tyr Lys Asp Gly Trp Thr Glu Ala Val Lys
785                 790                 795                 800
Ala Phe Tyr Ala Gly Met Met Glu Glu Leu Leu Val Ser Lys Ser Tyr
                805                 810                 815
```

```
Phe Leu Gly Asn Asn Lys His Arg His Val Asp Ile Ile Arg Asp Val
                820                 825                 830

Gly Asn Met Val His Val His Phe Ala Ser Gln Val Phe Gly Leu Pro
            835                 840                 845

Leu Lys Thr Ala Lys Asn Pro Thr Gly Val Phe Thr Glu Gln Glu Met
        850                 855                 860

Tyr Gly Ile Leu Ala Ala Ile Phe Thr Thr Ile Phe Phe Asp Leu Asp
865                 870                 875                 880

Pro Ser Lys Ser Phe Pro Leu Arg Thr Lys Thr Arg Glu Val Cys Gln
                885                 890                 895

Lys Leu Ala Lys Leu Val Glu Ala Asn Val Lys Leu Ile Asn Lys Ile
            900                 905                 910

Pro Trp Ser Arg Gly Met Phe Val Gly Lys Pro Ala Lys Asp Glu Pro
        915                 920                 925

Leu Ser Ile Tyr Gly Lys Thr Met Ile Lys Gly Leu Lys Ala His Gly
    930                 935                 940

Leu Ser Asp Tyr Asp Ile Ala Trp Ser His Val Val Pro Thr Ser Gly
945                 950                 955                 960

Ala Met Val Pro Asn Gln Ala Gln Val Phe Ala Gln Ala Val Asp Tyr
                965                 970                 975

Tyr Leu Ser Pro Ala Gly Met His Tyr Ile Pro Glu Ile His Met Val
            980                 985                 990

Ala Leu Gln Pro Ser Thr Pro Glu Thr Asp Ala Leu Leu Leu Gly Tyr
        995                 1000                1005

Ala Met Glu Gly Ile Arg Leu Ala Gly Thr Phe Gly Ser Tyr Arg
        1010                1015                1020

Glu Ala Ala Val Asp Asp Val Lys Glu Asp Asn Gly Arg Gln
        1025                1030                1035

Val Pro Val Lys Ala Gly Asp Arg Val Phe Ser Phe Val Asp
        1040                1045                1050

Ala Ala Arg Asp Pro Lys His Phe Pro Asp Pro Glu Val Val Asn
        1055                1060                1065

Pro Arg Arg Pro Ala Lys Lys Tyr Ile His Tyr Gly Val Gly Pro
        1070                1075                1080

His Ala Cys Leu Gly Arg Asp Ala Ser Gln Ile Ala Ile Thr Glu
        1085                1090                1095

Met Phe Arg Cys Leu Phe Arg Arg Asn Val Arg Arg Val Pro
        1100                1105                1110

Gly Pro Gln Gly Glu Leu Lys Lys Val Pro Arg Pro Gly Gly Phe
        1115                1120                1125

Tyr Val Tyr Met Arg Glu Asp Trp Gly Gly Leu Phe Pro Phe Pro
        1130                1135                1140

Val Thr Met Arg Val Met Trp Asp Asp Glu
        1145                1150

<210> SEQ ID NO 59
<211> LENGTH: 1161
<212> TYPE: PRT
<213> ORGANISM: Glomerella cingulate

<400> SEQUENCE: 59

Met Ala Phe Asn Thr Lys Phe Gln Ala Gly Glu Ser Tyr Gly Asp Glu
1               5                   10                  15

Arg Lys Gly Ser Asn Asn Phe Phe Ala Asp Pro Lys Lys Val Ala Met
            20                  25                  30
```

```
Asp Ile Ile Lys Asp Leu Gly Gly Ala His Gly Gln Leu Asn Leu Leu
         35                  40                  45

Glu Val Thr Ala Leu Val Gln Gln Leu Leu Gln Lys Gly Glu Pro Leu
 50                  55                  60

Asp Asp Lys Lys Gly Thr Thr Glu Ala Leu Ile Gly Ile Leu Thr Ser
 65              70                  75                  80

Leu Pro Ser Gly Ser Asn Thr Arg Val Gln Leu Thr Asn Lys Leu Ile
                 85                  90                  95

Asp Thr Leu Trp Gly Asn Leu Gln His Pro Pro Leu Ser Tyr Val Gly
             100                 105                 110

Gly Asp Val Lys Tyr Glu Val Val Lys Thr Lys Glu Gln Leu Ala Lys
             115                 120                 125

Glu Gln Ala Asp Leu Ala Ala Gln Gly Lys Ala Pro Gln Ser Pro Glu
         130                 135                 140

Glu Ser His Ile Thr Phe Lys Ala Pro Asp Phe Pro Asp Ile Thr Leu
145                 150                 155                 160

Arg Glu His Leu Pro Thr Pro Pro Asp Asn Tyr Lys Met Pro Asp Gly
                 165                 170                 175

Ser Tyr Asn Asn Ile Leu Glu Pro Asn Leu Gly Ala Ala Gly Thr Pro
             180                 185                 190

Tyr Ala Lys Thr Val Lys Thr Glu Lys Arg Leu Ala Gly Val Lys Pro
         195                 200                 205

Asp Pro Gly Leu Leu Phe Asp Leu Leu Leu Ala Arg Asp Asp Lys Lys
210                 215                 220

Phe Thr Glu Asn Pro Ala Gly Ile Ser Ser Met Leu Phe Tyr His Ala
225                 230                 235                 240

Ser Ile Ile Ile His Asp Ile Phe Arg Thr Asn Arg His Asp Leu Asn
                 245                 250                 255

Lys Ser Asp Thr Ser Ser Tyr Leu Asp Leu Ala Pro Leu Tyr Gly Ser
             260                 265                 270

Ser Phe Lys Asp Gln Leu Glu Ile Arg Thr Met Lys Glu Gly Lys Leu
         275                 280                 285

Lys Pro Asp Thr Phe His Glu Lys Arg Leu Leu Gly Gln Pro Ala Gly
         290                 295                 300

Val Asn Val Met Leu Val Leu Ser Ser Arg Phe His Asn Tyr Val Ala
305                 310                 315                 320

Asp Ile Leu Leu Lys Ile Asn Glu Asn Gly Arg Phe Thr Leu Gln Thr
                 325                 330                 335

Ala Lys Asp Ala Ala Pro Glu Asp Gln Ala Lys Ala Val Ala Lys Gln
             340                 345                 350

Asp His Asp Leu Phe Asn Val Ala Arg Leu Val Thr Gly Gly Leu Tyr
         355                 360                 365

Ile Asn Ile Cys Leu His Asp Tyr Leu Arg Ala Ile Thr Asn Thr His
         370                 375                 380

His Ser Lys Ser Asp Trp Thr Leu Asp Pro Arg Val Glu Ile Gly Lys
385                 390                 395                 400

Gln Phe Asp Gly Glu Gly Val Pro Arg Gly Val Gly Asn Gln Val Ser
                 405                 410                 415

Val Glu Phe Asn Leu Leu Tyr Arg Phe His Ser Cys Ile Ser Lys Lys
             420                 425                 430

Asp Glu Arg Trp Ile Asp Gly Phe Phe Ala Lys Leu Phe Pro Gly Arg
         435                 440                 445
```

```
Lys Pro Glu Asp Leu Gln Asn Val Gly Met Glu Leu Gly Ala Ala
450                 455                 460

Leu Met Lys Phe Glu Met Gly Ile Asp Lys Asp Pro Ser Lys Arg Thr
465                 470                 475                 480

Phe Asp Asp Leu Gln Arg Gly Glu Asp Gly Lys Phe Arg Asp Glu Asp
                485                 490                 495

Leu Val Arg Val Leu Lys Glu Ala Met Glu Asp Pro Ala Gly Thr Phe
                500                 505                 510

Gly Ala Arg Met Val Pro Lys Ala Leu Lys Ile Val Glu Ile Met Gly
                515                 520                 525

Ile Lys Gln Ala Arg Ala Trp Gln Val Ala Ser Leu Asn Glu Phe Arg
530                 535                 540

Asp Phe Phe Gly Leu Lys Arg His Asp Thr Phe Lys Asp Ile Asn Ser
545                 550                 555                 560

Asn Glu Glu Ile Ala Thr Leu Leu Glu Lys Leu Tyr Thr Asp Pro Asp
                565                 570                 575

Met Val Glu Leu Tyr Pro Gly Leu Met Ile Glu Asp Ile Lys Pro Val
                580                 585                 590

Arg Asn Thr Gly Ser Gly Ile Cys Pro Thr Tyr Ser Val Gly Arg Ala
                595                 600                 605

Val Leu Ser Asp Ala Val Thr Leu Val Arg Ser Asp Arg Phe Asn Thr
                610                 615                 620

Ile Asp Tyr Thr Val Ser Asn Leu Thr Ala Trp Gly Tyr Asn Glu Val
625                 630                 635                 640

Gln Gln Asp Tyr Lys Thr Leu Gly Gly Ser Met Leu Tyr Lys Leu Ile
                645                 650                 655

Gln Arg Gly Leu Pro Gly Trp Phe Pro Phe Asn Ser Ile Ala Val Met
                660                 665                 670

Gln Pro Met Tyr Thr Lys Lys Ala Asn Glu Arg Ile Ala Arg Glu Ile
                675                 680                 685

Gly Thr Phe Asn Gln Phe Thr Leu Asp Asp Pro Lys Ala Pro Pro Lys
                690                 695                 700

Pro Val Val Val Ala Ser Ser Glu Gly Ile Lys Arg Val Leu Gly Ser
705                 710                 715                 720

Pro Asp Lys Phe Val Val Pro Trp Leu Thr Pro Leu Asn Ala Leu Tyr
                725                 730                 735

Thr Asp Thr Lys Lys Asp Ile Ser Trp Phe Met Leu Ala Gly Asp Gly
                740                 745                 750

Ser Thr Asn Lys Gln Glu Lys Val Asn Phe Val Asn Ala Met Lys Lys
                755                 760                 765

Val Pro Asn Leu His Asn Ala Val His Gln Phe Ile Glu Arg Val Gly
                770                 775                 780

Arg Gln Leu Ile Glu Lys Glu Thr Phe Lys Leu Lys Glu Gly Leu Cys
785                 790                 795                 800

Gln Met Asp Ile Ile Arg Asp Val Ala Ile Pro Leu Asn Ala Gln Leu
                805                 810                 815

Leu Ala Asp Leu Phe Tyr Phe Asp Leu Arg His Glu Glu Asn Pro Gly
                820                 825                 830

Gly Thr Leu Ser Ala Thr Asp Leu Tyr Arg His Leu Leu Asn Ile Arg
                835                 840                 845

Ile Trp Gly Val Asn Asn Asn Asp Pro Gly Gln Ala Trp Asn Arg Arg
850                 855                 860

Arg Arg Ala Ala Glu Ser Ala Lys Val Ile Thr Asp Ser Thr Arg Lys
```

```
                865                 870                 875                 880
Leu Val Asp Glu Val Ser Arg Gly Arg Gly Leu Asn Leu Gly Phe Ile
                    885                 890                 895

Ser Ala Ile Asn Glu Val Ala Ser Arg Lys Thr His Ile Lys Lys Asp
            900                 905                 910

Ser Leu Arg Ser Cys Gly Tyr Lys Leu Val Glu Leu Leu Asn Gln
            915                 920                 925

Gly Gly Ser Pro Glu Lys Val Thr Asp Asn Val Trp Leu Thr Ala Phe
        930                 935                 940

Gly Gly Ile Gly Val Pro Val Thr Thr Phe Tyr Glu Val Met Glu Tyr
945                 950                 955                 960

Phe Leu Arg Pro Glu Asn Lys Ser Ile Trp Gly Val Gln Ala Leu
                965                 970                 975

Ala Gln Lys Asn Asp Glu Ala Gly Leu His Ala Tyr Val Asn Glu Ala
                980                 985                 990

Met Arg Leu Thr Ser Gly Gln Arg Asn Val Arg Ile Ala Thr Val Lys
                995                 1000                1005

Asp Glu Ile Asp Gly Gln Lys Val Glu Pro Gly Asn Ala Val Val
        1010                1015                1020

Met Leu Leu Gly Ala Ala Gly Arg Asn Pro Lys Glu Val Pro Asn
        1025                1030                1035

Ala Asp Lys Phe Asp Ala Lys Arg Ser Thr Asp His Ile Lys Pro
        1040                1045                1050

Phe Ser Tyr Gly Gln His Glu Cys Val Gly Gln Asp Val Ala Arg
        1055                1060                1065

Ala Phe Val Thr Gly Leu Val Lys Leu Val Ala Asp Leu Arg Gln
        1070                1075                1080

Leu Arg Pro Ala Pro Gly Glu Met Gly Lys Val Lys Thr Ile Gln
        1085                1090                1095

Val Gly Thr Glu Arg Ala Tyr Leu Asn Asp Ser Trp Ser Tyr Leu
        1100                1105                1110

Gly Phe Asp Ala Ser Thr Trp Lys Val His Phe Asp Gly His Gly
        1115                1120                1125

Gln Gly Thr Tyr Glu Gly Asp Pro Glu Pro Asn Lys Pro Ile Asp
        1130                1135                1140

Met Gly Arg Tyr Tyr Tyr Ile Leu Gln Lys Arg Lys Glu Ser Leu
        1145                1150                1155

Leu Lys Gly
        1160

<210> SEQ ID NO 60
<211> LENGTH: 1283
<212> TYPE: PRT
<213> ORGANISM: Fusarium oxysporum

<400> SEQUENCE: 60

Met Ala Glu His Lys Asn Gly Val Ala Thr Asn Gly Tyr Glu Lys Lys
1               5                   10                  15

Ser Ser Pro Ala Ser Ser Ser Thr Lys Ser Glu Ala Lys Pro Leu Pro
            20                  25                  30

Asn Gly Asp Lys Lys Asp Gly Ile Val Lys Ser Phe Lys Gln Leu Arg
        35                  40                  45

Val Ala Ser Lys Arg Pro Leu Pro Lys Glu Met Gly Asp Gly Ser Tyr
    50                  55                  60
```

```
Arg Val Val Glu Asn Arg Pro Gly Leu Lys Gln Asp Ile Arg Arg Leu
 65                  70                  75                  80

Arg Gly Arg Asp Leu Lys Thr Leu Leu Glu Ile Val Lys Ala Lys Val
                 85                  90                  95

Lys Gly Glu Thr Gln Gln Asp Asp Lys Thr Met Ile Met Glu Arg Thr
                100                 105                 110

Ile Gln Leu Val Ala Asn Leu Ser Asp His Ser Lys Val Gln Glu Ser
                115                 120                 125

Leu Thr Asn Ser Phe Ile Ser Gln Leu Trp Asn Ser Ile Asp His Pro
            130                 135                 140

Pro Met Leu Tyr Met Gly Asp Lys Phe Arg Phe Arg Gln Pro Asp Gly
145                 150                 155                 160

Ser Asn Asn Asn Pro Tyr Leu Pro Gln Leu Gly Ala Ala Arg Thr Pro
                165                 170                 175

Tyr Ser Arg Thr Val Arg Pro Lys Gly Met Ser Leu Gly Ala Gln Pro
                180                 185                 190

Asp Pro Glu Ala Ile Phe Glu Ser Val Phe Ala Arg Asp Ala Phe Arg
            195                 200                 205

Lys Asn Pro Asn Val Ser Ser Ile Leu Trp Tyr Trp Ala Thr Ile
210                 215                 220

Ile Ile His Asp Leu Phe Trp Thr Asn Leu Gln Asp Pro Asn Gln Asn
225                 230                 235                 240

Asp Ser Ser Ser Tyr Leu Asp Leu Ala Pro Leu Tyr Gly Ser Thr Glu
                245                 250                 255

Lys Asp Arg Asp Ser Ile Arg Thr Phe Lys Asp Gly Gln Leu Lys Pro
                260                 265                 270

Asp Cys Phe Ala Asp Lys Arg Leu Ile Gly Asn Pro Pro Gly Val Pro
            275                 280                 285

Ile Leu Leu Ile Met Phe Asn Arg Phe His Asn His Val Ala Thr Asn
            290                 295                 300

Leu Ala Asp Ile Asn Glu Gly Gly Arg Phe Ser Lys Pro Ala Glu His
305                 310                 315                 320

Leu Ser Pro Glu Ala Ala Asp Ala Ala Trp Lys Lys Arg Asp Thr Glu
                325                 330                 335

Leu Phe Glu Thr Ala Arg Leu Val Thr Ser Gly Leu Tyr Ile Asn Ile
                340                 345                 350

Thr Leu Ile Asp Tyr Val Arg Asn Ile Ile Asn Leu Asn Arg Val Asp
            355                 360                 365

Thr Thr Trp Thr Leu Asp Pro Arg Gln Glu Met Gly Val Ser Val Gly
            370                 375                 380

Thr Lys Asp Leu Ser Glu Ser Gly Thr Gly Asn Val Val Ser Ala Glu
385                 390                 395                 400

Phe Asn Leu Cys Tyr Arg Trp His Ser Cys Leu Ser Glu Met Asp Asp
                405                 410                 415

Lys Trp Val Gln Asp Phe Tyr Thr Glu Leu Leu Gly Glu Asn Tyr Gly
                420                 425                 430

Pro Met Asn Leu Gln Thr Met Met Lys Ala Leu Lys Ala Phe Glu Ala
            435                 440                 445

Ser Val Ala Asp Glu Pro Ser Glu Arg Thr Phe Gly Gly Phe Lys Arg
            450                 455                 460

Gly Pro Asp Gly Lys Phe Asn Asp Asp Glu Leu Val Glu Ala Leu Ala
465                 470                 475                 480

Thr Ala Ile Glu Gln Pro Gly Gly Ala Phe Gly Gly Arg Asn Val Pro
```

```
            485                 490                 495
Arg Ile Met Lys Pro Ile Glu Met Leu Gly Ile Met Arg Gly Arg Lys
            500                 505                 510

Trp Asn Leu Ala Gly Leu Asn Glu Phe Arg Lys His Phe Gly Leu Lys
            515                 520                 525

Ala Tyr Glu Thr Phe Glu Asp Ile Asn Ser Asp Pro Ser Val Ala Asp
            530                 535                 540

Ala Leu Arg Asn Leu Tyr Gln His Pro Asp Tyr Val Glu Leu Tyr Pro
545                 550                 555                 560

Gly Ile Val Ala Glu Glu Ala Lys Thr Pro Met Val Pro Gly Val Gly
                    565                 570                 575

Ile Ala Pro Thr Tyr Thr Ile Ser Arg Val Val Leu Ser Asp Ala Val
                580                 585                 590

Ala Leu Val Arg Gly Asp Arg Tyr Tyr Thr Thr Asp Tyr Asn Pro Arg
                595                 600                 605

His Leu Thr Asn Trp Gly Tyr Lys Glu Val Asp Tyr Asp Leu Lys Val
                610                 615                 620

Asn His Gly Cys Val Phe Tyr Lys Leu Phe Leu Arg Ala Phe Pro Gln
625                 630                 635                 640

His Phe Lys Gly Asn Ser Val Tyr Ala His Tyr Pro Met Val Ile Pro
                645                 650                 655

Ser Glu Asn Lys Lys Ile Leu Thr Asn Ile Lys Arg Ala Asp Arg Phe
                660                 665                 670

Asp Phe Ser Arg Pro Glu Pro Thr Ala Thr Arg Ile Asn Ile Ile Gly
                675                 680                 685

Tyr Asn Ala Ala Lys Tyr Ile Leu Glu Asp Gln Gln Lys Tyr Arg Val
690                 695                 700

Cys Trp Glu Glu Gly Leu Lys His Leu Met Gly Glu Ala Gly Gly Arg
705                 710                 715                 720

Phe Met Leu Ser Gly Asp Thr Ala Leu His Ala Gln Gln Arg Lys Cys
                725                 730                 735

Met Gly Lys Leu Leu Tyr Asn Asp Thr Trp Arg Asn Ala Val Lys Ser
                740                 745                 750

Phe Tyr Ala Thr Thr Ala Glu Lys Leu Leu Ala Glu Lys Ser Tyr Arg
                755                 760                 765

Leu Ala Gly Lys Met Gln Val Asp Val Val Arg Asp Val Gly Asn Val
                770                 775                 780

Ala His Thr His Phe Val Ala Arg Met Phe Asn Leu Pro Leu Lys Thr
785                 790                 795                 800

Ser Glu Asn Pro Lys Gly Val Phe Ser Glu Gln Glu Leu Tyr Met Ile
                805                 810                 815

Leu Ala Val Ile Phe Val Cys Ile Phe Phe Asp Ile Asp Pro Ala Lys
                820                 825                 830

Ser Phe Pro Leu Arg Gln Gly Ala Arg Glu Val Ala Gln Lys Leu Gly
                835                 840                 845

Gly Ile Ile Glu Met Asn Val Lys Leu Ala Asn Ser Ile Gly Val Lys
                850                 855                 860

Gly Leu Phe Thr Ser Lys Pro Asp Lys Asn Asp Asp Pro Leu Ala Arg
865                 870                 875                 880

Tyr Gly Glu Asn Met Ala Lys Gly Leu Lys Lys Ala Gly Leu Ser Thr
                885                 890                 895

Glu Asp Ile Val Trp Ser Gln Ile Leu Pro Thr Ala Gly Ala Met Val
                900                 905                 910
```

```
Pro Asn Gln Ala Gln Val Phe Ala Gln Thr Leu Asp Trp Tyr Leu Ser
    915                 920                 925

Pro Ala Gly Glu Lys Tyr Arg Pro Glu Leu Ala Arg Ile Ala Ala Leu
930                 935                 940

Glu Thr Gly Asp Glu Thr Asp Ala Leu Leu Gly Tyr Ala Met Glu
945                 950                 955                 960

Gly Ile Arg Met Ala Gly Thr Phe Gly Leu Tyr Arg Glu Ala Thr Gly
                965                 970                 975

Pro Asp Thr Ile His Glu Asp Gly Arg Ser Ile Pro Val Asn Ala
                980                 985                 990

Gly Asp Arg Val Phe Val Ser Phe Val Gln Ala Ala Gln Asp Pro Lys
            995                 1000                1005

Ile Phe Pro Asn Pro Gly Val Val Asp Pro Lys Arg Pro Leu Asp
    1010                1015                1020

Lys Tyr Ile His Tyr Gly Val Gly Pro His Ala Cys Leu Gly Arg
    1025                1030                1035

Asp Ile Ser Gln Val Ala Leu Thr Glu Leu Phe Arg Ala Val Phe
    1040                1045                1050

Arg Lys Lys Gly Val Arg Arg Val Pro Gly Ala Gln Gly Glu Leu
    1055                1060                1065

Lys Lys Val Pro Arg Pro Gly Gly Phe Phe Val Tyr Met Thr Glu
    1070                1075                1080

Asp Trp Gly Ser Ile Trp Pro Phe Pro Thr Ser Met Lys Ile Thr
    1085                1090                1095

Trp Asp Asp Gly Cys Gly Thr Asp Leu Phe Thr Leu Leu Phe Trp
    1100                1105                1110

Cys Arg Ser Val Pro Trp Trp Asp Leu Leu Pro Glu Thr Thr Gln
    1115                1120                1125

Ala Ala Pro Phe Ile Ile Ser Ser Phe Gln Ser Gln Gln Ile Tyr
    1130                1135                1140

Ser Pro Ala Glu Ile Ala Ala Val Leu Ala Leu Met Ala Phe Glu
    1145                1150                1155

Ser Gly Asp Phe Gln Tyr Lys Arg Asn His Tyr Pro Gly Arg Pro
    1160                1165                1170

Gly Gln Gly Thr Ala Asn Met Gln Met Pro Asn Tyr Asn Leu Leu
    1175                1180                1185

Tyr Ala Lys Ser Ile Pro Glu Leu Ala Lys Gly Trp Gln Gly Ile
    1190                1195                1200

Glu Ser Val Glu Gly Leu Ser Asp Gln Glu Leu Gly Asp Leu Leu
    1205                1210                1215

Asp Asp Val Thr Val Asp Lys Tyr Asn Phe Gly Ser Gly Pro Trp
    1220                1225                1230

Phe Leu Lys Thr Gln Cys Lys Glu Asp Val Arg Gln Ala Phe Lys
    1235                1240                1245

Thr Asp Val Asp Thr Gly Phe Gln Lys Tyr Ile Glu Glu Cys Val
    1250                1255                1260

Gly Thr Asp Leu Gln Pro Arg Leu Glu Tyr Phe Gln Arg Ala Lys
    1265                1270                1275

Thr Ala Phe Gly Leu
    1280

<210> SEQ ID NO 61
<211> LENGTH: 1079
```

<212> TYPE: PRT
<213> ORGANISM: Aspergillus fumigatus

<400> SEQUENCE: 61

```
Met Ser Glu Lys Gln Thr Gly Ser Ala Asn Gly Gly Leu Gly Lys Thr
1               5                   10                  15

Leu Ala Gln Leu Glu Gln Val Val Ala Ser Leu Arg Pro Leu Pro
            20                  25                  30

Ser Gln Thr Gly Asp Gly Thr Tyr Val Thr Glu Gln Val Lys Thr Gly
            35                  40                  45

Ile Leu Lys Asp Leu Ser His Val Asp Leu Gly Asp Leu Lys Thr Leu
50                  55                  60

Val Asp Val Ser Lys Ser Ala Leu Thr Gly Glu Ala Leu Asp Asp Arg
65                  70                  75                  80

Lys Tyr Ile Met Glu Arg Val Ile Gln Leu Ser Ala Gly Leu Pro Ser
                85                  90                  95

Thr Ser Gln Ile Gly Lys Glu Leu Thr Asn Thr Phe Leu Thr Thr Leu
            100                 105                 110

Trp Asn Asp Leu Glu His Pro Pro Ile Ser Tyr Leu Gly Arg Asp Ala
            115                 120                 125

Met Tyr Arg Arg Ala Asp Gly Ser Gly Asn Asn Val Leu Trp Pro His
130                 135                 140

Ile Gly Ala Ala Gly Thr Pro Tyr Ala Arg Ser Val Gln Pro Lys Thr
145                 150                 155                 160

Val Gln Ser Pro Asn Leu Pro Asp Pro Glu Thr Leu Phe Asp Cys Leu
                165                 170                 175

Leu Ala Arg Lys Glu Tyr Lys Glu His Pro Asn Lys Ile Ser Ser Val
            180                 185                 190

Leu Phe Tyr Ile Ala Ser Ile Ile His Asp Leu Phe Glu Thr Asp
            195                 200                 205

Arg Lys Asp Pro Ala Ile Ser Leu Thr Ser Ser Tyr Leu Asp Leu Ser
210                 215                 220

Pro Leu Tyr Gly Asn Asn Gln Gln Glu Gln Asp Leu Ile Arg Thr Phe
225                 230                 235                 240

Lys Asp Gly Lys Leu Lys Pro Asp Cys Phe Ser Thr Lys Arg Val Leu
                245                 250                 255

Gly Phe Pro Pro Gly Val Gly Val Val Leu Ile Met Phe Asn Arg Phe
            260                 265                 270

His Asn Tyr Val Val Glu Lys Leu Ala Met Ile Asn Glu Gly Gly Arg
            275                 280                 285

Phe Thr Lys Pro Gln Glu Ser Asp Thr Ala Ala Tyr Ala Lys Tyr Asp
290                 295                 300

Asn Asp Leu Phe Gln Thr Gly Arg Leu Val Thr Cys Gly Leu Tyr Val
305                 310                 315                 320

Asn Ile Ile Leu Lys Asp Tyr Val Arg Thr Ile Leu Asn Ile Asn Arg
                325                 330                 335

Thr Asp Ser Ile Trp Ser Leu Asp Pro Arg Ser Glu Met Lys Asp Gly
            340                 345                 350

Leu Leu Gly Arg Ala Ala Gln Ala Thr Gly Asn Gln Val Ala Ala
            355                 360                 365

Glu Phe Asn Leu Val Tyr Arg Trp His Ser Cys Ile Ser Gln Arg Asp
370                 375                 380

Gln Lys Trp Thr Glu Asp Met Tyr Gln Glu Leu Phe Pro Gly Gln Asp
385                 390                 395                 400
```

```
Pro Ser Lys Ile Ser Leu Gln Asp Phe Leu Arg Gly Leu Gly Arg Trp
            405                 410                 415
Glu Ala Lys Leu Pro Gly Pro Arg Glu Arg Pro Phe Ala Gly Leu
        420                 425                 430
Gln Arg Lys Ala Asp Gly Ser Tyr Asp Asp Asn Asp Leu Val Lys Ile
            435                 440                 445
Phe Glu Glu Ser Val Glu Asp Cys Ala Gly Ala Phe Gly Ala Leu His
    450                 455                 460
Val Pro Thr Val Phe Arg Ser Ile Glu Ala Leu Gly Ile Gln Gln Ala
465                 470                 475                 480
Arg Ser Trp Asn Leu Ala Thr Leu Asn Glu Phe Arg Lys Tyr Phe Asn
                485                 490                 495
Leu Ala Pro Tyr Lys Thr Phe Glu Glu Ile Asn Ser Asp Pro Tyr Val
            500                 505                 510
Ala Asp Gln Leu Lys Arg Leu Tyr Asp His Pro Asp Arg Val Glu Ile
            515                 520                 525
Tyr Pro Gly Ile Ile Val Glu Asp Ala Lys Glu Ser Met Ala Pro Gly
    530                 535                 540
Ser Gly Leu Cys Thr Asn Phe Thr Ile Ser Arg Ala Ile Leu Ser Asp
545                 550                 555                 560
Ala Val Ala Leu Val Arg Gly Asp Arg Phe His Thr Val Asp Phe Thr
                565                 570                 575
Pro Lys His Leu Thr Asn Trp Ala Tyr Asn Glu Ile Gln Pro Gln Asp
            580                 585                 590
Ser Val Asp Gln Thr His Val Phe Tyr Lys Leu Val Leu Arg Ala Phe
            595                 600                 605
Pro Asn His Phe Arg Gly Asp Ser Ile Tyr Ala His Phe Pro Leu Val
    610                 615                 620
Val Pro Ser Glu Asn Lys Lys Ile Leu Thr Lys Leu Gly Thr Ala Asp
625                 630                 635                 640
Lys Tyr Ser Trp Asp Arg Pro Asn Tyr Thr Pro Pro Gln Phe Ile
                645                 650                 655
Asn Ser His Ser Ala Cys Met Ser Ile Leu Ser Asp Gln Glu Thr Phe
            660                 665                 670
Lys Val Thr Trp Gly Ser Lys Ile Glu Phe Leu Met Arg His Asn Asn
            675                 680                 685
Gln Pro Tyr Gly Arg Asp Phe Met Leu Ser Gly Asp Arg Thr Pro Asn
    690                 695                 700
Ala Met Ser Arg Gln Met Met Gly Lys Ala Leu Tyr Arg Asp Lys Trp
705                 710                 715                 720
Glu Thr Glu Val Lys Arg Phe Tyr Glu Asn Ile Thr Leu Lys Leu Leu
                725                 730                 735
His Arg Tyr Ser Tyr Lys Leu Ala Gly Val Asn Gln Val Asp Val Val
            740                 745                 750
Arg Asp Ile Ala Asn Leu Ala Gln Val His Phe Cys Ala Ser Val Phe
            755                 760                 765
Ser Leu Pro Leu Lys Thr Glu Ser Asn Pro Arg Gly Ile Phe Thr Glu
    770                 775                 780
Ser Glu Leu Tyr Gln Ile Met Ala Val Val Phe Thr Ser Ile Phe Tyr
785                 790                 795                 800
Asp Ala Asp Ile Gly Lys Ser Phe Glu Leu Asn Gln Ala Ala Arg Ala
                805                 810                 815
```

```
Val Thr Gln Gln Leu Gly Gln Leu Thr Leu Ala Asn Val Glu Leu Ile
                820                 825                 830

Ala Lys Thr Gly Phe Ile Ala Asn Leu Val Asn Ser Leu His Arg His
            835                 840                 845

Asp Val Leu Ser Glu Tyr Gly Val His Met Ile Gln Arg Leu Leu Asp
        850                 855                 860

Ser Gly Met Pro Ala Pro Glu Ile Val Trp Thr His Val Leu Pro Thr
865                 870                 875                 880

Ala Gly Gly Met Val Ala Asn Gln Ala Gln Leu Phe Ser Gln Ser Leu
                885                 890                 895

Asp Tyr Tyr Leu Ser Glu Glu Gly Ser Val His Leu Pro Glu Ile Asn
        900                 905                 910

Arg Leu Ala Lys Glu Asp Thr Thr Glu Ala Asp Asp Leu Leu Leu Arg
        915                 920                 925

Tyr Phe Met Glu Gly Ala Arg Ile Arg Ser Ser Val Ala Leu Pro Arg
        930                 935                 940

Val Val Ala Gln Pro Thr Val Glu Asp Asn Gly Gln Lys Ile Thr
945                 950                 955                 960

Leu Lys Gln Gly Gln His Ile Ile Cys Asn Leu Val Ser Ala Ser Met
                965                 970                 975

Asp Pro Val Thr Phe Pro Glu Pro Asp Lys Val Lys Leu Asp Arg Asp
            980                 985                 990

Met Asn Leu Tyr Ala His Phe Gly Phe Gly Pro His Gln Cys Leu Gly
                995                1000                1005

Leu Gly Leu Cys Lys Thr Ala Leu Thr Thr Met Leu Lys Val Ile
   1010                1015                1020

Gly Arg Leu Asp Asn Leu Arg Arg Ala Pro Gly Gly Gln Gly Lys
   1025                1030                1035

Leu Lys Lys Leu Ser Gly Pro Gly Gly Ile Ala Met Tyr Met Thr
   1040                1045                1050

Pro Asp Gln Thr Ala Phe Phe Pro Phe Pro Thr Thr Met Lys Ile
   1055                1060                1065

Gln Trp Asp Gly Asp Leu Pro Glu Val Lys Glu
   1070                1075

<210> SEQ ID NO 62
<211> LENGTH: 1071
<212> TYPE: PRT
<213> ORGANISM: Aspergillus terreus

<400> SEQUENCE: 62

Met Gln Gly Ile Gly Lys Ala Ile Ser Gln Leu Glu Lys Val Ala Thr
1               5                   10                  15

Ala Ser Leu Arg Pro Leu Pro Thr Glu Thr Gly Asp Gly Ser Tyr Val
            20                  25                  30

Ala Glu Ser Thr Ala Thr Gly Leu Val Gln Asp Leu Pro His Val Asp
        35                  40                  45

Leu Gly Asp Leu Lys Thr Leu Leu Asp Val Thr Lys Asn Ala Ala Thr
    50                  55                  60

Gly Glu Pro Ile Asp Asp Lys Gly Tyr Val Met Glu Arg Leu Ile Gln
65                  70                  75                  80

Leu Ala Ser Gly Leu Pro Ser Thr Ser Arg Asn Ala Lys Gln Leu Thr
                85                  90                  95

Ser Ala Phe Leu Asn Gln Leu Trp Asn Asp Leu Asp His Pro Pro Val
            100                 105                 110
```

-continued

```
Ser Thr Val Gly Gly Glu Tyr Ser His Arg Ser Ala Asp Gly Ser Gly
        115                 120                 125

Asn Asn Ile Leu Trp Pro Gly Ile Gly Ala Ala Gly Ser His Tyr Ala
130                 135                 140

Arg Ser Val Gln Pro Lys Thr Met Gln Ser Pro Ser Leu Pro Asp Pro
145                 150                 155                 160

Glu Ala Leu Phe Asp Ser Leu Leu Ala Arg Lys Asp Phe Lys Glu His
                165                 170                 175

Pro Asn Lys Ile Ser Ser Val Leu Phe Tyr Ile Ala Ser Ile Ile Ile
                180                 185                 190

His Asp Leu Phe Gln Thr Asp His Arg Asp Ser Ser Ile Asn Arg Thr
            195                 200                 205

Ser Ser Tyr Leu Asp Leu Ser Pro Leu Tyr Gly Asn Asn Gln Asp Glu
        210                 215                 220

Gln Tyr Leu Met Arg Thr Phe Lys Asp Gly Lys Leu Lys Pro Asp Cys
225                 230                 235                 240

Phe Ser Ser Lys Arg Ile Leu Gly Phe Pro Pro Gly Val Gly Val Leu
                245                 250                 255

Leu Ile Met Phe Asn Arg Phe His Asn Tyr Val Val Glu Gln Leu Ala
                260                 265                 270

Ala Val Asn Glu Gly Gly Arg Phe Thr Lys Pro Ser Glu Ser Asn Asp
            275                 280                 285

Lys Glu Tyr Ala Lys Tyr Asp Asn Asn Leu Phe Gln Thr Gly Arg Leu
        290                 295                 300

Val Thr Cys Gly Leu Tyr Ile Asn Ile Ile Leu Lys Asp Tyr Val Arg
305                 310                 315                 320

Thr Ile Leu Asn Ile Asn Arg Thr Asn Ser Thr Trp Ser Leu Asp Pro
                325                 330                 335

Arg Met Asp Met Lys Asp Gly Leu Leu Gly Asp Ala Ala Pro Leu Ala
            340                 345                 350

Thr Gly Asn Gln Val Ser Ala Glu Phe Asn Leu Ile Tyr Arg Trp His
        355                 360                 365

Ser Cys Ile Ser Gln Arg Asp Glu Lys Trp Thr Thr Asp Leu Tyr Asn
        370                 375                 380

Asp Ile Phe Ser Asp Lys Gly Gln Glu Asp Ile Pro Leu Asn Glu Phe
385                 390                 395                 400

Met Met Gly Val Gly Lys Trp Glu Ala Gly Leu Pro Gln Gln Pro Ala
                405                 410                 415

Glu Arg Pro Phe Ala Gly Leu Lys Arg Lys Pro Asn Gly Leu Phe Asp
            420                 425                 430

Asp Asp Asp Leu Val Thr Ile Phe Lys Glu Ser Val Gly Asp Cys Ala
        435                 440                 445

Gly Ala Phe Gly Ala Ser His Val Pro Thr Ile Phe Lys Ser Ile Glu
        450                 455                 460

Ser Leu Gly Ile Lys Gln Ala Arg Ala Trp Asn Leu Ala Thr Leu Asn
465                 470                 475                 480

Glu Leu Arg Gln Tyr Phe Gly Leu Thr Pro His Lys Thr Phe Glu Asp
                485                 490                 495

Ile Asn Ser Asp Pro Tyr Ile Ser Glu Gln Leu Arg Arg Leu Tyr Asp
            500                 505                 510

His Pro Asp Gln Val Glu Ile Tyr Pro Gly Val Ile Val Glu Glu Thr
        515                 520                 525
```

```
Lys Glu Ser Met Leu Pro Gly Ser Gly Leu Cys Thr Asn Phe Thr Ile
    530                 535                 540

Ser Arg Ala Ile Leu Ser Asp Ala Val Ala Leu Val Arg Gly Asp Arg
545                 550                 555                 560

Phe Tyr Thr Val Asp Tyr Thr Pro Lys Gln Leu Thr Asn Trp Ala Phe
                565                 570                 575

Thr Glu Ile Gln Pro Lys Asp Ser Val Asp Gln Gly His Met Phe His
            580                 585                 590

Lys Leu Val Tyr Arg Ala Phe Pro Asn Tyr Phe Lys Gly Asn Ser Val
        595                 600                 605

Tyr Ala His Phe Pro Met Val Val Pro Ser Glu Asn Gln Lys Ile Leu
    610                 615                 620

Thr Ala Leu Gly Ser Ala Glu Lys Tyr Ser Trp Asp Lys Pro Gly Phe
625                 630                 635                 640

Ile His Pro Pro Gln Phe Ile Asn Ser His Ser Thr Cys Val Ser Ile
                645                 650                 655

Leu Ala Asp Gln Glu Thr Phe Lys Val Ser Trp Gly Asp Lys Ile Glu
            660                 665                 670

Phe Leu Met Ser Asn His Asp Lys Ile Tyr Gly Lys Asp Phe Met Leu
        675                 680                 685

Ser Gly Asp Arg Leu Pro Asn Ala Glu Ser Arg Lys Met Met Gly Ala
    690                 695                 700

Ala Leu Tyr Thr Asp Gln Trp Glu Glu Val Lys Lys Phe Tyr Glu
705                 710                 715                 720

Lys Ile Thr Leu Lys Leu Leu Lys Lys His Ser Tyr Lys Ile Ala Gly
                725                 730                 735

Val Asn Gln Val Asp Ile Val Arg Asp Val Ala Asn Leu Ala Gln Val
            740                 745                 750

Asn Phe Cys Ala Asn Val Phe Ser Leu Pro Leu Lys Thr Glu Ala Ser
        755                 760                 765

Pro Arg Gly Ile Phe Thr Glu Ser Glu Leu Tyr Met Ile Met Ala Ala
    770                 775                 780

Val Phe Ala Ala Ile Phe Tyr Asp Ala Asp Pro Ala Asn Ser Phe Ala
785                 790                 795                 800

Leu Asn Gln Ala Ala Arg Glu Val Thr Gln Gln Leu Gly Gln Val Thr
                805                 810                 815

Met Ala Asn Val Glu Leu Ile His Lys Thr Gly Phe Ile Ser Asn Leu
            820                 825                 830

Val Asn Gly Leu Gln Arg His Asp Val Leu Ser Asn Tyr Gly Ile His
        835                 840                 845

Met Ile Gln Arg Leu Leu Ala Ser Gly Leu Pro Ala Ser Glu Ile Val
    850                 855                 860

Trp Thr His Leu Leu Pro Thr Ala Gly Gly Met Val Ala Asn Gln Gly
865                 870                 875                 880

Gln Leu Phe Ser Gln Cys Leu Asp Tyr Tyr Leu Ser Glu Glu Gly Ser
                885                 890                 895

Val His Leu Pro Glu Ile Asn Arg Leu Ala Lys Glu Asn Thr Pro Glu
            900                 905                 910

Ala Asp Glu Leu Leu Arg Tyr Phe Met Glu Gly Ala Arg Leu Arg
        915                 920                 925

Ser Ser Val Gly Leu Pro Arg Val Val Ala Lys Pro Thr Val Ile Asp
    930                 935                 940

Asp Asn Gly Thr Lys Leu Thr Leu Lys Glu Gly Gln His Ile Leu Cys
```

```
945                 950                 955                 960
Asn Leu Val Ala Ala Ser His Asp Pro Val Ser Phe Pro Glu Pro Glu
                965                 970                 975
Lys Val Arg Leu Asp Arg Asp Met Asp Leu Tyr Val His Phe Gly Ser
                980                 985                 990
Gly Pro His Lys Cys Leu Gly Phe Gly Leu Cys Lys Leu Gly Leu Thr
                995                 1000                1005
Thr Met Leu Lys Val Val Gly Gly Leu Asp Asn Leu Arg Arg Ala
1010                1015                1020
Pro Gly Pro Gln Gly Gln Leu Lys Arg Leu Ala Gly Pro Gly Gly
1025                1030                1035
Ile Ser Lys Tyr Met Thr Ala Asp Gln Ser Gly Phe Phe Pro Phe
1040                1045                1050
Pro Thr Thr Met Lys Ile Gln Trp Asp Gly Asp Leu Pro Glu Pro
1055                1060                1065
Ala Ser Asp
1070

<210> SEQ ID NO 63
<211> LENGTH: 1080
<212> TYPE: PRT
<213> ORGANISM: Aspergillus kawachii

<400> SEQUENCE: 63

Met Ser Gly Ser Asn Asn His Ser Ile Val Asn Gly Ile Gly Ser Thr
1               5                   10                  15
Ile Ser Gln Val Glu Lys Ala Ile Ala Ser Leu Arg Pro Leu Pro
                20                  25                  30
Thr Ala Thr Gly Asn Gly Thr Tyr Val Thr Glu Pro Ala Gln Thr Gly
            35                  40                  45
Ile Val Lys Asp Leu Ser His Val Asp Leu Thr Asp Phe Lys Ala Leu
        50                  55                  60
Leu Glu Val Val Lys Asp Ala Val Thr Gly Gln Pro Val Asp Asp Arg
65                  70                  75                  80
His Tyr Ile Met Glu Arg Val Ile Gln Leu Ala Ala Gly Leu Pro Ser
                85                  90                  95
Thr Ser Lys Ser Gly Lys Asp Leu Thr Asn Thr Phe Leu Lys Gln Leu
                100                 105                 110
Trp Asn Asp Leu Glu His Pro Pro Ile Ser Tyr Leu Gly Arg Asn Thr
            115                 120                 125
Ser Tyr Arg Lys Ala Asp Gly Ser Gly Asn Asn Phe Leu Trp Pro His
        130                 135                 140
Ile Gly Ala Ala Gly Ser His Tyr Ala Arg Ser Val Arg Pro Thr Thr
145                 150                 155                 160
Val Gln Ser Pro Ser Leu Pro Asp Pro Ser Thr Leu Phe Glu Ser Leu
                165                 170                 175
Leu Glu Arg Lys Glu Tyr Lys Glu His Pro Asn Lys Ile Ser Ser Val
                180                 185                 190
Leu Phe Tyr Leu Ala Ser Ile Ile Ile His Asp Leu Phe Gln Thr Asp
            195                 200                 205
Arg Asn Asp Tyr Thr Leu Asn Lys Thr Ser Ser Tyr Leu Asp Leu Ser
        210                 215                 220
Pro Leu Tyr Gly Asn Asn Gln Asp Glu Gln Asn Leu Val Arg Ser Phe
225                 230                 235                 240
```

-continued

```
Lys Asp Gly Lys Leu Lys Pro Asp Cys Phe Ser Ser Lys Arg Val Leu
                245                 250                 255
Gly Phe Pro Pro Gly Val Gly Val Leu Leu Met Phe Asn Arg Phe
            260                 265                 270
His Asn Tyr Val Val Glu Asn Leu Ala Thr Ile Asn Glu Gly Gly Arg
                275                 280                 285
Phe Thr Lys Pro Asp Glu Ser Asp Val Asp Ala Ser Thr Arg Tyr Asp
            290                 295                 300
Asn Asp Leu Phe Gln Thr Gly Arg Leu Val Thr Cys Gly Leu Tyr Ile
305                 310                 315                 320
Asn Ile Ile Leu Lys Asp Tyr Val Arg Thr Ile Leu Asn Ile Asn Arg
                325                 330                 335
Thr Asp Ser Leu Trp Ser Leu Asp Pro Arg Ala Asp Ile Gln Asp Ser
            340                 345                 350
Leu Leu Gly Ser Ala Pro Ala Glu Ala Thr Gly Asn Gln Val Ser Ala
            355                 360                 365
Glu Phe Asn Leu Val Tyr Arg Trp His Ala Cys Val Ser Gln Arg Asp
            370                 375                 380
Glu Lys Trp Thr Gln Asp Leu Tyr Lys Asp Leu Phe Pro Gly Lys Asp
385                 390                 395                 400
Pro Asn Asn Val Ser Leu Pro Glu Phe Leu Arg Gly Val Ala Lys Trp
                405                 410                 415
Glu Ala Ser Leu Pro Glu Gln Pro Pro Asp Arg Pro Phe Ala Gly Leu
            420                 425                 430
Gln Arg Asn Ala Asp Gly Ala Phe Asp Asp Asp Leu Ala Asn Met
            435                 440                 445
Phe Ala Asp Gly Val Glu Asp Cys Ala Gly Ala Phe Gly Ala Gly Asn
450                 455                 460
Ile Pro Ser Val Phe Arg Asn Ile Glu Ala Leu Gly Ile Leu Gln Ala
465                 470                 475                 480
Arg Ser Trp Asn Leu Ala Thr Leu Asn Glu Phe Arg Lys Phe Phe Asp
                485                 490                 495
Leu Ala Pro Tyr Lys Thr Phe Glu Glu Ile Asn Pro Asp Pro Tyr Ile
            500                 505                 510
Ala Ala Gln Leu Lys Asn Leu Tyr Asp Glu Pro Asp Leu Val Glu Met
            515                 520                 525
Tyr Pro Gly Val Ile Val Glu Ala Thr Lys Asp Ala Val Val Pro Gly
            530                 535                 540
Ser Gly Leu Cys Thr Asn Phe Thr Ile Ser Arg Ala Ile Leu Ser Asp
545                 550                 555                 560
Ala Val Ser Leu Val Arg Gly Asp Arg Phe Tyr Thr Val Asp Tyr Thr
                565                 570                 575
Pro Lys His Leu Thr Asn Trp Ala Tyr His Glu Ile Gln Pro Gln Asp
            580                 585                 590
Ser Val Asp Gln Gly Gln Val Phe Tyr Lys Leu Val Leu Arg Ala Phe
            595                 600                 605
Pro Asn His Phe Lys Gly Asp Ser Ile Tyr Ala His Phe Pro Leu Val
            610                 615                 620
Ile Pro Ser Glu Asn Lys Lys Ile Leu Glu Lys Leu Ser Val Ala Gln
625                 630                 635                 640
Asp Tyr Ser Trp Gly Arg Pro Ser Tyr Thr Pro Thr Pro Gln Phe Ile
                645                 650                 655
Ser Ser Asn Ala Ala Cys Ile Ser Val Leu Asn Asp Gln Glu Ala Phe
```

```
            660                 665                 670
Lys Val Thr Trp Gly Ser Lys Ile Glu Phe Leu Met Arg His Asn Asn
    675                 680                 685

His Pro Tyr Gly Arg Asp Phe Met Leu Ser Gly Asp Lys Pro Pro Asn
    690                 695                 700

Ala Ala Ser Arg Arg Met Met Gly Ser Ala Leu Tyr Arg Asp Lys Trp
705                 710                 715                 720

Glu Ser Glu Val Lys Arg Phe Tyr Glu Asp Ile Thr Ile Lys Leu Leu
                725                 730                 735

Arg Gln His Ser Tyr Lys Leu Gly Gly Thr Asn Gln Val Asp Ile Val
            740                 745                 750

Arg Asp Val Ala Asn Tyr Ala Gln Val His Phe Cys Ala Asn Val Phe
        755                 760                 765

Ser Leu Pro Leu Lys Thr Glu Ser Asn Pro Arg Gly Ile Phe Thr Glu
    770                 775                 780

Ala Glu Leu Tyr Glu Ile Leu Ala Leu Val Phe Ala Ser Ile Phe Tyr
785                 790                 795                 800

Asp Ala Asp Val Gly Thr Ser Phe Gln Leu Asn His Thr Ala Arg Asp
                805                 810                 815

Val Thr Gln Gln Leu Gly Asp Leu Thr Met Ala Asn Val Asp Phe Val
            820                 825                 830

Asn Lys Ala Gly Phe Ile Ala Asn Ile Val Ser Ser Leu His Arg His
        835                 840                 845

Asp Val Leu Ser Glu Tyr Gly Glu His Met Ile Gln Arg Leu Leu His
    850                 855                 860

Asn Asn Ile Pro Pro Ala Asp Ile Val Trp Thr His Leu Leu Pro Thr
865                 870                 875                 880

Ala Gly Gly Met Val Ala Asn Gln Ala Gln Leu Phe Ser Gln Cys Leu
                885                 890                 895

Asp Tyr Tyr Leu Ser Asp Glu Gly Ser Val His Leu Pro Asp Ile Lys
            900                 905                 910

Arg Leu Ala Gln Glu Asn Thr Ser Glu Ala Asp Ser Leu Leu Leu Arg
        915                 920                 925

Tyr Phe Met Glu Gly Ala Arg Leu Arg Ser Ser Val Gly Leu Pro Arg
    930                 935                 940

Leu Val Ala Lys Pro Thr Val Asp Asp Gly Gly Ser Lys Tyr Thr
945                 950                 955                 960

Leu Lys Pro Gly Gln Ser Val Leu Cys Asn Leu Val Ser Ala Ser Met
                965                 970                 975

Asp Pro Arg Ser Phe Pro Glu Pro Glu Lys Val Lys Leu Asp Arg Asp
            980                 985                 990

Met Ser Leu Tyr Ala His Phe Gly Phe Gly Pro His Gln Cys Leu Gly
        995                 1000                1005

Met Gly Ile Cys Lys Leu Ala Leu Thr Thr Met Leu Arg Val Val
    1010                1015                1020

Gly Arg Leu Asp Asn Leu Arg Arg Ala Pro Gly Ser Gln Gly Gln
    1025                1030                1035

Leu Lys Arg Ile Ala Gly Pro Gly Gly Ile Ser Met Tyr Met Thr
    1040                1045                1050

Ala Asp Gln Ser Ser Tyr Trp Pro Phe Pro Ser Thr Met Lys Ile
    1055                1060                1065

Gln Trp Asp Gly Asp Leu Pro Ser Leu Ala Thr Asn
    1070                1075                1080
```

<210> SEQ ID NO 64
<211> LENGTH: 1080
<212> TYPE: PRT
<213> ORGANISM: Aspergillus clavatus

<400> SEQUENCE: 64

```
Met Ser Gly Lys Arg Glu Glu Ser Thr Asn Gly Gly Ile Gly Lys Thr
1               5                   10                  15

Ile Ala Gln Ile Glu Lys Val Val Thr Ala Ser Leu Arg Pro Leu Pro
            20                  25                  30

Ser Lys Thr Gly Asp Gly Thr Tyr Val Thr Glu Ala Val Lys Thr Gly
        35                  40                  45

Leu Leu Lys Asp Leu Ser His Val Asp Leu Gly Asp Leu Lys Thr Leu
    50                  55                  60

Leu Glu Val Ser Lys Ser Ala Leu Thr Gly Glu Ala Val Asp Asp Lys
65                  70                  75                  80

Lys Tyr Ile Met Glu Arg Val Val Gln Leu Ala Ala Gly Leu Pro Ser
                85                  90                  95

Thr Ser Gln Ile Gly Lys Asp Met Thr Asn Thr Phe Leu Thr Thr Leu
            100                 105                 110

Trp Asn Asp Leu Glu His Pro Pro Ile Ser Tyr Leu Gly Arg Asp Ala
        115                 120                 125

Met Tyr Arg Lys Ala Asp Gly Ser Gly Asn Asn Ile Leu Trp Pro His
    130                 135                 140

Ile Gly Ala Ala Gly Thr Pro Tyr Ala Arg Ser Val Arg Pro Lys Thr
145                 150                 155                 160

Met Gln Ser Pro Asn Leu Pro Asp Pro Glu Thr Leu Phe Asp Cys Leu
                165                 170                 175

Leu Ala Arg Lys Glu Tyr Lys Glu His Pro Asn Lys Ile Ser Ser Val
            180                 185                 190

Leu Phe Tyr Ile Ala Ser Ile Ile His Asp Ile Phe Gln Thr Asp
        195                 200                 205

Arg Lys Asp Pro Thr Val Ser Leu Thr Ser Ser Tyr Leu Asp Leu Ser
    210                 215                 220

Pro Leu Tyr Gly Asn Asn Gln Asp Glu Gln Asn Leu Val Arg Thr Phe
225                 230                 235                 240

Lys Asp Gly Lys Leu Lys Pro Asp Cys Phe Ser Thr Lys Arg Val Leu
                245                 250                 255

Gly Phe Pro Pro Gly Val Gly Val Leu Leu Ile Met Phe Asn Arg Phe
            260                 265                 270

His Asn His Val Val Glu Asn Leu Ala Leu Ile Asn Glu Gly Gly Arg
        275                 280                 285

Phe Thr Lys Pro Gln Glu Ser Asp Ala Gln Ala Tyr Ala Lys Tyr Asp
    290                 295                 300

Asn Asp Leu Phe Gln Thr Gly Arg Leu Ile Thr Cys Gly Leu Tyr Val
305                 310                 315                 320

Asn Ile Ile Leu Lys Asp Tyr Val Arg Thr Ile Leu Asn Ile Asn Arg
                325                 330                 335

Thr Asp Ser Ile Trp Ser Leu Asp Pro Arg Ala Asp Met Lys Asp Gly
            340                 345                 350

Leu Leu Gly Glu Ala Ala Ala Gln Ala Thr Gly Asn Gln Val Ser Ala
        355                 360                 365

Glu Phe Asn Leu Val Tyr Arg Trp His Ser Cys Ile Ser Lys Arg Asp
```

```
                370                 375                 380
Gln Lys Trp Thr Glu Asp Met Tyr Gln Glu Val Phe Pro Gly Gln Asp
385                 390                 395                 400

Pro Ser Lys Leu Pro Leu Gln Asp Phe Met Arg Gly Leu Gly Arg Trp
                405                 410                 415

Glu Ala Lys Leu Pro Gly Pro Gln Glu Arg Pro Phe Ala Gly Leu
                420                 425                 430

Gln Arg Lys Ala Asp Gly Ser Tyr Asp Asp Asp Leu Val Lys Ile
        435                 440                 445

Phe Gly Asp Ser Val Glu Asp Cys Ala Gly Ala Phe Gly Val Leu His
        450                 455                 460

Val Pro Thr Val Phe Arg Ser Ile Glu Ala Leu Gly Ile Gln Gln Ala
465                 470                 475                 480

Arg Ser Trp Asn Leu Ala Thr Leu Asn Glu Phe Arg Asn Tyr Phe Asn
                485                 490                 495

Leu Ala Pro Tyr Lys Thr Phe Glu Glu Ile Asn Pro Asp Pro Tyr Val
                500                 505                 510

Ala Asp Gln Leu Arg Arg Leu Tyr Asp His Pro Asp Arg Val Glu Ile
        515                 520                 525

Tyr Pro Gly Ile Ile Val Glu Asp Thr Lys Glu Ser Met Ala Pro Gly
        530                 535                 540

Ser Gly Leu Cys Thr Asn Phe Thr Ile Ser Arg Ala Ile Leu Ser Asp
545                 550                 555                 560

Ala Val Ala Leu Val Arg Gly Asp Arg Phe His Thr Val Asp Phe Thr
                565                 570                 575

Pro Lys His Leu Thr Asn Trp Ala Tyr Asn Glu Ile Gln Pro Gln Glu
                580                 585                 590

Ser Val Asp Gln Thr His Val Leu Tyr Lys Leu Val Phe Arg Ala Phe
        595                 600                 605

Pro Asn His Phe Lys Gly Asp Ser Ile Tyr Ala His Phe Pro Leu Val
        610                 615                 620

Ile Pro Ser Glu Asn Lys Lys Ile Leu Thr Lys Leu Gly Thr Ala Asp
625                 630                 635                 640

Lys Tyr Ser Trp Asp Arg Pro Ser Phe Thr His Pro Pro Gln Phe Ile
                645                 650                 655

Asn Ser His Ser Ala Cys Met Ser Ile Leu Ala Asp Gln Glu Thr Phe
                660                 665                 670

Lys Val Ser Trp Gly Lys Lys Ile Glu Phe Leu Met Arg His Asn Asp
        675                 680                 685

Gln Pro His Gly Arg Asp Phe Met Leu Ser Gly Asp Lys Pro Pro Asn
        690                 695                 700

Ala Glu Ser Arg Gln Met Met Gly Lys Ala Leu Tyr Arg Asn Lys Trp
705                 710                 715                 720

Glu Thr Glu Val Lys Asp Phe Tyr Glu Glu Ile Thr Leu Lys Leu Leu
                725                 730                 735

His Arg Asn Ser Tyr Lys Leu Ala Gly Thr Asn Gln Val Asp Ile Val
                740                 745                 750

Arg Asp Val Ala Asn Leu Ala Gln Val Tyr Phe Cys Ala Ser Val Phe
        755                 760                 765

Ser Leu Pro Leu Lys Thr Glu Ser Asn Pro Arg Gly Val Phe Thr Glu
        770                 775                 780

Ser Glu Leu Tyr Gln Ile Met Ala Val Val Phe Thr Ser Ile Phe Tyr
785                 790                 795                 800
```

Asp Ala Asp Val Cys Lys Ser Phe Glu Leu Asn Gln Gly Ala Arg Ala
             805                 810                 815

Val Thr Gln Gln Leu Gly Gln Leu Thr Met Ala Asn Val Glu Leu Ile
         820                 825                 830

Glu Lys Thr Gly Phe Ile Ala Asn Leu Val Asn Ser Leu His Arg His
     835                 840                 845

Asp Ala Leu Thr Glu Tyr Gly Val His Met Ile Gln Arg Leu Leu Asp
 850                 855                 860

Thr Gly Thr Pro Ala Ala Glu Ile Val Trp Thr His Val Leu Pro Thr
865                 870                 875                 880

Ala Gly Gly Met Val Ala Asn Gln Ala Gln Leu Phe Ser Gln Cys Leu
                 885                 890                 895

Asp Tyr Tyr Leu Ser Asp Glu Gly Ser Ile His Leu Pro Glu Ile Asn
             900                 905                 910

Arg Leu Ala Lys Gln Asp Thr Pro Glu Ala Asp Leu Leu Leu Arg
         915                 920                 925

Tyr Phe Met Glu Gly Ala Arg Leu Arg Ser Ser Val Ala Leu Pro Arg
     930                 935                 940

Val Val Ala Gln Pro Thr Val Glu Asp Asn Gly Gln Lys Val Ile
945                 950                 955                 960

Leu Lys Glu Gly Gln His Ile Leu Cys Asn Leu Val Ser Ala Ser Met
                 965                 970                 975

Asp Pro Ala Ser Phe Pro Glu Pro Lys Val Lys Leu Asp Arg Asp
             980                 985                 990

Met Asn Leu Tyr Ala His Phe Gly Phe Gly Pro His Gln Cys Leu Gly
         995                 1000                1005

Ile Gly Leu Cys Lys Leu Ala Leu Thr Thr Met Leu Lys Val Val
    1010                1015                1020

Gly Arg Leu Asp Asn Leu Arg Arg Ala Pro Gly Gly Gln Gly Arg
    1025                1030                1035

Leu Lys Lys Leu Ser Gly Pro Gly Gly Ile Ala Met Tyr Met Thr
    1040                1045                1050

Pro Asp Gln Ser Gly Phe Phe Pro Phe Pro Thr Thr Met Lys Ile
    1055                1060                1065

Gln Trp Asp Gly Asp Leu Pro Pro Leu Lys Thr Glu
    1070                1075                1080

<210> SEQ ID NO 65
<211> LENGTH: 1080
<212> TYPE: PRT
<213> ORGANISM: Aspergillus niger

<400> SEQUENCE: 65

Met Ser Gly Ala Asn Asn His Ser Ile Val Asn Gly Ile Gly Ser Thr
1               5                   10                  15

Ile Ser Gln Val Glu Lys Ala Ile Ser Ala Ser Leu Arg Pro Leu Pro
             20                  25                  30

Thr Ala Thr Gly Asn Gly Thr Tyr Ile Thr Glu Pro Asp Gln Thr Gly
         35                  40                  45

Ile Val Lys Asp Leu Ser His Val Asp Phe Thr Asp Ile Lys Ala Leu
     50                  55                  60

Leu Glu Val Ile Lys Asp Ala Val Thr Gly Gln Pro Val Asp Asp Arg
65                  70                  75                  80

His Tyr Ile Met Glu Arg Val Ile Gln Leu Ala Ala Gly Leu Pro Ser

```
                         85                  90                  95
Thr Ser Lys Asn Gly Lys Asp Leu Thr Asn Ala Phe Leu Lys Gln Leu
            100                 105                 110

Trp Asn Asp Leu Glu His Pro Pro Ile Ser Tyr Leu Gly Arg Asp Ser
            115                 120                 125

Ser Tyr Arg Lys Ala Asp Gly Ser Gly Asn Asn Phe Leu Trp Pro His
            130                 135                 140

Ile Gly Ala Ala Gly Ser His Tyr Ala Arg Ser Val Arg Pro Thr Thr
145                 150                 155                 160

Val Gln Ser Pro Ser Leu Pro Asp Pro Ser Thr Leu Phe Ala Ser Leu
                165                 170                 175

Leu Glu Arg Lys Glu Tyr Lys Glu His Pro Asn Lys Ile Ser Ser Val
            180                 185                 190

Leu Phe Tyr Leu Ala Ser Val Ile Ile His Asp Leu Phe Gln Thr Asp
            195                 200                 205

Arg Ser Asp Phe Thr Leu Asn Lys Thr Ser Ser Tyr Leu Asp Leu Ser
            210                 215                 220

Pro Leu Tyr Gly Asn Asn Gln Asp Glu Gln Asp Leu Val Arg Thr Phe
225                 230                 235                 240

Lys Asp Gly Lys Leu Lys Pro Asp Cys Phe Ser Ser Lys Arg Val Leu
                245                 250                 255

Gly Phe Pro Pro Gly Val Gly Val Leu Leu Leu Met Phe Asn Arg Phe
            260                 265                 270

His Asn Tyr Val Val Glu Asn Leu Ala Thr Ile Asn Glu Gly Gly Arg
            275                 280                 285

Phe Thr Lys Pro Asp Glu Ser Asp Val Asp Ala Ser Thr Lys Tyr Asp
290                 295                 300

Asn Asp Leu Phe Gln Thr Gly Arg Leu Val Thr Cys Gly Leu Tyr Ile
305                 310                 315                 320

Asn Ile Ile Leu Lys Asp Tyr Val Arg Thr Ile Leu Asn Ile Asn Arg
                325                 330                 335

Thr Asp Ser Leu Trp Ser Leu Asp Pro Arg Ala Asp Ile Gln Asp Ser
            340                 345                 350

Leu Leu Gly Ser Ala Pro Ala Glu Ala Thr Gly Asn Gln Val Ser Ala
            355                 360                 365

Glu Phe Asn Leu Val Tyr Arg Trp His Ala Cys Ile Ser Gln Arg Asp
            370                 375                 380

Glu Lys Trp Thr Gln Asp Leu Tyr Lys Asp Leu Phe Pro Gly Lys Asp
385                 390                 395                 400

Pro Asn Asn Val Ser Leu Gln Glu Phe Ile Arg Gly Val Ala Lys Trp
                405                 410                 415

Glu Ala Ser Leu Pro Glu Gln Pro Asp Arg Pro Phe Ala Gly Leu
            420                 425                 430

Gln Arg Asn Ala Asp Gly Ala Phe Asp Asp Gly Asp Leu Ala Asn Met
            435                 440                 445

Phe Ala Asp Gly Val Glu Asp Cys Ala Gly Ala Phe Gly Ala Gly Asn
            450                 455                 460

Ile Pro Ser Val Phe Arg Asn Ile Glu Ala Leu Gly Ile Leu Gln Ala
465                 470                 475                 480

Arg Ser Trp Asn Leu Ala Thr Leu Asn Glu Phe Arg Lys Phe Phe Asp
            485                 490                 495

Leu Ala Pro Tyr Lys Thr Phe Glu Glu Ile Asn Pro Asp Pro Tyr Ile
            500                 505                 510
```

```
Ala Ala Gln Leu Lys Asn Leu Tyr Asp Glu Pro Asp Leu Val Glu Met
        515                 520                 525

Tyr Pro Gly Val Ile Val Glu Ala Thr Lys Asp Ala Ile Val Pro Gly
    530                 535                 540

Ser Gly Leu Cys Thr Asn Phe Thr Ile Ser Arg Ala Ile Leu Ser Asp
545                 550                 555                 560

Ala Val Ser Leu Val Arg Gly Asp Arg Phe Tyr Thr Val Asp Tyr Thr
                565                 570                 575

Pro Lys His Leu Thr Asn Trp Ala Tyr Asn Glu Ile Gln Pro Gln Asp
            580                 585                 590

Ser Val Asp Gln Gly Gln Val Phe Tyr Lys Leu Val Leu Arg Ala Phe
        595                 600                 605

Pro Asn His Phe Lys Gly Asp Ser Val Tyr Ala His Phe Pro Leu Val
    610                 615                 620

Ile Pro Ser Glu Asn Lys Lys Ile Leu Glu Lys Leu Ser Val Ala Gln
625                 630                 635                 640

Asp Tyr Ser Trp Gly Arg Pro Ser Tyr Thr Pro Leu Pro Gln Phe Ile
                645                 650                 655

Ser Ser Asn Ala Ala Cys Ile Ser Val Leu Asn Asp Gln Glu Ala Phe
            660                 665                 670

Lys Val Thr Trp Gly Ser Lys Ile Glu Phe Leu Met Arg His Asn Asn
        675                 680                 685

His Pro Tyr Gly Arg Asp Phe Met Leu Ser Gly Asp Lys Pro Asn
    690                 695                 700

Ala Ala Ser Arg Arg Met Met Gly Ser Ala Leu Tyr Arg Asp Lys Trp
705                 710                 715                 720

Glu Ser Glu Val Lys Arg Phe Tyr Glu Asp Ile Thr Ile Lys Leu Leu
                725                 730                 735

Arg Gln His Ser Tyr Gln Leu Gly Gly Val Asn Gln Val Asp Ile Val
            740                 745                 750

Arg Asp Val Ala Asn Tyr Ala Gln Val His Phe Cys Ala Asn Val Phe
        755                 760                 765

Ser Leu Pro Leu Lys Thr Glu Ser Asn Pro Arg Gly Ile Phe Ala Glu
    770                 775                 780

Ser Glu Leu Tyr Glu Ile Leu Ala Leu Val Phe Ala Ser Ile Phe Tyr
785                 790                 795                 800

Asp Ala Asp Val Gly Thr Ser Phe Gln Leu Asn Gln Thr Ala Arg Asp
                805                 810                 815

Val Thr Gln Gln Leu Gly Glu Leu Thr Met Ala Asn Val Asp Phe Val
            820                 825                 830

Asn Lys Ala Gly Phe Ile Ala Asn Leu Val Ser Ser Leu His Arg His
        835                 840                 845

Asp Val Leu Ser Glu Tyr Gly Glu His Met Ile Gln Arg Leu Leu His
    850                 855                 860

Ser Asn Val Pro Pro Ala Glu Ile Val Trp Thr His Leu Leu Pro Thr
865                 870                 875                 880

Ala Gly Gly Met Val Ala Asn Gln Ala Gln Leu Phe Ser Gln Cys Leu
                885                 890                 895

Asp Tyr Tyr Leu Ser Asp Glu Gly Ser Ile His Leu Pro Asp Ile Lys
            900                 905                 910

Arg Leu Ala Lys Glu Asn Thr Ser Glu Ala Asp Ala Leu Leu Leu Arg
        915                 920                 925
```

```
Tyr Phe Met Glu Gly Ala Arg Leu Arg Ser Ser Val Gly Leu Pro Arg
    930                 935                 940

Leu Val Ala Lys Pro Thr Val Asp Asp Gly Gly Lys Tyr Thr
945                 950                 955                 960

Leu Lys Pro Gly Gln Ser Val Leu Cys Asn Leu Val Ser Ala Ser Met
                965                 970                 975

Asp Pro Arg Ser Phe Pro Glu Pro Lys Val Lys Leu Asp Arg Asp
                980                 985                 990

Met Ser Leu Tyr Ala His Phe Gly Phe Gly Pro His Gln Cys Leu Gly
                995                 1000                1005

Met Gly Ile Cys Lys Leu Ala Leu Thr Thr Met Leu Arg Val Val
    1010                1015                1020

Gly Arg Leu Asp Asn Leu Arg Arg Ala Pro Gly Ser Gln Gly Gln
    1025                1030                1035

Leu Lys Lys Ile Ala Gly Pro Gly Gly Ile Ser Met Tyr Met Thr
    1040                1045                1050

Ala Asp Gln Ser Ser Tyr Trp Pro Phe Pro Ser Thr Met Lys Ile
    1055                1060                1065

Gln Trp Asp Gly Asp Leu Pro Ser Leu Ala Thr Asn
    1070                1075                1080

<210> SEQ ID NO 66
<211> LENGTH: 1127
<212> TYPE: PRT
<213> ORGANISM: Glomerella cingulate

<400> SEQUENCE: 66

Met Ser Gln Gln Ser His Thr Glu Gln Phe Pro Lys Asn Gln Pro Pro
1               5                   10                  15

Leu Ala Glu Arg Leu Ala Ser Ala Arg Gln Leu Val Thr Lys Ala Ile
                20                  25                  30

Ser Ala Val Pro Pro His Pro Glu Pro Leu Pro Ser Pro Asn Ser Asp
            35                  40                  45

Gln Gly Glu Pro Ser Asn Leu Leu Gln Asp Val Lys Lys Leu Gly Phe
        50                  55                  60

Asp Asp Phe Asp Thr Leu Val His Phe Phe Ser Ser Ala Val Glu Gly
65                  70                  75                  80

Gln Ile Asn Asp Asn Glu Leu Leu Leu Glu Asn Leu Ile Gln Leu Phe
                85                  90                  95

Ala Lys Leu Pro Gln Asn Ser Val Lys Gly Lys Arg Leu Glu Asn Gly
                100                 105                 110

Leu Ile Asn Gln Leu Trp Asn Gly Ile Asp His Pro Pro Met Thr Thr
            115                 120                 125

Leu Gly Glu Asp His Lys Tyr Arg Ala Ala Asp Gly Ser Gly Asn Ala
        130                 135                 140

Ile His Asp Pro Lys Met Gly Ala Ala Gly Gln Pro Tyr Ala Arg Ser
145                 150                 155                 160

Thr Pro Ala Lys Ser Tyr Gln Asn Pro Asn Gln Pro Glu Pro Glu Met
                165                 170                 175

Ile Phe Asp Met Leu Phe Ala Arg Gly Gly Glu Phe Lys Pro His Pro
                180                 185                 190

Asn Lys Ile Ser Ser Phe Met Phe Tyr Leu Ala Thr Ile Ile Thr His
            195                 200                 205

Asp Ile Phe Gln Thr Lys Asn Gly Thr Ser Pro Ile Asn Gln Thr Ser
        210                 215                 220
```

-continued

Ser Tyr Leu Asp Leu Ala Pro Leu Tyr Gly Arg Asn Gln Ala Glu Gln
225                 230                 235                 240

Asp Leu Met Arg Thr Lys Lys Asn Gly Leu Leu Lys Pro Asp Thr Phe
            245                 250                 255

Ser Ser Lys Arg Val Leu Gly Phe Pro Pro Gly Val Gly Thr Leu Leu
        260                 265                 270

Ile Met Phe Asn Arg Tyr His Asn Tyr Val Ala Thr Asn Leu Ala Thr
    275                 280                 285

Ile Asn Glu Gly Gly Arg Phe Gln Lys Pro Thr Gly Asp Asp Pro Glu
290                 295                 300

Lys Thr Ala Lys Tyr Asp Asn Asp Leu Phe Gln Thr Ala Arg Leu Ile
305                 310                 315                 320

Thr Cys Gly Leu Tyr Val Ser Ile Ile Leu Arg Asp Tyr Val Arg Thr
                325                 330                 335

Ile Leu Gly Met Asn Arg Thr Ala Ser Ser Trp Ala Leu Asp Pro Arg
            340                 345                 350

Thr Asn Glu Gly Lys Ser Ile Leu Ser Gln Gln Thr Pro Glu Gly Thr
                355                 360                 365

Gly Asn Gln Val Ser Val Glu Phe Asn Leu Ile Tyr Arg Trp His Asn
370                 375                 380

Thr Ile Ser Pro Lys Asp Glu Gln Trp Thr Lys Asp Val Met Lys Lys
385                 390                 395                 400

Val Leu Gly Lys Asp Pro Thr Glu Met Ser Leu Met Glu Phe Gly His
                405                 410                 415

Ala Met Arg Asp Trp Glu Gln Glu Ile Pro Asp Pro Ala Gln Arg
                420                 425                 430

Gly Phe Met Asp Leu Pro Arg Asn Ala Asp Gly Thr Leu Asn Glu Ala
            435                 440                 445

Asp Leu Ala Lys Ile Phe Lys Glu Ser Val Asp Val Ala Gly Ser
    450                 455                 460

Tyr Gly Ala Asn Arg Ile Pro Glu Val Met Arg Pro Ile Glu Leu Met
465                 470                 475                 480

Gly Ile Met Ala Ser Arg Ser Trp Asn Cys Ala Thr Leu Asn Glu Phe
                485                 490                 495

Arg Glu His Phe Gly Leu Thr Arg His Pro Thr Phe Glu Asp Ile Asn
            500                 505                 510

Pro Asp Lys Glu Val Ala Ala Lys Leu Arg Phe Leu Tyr Gly Ser Pro
    515                 520                 525

Asp Ala Val Glu Leu Tyr Pro Gly Leu Met Ala Glu Lys Ala Lys Pro
    530                 535                 540

Pro Met Ala Pro Gly Ser Gly Leu Cys Gly Asn Phe Thr Met Thr Arg
545                 550                 555                 560

Ala Ile Leu Ser Asp Ala Val Ala Leu Val Arg Gly Asp Arg Phe Tyr
                565                 570                 575

Thr Ile Asp Tyr Thr Pro Lys Asn Leu Thr Asn Trp Gly Phe Asn Gln
            580                 585                 590

Ala Ser Tyr Asp Leu Asn Val Asp Gln Ser His Val Leu Tyr Lys Leu
    595                 600                 605

Val Phe Arg Ala Phe Pro Asn Ser Phe Gln Asn Asn Ser Ile Tyr Ala
    610                 615                 620

His Phe Pro Phe Val Ile Pro Ser Glu Asn Lys Lys Ile Leu Glu Ser
625                 630                 635                 640

```
Ile Asp Lys Ala Tyr Leu Tyr Thr Trp Asp Glu Pro Lys Thr Lys Thr
            645                 650                 655

Pro Leu Ile Pro Ile Leu Ser His Lys Ala Val Ser Glu Val Leu Tyr
            660                 665                 670

Asn Gln Gln Asp Phe Lys Val Ile Thr Gly Asp Ala Ile Asn His Leu
            675                 680                 685

Val Ala Gln Pro Asn Lys Pro His Tyr Gly Lys Asp Phe Cys Leu Ser
    690                 695                 700

Gly Asp Gly Lys Glu His Ala Lys Asn Arg Thr Leu Val Arg Lys Ser
705                 710                 715                 720

Leu Ile Ser Gly Pro Trp Glu Thr Glu Ile Trp Lys Trp Tyr Thr His
                725                 730                 735

Met Thr Pro Lys Ile Leu Asn Leu Asn Ser Phe Pro Ile Pro Gly Asn
            740                 745                 750

Lys Arg Glu Ile Asp Leu Val Arg Asp Val Ile Asn Val Thr Asn Thr
            755                 760                 765

Arg Phe Asn Ala Ala Leu Phe Cys Met Pro Ile Lys Asn Glu Glu Ser
770                 775                 780

Pro Trp Gly Val Tyr Thr Asp Gln Glu Leu Tyr Ser Val Leu Gly Ala
785                 790                 795                 800

Leu Phe Gln Ala Val Phe Met Asp Ala Asp Ile Gly Asn Ser Phe Lys
                805                 810                 815

Leu Arg Thr Ile Ala Arg Glu Leu Ala Gln Asp Leu Gly Lys Val Val
                820                 825                 830

Met Leu Ile Ala Gln Thr Ile Lys Lys Ala Gly Leu Ile Thr Asp Ile
            835                 840                 845

Val Ala Lys Ile Arg Glu Gly Glu Ala Ser Leu Pro Thr Tyr Gly Asn
850                 855                 860

His Leu Ile Glu Arg Met Leu Ser Asp Gly Lys Asp Val Glu Glu Val
865                 870                 875                 880

Val Trp Gly Thr Ile Met Pro Val Ile Thr Ala Asn Val Ala Asn Gln
                885                 890                 895

Ser Gln Val Thr Ser Leu Cys Val Asp Tyr Tyr Leu Asp Lys Glu Gly
            900                 905                 910

Lys Lys His Leu Pro Glu Leu Tyr Arg Leu Ala His Glu Asn Thr Pro
    915                 920                 925

Glu Ala Asp Glu Thr Leu Leu Lys Tyr Met Leu Glu Gly Cys Arg Leu
            930                 935                 940

Arg Gly Pro Val Ala Val Tyr Arg Glu Ala Thr Ser Thr Gln Val Ile
945                 950                 955                 960

Thr Asp Tyr Ser Pro Cys Leu Pro Ser Glu Ser Asp Pro Thr Gly Arg
                965                 970                 975

Asp Pro Ile Thr Asn Pro Asp Ile Glu Gly Thr Lys Arg Glu Val Lys
            980                 985                 990

Ile Pro Arg Gly Tyr Arg Val Val     Cys Asn Phe Ala Thr  Ala Gly Arg
            995                 1000                1005

Asp Pro  Ala Ile Phe Glu Asp  Pro Asn Glu Val Arg  Leu Asp Arg
    1010                1015                1020

Pro Leu  Asp Ser Tyr Val His  Phe Gly Leu Gly Pro  His Trp Cys
    1025                1030                1035

Ala Gly  Lys Glu Met Ser Arg  Val Gly Gln Thr Ser  Leu Phe Lys
    1040                1045                1050

Gln Ile  Val Gly Leu Lys Asn  Leu Arg Arg Ala Pro  Gly Gly Arg
```

```
             1055                1060                1065
Gly  Glu   Met  Lys  Asn  Phe  Pro  Ala  Ser  Pro  Trp  Asn  Gly  Gln  Val
           1070                1075                1080

Gly  Leu   Pro  Val  Glu  Gly  Gln  Asn  Gly  Ser  Ala  Ala  His  Gln  Gln
           1085                1090                1095

Pro  Trp   Leu  Gly  Leu  Arg  Ala  Phe  Met  Thr  Val  Asp  Gln  Ser  Ser
           1100                1105                1110

Leu  Trp   Pro  Ile  Pro  Thr  Thr  Met  Arg  Val  Gln  Trp  Asp  Glu
           1115                1120                1125
```

<210> SEQ ID NO 67
<211> LENGTH: 1165
<212> TYPE: PRT
<213> ORGANISM: Gaeumannomyces graminis

<400> SEQUENCE: 67

```
Met  Thr  Val  Ser  Thr  His  His  Asp  Asp  Ser  Pro  Gly  Leu  Ser  Gly  Arg
1                  5                   10                  15

Leu  Arg  Asp  Leu  Leu  His  His  Val  Phe  Gly  Asn  Gln  Lys  Ser  Pro  Thr
                 20                  25                  30

Val  Tyr  Pro  Asn  Ala  Pro  Gly  Asn  Ser  Ala  Lys  Pro  Val  Pro  Thr  Gly
             35                  40                  45

Leu  Ala  Asp  Asp  Ile  Asp  Lys  Leu  Gly  Phe  Lys  Asp  Ile  Asp  Thr  Leu
         50                  55                  60

Leu  Ile  Phe  Leu  Asn  Ser  Ala  Val  Lys  Gly  Val  Asn  Asp  Asp  Gln  Gln
65                   70                  75                  80

Phe  Leu  Leu  Glu  Lys  Met  Ile  Gln  Leu  Leu  Ala  Lys  Leu  Pro  Pro  Ala
                 85                  90                  95

Ser  Arg  Glu  Gly  Lys  Lys  Leu  Thr  Asp  Gly  Leu  Ile  Asn  Asp  Leu  Trp
            100                 105                 110

Asp  Ser  Leu  Asp  His  Pro  Val  Ala  Ser  Leu  Gly  Lys  Gly  Phe  Ser
            115                 120                 125

Phe  Arg  Glu  Pro  Asp  Gly  Ser  Asn  Asn  Asn  Ile  His  Leu  Pro  Ser  Leu
        130                 135                 140

Gly  Ala  Ala  Asn  Thr  Pro  Tyr  Ala  Arg  Ser  Thr  Lys  Pro  Leu  Val  Phe
145                 150                 155                 160

Gln  Asn  Pro  Asn  Pro  Pro  Asp  Pro  Ala  Thr  Ile  Phe  Asp  Thr  Leu  Met
                165                 170                 175

Val  Arg  Asp  Pro  Ala  Lys  Phe  Arg  Pro  His  Pro  Asn  Lys  Ile  Ser  Ser
            180                 185                 190

Met  Leu  Phe  Tyr  Leu  Ala  Thr  Ile  Ile  Thr  His  Asp  Ile  Phe  Gln  Thr
        195                 200                 205

Ser  Pro  Arg  Asp  Phe  Asn  Ile  Asn  Leu  Thr  Ser  Ser  Tyr  Leu  Asp  Leu
    210                 215                 220

Ser  Pro  Leu  Tyr  Gly  Arg  Asn  His  Asp  Glu  Gln  Met  Ala  Val  Arg  Thr
225                 230                 235                 240

Gly  Lys  Asp  Gly  Leu  Leu  Lys  Pro  Asp  Thr  Phe  Ser  Ser  Lys  Arg  Val
                245                 250                 255

Ile  Gly  Phe  Pro  Pro  Gly  Val  Gly  Ala  Phe  Leu  Ile  Met  Phe  Asn  Arg
            260                 265                 270

Phe  His  Asn  Tyr  Val  Val  Thr  Gln  Leu  Ala  Lys  Ile  Asn  Glu  Gly  Gly
        275                 280                 285

Arg  Phe  Lys  Arg  Pro  Thr  Thr  Pro  Asp  Asp  Thr  Ala  Gly  Trp  Glu  Thr
    290                 295                 300
```

-continued

Tyr Asp Asn Ser Leu Phe Gln Thr Gly Arg Leu Ile Thr Cys Gly Leu
305                 310                 315                 320

Tyr Ile Asn Ile Val Leu Gly Asp Tyr Val Arg Thr Ile Leu Asn Leu
            325                 330                 335

Asn Arg Ala Asn Thr Thr Trp Asn Leu Asp Pro Arg Thr Lys Glu Gly
        340                 345                 350

Lys Ser Leu Leu Ser Lys Pro Thr Pro Glu Ala Val Gly Asn Gln Val
            355                 360                 365

Ser Val Glu Phe Asn Leu Ile Tyr Arg Trp His Cys Thr Ile Ser Glu
370                 375                 380

Arg Asp Asp Lys Trp Thr Thr Asn Ala Met Arg Glu Ala Leu Gly Gly
385                 390                 395                 400

Gln Asp Pro Ala Thr Ala Lys Met Glu Asp Val Met Arg Ala Leu Gly
                405                 410                 415

Met Phe Glu Lys Asn Ile Pro Asp Glu Pro Glu Lys Arg Thr Leu Ala
                420                 425                 430

Gly Leu Thr Arg Gln Ser Asp Gly Ala Phe Asp Thr Glu Leu Val
            435                 440                 445

Lys Ile Leu Gln Glu Ser Ile Glu Asp Val Ala Gly Ala Phe Gly Pro
450                 455                 460

Asn His Val Pro Ala Cys Met Arg Ala Ile Glu Ile Leu Gly Ile Lys
465                 470                 475                 480

Gln Ser Arg Thr Trp Asn Val Ala Thr Leu Asn Glu Phe Arg Gln Phe
            485                 490                 495

Ile Gly Leu Thr Pro His Asp Ser Phe Tyr His Met Asn Pro Asp Pro
            500                 505                 510

Lys Ile Cys Lys Ile Leu Ala Gln Met Tyr Asp Ser Pro Asp Ala Val
            515                 520                 525

Glu Leu Tyr Pro Gly Ile Met Ala Glu Ala Lys Pro Pro Phe Ser
530                 535                 540

Pro Gly Ser Gly Leu Cys Pro Pro Tyr Thr Thr Ser Arg Ala Ile Leu
545                 550                 555                 560

Ser Asp Ala Val Ser Leu Val Arg Gly Asp Arg Phe Tyr Thr Val Asp
            565                 570                 575

Tyr Thr Pro Arg Asn Ile Thr Asn Trp Gly Phe Asn Glu Ala Ser Thr
            580                 585                 590

Asp Lys Ala Val Asp Trp Gly His Val Ile Tyr Lys Leu Phe Phe Arg
            595                 600                 605

Ala Phe Pro Asn His Phe Leu Pro Asn Ser Val Tyr Ala His Phe Pro
610                 615                 620

Phe Val Val Pro Ser Glu Asn Lys Leu Ile Phe Glu Gly Leu Gly Ala
625                 630                 635                 640

Ala Asn Lys Tyr Ser Trp Asp Pro Pro Lys Ala Arg Ala Pro Ile Gln
            645                 650                 655

Phe Ile Arg Ser His Lys Ala Val Leu Glu Val Leu Ser Asn Gln Lys
            660                 665                 670

Asp Tyr Lys Val Thr Trp Gly Pro Ala Ile Lys Met Leu Ser Gly Asp
            675                 680                 685

Pro Ala Thr Ser Phe Ala Leu Ala Gly Asp Glu Pro Ala Asn Ala Ala
            690                 695                 700

Ser Arg His His Val Ile Ala Ala Leu Thr Ala Pro Lys Gln Trp Arg
705                 710                 715                 720

Asp Glu Val Arg Arg Phe Tyr Glu Val Thr Thr Arg Asp Leu Leu Arg

```
              725                 730                 735
Arg His Gly Ala Pro Val His Gly Val Gly Ala Gly Pro Arg Thr His
                740                 745                 750
Glu Val Asp Val Ile Arg Asp Val Ile Gly Leu Ala His Ala Arg Phe
                755                 760                 765
Met Ala Ser Leu Phe Ser Leu Pro Leu Lys Glu Gly Lys Glu Glu
    770                 775                 780
Gly Ala Tyr Gly Glu His Glu Leu Tyr Arg Ser Leu Val Thr Ile Phe
785                 790                 795                 800
Ala Ala Ile Phe Trp Asp Ser Asp Val Cys Asn Ser Leu Lys Leu His
                805                 810                 815
Gln Ala Ser Lys Ala Ala Asp Lys Met Ser Ala Leu Ile Ala Glu
                820                 825                 830
His Val Arg Glu Met Glu Ala Gly Thr Gly Phe Leu Gly Ala Leu Gly
                835                 840                 845
Lys Leu Lys Asp Leu Ile Thr Gly Asn Asp Val His Ala Asn Gly Asn
850                 855                 860
Gly Val Tyr Thr Asn Gly Asn Gly Val Tyr Thr Asn Gly Asn Gly Val
865                 870                 875                 880
His Thr Asn Gly Asn Gly Val His Thr Asn Gly Asn Gly Val Pro His
                885                 890                 895
Ala Ala Pro Ser Leu Arg Ser Phe Gly Asp Gln Leu Leu Gln Arg Met
                900                 905                 910
Leu Ser Gln Asp Gly Arg Ser Ile Glu Glu Thr Val Ser Gly Thr Ile
                915                 920                 925
Leu Pro Val Val Met Ala Gly Thr Ala Asn Gln Thr Gln Leu Leu Ala
930                 935                 940
Gln Cys Leu Asp Tyr Tyr Leu Gly Val Gly Glu Lys His Leu Pro Glu
945                 950                 955                 960
Met Lys Arg Leu Ala Met Leu Asn Thr Ser Glu Ala Asp Glu Lys Leu
                965                 970                 975
Leu Lys Tyr Thr Met Glu Gly Cys Arg Ile Arg Gly Cys Val Ala Leu
                980                 985                 990
Tyr Arg Ala Val Val Thr Asp Gln Ala Val Asp Asp Thr Ile Pro Cys
                995                 1000                1005
Ile Pro Asn Lys Asp Asp Pro Thr Phe Ala Arg Pro Leu Ser Asn
    1010                1015                1020
Pro Gln Val Ala Glu Ser Ala Arg Thr Leu Lys Leu Ser Thr Gly
    1025                1030                1035
Thr Arg Met Leu Val Asp Leu Thr Thr Ala Ser His Asp Pro Ala
    1040                1045                1050
Ala Phe Pro Asp Pro Asp Glu Val Arg Leu Asp Arg Pro Leu Glu
    1055                1060                1065
Ser Tyr Val His Phe Gly Leu Gly Pro His Arg Cys Ala Gly Glu
    1070                1075                1080
Pro Ile Ser Gln Ile Ala Leu Ser Ser Val Met Lys Val Leu Leu
    1085                1090                1095
Gln Leu Asp Gly Leu Arg Arg Ala Ala Gly Pro Arg Gly Glu Ile
    1100                1105                1110
Arg Ser Tyr Pro Ala Ser Gln Trp Pro Gly Gln Ala Gly Arg Pro
    1115                1120                1125
Pro Arg Asp Pro Ala Trp Ser Gly Leu Arg Thr Phe Thr Ser Ala
    1130                1135                1140
```

Asp Gln Ser Ala Phe Ser Pro Leu Ala Thr Thr Met Lys Ile Asn
        1145               1150                1155

Trp Glu Gly Arg Gly Asp Leu
        1160            1165

<210> SEQ ID NO 68
<211> LENGTH: 1171
<212> TYPE: PRT
<213> ORGANISM: Magnaporthe oryzae

<400> SEQUENCE: 68

Met Ala Ser Ser Ser Ser Gly Ser Ser Thr Arg Ser Ser Ser Pro
1               5                   10                  15

Ser Asp Pro Pro Ser Ser Phe Phe Gln Lys Leu Gly Ala Phe Leu Gly
            20                  25                  30

Leu Phe Ser Lys Pro Gln Pro Pro Arg Pro Asp Tyr Pro His Ala Pro
            35                  40                  45

Gly Asn Ser Ala Arg Glu Glu Gln Thr Asp Ile Thr Glu Asp Ile Gln
    50                  55                  60

Lys Leu Gly Phe Lys Asp Val Glu Thr Leu Leu Leu Tyr Leu Asn Ser
65                  70                  75                  80

Ser Val Lys Gly Val Asn Asp Asp Lys Gln Leu Leu Leu Glu Arg Leu
                85                  90                  95

Ile Gln Leu Leu Ser Lys Leu Pro Pro Thr Ser Thr Asn Gly Lys Lys
            100                 105                 110

Val Thr Asp Gly Leu Ile Thr Gly Leu Trp Glu Ser Leu Asp His Pro
            115                 120                 125

Pro Val Ser Ser Leu Gly Glu Lys Tyr Arg Phe Arg Glu Ala Asp Gly
            130                 135                 140

Ser Asn Asn Asn Ile His Asn Pro Thr Leu Gly Val Ala Gly Ser His
145                 150                 155                 160

Tyr Ala Arg Ser Ala Lys Pro Met Val Tyr Gln Asn Pro Asn Pro Pro
                165                 170                 175

Ala Pro Glu Thr Ile Phe Asp Thr Leu Met Ala Arg Asp Pro Ala Lys
            180                 185                 190

Phe Arg Pro His Pro Asn Gln Ile Ser Ser Val Leu Phe Tyr Phe Ala
            195                 200                 205

Thr Ile Ile Thr His Asp Ile Phe Gln Thr Ser Ser Arg Asp Pro Ser
            210                 215                 220

Ile Asn Leu Thr Ser Ser Tyr Leu Asp Leu Ser Pro Leu Tyr Gly Arg
225                 230                 235                 240

Asn Leu Glu Glu Gln Leu Ser Val Arg Ala Met Lys Asp Gly Leu Leu
                245                 250                 255

Lys Pro Asp Thr Phe Cys Ser Lys Arg Val His Gly Phe Pro Pro Gly
            260                 265                 270

Val Gly Val Leu Leu Ile Met Phe Asn Arg Phe His Asn Tyr Val Val
            275                 280                 285

Thr Ser Leu Ala Lys Ile Asn Glu Gly Asn Arg Phe Lys Lys Pro Val
            290                 295                 300

Gly Asp Asp Thr Ala Ala Trp Glu Lys Tyr Asp Asn Asp Leu Phe Gln
305                 310                 315                 320

Thr Gly Arg Leu Ile Thr Cys Gly Leu Tyr Val Asn Ile Val Leu Val
            325                 330                 335

Asp Tyr Val Arg Thr Ile Leu Asn Leu Asn Arg Val Asp Ser Ser Trp

```
               340                 345                 350
Ile Leu Asp Pro Arg Thr Glu Glu Gly Lys Ser Leu Leu Ser Lys Pro
            355                 360                 365

Thr Pro Glu Ala Val Gly Asn Gln Val Ser Val Glu Phe Asn Leu Ile
        370                 375                 380

Tyr Arg Trp His Cys Gly Met Ser Gln Arg Asp Asp Lys Trp Thr Thr
385                 390                 395                 400

Asp Met Leu Thr Glu Ala Leu Gly Gly Lys Asp Pro Ala Thr Ala Thr
                405                 410                 415

Leu Pro Glu Phe Phe Gly Ala Leu Gly Arg Phe Glu Ser Ser Phe Pro
            420                 425                 430

Asn Glu Pro Glu Lys Arg Thr Leu Ala Gly Leu Lys Arg Gln Glu Asp
        435                 440                 445

Gly Ser Phe Glu Asp Glu Gly Leu Ile Lys Ile Met Gln Glu Ser Ile
    450                 455                 460

Glu Glu Val Ala Gly Ala Phe Gly Pro Asn His Val Pro Ala Cys Met
465                 470                 475                 480

Arg Ala Ile Glu Ile Leu Gly Met Asn Gln Ala Arg Ser Trp Asn Val
                485                 490                 495

Ala Thr Leu Asn Glu Phe Arg Glu Phe Ile Gly Leu Lys Arg Tyr Asp
            500                 505                 510

Thr Phe Glu Asp Ile Asn Pro Asp Pro Lys Val Ala Asn Leu Leu Ala
        515                 520                 525

Glu Phe Tyr Gly Ser Pro Asp Ala Val Glu Leu Tyr Pro Gly Ile Asn
    530                 535                 540

Ala Glu Ala Pro Lys Pro Val Ile Val Pro Gly Ser Gly Leu Cys Pro
545                 550                 555                 560

Pro Ser Thr Thr Gly Arg Ala Ile Leu Ser Asp Ala Val Thr Leu Val
                565                 570                 575

Arg Gly Asp Arg Phe Phe Thr Val Asp Tyr Thr Pro Arg Asn Leu Thr
            580                 585                 590

Asn Phe Gly Tyr Gln Glu Ala Ala Thr Asp Lys Ser Val Asp Asn Gly
        595                 600                 605

Asn Val Ile Tyr Lys Leu Phe Phe Arg Ala Phe Pro Asn His Tyr Ala
    610                 615                 620

Gln Asn Ser Ile Tyr Ala His Phe Pro Phe Val Ile Pro Ser Glu Asn
625                 630                 635                 640

Lys Lys Ile Met Glu Ser Leu Gly Leu Ala Asp Lys Tyr Ser Trp Gln
                645                 650                 655

Pro Pro Gln Arg Lys Pro Ala Thr Gln Met Ile Arg Ser His Ala Ala
            660                 665                 670

Ala Val Lys Ile Leu Asn Asn Gln Lys Asp Phe Lys Val Val Trp Gly
        675                 680                 685

Glu Ser Ile Gly Phe Leu Thr Lys Phe Pro Thr Gly Glu Asn Pro Gly
    690                 695                 700

Leu Gly Phe Ala Leu Ala Gly Asp Ala Pro Ala Asn Gln Gln Ser Arg
705                 710                 715                 720

Asp Gln Leu Met Lys Cys Ile Phe Ser Pro Lys Ala Trp Glu Asp Glu
                725                 730                 735

Val Arg Gln Phe Cys Glu Ala Thr Thr Trp Asp Leu Leu Arg Arg Tyr
            740                 745                 750

Ser Ala Lys Val Gln Asp Lys Gly Pro His Leu Lys Val His Thr His
        755                 760                 765
```

-continued

```
Glu Ile Asp Val Ile Arg Asp Val Ile Ser Leu Ala Asn Ala Arg Phe
    770             775             780

Phe Ala Ala Val Tyr Ser Leu Pro Leu Lys Thr Glu Asn Gly Asp Asp
785             790             795             800

Gly Val Tyr Ser Asp His Glu Met Tyr Arg Ser Leu Met Leu Ile Phe
            805             810             815

Ser Ala Ile Phe Trp Asp Asn Asp Val Ser Lys Ser Phe Lys Leu Arg
        820             825             830

Arg Asp Ala Arg Ala Ala Thr Gln Lys Leu Gly Ala Leu Val Glu Lys
    835             840             845

His Ile Val Glu Met Gly Ser Leu Phe His Ser Phe Lys His Ser His
    850             855             860

Ser Ala Val Ser Asp Lys Thr Asn Gly Leu Ala Asn Gly Gly Ala Asn
865             870             875             880

Gly His Ala Asn Gly Asn Ala Asn Gly His Thr Asn Gly Asn Gly Ile
            885             890             895

His Gln Asn Gly Gly Ala Ala Pro Ser Met Leu Arg Ser Tyr Gly Asp
        900             905             910

Leu Met Leu Arg Arg Met Ile Glu Ala Tyr Gly Glu Gly Lys Ser Val
        915             920             925

Lys Glu Ala Val Tyr Gly Gln Ile Met Pro Ser Ile Ala Ala Gly Thr
    930             935             940

Ala Asn Gln Thr Gln Ile Met Ala Gln Cys Leu Asp Tyr Tyr Met Ser
945             950             955             960

Asp Asp Gly Ala Glu His Leu Pro Glu Met Lys Arg Leu Ala Ser Leu
            965             970             975

Glu Thr Pro Glu Ala Phe Asn Thr Leu Met Lys Tyr Leu Phe Glu Gly
        980             985             990

Ala Arg Ile Arg Asn Thr Thr Ala  Val Pro Arg Leu Val  Ala Thr Asp
        995             1000            1005

Gln Thr  Val Glu Asp Asn Ile  Pro Cys Leu Pro Asp  Pro Lys Asp
    1010            1015            1020

Ser Thr  Phe Leu Arg Pro Ile  Pro Asn Pro Gln Gln  Ala Glu Thr
    1025            1030            1035

Thr Arg  Thr Val Lys Leu Ser  Arg Gly Ser Met Val  Leu Val Asp
    1040            1045            1050

Leu Thr  Val Ala Ala His Asp  Ala Thr Ala Phe Pro  Asp Pro Glu
    1055            1060            1065

Lys Val  Arg Leu Asp Arg Asp  Leu Asp Ser Tyr Thr  Phe Phe Gly
    1070            1075            1080

Leu Gly  Pro His Arg Cys Ala  Gly Asp Lys Val Val  Arg Ile Thr
    1085            1090            1095

Met Thr  Ala Val Phe Lys Val  Leu Leu Gln Leu Asp  Gly Leu Arg
    1100            1105            1110

Arg Ala  Glu Gly Gly Arg Gly  Val Phe Lys Ser Leu  Pro Ala Ser
    1115            1120            1125

Gln Trp  Asn Gly Gln Ala Gly  Arg Val Ala Gly Glu  Lys Pro Gln
    1130            1135            1140

Trp Ser  Gly Leu Arg Thr Tyr  Val Asn Ala Asp Glu  Ser Ala Phe
    1145            1150            1155

Ser Gln  Thr Pro Met Asn Met  Lys Ile Arg Trp Asp  Asp
    1160            1165            1170
```

<210> SEQ ID NO 69
<211> LENGTH: 1079
<212> TYPE: PRT
<213> ORGANISM: Penicillium oxalicum

<400> SEQUENCE: 69

```
Met Val Gly His His Gly Ser Glu Thr His Gly Glu Lys Ser Pro Leu
1               5                   10                  15

Val Gln Ile Glu Gln Val Phe Lys Ala Ala Leu Arg Pro Leu Pro Thr
            20                  25                  30

Glu Thr Gly Asp Gly Thr Tyr Val Lys Asp Thr Lys Leu Thr Gly Leu
        35                  40                  45

Ala Gln Asp Leu Ser His Val Asp Leu Val Asp Val Lys Thr Leu Ala
    50                  55                  60

Asp Val Ala Lys Asn Ala Ile Thr Gly Glu Ala Met Asn Asp Arg Glu
65                  70                  75                  80

Tyr Ile Met Glu Arg Val Ile Gln Leu Ala Ala Gly Leu Pro Thr Thr
                85                  90                  95

Ser Lys Asn Gly Arg Asp Leu Thr Asn Thr Phe Leu Ser Thr Leu Trp
            100                 105                 110

Asn Asp Leu Gln His Pro Pro Thr Ser Tyr Leu Gly Arg Asp Ser Ala
        115                 120                 125

Tyr Arg Gln Ala Asp Gly Ser Gly Asn Asn Pro Phe Trp Pro Asn Ile
    130                 135                 140

Gly Ala Ala Gly Thr Pro Tyr Ala Arg Ser Val Arg Pro Gln Thr Met
145                 150                 155                 160

Gln Pro Gly Ala Leu Pro Glu Pro Glu Thr Leu Phe Asp Ser Leu Leu
                165                 170                 175

Ala Arg Gln Lys Phe Lys Glu His Pro Asn Lys Ile Ser Ser Val Leu
            180                 185                 190

Phe Tyr Leu Ala Ser Ile Ile Ile His Asp Leu Phe Gln Thr Asp Pro
        195                 200                 205

Arg Asn Pro Thr Val Ser Leu Ser Ser Ser Tyr Leu Asp Leu Gly Pro
    210                 215                 220

Leu Tyr Gly Asn Asn Gln Asp Glu Gln Asn Ala Val Arg Thr Phe Lys
225                 230                 235                 240

Asp Gly Lys Leu Lys Pro Asp Cys Phe Ser Ser Lys Arg Ile Leu Gly
                245                 250                 255

Phe Pro Pro Gly Val Gly Val Leu Leu Ile Met Phe Asn Arg Phe His
            260                 265                 270

Asn Tyr Val Ala Glu Gln Leu Ala Gln Ile Asn Glu Gly Gly Arg Phe
        275                 280                 285

Thr Lys Pro Ala Glu Ser Asn Thr Lys Ala Tyr Ala Thr Trp Asp Asn
    290                 295                 300

Asp Leu Phe Gln Thr Ser Arg Leu Val Thr Cys Gly Leu Tyr Val Asn
305                 310                 315                 320

Ile Ile Leu Lys Asp Tyr Val Arg Thr Ile Leu Asn Ile Asn Arg Thr
                325                 330                 335

Asp Ser Thr Trp Ser Leu Asp Pro Arg Ala Glu Met Lys Asp Gly Val
            340                 345                 350

Leu Ser His Ala Ala Lys Gln Ala Thr Gly Asn Gln Val Ser Ala Glu
        355                 360                 365

Phe Asn Leu Val Tyr Arg Trp His Ser Cys Ile Ser Ala Arg Asp Gln
    370                 375                 380
```

```
Gln Trp Ser Glu Asp Leu Tyr Arg Glu Leu Phe Asn Gly Gln Asp Pro
385                 390                 395                 400

Asn Thr Leu Ser Thr Gln Gln Phe Ile Met Gly Val Gly Arg Trp Glu
            405                 410                 415

Gly Thr Leu Pro Gln Asp Pro Met Glu Arg Pro Phe Ala Lys Leu Gln
        420                 425                 430

Arg Gln Ala Asp Gly Arg Phe Ser Asp Asp Leu Val Arg Phe Phe
    435                 440                 445

Glu Glu Ser Val Glu Asp Val Ala Gly Ala Phe Gly Ala Ser Asn Val
450                 455                 460

Pro Thr Val Phe Arg Thr Ile Glu Val Leu Gly Ile Lys Gln Ala Arg
465                 470                 475                 480

Ser Trp Asn Leu Ala Thr Leu Asn Glu Phe Arg Ser Phe Phe Asn Leu
            485                 490                 495

Gln Pro Tyr Lys Thr Phe Glu Glu Ile Asn Ser Asp Pro Tyr Ile Ala
            500                 505                 510

Asp Gln Leu Arg His Leu Tyr Asp His Pro Asp Gln Val Glu Leu Tyr
            515                 520                 525

Pro Gly Leu Val Val Glu Asp Ala Lys Glu Pro Met Leu Pro Gly Ser
    530                 535                 540

Gly Leu Cys Thr Asn Tyr Thr Thr Ser Arg Ala Ile Leu Ser Asp Ala
545                 550                 555                 560

Val Thr Leu Val Arg Gly Asp Arg Phe Tyr Thr Val Asp Tyr Thr Pro
                565                 570                 575

Lys His Leu Thr Asn Trp Ala Phe Asn Glu Ile Ser Tyr Asp Asp Ser
            580                 585                 590

Val Asp Asn Gly Ala Ile Phe Tyr Lys Leu Val Leu Arg Ala Phe Pro
            595                 600                 605

Asn His Val Arg Gly Asp Ser Val Tyr Ala His Phe Pro Met Val Val
        610                 615                 620

Pro Ser Glu Asn Lys Lys Ile Leu Thr Ser Leu Gly Lys Ser Glu Lys
625                 630                 635                 640

Tyr Ser Tyr Ser Arg Pro Thr Tyr Thr Pro Pro Arg Met Ile Lys
                645                 650                 655

Ser His Gly Ala Cys Met Ser Ile Leu Ala Asp Lys Glu Thr Phe Lys
            660                 665                 670

Val Thr Trp Gly Gln Lys Leu Glu Phe Ile Leu Ser Arg Asp Gly His
            675                 680                 685

Ser Tyr Gly Gly Asp Phe Met Leu Ser Gly Asp Lys Ala Pro His Ala
        690                 695                 700

Gln Ser Arg Lys Met Ile Gly Asn Ala Leu Tyr Arg Asp Gln Trp Lys
705                 710                 715                 720

Ser Glu Val Arg Ser Phe Tyr Glu Ser Ile Thr Leu Gln Leu Leu Arg
                725                 730                 735

Gln Lys Ser Tyr Lys Leu Ala Gly Val Asn Gln Val Asp Ile Val Arg
            740                 745                 750

Asp Val Ser Asn Leu Ala Gln Ile His Phe Cys Ala Asn Ile Phe Ser
            755                 760                 765

Leu Pro Leu Lys Thr Glu Ser Asn Pro His Gly Val Phe Thr Glu Gln
        770                 775                 780

Glu Leu Tyr Glu Ile Met Ala Leu Val Phe Thr Cys Ile Phe Tyr Asp
785                 790                 795                 800
```

-continued

```
Val Glu Val Thr Lys Ser Phe Gln Leu Glu Gln Ala Ser Arg Gln Val
            805                 810                 815

Ala Gln Gln Leu Gly Glu Leu Val Met Ala Asn Val Asp Leu Val Ser
        820                 825                 830

Lys Ser Gly Phe Val Ala Asp Ile Ile Ser Arg Leu Arg Arg His Glu
    835                 840                 845

His Leu Thr Asp Tyr Gly Val His Met Ile Gln Arg Leu Leu Asp Ser
850                 855                 860

Gly Leu Pro Pro Lys Glu Ile Val Trp Thr His Ile Leu Pro Ser Ala
865                 870                 875                 880

Ser Ser Met Val Ala Asn Gln Ala Gln Leu Phe Ile Gln Cys Leu Asp
            885                 890                 895

Phe Tyr Leu Lys Pro Glu Asn Ala His His Leu Ala Asp Ile Gln Arg
        900                 905                 910

Leu Ser Lys Glu Asp Thr Pro Glu Ser Asp Glu Leu Leu Leu Arg Tyr
    915                 920                 925

Phe Met Glu Gly Gly Arg Ile Cys Ser Ser Val Ala Leu Pro Arg Val
930                 935                 940

Val Ala Lys Ser Thr Val Ile Glu Asp Asn Gly Glu Gln Val Ser Leu
945                 950                 955                 960

Lys Glu Gly Glu Ala Ile Phe Leu Asn Leu Val Ser Ala Ser His Asp
            965                 970                 975

Pro Lys Ala Trp Pro Asp Pro Glu Glu Val Arg Leu Asp Arg Asp Leu
        980                 985                 990

Asn Gln Tyr Ala His Phe Gly Phe  Gly Pro His Gln Cys  Leu Gly Leu
    995                 1000                1005

Gly Val  Cys Gln Val Ala Leu  Pro Thr Met Leu Arg  Val Val Gly
    1010                1015                1020

Gln Leu  Gln Asn Leu Arg Arg  Ala Pro Gly Leu Gln  Gly Gln Leu
    1025                1030                1035

Lys Lys  Leu Pro Ala Leu Gly  Gly Leu Thr Met Tyr  Met Asp Ala
    1040                1045                1050

Asp His  Ser Ser Ile Ser Pro  Tyr Pro Ser Thr Met  Lys Ile Gln
    1055                1060                1065

Trp Asp  Gly Glu Leu Pro Lys  Ala Arg Tyr Thr
    1070                1075

<210> SEQ ID NO 70
<211> LENGTH: 1074
<212> TYPE: PRT
<213> ORGANISM: Penicillium chrysogenum

<400> SEQUENCE: 70

Met Ala Glu Lys Glu Ser Asn Ser Ser Gly Lys Ile Ala Gln Leu Glu
1               5                   10                  15

Gln Val Val Ala Ala Ala Leu Arg Pro Leu Pro Thr Gln Thr Gly Asp
            20                  25                  30

Gly Ser Tyr Val Gln Glu Pro Thr Val Thr Gly Leu Ala Lys Asp Leu
        35                  40                  45

Leu Asn Phe Asp Leu Lys Asp Ala Lys Thr Leu Ala Asp Met Ala Lys
    50                  55                  60

Thr Ala Val Thr Gly Lys Ala Val Asn Asp Arg Asp Tyr Ile Met Glu
65                  70                  75                  80

Arg Val Ile Gln Leu Ala Ser Gly Leu Pro Ser Thr Ser Arg Asn Gly
            85                  90                  95
```

```
Lys Glu Leu Thr Asn Thr Phe Leu Thr Gln Leu Trp Gly Asp Leu Glu
            100                 105                 110

His Pro Pro Ile Ser Tyr Leu Gly Arg Asp Ala Ala Tyr Arg Lys Ala
            115                 120                 125

Asp Gly Ser Gly Asn Asn Thr Phe Trp Pro Gln Ile Gly Ala Ala Asn
            130                 135                 140

Thr Pro Tyr Ala Arg Ser Val Arg Pro Lys Thr Met Gln Pro Val Ala
145                 150                 155                 160

Leu Pro Glu Pro Glu Ala Leu Phe Asp Ser Leu Leu Ala Arg Lys Asp
                165                 170                 175

Phe Lys Glu His Pro Asn Lys Ile Ser Ser Val Leu Phe His Leu Ala
            180                 185                 190

Ser Ile Ile His Asp Leu Phe Gln Thr Asp Pro Arg Asp Gln Thr
            195                 200                 205

Lys Ser Leu Thr Ser Ser Tyr Leu Asp Leu Ser Pro Leu Tyr Gly Asn
            210                 215                 220

Asn Gln Lys Glu Gln Asp Thr Val Arg Ala Phe Lys Asp Gly Lys Leu
225                 230                 235                 240

Lys Pro Asp Cys Phe Ser Thr Lys Arg Val Leu Gly Phe Pro Pro Gly
            245                 250                 255

Val Gly Val Ile Leu Ile Met Phe Asn Arg Phe His Asn Ser Val Val
            260                 265                 270

Thr Gln Leu Ala Ala Ile Asn Glu Gly Gly Arg Phe Thr Lys Pro Asp
            275                 280                 285

Glu Ser Asn Ala Glu Ala Tyr Ala Thr Trp Asp Asn Asp Leu Phe Gln
            290                 295                 300

Thr Ala Arg Leu Val Thr Cys Gly Leu Tyr Ile Asn Ile Ile Leu Lys
305                 310                 315                 320

Asp Tyr Val Arg Thr Ile Leu Asn Val Asn Arg Thr Asp Ser Leu Trp
            325                 330                 335

Ser Leu Asp Pro Arg Ala Asp Ile Arg Asp Gly Leu Leu Gly Glu Ala
            340                 345                 350

Pro Ala Gln Ala Thr Gly Asn Gln Val Ser Ala Glu Phe Asn Leu Val
            355                 360                 365

Tyr Arg Trp His Ser Cys Val Ser Ser Arg Asp Glu Lys Trp Ser Glu
            370                 375                 380

Asp Leu Tyr Lys Glu Ile Phe Asp Gly Lys Asp Pro Lys Glu Ile Ser
385                 390                 395                 400

Met Gln Gln Phe Thr Gly Gly Leu Arg Gln Trp Glu Ser Lys Leu Pro
                405                 410                 415

Ala Asp Pro Gln Glu Arg Pro Phe Ala Lys Leu Gln Arg Gln Ala Asp
            420                 425                 430

Gly Lys Phe Asp Asp Asn Asp Leu Val Lys Ile Phe Glu Glu Ser Val
            435                 440                 445

Glu Asp Pro Ala Gly Ala Phe Gly Ala Leu Asn Val Pro Asp Val Phe
            450                 455                 460

Arg Gly Ile Glu Val Leu Gly Ile Lys Gln Ala Arg Ser Trp Asn Leu
465                 470                 475                 480

Ala Thr Leu Asn Glu Phe Arg Gln Tyr Phe Gly Leu Ala Ala Tyr Gln
            485                 490                 495

Thr Phe Glu Glu Ile Asn Pro Asp Pro Tyr Val Ala Asn Gln Leu Lys
            500                 505                 510
```

-continued

His Phe Tyr Asp His Pro Asp Leu Val Glu Leu Tyr Pro Gly Leu Val
              515                 520                 525

Val Glu Glu Thr Lys Gln Ala Met Thr Pro Gly Ser Gly Leu Cys Thr
    530                 535                 540

Asn Phe Thr Thr Ser Arg Ala Ile Leu Ser Asp Ala Val Ala Leu Val
545                 550                 555                 560

Arg Gly Asp Arg Phe Tyr Thr Val Asp Phe Thr Pro Lys His Leu Thr
                565                 570                 575

Asn Trp Ala Phe Asn Glu Ile Asn Asn Asp Val Ser Val Asp Gly Gly
                580                 585                 590

Gln Val Phe Tyr Lys Leu Ile Leu Lys Ala Phe Pro Asn His Phe Arg
            595                 600                 605

Gly Asp Ser Val Tyr Ala His Phe Pro Leu Val Val Pro Asp Glu Asn
        610                 615                 620

Lys Lys Ile Leu Thr Ser Leu Gly Lys Val Lys Thr Tyr Ser Phe Asp
625                 630                 635                 640

Arg Pro Phe Tyr Lys Ala Pro Pro Leu Phe Ile Asn Ser His Ser Ala
                645                 650                 655

Cys Thr Lys Ile Leu Lys Asp Gln Glu Gly Phe Lys Val Val Trp Gly
            660                 665                 670

Glu Lys Ile Gln Phe Leu Met Glu Asn Ser Gly Arg Pro Tyr Gly Arg
        675                 680                 685

Asp Phe Ala Leu Ser Gly Asp Leu Pro Ala Asn Ala Ser Arg Lys
        690                 695                 700

Met Ile Gly Ala Ala Leu His Arg Asp Lys Trp Glu Ser Glu Val Lys
705                 710                 715                 720

Ala Phe Tyr Glu Asp Ile Thr Leu Lys Leu Leu Glu Arg Asn Ser Phe
                725                 730                 735

Lys Val Ala Gly Val Asn Gln Val Asp Ile Val Arg Asp Val Ala Val
            740                 745                 750

Leu Ala Gln Val Asn Phe Cys Ala Asn Val Phe Ser Leu Ser Leu Lys
        755                 760                 765

Thr Glu Ser Asn Pro Arg Gly Val Phe Ser Glu Gln Glu Leu Tyr Gln
770                 775                 780

Ile Leu Ala Val Ile Phe Ala Ser Ile Phe Tyr Asp Val Asp Val Ser
785                 790                 795                 800

Lys Ser Leu Gln Leu Cys Gln Thr Ala Arg Asn Val Ala Gln Gln Leu
                805                 810                 815

Gly Glu Leu Thr Leu Ala Asn Val Glu Leu Val Ala Lys Thr Gly Phe
            820                 825                 830

Ile Ser Asn Leu Val Asn Arg Leu His Arg His Asp Ile Leu Ser Glu
        835                 840                 845

Tyr Gly Ile His Met Ile Gln Arg Leu Leu Asp Ser Gln Leu Pro Val
    850                 855                 860

Lys Asp Val Val Trp Ser His Ile Leu Pro Thr Ala Gly Ala Leu Val
865                 870                 875                 880

Ala Asn Gln Gly Gln Leu Phe Ser Gln Cys Ile Asp Tyr Tyr Leu Ser
                885                 890                 895

Glu Glu Ala Ala Glu His Leu Ala Glu Ile Gln Arg Leu Ser Arg Glu
            900                 905                 910

Asp Thr Pro Glu Ala Asp Glu Leu Leu Val Arg Tyr Phe Met Glu Gly
        915                 920                 925

Ala Arg Leu Arg Cys Ser Val Ala Leu Pro Arg Phe Ala Thr Lys Pro

-continued

```
                930                 935                 940
Thr Val Val Asp Asp Asn Gly Lys Arg Val Thr Leu Lys Ala Gly Gln
945                 950                 955                 960

Glu Ile Ile Cys Asn Leu Val Val Ala Gly Arg Asp Pro Val Ala Phe
                965                 970                 975

Pro Asp Pro Asp Lys Val Arg Leu Asp Arg Asp Met Ser Leu Tyr Thr
            980                 985                 990

His Phe Gly Phe Gly Pro His Glu Cys Leu Gly Val Lys Met Cys Pro
            995                 1000                1005

Leu Ala Leu Ser Thr Met Leu Lys Val Leu Gly Arg Leu Asp Asn
    1010                1015                1020

Val Arg Arg Ala Pro Gly Pro Gln Gly His Leu Lys Arg Leu Asp
    1025                1030                1035

Gly Leu Gly Gly Ile Ala Met Tyr Met Asp Ala Glu His Ser Ser
    1040                1045                1050

Phe Ser Pro Phe Pro Met Thr Met Lys Ile Gln Trp Asp Gly Asp
    1055                1060                1065

Leu Pro Ala Arg Arg Glu
    1070
```

<210> SEQ ID NO 71
<211> LENGTH: 1121
<212> TYPE: PRT
<213> ORGANISM: Penicillium digitatum

<400> SEQUENCE: 71

```
Met Leu Arg Arg Ile Ser Thr Gln Phe Lys Arg Ser Lys Asp Leu Lys
1               5                   10                  15

Asp Ser Lys Asp Phe Lys Asp Ser Asn Gly Glu Asn Thr Glu Asn Ser
            20                  25                  30

Thr Glu Lys Asn Ser Lys Arg Ala Ser Lys Val Ser Pro Thr Arg Lys
        35                  40                  45

Ser Phe Ser Ala Lys Glu Glu His His Val Val Lys Arg Ala Glu Val
50                  55                  60

Val Ala Val Phe Glu Lys Phe Ala Gln Ala Ile His Ala Ser Lys Glu
65                  70                  75                  80

Pro Leu Pro Asn Gln Thr Ser Asp Gly Ala Tyr Leu Lys His Asp Lys
                85                  90                  95

Ser Ser Gly Leu Ile Asn Asp Ile Lys Ser Leu Gly Phe Arg Glu Leu
            100                 105                 110

Asn Thr Val Lys Asp Leu Ile Ala Ser Lys Ala Ser Gly Glu Leu Val
        115                 120                 125

Asp Asp Lys Thr Tyr Leu Met Glu Arg Ile Ile Gln Met Val Ala Asp
    130                 135                 140

Leu Pro Gly Asn Ser Lys Asn Arg Thr Glu Leu Thr Ser Leu Phe Leu
145                 150                 155                 160

Asp Glu Leu Trp Asn Ser Ile Pro His Pro Leu Ser Tyr Met Gly
                165                 170                 175

Asp Glu Tyr Lys Tyr Arg Ser Ala Asp Gly Ser Asn Asn Pro Thr
            180                 185                 190

Leu Pro Trp Leu Gly Ala Ala Asn Thr Ala Tyr Cys Arg Thr Ile Pro
        195                 200                 205

Pro Leu Thr Ile Gln Pro Ser Gly Leu Pro Asp Ala Gly Leu Ile Phe
    210                 215                 220
```

```
Asp Thr Leu Phe Ala Arg Gln Glu Phe Thr Pro His Pro Asn Lys Val
225                 230                 235                 240

Ser Ser Val Phe Phe Asp Trp Ala Ser Leu Ile Ile His Asp Ile Phe
            245                 250                 255

Gln Thr Asp Tyr Arg Gln His Leu Asn Lys Thr Ser Ala Tyr Leu
        260                 265                 270

Asp Leu Ser Ile Leu Tyr Gly Asp Val Gln Glu Gln Asp Leu Ile
    275                 280                 285

Arg Ser His Gln Asp Gly Lys Leu Lys Pro Asp Cys Phe Ser Glu Gly
290                 295                 300

Arg Leu Gln Ala Leu Pro Ala Ala Cys Gly Val Leu Leu Val Met Leu
305                 310                 315                 320

Asn Arg Phe His Asn His Val Val Thr Gln Leu Ala Glu Ile Asn Glu
                325                 330                 335

Asn Gly Arg Phe Ser Lys Pro Arg Pro Gly Leu Ser Glu Glu Asp Ala
                340                 345                 350

Lys Lys Val Trp Thr Lys Arg Asp Glu Asp Leu Phe Gln Thr Gly Arg
            355                 360                 365

Leu Ile Thr Cys Gly Leu Tyr Ile Asn Ile Thr Leu Tyr Asp Tyr Leu
370                 375                 380

Arg Thr Ile Val Asn Leu Asn Arg Thr Asn Ser Thr Trp Cys Leu Asp
385                 390                 395                 400

Pro Arg Ala Gln Val Glu Lys Ala Gly Ala Thr Pro Ser Gly Leu Gly
                405                 410                 415

Asn Gln Cys Ser Val Glu Phe Asn Leu Ala Tyr Arg Trp His Ser Thr
                420                 425                 430

Ile Ser Gln Gly Asp Glu Lys Trp Ile Glu Gln Ile Tyr His Asp Leu
            435                 440                 445

Met Gly Lys Pro Ala Glu Glu Val Thr Met Pro Glu Leu Leu Met Gly
    450                 455                 460

Leu Lys Lys Val Glu Gly Leu Leu Asp Thr Asp Pro Ala Lys Arg Thr
465                 470                 475                 480

Phe Ala Arg Leu Gln Arg Asn Glu Asp Gly Phe Phe Asn Asp Gly Glu
                485                 490                 495

Leu Val Asn Ile Leu Thr His Ala Thr Glu Asp Val Ala Ser Ser Phe
            500                 505                 510

Gly Pro Arg Asn Val Pro Lys Ala Met Arg Ser Ile Glu Ile Leu Gly
        515                 520                 525

Ile Glu Ala Ser Arg Arg Trp Asn Val Gly Ser Leu Asn Glu Phe Arg
    530                 535                 540

Lys His Phe Gly Leu Lys Pro Tyr Glu Thr Phe Glu Glu Val Asn Ser
545                 550                 555                 560

Asn Pro Glu Ile Ser Asn Thr Leu Arg His Leu Tyr Asp His Pro Asp
                565                 570                 575

Phe Ile Glu Leu Tyr Pro Gly Ile Val Thr Glu Ala Lys Glu Pro
            580                 585                 590

Met Ile Pro Gly Val Gly Ile Ala Pro Thr Tyr Thr Ile Ser Arg Ala
        595                 600                 605

Val Leu Ser Asp Ala Val Ala Leu Val Arg Gly Asp Arg His Tyr Thr
    610                 615                 620

Ile Asp Tyr Asn Pro Arg Asn Leu Thr Asn Trp Gly Tyr Asn Glu Cys
625                 630                 635                 640

Arg Tyr Asp Leu Asn Ile Asn Gln Gly Cys Ile Phe Tyr Lys Leu Ala
```

```
            645                 650                 655
Thr Arg Ala Phe Pro Asn His Tyr Arg Pro Asp Ser Ile Tyr Ala His
            660                 665                 670

Tyr Pro Met Thr Ile Pro Ser Glu Asn Arg Asn Ile Met Lys Asp Leu
            675                 680                 685

Gly Arg Glu Gln Asp Tyr Ser Trp Asp Lys Pro Ala Phe Ile Glu Pro
            690                 695                 700

Arg Val Asn Leu Ala Ser His Gln Asn Ala Lys Leu Leu Glu Asn
705                 710                 715                 720

Gln Arg Asp Phe Arg Pro Ser Trp Ala Arg Ser Val Ser Glu Leu Phe
            725                 730                 735

Gly Lys Gly Glu Phe Asp Thr Lys Gln Arg Glu Ala Ile Gly Lys Ala
            740                 745                 750

Leu Asn Thr Glu Asp Phe Pro Lys Leu Val Lys Thr Phe Tyr Glu Asp
            755                 760                 765

Ile Thr Glu Arg Leu Ile Val Glu Lys Gly Gly Gln Leu Gly Lys Ile
            770                 775                 780

Asn Gln Ile Asp Ile Thr Arg Asp Val Gly Asn Leu Ala His Val His
785                 790                 795                 800

Phe Ala Ser Thr Ile Phe Gly Ile Pro Leu Lys Thr Glu Gln Ser Pro
            805                 810                 815

Gln Gly Leu Phe Thr Glu His Glu Met Tyr Met Ile Leu Ser Thr Ile
            820                 825                 830

Phe Ser Ala Leu Phe Phe Asp Val Asp Ala Pro Arg Ser Tyr Ala Leu
            835                 840                 845

Asn His Ala Ala Ser Ala Val Ser Thr Gln Leu Gly Gln Val Val Glu
850                 855                 860

Ala Thr Val Lys Ala Asp Thr Asn Ser Gly Leu Phe Ser Gly Ile Met
865                 870                 875                 880

Asp Ser Phe Arg Pro His Asp Asn Ala Leu Arg Glu Phe Gly Thr Glu
            885                 890                 895

Ala Val Arg Arg Met Lys Glu Ala Gly Ser Ser Ala Ser Asp Ile Thr
            900                 905                 910

Trp Ser Ala Ile Ile Pro Thr Ile Val Gly Leu Val Pro Ser Gln Gly
            915                 920                 925

Gln Val Phe Thr Gln Ile Ile Glu Phe Tyr Thr Ala Pro Glu Asn Gln
            930                 935                 940

Ala His Leu Ala Ala Ile His Ser Leu Thr Lys Thr Asp Ser Ala Glu
945                 950                 955                 960

Ser Asp Glu Lys Leu His Arg Tyr Cys Leu Glu Ala Ile Arg Leu Asn
            965                 970                 975

Gly Thr Phe Gly Ala Phe Arg Glu Ala Lys Glu Ala Val Thr Ile Glu
            980                 985                 990

Glu Asp Gly Lys Val Tyr Ala Val Gln Pro Gly Gln Gln Val Phe Ala
            995                 1000                1005

Ser Phe Asn Gln Ala Asn His Asp Pro Ser Val Phe Pro Glu Pro
            1010                1015                1020

Tyr Gln Val Asn Leu His Arg Pro Leu Asn Ser Tyr Ile Asn His
            1025                1030                1035

Gly Gln Gly Pro Thr Thr Gly Phe Gly Glu Gln Ile Thr Lys Ile
            1040                1045                1050

Ala Leu Val Ala Met Leu Arg Val Val Gly Arg Leu Gln Gly Leu
            1055                1060                1065
```

```
Arg  Arg  Ala  Ala  Gly  Ala  Gln  Gly  Gln  Leu  Gln  Lys  Ile  Pro  Gln
    1070               1075                    1080

Glu  Gly  Gly  Tyr  Tyr  Val  Tyr  Leu  Arg  Gly  Asp  Gly  Ala  Ala  Tyr
    1085               1090                    1095

Cys  Pro  Phe  Pro  Met  Ser  Leu  Lys  Leu  His  Trp  Asp  Gly  Pro  Val
    1100               1105                    1110

Gly  Gln  Lys  Lys  Thr  Pro  Ser  Ser
    1115               1120

<210> SEQ ID NO 72
<211> LENGTH: 805
<212> TYPE: PRT
<213> ORGANISM: Acaryochloris marina

<400> SEQUENCE: 72

Met  Asp  Ser  Arg  Asp  Pro  Arg  Thr  Glu  His  Val  Asp  Glu  Phe  Lys
1                    5                   10                   15

Lys  Leu  Ile  Ser  Asn  Ile  Ala  Arg  Ala  Phe  Gly  Arg  Thr  Ala  Gln  Ile
                20                   25                   30

Lys  Gly  Arg  Arg  Ala  Thr  His  Ser  Tyr  Gly  Thr  Val  Ala  Lys  Gly  Val
         35                   40                        45

Leu  Lys  Val  Leu  Asp  Thr  Leu  Asp  Ile  Pro  Gln  His  Gln  Ile  Phe  Ser
    50                   55                   60

Ala  Gly  Lys  Gln  Tyr  Pro  Val  Leu  Leu  Arg  His  Ala  Asn  Ile  Lys  Gly
65                   70                   75                        80

Phe  Arg  Asp  Asp  Ala  Ile  Leu  Asp  Gly  Arg  Gly  Ala  Thr  Val  Arg  Val
                85                   90                        95

Leu  Ala  Gly  Asp  Ala  Gln  Ala  Pro  Leu  Ser  Asp  Leu  Asn  Leu  Asp  Glu
              100                  105                  110

Gly  Ile  Val  Asp  Ile  Leu  Met  Ser  Thr  Gly  Arg  Ser  Phe  Ile  Leu  Ala
              115                  120                  125

Glu  Ala  Leu  Ser  Phe  Ala  Arg  Trp  Ala  Ala  Gly  Pro  Met  Lys  Ser  Arg
     130                  135                  140

Ala  Ala  Met  Leu  Gln  Glu  Phe  Pro  Lys  Ile  Ala  Pro  Ile  Phe  His  Glu
145                  150                  155                       160

Ile  Ile  Arg  Asp  Pro  Asp  Ser  Tyr  Thr  Gln  Leu  His  Tyr  Tyr  Ser  Glu
                165                  170                       175

Thr  Thr  Tyr  Ser  Phe  Thr  Ser  Leu  Asn  Gln  Gln  Ser  Phe  Phe  Leu  Arg
              180                  185                  190

Tyr  Arg  Leu  Val  Asn  Arg  Gln  Asn  Pro  Ser  Ala  Asp  Thr  Gly  Trp  Leu
         195                  200                  205

Lys  Pro  Glu  Glu  Val  Lys  Leu  Pro  Leu  Asp  Tyr  Leu  Pro  Arg  Val  Ala
    210                  215                  220

Ser  Asp  Thr  Arg  Pro  Glu  Thr  Tyr  Leu  Gln  Asp  Asp  Phe  Arg  Gln  Gln
225                  230                  235                       240

Val  Arg  Ser  Thr  Gly  Val  Ser  Tyr  Leu  Leu  Gln  Ile  Gln  Leu  Gln  Pro
                245                  250                       255

Val  Ser  Asp  Asp  Ala  Ala  Met  Asn  Glu  Thr  Ala  Lys  Asp  Cys  Thr  Ile
              260                  265                  270

Pro  Trp  Glu  Glu  Glu  Asp  His  Pro  Phe  His  Asp  Val  Ala  Val  Leu  Asp
              275                  280                  285

Leu  Gly  Ser  Ile  Leu  Pro  Asp  Glu  Leu  Ala  Glu  Ala  Leu  Glu  Phe  Asn
     290                  295                  300

Pro  Tyr  Asn  Ala  Pro  Pro  Glu  Leu  Ser  Leu  Ile  Leu  Ala  Lys  Thr  Ala
```

```
            305                 310                 315                 320
Arg Glu Thr Ala Ser Val Asn His Leu Arg Ser Val Val Tyr Gln Ile
                325                 330                 335

Ser Ala Asn Met Arg Lys Tyr Gln Thr Pro Ser Ser Ser Leu Val Asp
                340                 345                 350

Trp Gly Ser Gly His Gln Pro Ser Leu Pro Glu Gln Tyr Pro Tyr Gly
                355                 360                 365

Thr Gly Lys Thr Pro Ser Phe Asp Asn Thr Lys Pro Leu Pro Ala Arg
            370                 375                 380

Val Lys Pro Lys Pro Arg Tyr Trp Ala Asn Phe Gly Leu Lys Leu Ile
385                 390                 395                 400

Pro Asn Gln Gln Leu Asp Pro Asp Leu Pro Glu Leu Gly Ile Thr Gly
                405                 410                 415

Ala Leu Asp Leu Met Gly Thr Ser Val Val Ser Tyr Met Pro Pro Asn
                420                 425                 430

Leu Thr Arg Thr Arg Leu Asp Lys Phe Ser Asp Asp Phe Phe Val Glu
                435                 440                 445

Arg Arg Leu Asn Gly Phe Asn Pro Gly Lys Leu Asn Arg Val Thr Gly
            450                 455                 460

His Ala Trp Gln Tyr Gln Val Cys Tyr Asp Cys Ser Lys His Gln Val
465                 470                 475                 480

Glu Pro Ala Gly Ile Leu Pro Thr Lys Ile Thr Ala Arg Phe Asn Phe
                485                 490                 495

Cys Gly Gln Tyr Leu His Pro His Ser Ile Gln Phe Thr Leu Asn Gly
                500                 505                 510

Gln Thr Glu Thr Gln Gln Pro Gly Asp Glu Asn Trp Glu Trp Ser Lys
            515                 520                 525

Arg Leu Phe Arg Cys Ala Glu Phe Val Phe Gln Glu Ala Gln Ser His
            530                 535                 540

Leu Gly Arg Thr His Met Asn Leu Asp Gln Tyr Ala Met Ala Tyr Tyr
545                 550                 555                 560

Arg Asn Val Val Asn Asn Pro Ile Arg Leu Leu Glu Pro His Leu
                565                 570                 575

Glu Gly Leu Leu Ser Ile Asn Lys Leu Gly Ala Asn Leu Ile Ser Gly
                580                 585                 590

Pro Thr Gly Phe Ile Pro Glu Ala Ser Ser Leu Thr Pro Glu Ser Val
            595                 600                 605

Asp Asp Val Leu Lys Asp Glu Ile Ser His Leu Ser Tyr His Trp Thr
610                 615                 620

Pro His Arg Gln Thr Leu Pro Asp Arg Val Leu Asn Asn His Tyr Asp
625                 630                 635                 640

Pro Ala Ala Ile Ala Met Trp Asn Leu Leu Thr Gln Tyr Val Arg Glu
                645                 650                 655

Phe Phe Glu Asp His Gln Ala Gly Met Glu Glu Tyr Trp Ser Glu Ile
                660                 665                 670

Gln Ala Met Ser His Asp Leu Val Thr His Ser Ile Leu Lys Pro Glu
            675                 680                 685

Leu Gly Thr Leu Ala Val Gln Asn Asn Ala Asp Leu Gln Gln Leu Cys
            690                 695                 700

Val Tyr Val Ile Phe Leu Ser Ser Phe Phe His Ser Trp Val Asn Asn
705                 710                 715                 720

Lys Gln Tyr Glu Asp Gly Gly Asp Val Ser Tyr Ser Thr Ile Gly Leu
                725                 730                 735
```

```
Trp Asp Thr Arg His Pro Lys Tyr Asp Pro Leu Arg Val Ala Glu Arg
                740                 745                 750

Glu Ala Lys Gln Val Thr Leu Leu Trp Thr Leu Ser His Val Arg Tyr
            755                 760                 765

Asn Pro Ile Met Asp Val Gly Pro Thr Ala Leu Lys Asn Leu Leu Trp
770                 775                 780

Gln Gln Arg Gln His Ile Glu Pro Gly Ile Pro Leu Ala Asn Leu Met
785                 790                 795                 800

Met Ser Thr Asn Ile
            805

<210> SEQ ID NO 73
<211> LENGTH: 822
<212> TYPE: PRT
<213> ORGANISM: Nostoc sp.

<400> SEQUENCE: 73

Met Thr Asn Glu Ile Gln Asn Pro Val Asp His Leu Val Gly Asp Pro
1               5                   10                  15

Arg Val Arg Asp Ile Glu Pro Lys Phe Ser Lys Ile Ile Ser Asp Ile
            20                  25                  30

Ala Arg Val Phe Gly Gln Met Ala Gln Leu Lys Gly Arg Arg Ala Thr
        35                  40                  45

His Ser Phe Gly Thr Val Ala Lys Gly Val Leu Glu Val Val Lys Gln
    50                  55                  60

Pro Asp Ile Pro Pro His Arg Leu Leu Glu Ala Gly Lys Lys Phe Pro
65                  70                  75                  80

Val Leu Leu Arg His Ala Asn Ile Lys Gly Phe Arg Asp Asp Ala Ile
                85                  90                  95

Leu Asp Gly Arg Gly Ala Thr Leu Arg Ile Leu Asn Gly Pro Ala Asp
            100                 105                 110

Ala Pro Ile Thr Ala Leu Asp Leu His Thr Pro Ile Leu Asp Val Leu
        115                 120                 125

Met Ser Thr Gly Arg Cys Phe Ile Leu Pro Asp Ala Ala Ser Phe Ser
    130                 135                 140

Arg Trp Val Ala Ser Pro Leu Gln Asp Arg Ala Lys Leu Leu Val Glu
145                 150                 155                 160

Phe Pro Lys Ile Thr Pro Ile Phe Ala Glu Ile Ile Arg Asn Pro Asp
                165                 170                 175

Ser Tyr Thr Lys Leu His Tyr Tyr Ser Glu Thr Thr Tyr Leu Phe Ile
            180                 185                 190

Gly Leu Asp Gly Lys Gln Tyr Tyr Leu Arg Tyr Arg Leu Ile Asn Ser
        195                 200                 205

Asp Arg Ser Ala Asp Thr Gly Phe Ile Asn Ser Ala Asp Leu Arg Leu
    210                 215                 220

Pro Leu Asp Tyr Leu Pro Arg Leu Glu Asp Thr Arg Pro Glu Thr
225                 230                 235                 240

Tyr Leu Gln Asn Asp Tyr Gln Gln Lys Val Lys Asn Gly Gly Val Lys
                245                 250                 255

Tyr Ile Leu Gln Phe Gln Leu Arg Ala Val Ser Asp Asn Gln Ala Ala
            260                 265                 270

Asn Glu Glu Ala Lys Asp Cys Thr Ile Pro Trp Asp Glu Thr Gln Tyr
        275                 280                 285

Pro Cys Lys Asp Val Ala Val Ile Ser Leu Thr Glu Ile Val Pro Ser
```

```
            290                 295                 300
Glu Leu Ala Glu Pro Leu Glu Phe Asn Pro Tyr His Ala Pro Pro Asp
305                 310                 315                 320

Leu Ser Leu Ile Leu Ala His Ser Ile Asn Glu Thr Ala Ser Val Asn
                325                 330                 335

His Leu Arg Ser Val Val Tyr Gln Ile Ser Ala Asn Met Arg Lys Phe
            340                 345                 350

Gln Gln Pro Ser Ala Glu Leu Val Asp Trp Gly Ile Lys Gly Asn Gln
        355                 360                 365

Pro Asp Pro Lys Gln Val Tyr Thr Tyr Tyr Gly Gln Ile Gly Gln Asp
    370                 375                 380

Ile Pro Arg Tyr Asp Phe Arg Arg Pro Leu Pro Asp Arg Val Lys Pro
385                 390                 395                 400

Lys Pro Arg Tyr Ile Ala Asn Phe Gly Leu His Leu Phe Pro Ala Arg
                405                 410                 415

Pro Leu Gly Ser Ile Pro Met Leu Gly Ile Val Gly Val Ala Glu Thr
            420                 425                 430

Met Gln Ala Leu Gly Gln Thr Ala Pro Gln Trp Met Pro Ala Asn Leu
        435                 440                 445

Thr Arg Thr Arg Pro Asp Lys Tyr Glu Asp Gln Phe Phe Val Glu Arg
    450                 455                 460

Arg Leu Asn Gly Phe Asn Pro Gly Lys Phe Asn Arg Val His Thr Phe
465                 470                 475                 480

Glu Pro Trp Gln Tyr Thr Ile Arg Tyr Asp Cys Arg Lys Tyr Lys Val
                485                 490                 495

Glu Glu Ala Gly Ile Leu Pro Ala Glu Ile Glu Ala Arg Phe Lys Phe
            500                 505                 510

Glu Asp His Asn Leu His Leu His Ser Ile Lys Phe Ile Leu Asn Gly
        515                 520                 525

Lys Thr Glu Thr His Lys Pro Gly Asp Ala Asp Trp Glu Trp Ser Lys
    530                 535                 540

Arg Leu Phe Arg Thr Ala Glu Phe Val Phe Gln Glu Ile Gln Ser His
545                 550                 555                 560

Leu Gly Arg Thr His Met Asn Leu Asp Gln Tyr Ala Met Ala Tyr Tyr
                565                 570                 575

Arg Asn Val Val Asn Asn Pro Ile Arg Leu Leu Leu Glu Pro His Phe
            580                 585                 590

Asp Gly Leu Leu Asn Ile Asn Ser Leu Gly Ala Ala Leu Ile Leu Gly
        595                 600                 605

Ala Thr Gly Phe Ile Pro Glu Ala Ser Ser Leu Ser Pro Glu Glu Val
    610                 615                 620

Asp Ile Val Leu Lys Asp Glu Ile Ser Arg Leu Ser Tyr Arg Asn Trp
625                 630                 635                 640

Ser Pro His Ile Gln Ala Leu Lys Asp Glu Val Gln Asn Asn His Phe
                645                 650                 655

Asp Arg Ala Ala Leu Ser Val Trp Glu Ala Ile Glu Glu Tyr Val Ser
            660                 665                 670

Glu Phe Phe Gln Lys Gln Glu Ala Gly Ile Lys Ala Tyr Trp Ser Glu
        675                 680                 685

Ile Gly Gly Met Ser Glu Asp Leu Val Lys His Ser Val Leu Gly Gln
    690                 695                 700

Lys Ser Gln Ser Leu Ala Ile Ala Asn Ile Asn Asp Leu Lys Gln Leu
705                 710                 715                 720
```

```
Cys Ile Tyr Val Ile Tyr Leu Ser Ser Phe Phe His Ser Trp Val Asn
                725                 730                 735

Asn Lys Gln Tyr Asp Asp Gly Gly Asp Pro Ala Tyr Ala Ser Ile Gly
            740                 745                 750

Leu Trp Asp Gly His Asn Pro Gln Tyr Asn Pro Ile Thr Val Ala Glu
        755                 760                 765

Lys His Ala Arg Gln Val Thr Leu Leu Trp Thr Leu Ser Ser Val Arg
    770                 775                 780

Tyr Asn Pro Val Met Glu Val Gly Pro Ala Leu Lys Asp Arg Leu
785                 790                 795                 800

Trp Lys Arg Arg Lys Ile Ile Gln Pro Gly Ile Pro Val Glu Ser Ile
            805                 810                 815

Met Met Ser Thr Asn Ile
            820

<210> SEQ ID NO 74
<211> LENGTH: 371
<212> TYPE: PRT
<213> ORGANISM: Agrocybe aegerita

<400> SEQUENCE: 74

Met Lys Tyr Phe Pro Leu Phe Pro Thr Leu Val Phe Ala Ala Arg Val
1               5                   10                  15

Val Ala Phe Pro Ala Tyr Ala Ser Leu Ala Gly Leu Ser Gln Gln Glu
            20                  25                  30

Leu Asp Ala Ile Ile Pro Thr Leu Glu Ala Arg Glu Pro Gly Leu Pro
        35                  40                  45

Pro Gly Pro Leu Glu Asn Ser Ser Ala Lys Leu Val Asn Asp Glu Ala
    50                  55                  60

His Pro Trp Lys Pro Leu Arg Pro Gly Asp Ile Arg Gly Pro Cys Pro
65                  70                  75                  80

Gly Leu Asn Thr Leu Ala Ser His Gly Tyr Leu Pro Arg Asn Gly Val
                85                  90                  95

Ala Thr Pro Val Gln Ile Ile Asn Ala Val Gln Glu Gly Leu Asn Phe
            100                 105                 110

Asp Asn Gln Ala Ala Val Phe Ala Thr Tyr Ala Ala His Leu Val Asp
        115                 120                 125

Gly Asn Leu Ile Thr Asp Leu Leu Ser Ile Gly Arg Lys Thr Arg Leu
    130                 135                 140

Thr Gly Pro Asp Pro Pro Pro Ala Ser Val Gly Gly Leu Asn Glu
145                 150                 155                 160

His Gly Thr Phe Glu Gly Asp Ala Ser Met Thr Arg Gly Asp Ala Phe
                165                 170                 175

Phe Gly Asn Asn His Asp Phe Asn Glu Thr Leu Phe Glu Gln Leu Val
            180                 185                 190

Asp Tyr Ser Asn Arg Phe Gly Gly Lys Tyr Asn Leu Thr Val Ala
        195                 200                 205

Gly Glu Leu Arg Phe Lys Arg Ile Gln Asp Ser Ile Ala Thr Asn Pro
    210                 215                 220

Asn Phe Ser Phe Val Asp Phe Arg Phe Thr Ala Tyr Gly Glu Thr
225                 230                 235                 240

Thr Phe Pro Ala Asn Leu Phe Val Asp Gly Arg Arg Asp Asp Gly Gln
                245                 250                 255

Leu Asp Met Asp Ala Ala Arg Ser Phe Phe Gln Phe Ser Arg Met Pro
```

```
                260                 265                 270
Asp Asp Phe Phe Arg Ala Pro Ser Pro Arg Ser Gly Thr Gly Val Glu
            275                 280                 285
Val Val Ile Gln Ala His Pro Met Gln Pro Gly Arg Asn Val Gly Lys
            290                 295                 300
Ile Asn Ser Tyr Thr Val Asp Pro Thr Ser Ser Asp Phe Ser Thr Pro
305                 310                 315                 320
Cys Leu Met Tyr Glu Lys Phe Val Asn Ile Thr Val Lys Ser Leu Tyr
            325                 330                 335
Pro Asn Pro Thr Val Gln Leu Arg Lys Ala Leu Asn Thr Asn Leu Asp
            340                 345                 350
Phe Phe Phe Gln Gly Val Ala Ala Gly Cys Thr Gln Val Phe Pro Tyr
            355                 360                 365
Gly Arg Asp
        370

<210> SEQ ID NO 75
<211> LENGTH: 417
<212> TYPE: PRT
<213> ORGANISM: Bacillus subtilis

<400> SEQUENCE: 75

Met Asn Glu Gln Ile Pro His Asp Lys Ser Leu Asp Asn Ser Leu Thr
1               5                   10                  15
Leu Leu Lys Glu Gly Tyr Leu Phe Ile Lys Asn Arg Thr Glu Arg Tyr
            20                  25                  30
Asn Ser Asp Leu Phe Gln Ala Arg Leu Leu Gly Lys Asn Phe Ile Cys
        35                  40                  45
Met Thr Gly Ala Glu Ala Ala Lys Val Phe Tyr Asp Thr Asp Arg Phe
    50                  55                  60
Gln Arg Gln Asn Ala Leu Pro Lys Arg Val Gln Lys Ser Leu Phe Gly
65                  70                  75                  80
Val Asn Ala Ile Gln Gly Met Asp Gly Ser Ala His Ile His Arg Lys
                85                  90                  95
Met Leu Phe Leu Ser Leu Met Thr Pro Pro His Gln Lys Arg Leu Ala
            100                 105                 110
Glu Leu Met Thr Glu Glu Trp Lys Ala Ala Val Thr Arg Trp Glu Lys
            115                 120                 125
Ala Asp Glu Val Val Leu Phe Glu Glu Ala Lys Glu Ile Leu Cys Arg
        130                 135                 140
Val Ala Cys Tyr Trp Ala Gly Val Pro Leu Lys Glu Thr Glu Val Lys
145                 150                 155                 160
Glu Arg Ala Asp Asp Phe Ile Asp Met Val Asp Ala Phe Gly Ala Val
                165                 170                 175
Gly Pro Arg His Trp Lys Gly Arg Arg Ala Arg Pro Arg Ala Glu Glu
            180                 185                 190
Trp Ile Glu Val Met Ile Glu Asp Ala Arg Ala Gly Leu Leu Lys Thr
            195                 200                 205
Thr Ser Gly Thr Ala Leu His Glu Met Ala Phe His Thr Gln Glu Asp
        210                 215                 220
Gly Ser Gln Leu Asp Ser Arg Met Ala Ala Ile Glu Leu Ile Asn Val
225                 230                 235                 240
Leu Arg Pro Ile Val Ala Ile Ser Tyr Phe Leu Val Phe Ser Ala Leu
                245                 250                 255
```

Ala Leu His Glu His Pro Lys Tyr Lys Glu Trp Leu Arg Ser Gly Asn
           260                 265                 270

Ser Arg Glu Arg Glu Met Phe Val Gln Glu Val Arg Arg Tyr Tyr Pro
        275                 280                 285

Phe Gly Pro Phe Leu Gly Ala Leu Val Lys Lys Asp Phe Val Trp Asn
        290                 295                 300

Asn Cys Glu Phe Lys Lys Gly Thr Ser Val Leu Leu Asp Leu Tyr Gly
305                 310                 315                 320

Thr Asn His Asp Pro Arg Leu Trp Asp His Pro Asp Glu Phe Arg Pro
                325                 330                 335

Glu Arg Phe Ala Glu Arg Glu Asn Leu Phe Asp Met Ile Pro Gln
                340                 345                 350

Gly Gly Gly His Ala Glu Lys Gly His Arg Cys Pro Gly Glu Gly Ile
                355                 360                 365

Thr Ile Glu Val Met Lys Ala Ser Leu Asp Phe Leu Val His Gln Ile
        370                 375                 380

Glu Tyr Asp Val Pro Glu Gln Ser Leu His Tyr Ser Leu Ala Arg Met
385                 390                 395                 400

Pro Ser Leu Pro Glu Ser Gly Phe Val Met Ser Gly Ile Arg Arg Lys
                405                 410                 415

Ser

<210> SEQ ID NO 76
<211> LENGTH: 415
<212> TYPE: PRT
<213> ORGANISM: Sphingomonas paucimobilis

<400> SEQUENCE: 76

Met Pro Lys Thr Pro His Thr Lys Gly Pro Asp Glu Thr Leu Ser Leu
1               5                   10                  15

Leu Ala Asp Pro Tyr Arg Phe Ile Ser Arg Gln Cys Gln Arg Leu Gly
                20                  25                  30

Ala Asn Ala Phe Glu Ser Arg Phe Leu Leu Lys Lys Thr Asn Cys Leu
            35                  40                  45

Lys Gly Ala Lys Ala Ala Glu Ile Phe Tyr Asp Thr Thr Arg Phe Glu
50                  55                  60

Arg Glu Gly Ala Met Pro Val Ala Ile Gln Lys Thr Leu Leu Gly Gln
65                  70                  75                  80

Gly Gly Val Gln Gly Leu Asp Gly Glu Thr His Arg His Arg Lys Gln
                85                  90                  95

Met Phe Met Gly Leu Met Thr Pro Glu Arg Val Arg Ala Leu Ala Gln
            100                 105                 110

Leu Phe Glu Ala Glu Trp Arg Arg Ala Val Pro Gly Trp Thr Arg Lys
        115                 120                 125

Gly Glu Ile Val Phe Tyr Asp Glu Leu His Glu Pro Leu Thr Arg Ala
    130                 135                 140

Val Cys Ala Trp Ala Gly Val Pro Leu Pro Asp Asp Glu Ala Gly Asn
145                 150                 155                 160

Arg Ala Gly Glu Leu Arg Ala Leu Phe Asp Ala Ala Gly Ser Ala Ser
                165                 170                 175

Pro Arg His Leu Trp Ser Arg Leu Ala Arg Arg Val Asp Ala Trp
            180                 185                 190

Ala Lys Arg Ile Ile Glu Gly Ile Arg Ala Gly Ser Ile Gly Ser Gly
        195                 200                 205

```
Ser Gly Thr Ala Ala Tyr Ala Ile Ala Trp His Arg Asp Arg His Asp
    210                 215                 220

Asp Leu Leu Ser Pro His Val Ala Ala Val Glu Leu Val Asn Val Leu
225                 230                 235                 240

Arg Pro Thr Val Ala Ile Ala Val Tyr Ile Thr Phe Val Ala His Ala
                245                 250                 255

Leu Gln Thr Cys Ser Gly Ile Arg Ala Ala Leu Val Gln Gln Pro Asp
            260                 265                 270

Tyr Ala Glu Leu Phe Val Gln Glu Val Arg Arg Phe Tyr Pro Phe Phe
        275                 280                 285

Pro Ala Val Val Ala Arg Ala Ser Gln Asp Phe Glu Trp Glu Gly Met
290                 295                 300

Ala Phe Pro Glu Gly Arg Gln Val Val Leu Asp Leu Tyr Gly Ser Asn
305                 310                 315                 320

His Asp Ala Ala Thr Trp Ala Asp Pro Gln Glu Phe Arg Pro Glu Arg
                325                 330                 335

Phe Arg Ala Trp Asp Glu Asp Ser Phe Asn Phe Ile Pro Gln Gly Gly
            340                 345                 350

Gly Asp His Tyr Leu Gly His Arg Cys Pro Gly Glu Trp Ile Val Leu
        355                 360                 365

Ala Ile Met Lys Val Ala Ala His Leu Leu Val Asn Ala Met Arg Tyr
370                 375                 380

Asp Val Pro Asp Gln Asp Leu Ser Ile Asp Phe Ala Arg Leu Pro Ala
385                 390                 395                 400

Leu Pro Lys Ser Gly Phe Val Met Arg Asn Val His Ile Gly Gly
                405                 410                 415
```

<210> SEQ ID NO 77
<211> LENGTH: 418
<212> TYPE: PRT
<213> ORGANISM: Clostridium acetobutylicum

<400> SEQUENCE: 77

```
Met Leu Leu Lys Glu Asn Thr Ala Lys Asp Lys Gly Ile Asp Ser Thr
1               5                   10                  15

Leu Asp Leu Leu Lys Glu Gly Tyr Leu Phe Ile Lys Asn Arg Ala Asp
                20                  25                  30

His Tyr Gln Ser Asp Leu Phe Glu Thr Arg Leu Met Gly Gln Arg Ile
            35                  40                  45

Ile Cys Met Thr Gly Glu Glu Ala Ala Arg Ile Phe Tyr Asp Ser Asp
        50                  55                  60

Lys Phe Lys Arg Gln Gly Ala Ala Pro Lys Arg Val Gln Glu Thr Leu
65                  70                  75                  80

Leu Gly Glu Asn Ala Ile Gln Thr Leu Asp Gly Glu Ser His Leu His
                85                  90                  95

Arg Lys Lys Leu Phe Met Leu Leu Thr Asn Gln Val Gln Gln Lys Arg
            100                 105                 110

Leu Ala Glu Leu Thr Thr Glu Lys Trp Glu Ala Ser Ala Ser Lys Trp
        115                 120                 125

His Thr Lys Ser Ile Val Leu Phe Asn Glu Ala Asn Glu Ile Leu Cys
130                 135                 140

Gln Val Ala Cys His Trp Ala Gly Val Pro Leu Met Glu Ser Asp Ile
145                 150                 155                 160

Lys Asn Arg Ala Glu Asp Phe Ser Ser Met Ile Asp Ser Phe Gly Ala
                165                 170                 175
```

Val Gly Pro Arg His Trp Lys Gly Lys Lys Ala Arg Asn Thr Ile Glu
            180                 185                 190

Ala Trp Ile Lys Glu Ile Ile Glu Asn Val Arg Ser Gly Arg Ile Arg
        195                 200                 205

Ala Glu Glu Gly Ser Pro Leu His Glu Ile Ala Phe Tyr Ile Asp Val
    210                 215                 220

Asn Gly Gln Gln Met Pro Ala Glu Met Ala Ala Ile Glu Leu Ile Asn
225                 230                 235                 240

Ile Leu Arg Pro Ile Val Ala Ile Ser Thr Phe Ile Thr Phe Ser Ala
                245                 250                 255

Leu Ala Leu Tyr Glu His Ser Glu Tyr Arg Gly Lys Leu Gln Ser Lys
            260                 265                 270

Asp Ile Arg Tyr Leu Glu Met Phe Thr Gln Glu Val Arg Arg Tyr Tyr
        275                 280                 285

Pro Phe Ala Pro Phe Val Gly Ala Arg Val Arg Lys Asp Phe Leu Trp
    290                 295                 300

Asn Asn Cys Glu Phe Lys Lys Glu Met Leu Val Leu Leu Asp Ile Tyr
305                 310                 315                 320

Gly Thr Asn His Asp Ser Arg Ile Trp Gln Lys Pro Tyr Glu Phe Ile
                325                 330                 335

Pro Asp Arg Phe Arg Ser Tyr Lys Gly Asn Leu Phe Asp Phe Ile Pro
            340                 345                 350

Gln Gly Gly Gly Asp Pro Ser Ser Thr His Arg Cys Pro Gly Glu Gly
        355                 360                 365

Ile Thr Leu Glu Ile Met Lys Thr Ser Leu Asp Phe Leu Ser Thr Lys
    370                 375                 380

Ile Asp Phe Thr Val Pro Asp Gln Asp Leu Ser Tyr Ser Leu Ser Lys
385                 390                 395                 400

Ile Pro Thr Leu Pro Lys Ser Gly Phe Ile Ile Asp Asn Ile Asn Leu
                405                 410                 415

Lys Leu

<210> SEQ ID NO 78
<211> LENGTH: 646
<212> TYPE: PRT
<213> ORGANISM: Elizabethkingia meningoseptica

<400> SEQUENCE: 78

Met Asn Pro Ile Thr Ser Lys Phe Asp Lys Val Leu Asn Ala Ser Ser
1               5                   10                  15

Glu Tyr Gly His Val Asn His Glu Pro Asp Ser Ser Lys Glu Gln Gln
            20                  25                  30

Arg Asn Thr Pro Gln Lys Ser Met Pro Phe Ser Asp Gln Ile Gly Asn
        35                  40                  45

Tyr Gln Arg Asn Lys Gly Ile Pro Val Gln Ser Tyr Asp Asn Ser Lys
    50                  55                  60

Ile Tyr Ile Ile Gly Ser Gly Ile Ala Gly Met Ser Ala Ala Tyr Tyr
65                  70                  75                  80

Phe Ile Arg Asp Gly His Val Pro Ala Lys Asn Ile Thr Phe Leu Glu
                85                  90                  95

Gln Leu His Ile Asp Gly Gly Ser Leu Asp Gly Ala Gly Asn Pro Thr
            100                 105                 110

Asp Gly Tyr Ile Ile Arg Gly Gly Arg Glu Met Asp Met Thr Tyr Glu
        115                 120                 125

```
Asn Leu Trp Asp Met Phe Gln Asp Ile Pro Ala Leu Glu Met Pro Ala
            130                 135                 140

Pro Tyr Ser Val Leu Asp Glu Tyr Arg Leu Ile Asn Asp Asn Asp Ser
145                 150                 155                 160

Asn Tyr Ser Lys Ala Arg Leu Ile Asn Asn Lys Gly Glu Ile Lys Asp
                165                 170                 175

Phe Ser Lys Phe Gly Leu Asn Lys Met Asp Gln Leu Ala Ile Ile Arg
            180                 185                 190

Leu Leu Leu Lys Asn Lys Glu Glu Leu Asp Asp Leu Thr Ile Glu Asp
                195                 200                 205

Tyr Phe Ser Glu Ser Phe Leu Lys Ser Asn Phe Trp Thr Phe Trp Arg
210                 215                 220

Thr Met Phe Ala Phe Glu Asn Trp His Ser Leu Leu Glu Leu Lys Leu
225                 230                 235                 240

Tyr Met His Arg Phe Leu His Ala Ile Asp Gly Leu Asn Asp Leu Ser
                245                 250                 255

Ser Leu Val Phe Pro Lys Tyr Asn Gln Tyr Asp Thr Phe Val Thr Pro
            260                 265                 270

Leu Arg Lys Phe Leu Gln Glu Lys Gly Val Asn Ile His Leu Asn Thr
            275                 280                 285

Leu Val Lys Asp Leu Asp Ile His Ile Asn Thr Glu Gly Lys Val Val
290                 295                 300

Glu Gly Ile Ile Thr Glu Gln Asp Gly Lys Glu Val Lys Ile Pro Val
305                 310                 315                 320

Gly Lys Asn Asp Tyr Val Ile Val Thr Thr Gly Ser Met Thr Glu Asp
                325                 330                 335

Thr Phe Tyr Gly Asn Asn Lys Thr Ala Pro Ile Ile Gly Ile Asp Asn
            340                 345                 350

Ser Thr Ser Gly Gln Ser Ala Gly Trp Lys Leu Trp Lys Asn Leu Ala
            355                 360                 365

Ala Lys Ser Glu Ile Phe Gly Lys Pro Glu Lys Phe Cys Ser Asn Ile
370                 375                 380

Glu Lys Ser Ala Trp Glu Ser Ala Thr Leu Thr Cys Lys Pro Ser Ala
385                 390                 395                 400

Leu Ile Asp Lys Leu Lys Glu Tyr Ser Val Asn Asp Pro Tyr Ser Gly
                405                 410                 415

Lys Thr Val Thr Gly Gly Ile Ile Thr Ile Thr Asp Ser Asn Trp Leu
            420                 425                 430

Met Ser Phe Thr Cys Asn Arg Gln Pro His Phe Pro Glu Gln Pro Asp
            435                 440                 445

Asp Val Leu Val Leu Trp Val Tyr Ala Leu Phe Met Asp Lys Glu Gly
450                 455                 460

Asn Tyr Ile Lys Lys Thr Met Leu Glu Cys Thr Gly Asp Glu Ile Leu
465                 470                 475                 480

Ala Glu Leu Cys Tyr His Leu Gly Ile Glu Asp Gln Leu Glu Asn Val
                485                 490                 495

Gln Lys Asn Thr Ile Val Arg Thr Ala Phe Met Pro Tyr Ile Thr Ser
            500                 505                 510

Met Phe Met Pro Arg Ala Lys Gly Asp Arg Pro Arg Val Val Pro Glu
            515                 520                 525

Gly Cys Lys Asn Leu Gly Leu Val Gly Gln Phe Val Glu Thr Asn Asn
530                 535                 540
```

```
Asp Val Val Phe Thr Met Glu Ser Ser Val Arg Thr Ala Arg Ile Ala
545                 550                 555                 560

Val Tyr Lys Leu Leu Asn Leu Asn Lys Gln Val Pro Asp Ile Asn Pro
            565                 570                 575

Leu Gln Tyr Asp Ile Arg His Leu Leu Lys Ala Ala Lys Thr Leu Asn
                580                 585                 590

Asp Asp Lys Pro Phe Val Gly Glu Gly Leu Leu Arg Lys Val Leu Lys
            595                 600                 605

Gly Thr Tyr Phe Glu His Val Leu Pro Ala Gly Ala Glu Glu Glu
610                 615                 620

Glu His Glu Ser Phe Ile Ala Glu His Val Asn Lys Phe Arg Glu Trp
625                 630                 635                 640

Val Lys Gly Ile Arg Gly
            645
```

```
<210> SEQ ID NO 79
<211> LENGTH: 589
<212> TYPE: PRT
<213> ORGANISM: Macrococcus caseolyticus

<400> SEQUENCE: 79

Met Tyr Tyr Ser Asn Gly Asn Tyr Glu Ala Phe Ala Arg Pro Lys Lys
1               5                   10                  15

Pro Glu Gly Val Asp Asn Lys Ser Ala Tyr Leu Val Gly Ser Gly Leu
            20                  25                  30

Ala Ser Leu Ala Ala Ala Ser Phe Leu Ile Arg Asp Gly Gln Met Lys
        35                  40                  45

Gly Glu Asn Ile His Ile Leu Glu Glu Leu Asp Leu Pro Gly Gly Ser
50                  55                  60

Leu Asp Gly Ile Leu Asn Pro Glu Arg Gly Tyr Ile Met Arg Gly Gly
65                  70                  75                  80

Arg Glu Met Glu Asn His Phe Glu Cys Leu Trp Asp Leu Phe Arg Ser
                85                  90                  95

Val Pro Ser Leu Glu Val Glu Asp Ala Ser Val Leu Asp Glu Phe Tyr
            100                 105                 110

Trp Leu Asn Lys Glu Asp Pro Asn Tyr Ser Lys Cys Arg Val Ile Glu
        115                 120                 125

Asn Arg Gly Gln Arg Leu Glu Ser Asp Gly Lys Met Thr Leu Thr Lys
130                 135                 140

Lys Ala Asn Lys Glu Ile Ile Gln Leu Cys Leu Met Lys Glu Glu Gln
145                 150                 155                 160

Leu Asn Asp Val Lys Ile Ser Asp Val Phe Ser Lys Asp Phe Leu Asp
                165                 170                 175

Ser Asn Phe Trp Ile Tyr Trp Lys Thr Met Phe Ala Phe Glu Pro Trp
            180                 185                 190

His Ser Ala Met Glu Met Arg Arg Tyr Leu Met Arg Phe Ile His His
        195                 200                 205

Ile Gly Gly Leu Ala Asp Phe Ser Ala Leu Lys Phe Thr Lys Phe Asn
210                 215                 220

Gln Phe Glu Ser Leu Val Met Pro Leu Ile Glu His Leu Lys Ala Lys
225                 230                 235                 240

Asn Val Thr Phe Glu Tyr Gly Val Thr Val Lys Asn Ile Gln Val Glu
                245                 250                 255

Cys Ser Lys Glu Ser Lys Val Ala Lys Ala Ile Asp Ile Val Arg Arg
            260                 265                 270
```

```
Gly Asn Glu Ser Ile Pro Leu Thr Glu Asn Asp Leu Val Phe Val
            275                 280                 285

Thr Asn Gly Ser Ile Thr Glu Ser Thr Thr Tyr Gly Asp Asn Asp Thr
290                 295                 300

Pro Ala Pro Pro Thr Ser Lys Pro Gly Gly Ala Trp Gln Leu Trp Glu
305                 310                 315                 320

Asn Leu Ser Thr Gln Cys Glu Glu Phe Gly Asn Pro Ala Lys Phe Tyr
            325                 330                 335

Lys Asp Leu Pro Glu Lys Ser Trp Phe Val Ser Ala Thr Ala Thr Thr
            340                 345                 350

Asn Asn Lys Glu Val Ile Asp Tyr Ile Gln Lys Ile Cys Lys Arg Asp
            355                 360                 365

Pro Leu Ser Gly Arg Thr Val Thr Gly Gly Ile Val Thr Val Asp Asp
            370                 375                 380

Ser Asn Trp Gln Leu Ser Phe Thr Leu Asn Arg Gln Gln Gln Phe Lys
385                 390                 395                 400

Asn Gln Pro Asp Asp Gln Val Ser Val Trp Ile Tyr Ala Leu Tyr Ser
            405                 410                 415

Asp Glu Arg Gly Glu Arg Thr Asn Lys Thr Ile Val Glu Cys Ser Gly
            420                 425                 430

Lys Glu Ile Cys Glu Glu Trp Leu Tyr His Met Gly Val Pro Glu Glu
            435                 440                 445

Lys Ile Ser Ala Leu Ala Ala Glu Cys Asn Thr Ile Pro Ser Tyr Met
            450                 455                 460

Pro Tyr Ile Thr Ala Tyr Phe Met Pro Arg Lys Glu Gly Asp Arg Pro
465                 470                 475                 480

Leu Val Val Pro His Gly Ser Lys Asn Ile Ala Phe Ile Gly Asn Phe
            485                 490                 495

Ala Glu Thr Glu Arg Asp Thr Val Phe Thr Thr Glu Tyr Ser Val Arg
            500                 505                 510

Thr Ala Met Glu Ala Val Tyr Lys Leu Leu Glu Val Asp Arg Gly Val
            515                 520                 525

Pro Glu Val Phe Ala Ser Val Tyr Asp Val Arg Ile Leu Leu His Ala
            530                 535                 540

Leu Ser Val Leu Asn Asp Gly Lys Lys Leu Asp Glu Ile Asp Met Pro
545                 550                 555                 560

Phe Tyr Glu Arg Leu Val Glu Lys Arg Leu Leu Lys Lys Ala Ser Gly
            565                 570                 575

Thr Phe Ile Glu Glu Leu Leu Glu Glu Ala Asn Leu Ile
            580                 585

<210> SEQ ID NO 80
<211> LENGTH: 590
<212> TYPE: PRT
<213> ORGANISM: Streptococcus pyogenes

<400> SEQUENCE: 80

Met Tyr Tyr Thr Ser Gly Asn Tyr Glu Ala Phe Ala Thr Pro Arg Lys
1               5                   10                  15

Pro Glu Gly Val Asp Gln Lys Ser Ala Tyr Ile Val Gly Thr Gly Leu
            20                  25                  30

Ala Gly Leu Ala Ala Ala Val Phe Leu Ile Arg Asp Gly His Met Ala
        35                  40                  45

Gly Glu Arg Ile His Leu Phe Glu Glu Leu Pro Leu Ala Gly Gly Ser
    50                  55                  60
```

-continued

Leu Asp Gly Ile Glu Lys Pro His Leu Gly Phe Val Thr Arg Gly Gly
65                  70                  75                  80

Arg Glu Met Glu Asn His Phe Glu Cys Met Trp Asp Met Tyr Arg Ser
                85                  90                  95

Ile Pro Ser Leu Glu Ile Pro Gly Ala Ser Tyr Leu Asp Glu Phe Tyr
            100                 105                 110

Trp Leu Asp Lys Asp Pro Asn Ser Ser Asn Cys Arg Leu Ile His
            115                 120                 125

Lys Arg Gly Asn Arg Val Asp Asp Gly Gln Tyr Thr Leu Gly Lys
        130                 135                 140

Gln Ser Lys Glu Leu Ile His Leu Ile Met Lys Thr Glu Glu Ser Leu
145                 150                 155                 160

Gly Asp Gln Thr Ile Glu Glu Phe Phe Ser Glu Asp Phe Phe Lys Ser
                165                 170                 175

Asn Phe Trp Val Tyr Trp Ala Thr Met Phe Ala Phe Glu Lys Trp His
            180                 185                 190

Ser Ala Val Glu Met Arg Arg Tyr Ala Met Arg Phe Ile His His Ile
            195                 200                 205

Asp Gly Leu Pro Asp Phe Thr Ser Leu Lys Phe Asn Lys Tyr Asn Gln
        210                 215                 220

Tyr Asp Ser Met Val Lys Pro Ile Ile Ala Tyr Leu Glu Ser His Asp
225                 230                 235                 240

Val Asp Ile Gln Phe Asp Thr Lys Val Thr Asp Ile Gln Val Glu Gln
                245                 250                 255

Thr Ala Gly Lys Lys Val Ala Lys Thr Ile His Met Thr Val Ser Gly
            260                 265                 270

Glu Ala Lys Ala Ile Glu Leu Thr Pro Asp Asp Leu Val Phe Val Thr
            275                 280                 285

Asn Gly Ser Ile Thr Glu Ser Ser Thr Tyr Gly Ser His His Glu Val
        290                 295                 300

Ala Lys Pro Thr Lys Ala Leu Gly Gly Ser Trp Asn Leu Trp Glu Asn
305                 310                 315                 320

Leu Ala Ala Gln Ser Asp Asp Phe Gly His Pro Lys Val Phe Tyr Gln
                325                 330                 335

Asp Leu Pro Ala Glu Ser Trp Phe Val Ser Ala Thr Ala Thr Ile Lys
            340                 345                 350

His Pro Ala Ile Glu Pro Tyr Ile Glu Arg Leu Thr His Arg Asp Leu
            355                 360                 365

His Asp Gly Lys Val Asn Thr Gly Gly Ile Ile Thr Ile Thr Asp Ser
        370                 375                 380

Asn Trp Met Met Ser Phe Ala Ile His Arg Gln Pro His Phe Lys Glu
385                 390                 395                 400

Gln Lys Glu Asn Glu Thr Thr Val Trp Ile Tyr Gly Leu Tyr Ser Asn
                405                 410                 415

Ser Glu Gly Asn Tyr Val His Lys Lys Ile Glu Glu Cys Thr Gly Gln
            420                 425                 430

Glu Ile Thr Glu Glu Trp Leu Tyr His Leu Gly Val Pro Val Asp Lys
            435                 440                 445

Ile Lys Asp Leu Ala Ser Gln Glu Tyr Ile Asn Thr Val Pro Val Tyr
        450                 455                 460

Met Pro Tyr Ile Thr Ser Tyr Phe Met Pro Arg Val Lys Gly Asp Arg
465                 470                 475                 480

```
Pro Lys Val Ile Pro Asp Gly Ser Val Asn Leu Ala Phe Ile Gly Asn
                485                 490                 495

Phe Ala Glu Ser Pro Ser Arg Asp Thr Val Phe Thr Thr Glu Tyr Ser
            500                 505                 510

Ile Arg Thr Ala Met Glu Ala Val Tyr Ser Phe Leu Asn Gly Glu Arg
        515                 520                 525

Gly Ile Pro Gln Gly Phe Asn Ser Ala Tyr Asp Ile Arg Glu Leu Leu
    530                 535                 540

Lys Ala Phe Tyr Tyr Leu Asn Asp Lys Lys Ala Ile Lys Asp Met Asp
545                 550                 555                 560

Leu Pro Ile Pro Ala Leu Ile Glu Lys Ile Gly His Lys Lys Ile Lys
            565                 570                 575

Asp Thr Phe Ile Glu Glu Leu Leu Lys Asp Ala Asn Leu Met
            580                 585                 590
```